United States Patent
Worrell et al.

(10) Patent No.: US 10,555,769 B2
(45) Date of Patent: Feb. 11, 2020

(54) FLEXIBLE CIRCUITS FOR ELECTROSURGICAL INSTRUMENT

(71) Applicant: Ethicon Endo-Surgery, LLC, Guaynabo, PR (US)

(72) Inventors: Barry C. Worrell, Centerville, OH (US); David C. Yates, West Chester, OH (US); Joseph D. Dennis, Wyoming, OH (US); Mark A. Davison, Mason, OH (US); Geoffrey S. Strobl, Williamsburg, OH (US)

(73) Assignee: Ethicon LLC, Guaynabo, PR (US)

( * ) Notice: Subject to any disclaimer, the term of this patent is extended or adjusted under 35 U.S.C. 154(b) by 702 days.

(21) Appl. No.: 15/050,102

(22) Filed: Feb. 22, 2016

(65) Prior Publication Data

US 2017/0238991 A1    Aug. 24, 2017

(51) Int. Cl.
*H01R 43/16* (2006.01)
*A61B 18/14* (2006.01)
(Continued)

(52) U.S. Cl.
CPC ......... *A61B 18/1445* (2013.01); *H05K 1/028* (2013.01); *H05K 1/034* (2013.01);
(Continued)

(58) Field of Classification Search
CPC .............. A61B 18/1445; A61B 18/085; A61B 5/04087; A61B 14/14; H05K 1/0313; H05K 1/0346; H05K 1/028; H05K 3/10; H05K 1/034; H05K 1/09; H05K 3/0011; H05K 3/061; Y10T 29/49128; Y10T 29/49155
(Continued)

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| AU | 2003241752 A1 | 9/2003 |
| CA | 2535467 A1 | 4/1993 |

(Continued)

OTHER PUBLICATIONS

Incropera et al., Fundamentals of Heat and Mass Transfer, Wiley, New York (1990). (Book—not attached).

(Continued)

*Primary Examiner* — Donghai D Nguyen

(57) ABSTRACT

The disclosure provides a method of manufacturing a flexible circuit electrode assembly and an apparatus manufactured by said method. According to the method, an electrically conductive sheet is laminated to an electrically insulative sheet. An electrode is formed on the electrically conductive sheet. An electrically insulative layer is formed on a tissue contacting surface of the electrode. The individual electrodes are separated from the laminated electrically insulative sheet and the electrically conductive sheet. In another method, a flexible circuit is vacuum formed to create a desired profile. The vacuum formed flexible circuit is trimmed. The trimmed vacuum formed flexible circuit is attached to a jaw member of a clamp jaw assembly.

22 Claims, 99 Drawing Sheets

(51) Int. Cl.
  *H05K 1/02* (2006.01)
  *H05K 1/03* (2006.01)
  *H05K 1/09* (2006.01)
  *H05K 3/00* (2006.01)
  *H05K 3/06* (2006.01)
  *H05K 3/10* (2006.01)
  *A61B 18/00* (2006.01)

(52) U.S. Cl.
  CPC ......... *H05K 1/0313* (2013.01); *H05K 1/0346* (2013.01); *H05K 1/09* (2013.01); *H05K 3/0011* (2013.01); *H05K 3/061* (2013.01); *H05K 3/10* (2013.01); *A61B 2018/00077* (2013.01); *A61B 2018/00083* (2013.01); *A61B 2018/1465* (2013.01); *H05K 2201/0154* (2013.01); *H05K 2201/05* (2013.01)

(58) Field of Classification Search
  USPC ........................... 29/831, 846, 874; 600/344
  See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A * | 9/1987 | Strand ................ A61B 5/04087 600/385 |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |

(56) References Cited

U.S. PATENT DOCUMENTS

| | | |
|---|---|---|
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,707 A | 8/1991 | Taheri |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A * | 9/1993 | DeLonzor .......... A61B 5/02427 600/344 |
| 5,254,129 A | 10/1993 | Alexander |
| 5,257,988 A | 11/1993 | L'Esperance, Jr. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,563 A | 6/1994 | Malis et al. |
| 5,318,564 A | 6/1994 | Eggers |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,449,370 A | 9/1995 | Vaitekunas |
| 5,451,053 A | 9/1995 | Garrido |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,471,988 A | 12/1995 | Fujio et al. |

(56) References Cited

U.S. PATENT DOCUMENTS

| | | |
|---|---|---|
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,155 A | 7/1998 | Beaupre et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |

(56) References Cited

U.S. PATENT DOCUMENTS

| | | |
|---|---|---|
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| H001904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |

(56) References Cited

U.S. PATENT DOCUMENTS

| | | |
|---|---|---|
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,409,722 B1 | 6/2002 | Hoey et al. |
| H002037 H | 7/2002 | Yates et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,142 B1 | 10/2002 | Faller et al. |
| 6,459,363 B1 | 10/2002 | Walker et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |

(56) References Cited

U.S. PATENT DOCUMENTS

| | | |
|---|---|---|
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,011,657 B2 | 3/2006 | Truckai et al. |
| 7,014,638 B2 | 3/2006 | Michelson |
| 7,025,732 B2 | 4/2006 | Thompson et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |

(56) References Cited

U.S. PATENT DOCUMENTS

| | | |
|---|---|---|
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,455,208 B2 | 11/2008 | Wales et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,145 B2 * | 1/2009 | Ehr .................. A61B 18/14 |
| | | 128/908 |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |

(56) References Cited

U.S. PATENT DOCUMENTS

| | | |
|---|---|---|
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,768 B2 | 5/2010 | Danek et al. |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 * | 6/2010 | Odom ............... A61B 18/1442 606/41 |
| 7,738,969 B2 | 6/2010 | Bleich |
| 7,740,594 B2 | 6/2010 | Hibner |
| 7,744,615 B2 | 6/2010 | Couture |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,871,392 B2 | 1/2011 | Sartor |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,770 B2 | 8/2011 | Swanson et al. |
| 8,020,743 B2 | 9/2011 | Shelton, IV |
| 8,028,885 B2 | 10/2011 | Smith et al. |
| 8,033,173 B2 | 10/2011 | Ehlert et al. |
| 8,038,693 B2 | 10/2011 | Allen |
| 8,048,070 B2 | 11/2011 | O'Brien et al. |

(56) References Cited

U.S. PATENT DOCUMENTS

| | | |
|---|---|---|
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,323 B2 | 1/2012 | Buysse et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,415 B2 | 7/2012 | Francischelli |
| 8,226,580 B2 | 7/2012 | Govari et al. |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,357,103 B2 | 1/2013 | Mark et al. |
| 8,357,149 B2 | 1/2013 | Govari et al. |
| 8,357,158 B2 | 1/2013 | McKenna et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,397,971 B2 | 3/2013 | Yates et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |

(56) References Cited

U.S. PATENT DOCUMENTS

| | | |
|---|---|---|
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,521,331 B2 | 8/2013 | Itkowitz |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,603,089 B2 | 12/2013 | Viola |
| 8,608,044 B2 | 12/2013 | Hueil et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,640,788 B2 | 2/2014 | Dachs, II et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,808,204 B2 | 8/2014 | Irisawa et al. |

(56) References Cited

U.S. PATENT DOCUMENTS

| | | |
|---|---|---|
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,039,731 B2 | 5/2015 | Joseph |
| 9,043,018 B2 | 5/2015 | Mohr |
| 9,044,227 B2 | 6/2015 | Shelton, IV et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |

(56) References Cited

U.S. PATENT DOCUMENTS

| | | |
|---|---|---|
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,574,644 B2 | 2/2017 | Parihar |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,636,135 B2 | 5/2017 | Stulen |
| 9,636,165 B2 | 5/2017 | Larson et al. |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,802,033 B2 | 10/2017 | Hibner et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,867,651 B2 | 1/2018 | Wham |

(56) References Cited

U.S. PATENT DOCUMENTS

| | | |
|---|---|---|
| 9,867,670 B2 | 1/2018 | Brannan et al. |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,907,563 B2 | 3/2018 | Germain et al. |
| 9,913,656 B2 | 3/2018 | Stulen |
| 9,913,680 B2 | 3/2018 | Voegele et al. |
| 9,918,730 B2 | 3/2018 | Trees et al. |
| 9,925,003 B2 | 3/2018 | Parihar et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,974,539 B2 | 5/2018 | Yates et al. |
| 9,987,033 B2 | 6/2018 | Neurohr et al. |
| 10,004,526 B2 | 6/2018 | Dycus et al. |
| 10,010,339 B2 | 7/2018 | Witt et al. |
| 10,010,341 B2 | 7/2018 | Houser et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,070,916 B2 | 9/2018 | Artale |
| 10,080,609 B2 | 9/2018 | Hancock et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,111,699 B2 | 10/2018 | Boudreaux |
| 10,111,703 B2 | 10/2018 | Cosman, Jr. et al. |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,130,412 B2 | 11/2018 | Wham |
| 10,154,848 B2 | 12/2018 | Chernov et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,179,022 B2 | 1/2019 | Yates et al. |
| 10,188,455 B2 | 1/2019 | Hancock et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,365 B2 | 2/2019 | Boudreaux et al. |
| 10,201,382 B2 | 2/2019 | Wiener et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055443 A1 | 3/2003 | Spotnitz |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0193153 A1 | 9/2004 | Sartor et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |

(56) References Cited

U.S. PATENT DOCUMENTS

| | | |
|---|---|---|
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0264995 A1 | 11/2006 | Fanton et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015575 A1 | 1/2008 | Odom et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0090763 A1 | 4/2009 | Zemlok et al. |
| 2009/0118751 A1 | 5/2009 | Wiener et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0254077 A1 | 10/2009 | Craig |
| 2009/0254080 A1 | 10/2009 | Honda |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0036370 A1 | 2/2010 | Mirel et al. |
| 2010/0042093 A9 | 2/2010 | Wham et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |

(56) References Cited

U.S. PATENT DOCUMENTS

| | | |
|---|---|---|
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0158307 A1 | 6/2010 | Kubota et al. |
| 2010/0168741 A1 | 7/2010 | Sanai et al. |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0028964 A1 | 2/2011 | Edwards |
| 2011/0125149 A1 | 5/2011 | El-Galley et al. |
| 2011/0125151 A1 | 5/2011 | Strauss et al. |
| 2011/0238010 A1 | 9/2011 | Kirschenman et al. |
| 2011/0270250 A1 | 11/2011 | Horner et al. |
| 2011/0276049 A1 | 11/2011 | Gerhardt |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0059289 A1 | 3/2012 | Nield et al. |
| 2012/0071863 A1 | 3/2012 | Lee et al. |
| 2012/0078139 A1 | 3/2012 | Aldridge et al. |
| 2012/0078244 A1 | 3/2012 | Worrell et al. |
| 2012/0080344 A1 | 4/2012 | Shelton, IV |
| 2012/0101495 A1 | 4/2012 | Young et al. |
| 2012/0109186 A1 | 5/2012 | Parrott et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0211542 A1 | 8/2012 | Racenet |
| 2012/0253328 A1 | 10/2012 | Cunningham et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0085510 A1 | 4/2013 | Stefanchik et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165916 A1 | 6/2013 | Mathur et al. |
| 2013/0165929 A1 | 6/2013 | Muir et al. |
| 2013/0214025 A1 | 8/2013 | Zemlok et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0121569 A1 | 5/2014 | Schafer et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0246475 A1 | 9/2014 | Hail et al. |
| 2014/0263541 A1 | 9/2014 | Leimbach et al. |
| 2014/0276659 A1 | 9/2014 | Juergens et al. |
| 2014/0276754 A1 | 9/2014 | Gilbert et al. |
| 2014/0276797 A1 | 9/2014 | Batchelor et al. |
| 2014/0276970 A1 | 9/2014 | Messerly et al. |
| 2014/0330271 A1 | 11/2014 | Dietz et al. |
| 2015/0032100 A1 | 1/2015 | Coulson et al. |
| 2015/0032150 A1 | 1/2015 | Ishida et al. |
| 2015/0080876 A1 | 3/2015 | Worrell et al. |
| 2015/0080887 A1 | 3/2015 | Sobajima et al. |
| 2015/0080912 A1 | 3/2015 | Sapre |
| 2015/0088178 A1 | 3/2015 | Stulen et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182277 A1 | 7/2015 | Wiener et al. |
| 2015/0230861 A1 | 8/2015 | Woloszko et al. |
| 2015/0257780 A1 | 9/2015 | Houser |
| 2015/0272659 A1 | 10/2015 | Boudreaux et al. |
| 2015/0272660 A1 | 10/2015 | Boudreaux et al. |
| 2015/0313667 A1 | 11/2015 | Allen, IV |
| 2015/0320480 A1 | 11/2015 | Cosman, Jr. et al. |
| 2015/0320481 A1 | 11/2015 | Cosman, Jr. et al. |
| 2015/0340586 A1 | 11/2015 | Wiener et al. |
| 2016/0030076 A1 | 2/2016 | Faller et al. |
| 2016/0045248 A1 | 2/2016 | Unger et al. |
| 2016/0051316 A1 | 2/2016 | Boudreaux |
| 2016/0074108 A1 | 3/2016 | Woodruff et al. |
| 2016/0128762 A1 | 5/2016 | Harris et al. |
| 2016/0144204 A1 | 5/2016 | Akagane |
| 2016/0157927 A1 | 6/2016 | Corbett et al. |
| 2016/0175029 A1 | 6/2016 | Witt et al. |
| 2016/0199123 A1 | 7/2016 | Thomas et al. |
| 2016/0199125 A1 | 7/2016 | Jones |
| 2016/0206342 A1 | 7/2016 | Robertson et al. |
| 2016/0228171 A1 | 8/2016 | Boudreaux |
| 2016/0262786 A1 | 9/2016 | Madan et al. |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0287311 A1 | 10/2016 | Friedrichs |
| 2016/0296249 A1 | 10/2016 | Robertson |
| 2016/0296250 A1 | 10/2016 | Olson et al. |
| 2016/0296251 A1 | 10/2016 | Olson et al. |
| 2016/0296252 A1 | 10/2016 | Olson et al. |
| 2016/0296268 A1 | 10/2016 | Gee et al. |
| 2016/0296270 A1 | 10/2016 | Strobl et al. |
| 2016/0317217 A1 | 11/2016 | Batross et al. |
| 2016/0338726 A1 | 11/2016 | Stulen et al. |
| 2016/0346001 A1 | 12/2016 | Vakharia et al. |
| 2016/0367273 A1 | 12/2016 | Robertson et al. |
| 2016/0367281 A1 | 12/2016 | Gee et al. |
| 2016/0374708 A1 | 12/2016 | Wiener et al. |
| 2016/0374709 A1 | 12/2016 | Timm et al. |
| 2016/0374712 A1 | 12/2016 | Stulen et al. |
| 2017/0000512 A1 | 1/2017 | Conlon et al. |
| 2017/0000516 A1 | 1/2017 | Stulen et al. |
| 2017/0000541 A1 | 1/2017 | Yates et al. |
| 2017/0000542 A1 | 1/2017 | Yates et al. |
| 2017/0000553 A1 | 1/2017 | Wiener et al. |
| 2017/0000554 A1 | 1/2017 | Yates et al. |
| 2017/0056056 A1 | 3/2017 | Wiener et al. |
| 2017/0056058 A1 | 3/2017 | Voegele et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |

(56) References Cited

U.S. PATENT DOCUMENTS

| | | |
|---|---|---|
| 2017/0086914 A1 | 3/2017 | Wiener et al. |
| 2017/0095267 A1 | 4/2017 | Messerly et al. |
| 2017/0105757 A1 | 4/2017 | Weir et al. |
| 2017/0105782 A1 | 4/2017 | Scheib et al. |
| 2017/0105786 A1 | 4/2017 | Scheib et al. |
| 2017/0105791 A1 | 4/2017 | Yates et al. |
| 2017/0143371 A1 | 5/2017 | Witt et al. |
| 2017/0143877 A1 | 5/2017 | Witt et al. |
| 2017/0189095 A1 | 7/2017 | Danziger et al. |
| 2017/0189096 A1 | 7/2017 | Danziger et al. |
| 2017/0196586 A1 | 7/2017 | Witt et al. |
| 2017/0196587 A1 | 7/2017 | Witt et al. |
| 2017/0202570 A1 | 7/2017 | Shelton, IV et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202592 A1 | 7/2017 | Shelton, IV et al. |
| 2017/0202593 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0245875 A1 | 8/2017 | Timm et al. |
| 2017/0312014 A1 | 11/2017 | Strobl et al. |
| 2017/0312015 A1 | 11/2017 | Worrell et al. |
| 2017/0312016 A1 | 11/2017 | Strobl et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0319228 A1 | 11/2017 | Worrell et al. |
| 2017/0319265 A1 | 11/2017 | Yates et al. |
| 2017/0325874 A1 | 11/2017 | Noack et al. |
| 2017/0348064 A1 | 12/2017 | Stewart et al. |
| 2018/0014872 A1 | 1/2018 | Dickerson |
| 2018/0028257 A1 | 2/2018 | Yates et al. |
| 2018/0036061 A1 | 2/2018 | Yates et al. |
| 2018/0036065 A1 | 2/2018 | Yates et al. |
| 2018/0042658 A1 | 2/2018 | Shelton, IV et al. |
| 2018/0064961 A1 | 3/2018 | Wiener et al. |
| 2018/0098785 A1 | 4/2018 | Price et al. |
| 2018/0098808 A1 | 4/2018 | Yates et al. |
| 2018/0116706 A9 | 5/2018 | Wiener et al. |
| 2018/0146976 A1 | 5/2018 | Clauda et al. |
| 2018/0177545 A1 | 6/2018 | Boudreaux et al. |
| 2018/0235691 A1 | 8/2018 | Voegele et al. |
| 2018/0280083 A1 | 10/2018 | Parihar et al. |
| 2019/0021783 A1 | 1/2019 | Asher et al. |

FOREIGN PATENT DOCUMENTS

| | | |
|---|---|---|
| CN | 1233944 A | 11/1999 |
| CN | 1253485 A | 5/2000 |
| CN | 2460047 Y | 11/2001 |
| CN | 1634601 A | 7/2005 |
| CN | 1640365 A | 7/2005 |
| CN | 1694649 A | 11/2005 |
| CN | 1775323 A | 5/2006 |
| CN | 1922563 A | 2/2007 |
| CN | 2868227 Y | 2/2007 |
| CN | 1951333 A | 4/2007 |
| CN | 101035482 A | 9/2007 |
| CN | 101040799 A | 9/2007 |
| CN | 101396300 A | 4/2009 |
| CN | 101467917 A | 7/2009 |
| CN | 101474081 A | 7/2009 |
| CN | 101674782 A | 3/2010 |
| CN | 101883531 A | 11/2010 |
| CN | 102160045 A | 8/2011 |
| CN | 202027624 U | 11/2011 |
| CN | 102834069 A | 12/2012 |
| CN | 101313865 B | 1/2013 |
| DE | 3904558 A1 | 8/1990 |
| DE | 9210327 U1 | 11/1992 |
| DE | 4300307 A1 | 7/1994 |
| DE | 4323585 A1 | 1/1995 |
| DE | 19608716 C1 | 4/1997 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0342448 A1 | 11/1989 |
| EP | 0443256 A1 | 8/1991 |
| EP | 0456470 A1 | 11/1991 |
| EP | 0238667 B1 | 2/1993 |
| EP | 0340803 B1 | 8/1993 |
| EP | 0598976 A2 | 6/1994 |
| EP | 0630612 A1 | 12/1994 |
| EP | 0424685 B1 | 5/1995 |
| EP | 0677275 A2 | 10/1995 |
| EP | 0482195 B1 | 1/1996 |
| EP | 0695535 A1 | 2/1996 |
| EP | 0705571 A1 | 4/1996 |
| EP | 0741996 B1 | 11/1996 |
| EP | 0612570 B1 | 6/1997 |
| EP | 0557806 B1 | 5/1998 |
| EP | 0640317 B1 | 9/1999 |
| EP | 1108394 A2 | 6/2001 |
| EP | 1138264 A1 | 10/2001 |
| EP | 0908148 B1 | 1/2002 |
| EP | 1229515 A2 | 8/2002 |
| EP | 0722696 B1 | 12/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1293172 B1 | 4/2006 |
| EP | 0875209 B1 | 5/2006 |
| EP | 1433425 B1 | 6/2006 |
| EP | 1256323 B1 | 8/2006 |
| EP | 1698289 A2 | 9/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1815950 A1 | 8/2007 |
| EP | 1839599 A1 | 10/2007 |
| EP | 1844720 A1 | 10/2007 |
| EP | 1862133 A1 | 12/2007 |
| EP | 1875875 A1 | 1/2008 |
| EP | 1878399 A1 | 1/2008 |
| EP | 1915953 A1 | 4/2008 |
| EP | 1532933 B1 | 5/2008 |
| EP | 1199045 B1 | 6/2008 |
| EP | 1707143 B1 | 6/2008 |
| EP | 1943957 A2 | 7/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1477104 B1 | 1/2009 |
| EP | 2014218 A2 | 1/2009 |
| EP | 1849424 B1 | 4/2009 |
| EP | 2042112 A2 | 4/2009 |

(56) References Cited

FOREIGN PATENT DOCUMENTS

| | | | |
|---|---|---|---|
| EP | 2042117 A1 | 4/2009 |
| EP | 2060238 A1 | 5/2009 |
| EP | 1832259 B1 | 6/2009 |
| EP | 2074959 A1 | 7/2009 |
| EP | 1810625 B1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 2106758 A1 | 10/2009 |
| EP | 2111813 A1 | 10/2009 |
| EP | 2131760 A1 | 12/2009 |
| EP | 1769766 B1 | 2/2010 |
| EP | 2151204 A1 | 2/2010 |
| EP | 2153791 A1 | 2/2010 |
| EP | 2200145 A1 | 6/2010 |
| EP | 1214913 B1 | 7/2010 |
| EP | 2238938 A1 | 10/2010 |
| EP | 2243439 A1 | 10/2010 |
| EP | 2298154 A2 | 3/2011 |
| EP | 2305144 A1 | 4/2011 |
| EP | 1510178 B1 | 6/2011 |
| EP | 1946708 B1 | 6/2011 |
| EP | 2335630 A1 | 6/2011 |
| EP | 1502551 B1 | 7/2011 |
| EP | 1728475 B1 | 8/2011 |
| EP | 2353518 A1 | 8/2011 |
| EP | 2361562 A1 | 8/2011 |
| EP | 2365608 A2 | 9/2011 |
| EP | 2420197 A2 | 2/2012 |
| EP | 2422721 A2 | 2/2012 |
| EP | 1927321 B1 | 4/2012 |
| EP | 2436327 A1 | 4/2012 |
| EP | 2529681 A1 | 12/2012 |
| EP | 1767164 B1 | 1/2013 |
| EP | 2316359 B1 | 3/2013 |
| EP | 2090238 B1 | 4/2013 |
| EP | 2578172 A2 | 4/2013 |
| EP | 1586275 B1 | 5/2013 |
| EP | 1616529 B1 | 9/2013 |
| EP | 1997438 B1 | 11/2013 |
| EP | 2668922 A1 | 12/2013 |
| EP | 2508143 B1 | 2/2014 |
| EP | 2583633 B1 | 10/2014 |
| EP | 2076195 B1 | 12/2015 |
| EP | 2113210 B1 | 3/2016 |
| EP | 2510891 B1 | 6/2016 |
| EP | 2227155 B1 | 7/2016 |
| EP | 2859858 B1 | 12/2016 |
| ES | 2115068 T3 | 6/1998 |
| GB | 1482943 A | 8/1977 |
| GB | 2032221 A | 4/1980 |
| GB | 2317566 A | 4/1998 |
| GB | 2379878 B | 11/2004 |
| GB | 2472216 A | 2/2011 |
| GB | 2447767 B | 8/2011 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04150847 A | 5/1992 |
| JP | H04152942 A | 5/1992 |
| JP | H 0541716 A | 2/1993 |
| JP | H0595955 A | 4/1993 |
| JP | H05115490 A | 5/1993 |
| JP | H0670938 A | 3/1994 |
| JP | H06104503 A | 4/1994 |
| JP | H06217988 A | 8/1994 |
| JP | H06507081 A | 8/1994 |
| JP | H 07500514 A | 1/1995 |
| JP | H07508910 A | 10/1995 |
| JP | H07308323 A | 11/1995 |
| JP | H0824266 A | 1/1996 |
| JP | H08229050 A | 9/1996 |
| JP | H08275951 A | 10/1996 |
| JP | H08299351 A | 11/1996 |
| JP | H08336544 A | 12/1996 |
| JP | H08336545 A | 12/1996 |
| JP | H09503146 A | 3/1997 |
| JP | H09130655 A | 5/1997 |
| JP | H09135553 A | 5/1997 |
| JP | H09140722 A | 6/1997 |
| JP | H105237 A | 1/1998 |
| JP | H10295700 A | 11/1998 |
| JP | H11501543 A | 2/1999 |
| JP | H11128238 A | 5/1999 |
| JP | H11192235 A | 7/1999 |
| JP | H11253451 A | 9/1999 |
| JP | H11318918 A | 11/1999 |
| JP | 2000041991 A | 2/2000 |
| JP | 2000070279 A | 3/2000 |
| JP | 2000210299 A | 8/2000 |
| JP | 2000271145 A | 10/2000 |
| JP | 2000287987 A | 10/2000 |
| JP | 2001029353 A | 2/2001 |
| JP | 2001502216 A | 2/2001 |
| JP | 2001309925 A | 11/2001 |
| JP | 2002059380 A | 2/2002 |
| JP | 2002177295 A | 6/2002 |
| JP | 2002186901 A | 7/2002 |
| JP | 2002204808 A | 7/2002 |
| JP | 2002238919 A | 8/2002 |
| JP | 2002263579 A | 9/2002 |
| JP | 2002301086 A | 10/2002 |
| JP | 2002306504 A | 10/2002 |
| JP | 2002330977 A | 11/2002 |
| JP | 2002542690 A | 12/2002 |
| JP | 2003000612 A | 1/2003 |
| JP | 2003010201 A | 1/2003 |
| JP | 2003510158 A | 3/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003530921 A | 10/2003 |
| JP | 2003310627 A | 11/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005040222 A | 2/2005 |
| JP | 2005066316 A | 3/2005 |
| JP | 2005074088 A | 3/2005 |
| JP | 2005507679 A | 3/2005 |
| JP | 2005534451 A | 11/2005 |
| JP | 2005337119 A | 12/2005 |
| JP | 2006006410 A | 1/2006 |
| JP | 2006068396 A | 3/2006 |
| JP | 2006075376 A | 3/2006 |
| JP | 2006081664 A | 3/2006 |
| JP | 2006114072 A | 4/2006 |
| JP | 2006512149 A | 4/2006 |
| JP | 2006116194 A | 5/2006 |
| JP | 2006158525 A | 6/2006 |
| JP | 2006217716 A | 8/2006 |
| JP | 2006218296 A | 8/2006 |
| JP | 2006288431 A | 10/2006 |
| JP | 2007037568 A | 2/2007 |
| JP | 2007050181 A | 3/2007 |

(56) References Cited

FOREIGN PATENT DOCUMENTS

| | | |
|---|---|---|
| JP | 2007-524459 A | 8/2007 |
| JP | 2007229454 A | 9/2007 |
| JP | 2007527747 A | 10/2007 |
| JP | 2007296369 A | 11/2007 |
| JP | 200801876 A | 1/2008 |
| JP | 2008018226 A | 1/2008 |
| JP | 200833644 A | 2/2008 |
| JP | 2008036390 A | 2/2008 |
| JP | 2008508065 A | 3/2008 |
| JP | 2008119250 A | 5/2008 |
| JP | 2008515562 A | 5/2008 |
| JP | 2008521503 A | 6/2008 |
| JP | 2008188160 A | 8/2008 |
| JP | D1339835 S | 8/2008 |
| JP | 2008212679 A | 9/2008 |
| JP | 2008536562 A | 9/2008 |
| JP | 2008284374 A | 11/2008 |
| JP | 2009511206 A | 3/2009 |
| JP | 2009082711 A | 4/2009 |
| JP | 2009517181 A | 4/2009 |
| JP | 4262923 B2 | 5/2009 |
| JP | 2009523567 A | 6/2009 |
| JP | 2009148557 A | 7/2009 |
| JP | 2009236177 A | 10/2009 |
| JP | 2009254819 A | 11/2009 |
| JP | 2010000336 A | 1/2010 |
| JP | 2010009686 A | 1/2010 |
| JP | 2010514923 A | 5/2010 |
| JP | 2010121865 A | 6/2010 |
| JP | 2010534522 A | 11/2010 |
| JP | 2010540186 A | 12/2010 |
| JP | 2011505198 A | 2/2011 |
| JP | 2012/075899 A | 4/2012 |
| JP | 2012071186 A | 4/2012 |
| JP | 2012235658 A | 11/2012 |
| JP | 5208761 B2 | 6/2013 |
| JP | 5714508 B2 | 5/2015 |
| JP | 2015515339 A | 5/2015 |
| JP | 5836543 B1 | 12/2015 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2304934 C2 | 8/2007 |
| RU | 2405603 C1 | 12/2010 |
| SU | 850068 A1 | 7/1981 |
| WO | WO-8103272 A1 | 11/1981 |
| WO | WO-9222259 A2 | 12/1992 |
| WO | WO-9307817 A1 | 4/1993 |
| WO | WO-9308757 A1 | 5/1993 |
| WO | WO-9314708 A1 | 8/1993 |
| WO | WO-9316646 A1 | 9/1993 |
| WO | WO-9320877 A1 | 10/1993 |
| WO | WO-9322973 A1 | 11/1993 |
| WO | WO-9400059 A1 | 1/1994 |
| WO | WO-9421183 A1 | 9/1994 |
| WO | WO-9424949 A1 | 11/1994 |
| WO | WO-9509572 A1 | 4/1995 |
| WO | WO-9510978 A1 | 4/1995 |
| WO | WO-9534259 A1 | 12/1995 |
| WO | WO-9630885 A1 | 10/1996 |
| WO | WO-9635382 A1 | 11/1996 |
| WO | WO-9639086 A1 | 12/1996 |
| WO | WO-9710764 A1 | 3/1997 |
| WO | WO-9800069 A1 | 1/1998 |
| WO | WO-9816156 A1 | 4/1998 |
| WO | WO-9826739 A1 | 6/1998 |
| WO | WO-9835621 A1 | 8/1998 |
| WO | WO-9837815 A1 | 9/1998 |
| WO | WO-9840020 A1 | 9/1998 |
| WO | WO-9847436 A1 | 10/1998 |
| WO | WO-9857588 A1 | 12/1998 |
| WO | WO-9920213 A1 | 4/1999 |
| WO | WO-9923960 A1 | 5/1999 |
| WO | WO-9940857 A1 | 8/1999 |
| WO | WO-9940861 A1 | 8/1999 |
| WO | WO-9952489 A1 | 10/1999 |
| WO | WO-0024330 A1 | 5/2000 |
| WO | WO-0024331 A1 | 5/2000 |
| WO | WO-0025691 A1 | 5/2000 |
| WO | WO-0064358 A2 | 11/2000 |
| WO | WO-0074585 A2 | 12/2000 |
| WO | WO-0124713 A1 | 4/2001 |
| WO | WO-0128444 A1 | 4/2001 |
| WO | WO-0154590 A1 | 8/2001 |
| WO | WO-0167970 A1 | 9/2001 |
| WO | WO-0172251 A1 | 10/2001 |
| WO | WO-0195810 A2 | 12/2001 |
| WO | WO-0224080 A2 | 3/2002 |
| WO | WO-0238057 A1 | 5/2002 |
| WO | WO-02062241 A1 | 8/2002 |
| WO | WO-02080797 A1 | 10/2002 |
| WO | WO-03001986 A2 | 1/2003 |
| WO | WO-03013374 A1 | 2/2003 |
| WO | WO-03020339 A2 | 3/2003 |
| WO | WO-03028541 A2 | 4/2003 |
| WO | WO-03030708 A2 | 4/2003 |
| WO | WO-03068046 A2 | 8/2003 |
| WO | WO-03082133 A1 | 10/2003 |
| WO | WO-2004011037 A2 | 2/2004 |
| WO | WO-2004012615 A1 | 2/2004 |
| WO | WO-2004026104 A2 | 4/2004 |
| WO | WO-2004032754 A2 | 4/2004 |
| WO | WO-2004032762 A1 | 4/2004 |
| WO | WO-2004032763 A2 | 4/2004 |
| WO | WO-2004037095 A2 | 5/2004 |
| WO | WO-2004060141 A2 | 7/2004 |
| WO | WO-2004078051 A2 | 9/2004 |
| WO | WO-2004098426 A1 | 11/2004 |
| WO | WO-2004112618 A2 | 12/2004 |
| WO | WO-2005052959 A2 | 6/2005 |
| WO | WO-2005117735 A1 | 12/2005 |
| WO | WO-2005122917 A1 | 12/2005 |
| WO | WO-2006012797 A2 | 2/2006 |
| WO | WO-2006021269 A1 | 3/2006 |
| WO | WO-2006036706 A1 | 4/2006 |
| WO | WO-2006042210 A2 | 4/2006 |
| WO | WO-2006055166 A2 | 5/2006 |
| WO | WO-2006058223 A2 | 6/2006 |
| WO | WO-2006063199 A2 | 6/2006 |
| WO | WO-2006083988 A1 | 8/2006 |
| WO | WO-2006101661 A2 | 9/2006 |
| WO | WO-2006119139 A2 | 11/2006 |
| WO | WO-2006119376 A2 | 11/2006 |
| WO | WO-2006129465 A1 | 12/2006 |
| WO | WO-2007008703 A2 | 1/2007 |
| WO | WO-2007008710 A2 | 1/2007 |
| WO | WO-2007038538 A1 | 4/2007 |
| WO | WO-2007040818 A1 | 4/2007 |
| WO | WO-2007047380 A2 | 4/2007 |
| WO | WO-2007047531 A2 | 4/2007 |
| WO | WO-2007056590 A2 | 5/2007 |
| WO | WO-2007087272 A2 | 8/2007 |
| WO | WO-2007089724 A2 | 8/2007 |
| WO | WO-2007143665 A2 | 12/2007 |
| WO | WO-2008016886 A2 | 2/2008 |
| WO | WO-2008020964 A2 | 2/2008 |
| WO | WO-2008042021 A1 | 4/2008 |
| WO | WO-2008045348 A2 | 4/2008 |
| WO | WO-2008049084 A2 | 4/2008 |
| WO | WO-2008051764 A2 | 5/2008 |
| WO | WO-2008089174 A2 | 7/2008 |
| WO | WO-2008099529 A1 | 8/2008 |
| WO | WO-2008101356 A1 | 8/2008 |
| WO | WO-2008118709 A1 | 10/2008 |
| WO | WO-2008130793 A1 | 10/2008 |
| WO | WO-2009010565 A1 | 1/2009 |
| WO | WO-2009018067 A1 | 2/2009 |
| WO | WO-2009018406 A2 | 2/2009 |
| WO | WO-2009022614 A1 | 2/2009 |
| WO | WO-2009027065 A1 | 3/2009 |
| WO | WO-2009036818 A1 | 3/2009 |
| WO | WO-2009039179 A1 | 3/2009 |
| WO | WO-2009046234 A2 | 4/2009 |

(56) References Cited

FOREIGN PATENT DOCUMENTS

| | | |
|---|---|---|
| WO | WO-2009059741 A1 | 5/2009 |
| WO | WO-2009073402 A2 | 6/2009 |
| WO | WO-2009082477 A2 | 7/2009 |
| WO | WO-2009088550 A2 | 7/2009 |
| WO | WO-2009120992 A2 | 10/2009 |
| WO | WO-2009141616 A1 | 11/2009 |
| WO | WO-2009149234 A1 | 12/2009 |
| WO | WO-2010017149 A1 | 2/2010 |
| WO | WO-2010017266 A1 | 2/2010 |
| WO | WO-2010068783 A1 | 6/2010 |
| WO | WO-2010104755 A1 | 9/2010 |
| WO | WO-2011008672 A2 | 1/2011 |
| WO | WO-2011/044338 A2 | 4/2011 |
| WO | WO-2011044343 A2 | 4/2011 |
| WO | WO-2011052939 A2 | 5/2011 |
| WO | WO-2011060031 A1 | 5/2011 |
| WO | WO-2011084768 A1 | 7/2011 |
| WO | WO-2011089717 A1 | 7/2011 |
| WO | WO-2011100321 A2 | 8/2011 |
| WO | WO-2011144911 A1 | 11/2011 |
| WO | WO-2012044597 A1 | 4/2012 |
| WO | WO-2012044606 A2 | 4/2012 |
| WO | WO-2012061638 A1 | 5/2012 |
| WO | WO-2012061722 A2 | 5/2012 |
| WO | WO-2012128362 A1 | 9/2012 |
| WO | WO-2012135705 A1 | 10/2012 |
| WO | WO-2012135721 A1 | 10/2012 |
| WO | WO-2012/150567 A1 | 11/2012 |
| WO | WO-2012166510 A1 | 12/2012 |
| WO | WO-2013018934 A1 | 2/2013 |
| WO | WO-2013034629 A1 | 3/2013 |
| WO | WO-2013062978 A2 | 5/2013 |
| WO | WO-2013102602 A2 | 7/2013 |
| WO | WO-2013154157 A1 | 10/2013 |
| WO | WO-2014092108 A1 | 6/2014 |
| WO | WO-2015197395 A8 | 12/2015 |
| WO | WO-2016009921 A1 | 1/2016 |

OTHER PUBLICATIONS

Glaser and Subak-Sharpe,Integrated Circuit Engineering, Addison-Wesley Publishing, Reading, MA (1979). (book—not attached).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wells et al., "Altered Mechanical Behavior of Epicardium Under Isothermal Biaxial Loading," Transactions of the ASME, Journal of Biomechanical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.

Douglas, S.C. "Introduction to Adaptive Filter". Digital Signal Processing Handbook. Ed. Vijay K. Madisetti and Douglas B. Williams. Boca Raton: CRC Press LLC, 1999.

Sullivan, "Optimal Choice for Number of Strands in a Litz-Wire Transformer Winding," IEEE Transactions on Power Electronics, vol. 14, No. 2, Mar. 1999, pp. 283-291.

National Semiconductors Temperature Sensor Handbook—http://www.national.com/appinfo/tempsensors/files/temphb.pdf; accessed online: Apr. 1, 2011.

Covidien Brochure, The LigaSure™ 5 mm Blunt Tip Sealer/Divider Family, dated Apr. 2013 (2 pages).

Covidien Brochure, The LigaSure Precise™ Instrument, dated Mar. 2011 (2 pages).

Kurt Gieck & Reiner Gieck, *Engineering Formulas* § Z.7 (7th ed. 1997).

Covidien Brochure, [Value Analysis Brief], LigaSure Advance™ Pistol Grip, dated Rev. Apr. 2010 (7 pages).

Wall et al., "Thermal modification of collagen," J Shoulder Elbow Surg, No. 8, pp. 339-344 (Jul./Aug. 1999).

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

F. A. Duck, "Optical Properties of Tissue Including Ultraviolet and Infrared Radiation," pp. 43-71 in Physical Properties of Tissue (1990).

Campbell et al, "Thermal Imaging in Surgery," p. 19-3, in Medical Infrared Imaging, N. A. Diakides and J. D. Bronzino, Eds. (2008).

Graff, K.F., "Elastic Wave Propagation in a Curved Sonic Transmission Line," IEEE Transactions on Sonics and Ultrasonics, SU-17(1), 1-6 (1970).

Makarov, S. N., Ochmann, M., Desinger, K., "The longitudinal vibration response of a curved fiber used for laser ultrasound surgical therapy," Journal of the Acoustical Society of America 102, 1191-1199 (1997).

Morley, L. S. D., "Elastic Waves in a Naturally Curved Rod," Quarterly Journal of Mechanics and Applied Mathematics, 14: 155-172 (1961).

Walsh, S. J., White, R. G., "Vibrational Power Transmission in Curved Beams," Journal of Sound and Vibration, 233(3), 455-488 (2000).

http://www.apicalinstr.com/generators.htm.

http://www.dotmed.com/listing/electrosurical-unit/ethicon/ultracision-g110-/1466724.

http://www.ethicon.com/gb-en/healthcare-professionals/products/energy-devices/capital//ge. . . .

http://www.medicalexpo.com/medical-manufacturer/electrosurgical-generator-6951.html.

http://www.megadyne.com/es_generator.php.

http://www.valleylab.com/product/es/generators/index.html.

Covidien 501(k) Summary Sonicision, dated Feb. 24, 2011 (7 pages).

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

Chen et al., "Heat-induced changes in the mechanics of a collagenous tissue: pseudoelastic behavior at 37° C.," Journal of Biomechanics, 31, pp. 211-216 (1998).

(56) References Cited

OTHER PUBLICATIONS

Henriques. F.C., "Studies in thermal injury V. The predictability and the significance of thermally induced rate processes leading to irreversible epidermal injury." Archives of Pathology, 434, pp. 489-502 (1947).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Technology Overview, printed from www.harmonicscalpel.com, Internet site, website accessed on Jun. 13, 2007, (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Fowler, K.R., "A Programmable, Arbitrary Waveform Electrosurgical Device," IEEE Engineering in Medicine and Biology Society 10th Annual International Conference, pp. 1324, 1325 (1988).

Gerhard, Glen C., "Surgical Electrotechnology: Quo Vadis?," IEEE Transactions on Biomedical Engineering, vol. BME-31, No. 12, pp. 787-792, Dec. 1984.

LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

http://www.4-traders.com/JOHNSON-JOHNSON-4832/news/Johnson-Johnson-Ethicon-E. . . .

Leonard I. Malis, M.D., "The Value of Irrigation During Bipolar Coagulation," 1989.

Hörmann et al., "Reversible and irreversible denaturation of collagen fibers." Biochemistry, 10, pp. 932-937 (1971).

Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

Jang, J. et al. "Neuro-fuzzy and Soft Computing." Prentice Hall, 1997, pp. 13-89, 199-293, 335-393, 453-496, 535-549.

Moraleda et al., A Temperature Sensor Based on a Polymer Optical Fiber Macro-Bend, Sensors 2013, 13, 13076-13089, doi: 10.3390/s131013076, ISSN 1424-8220.

\* cited by examiner

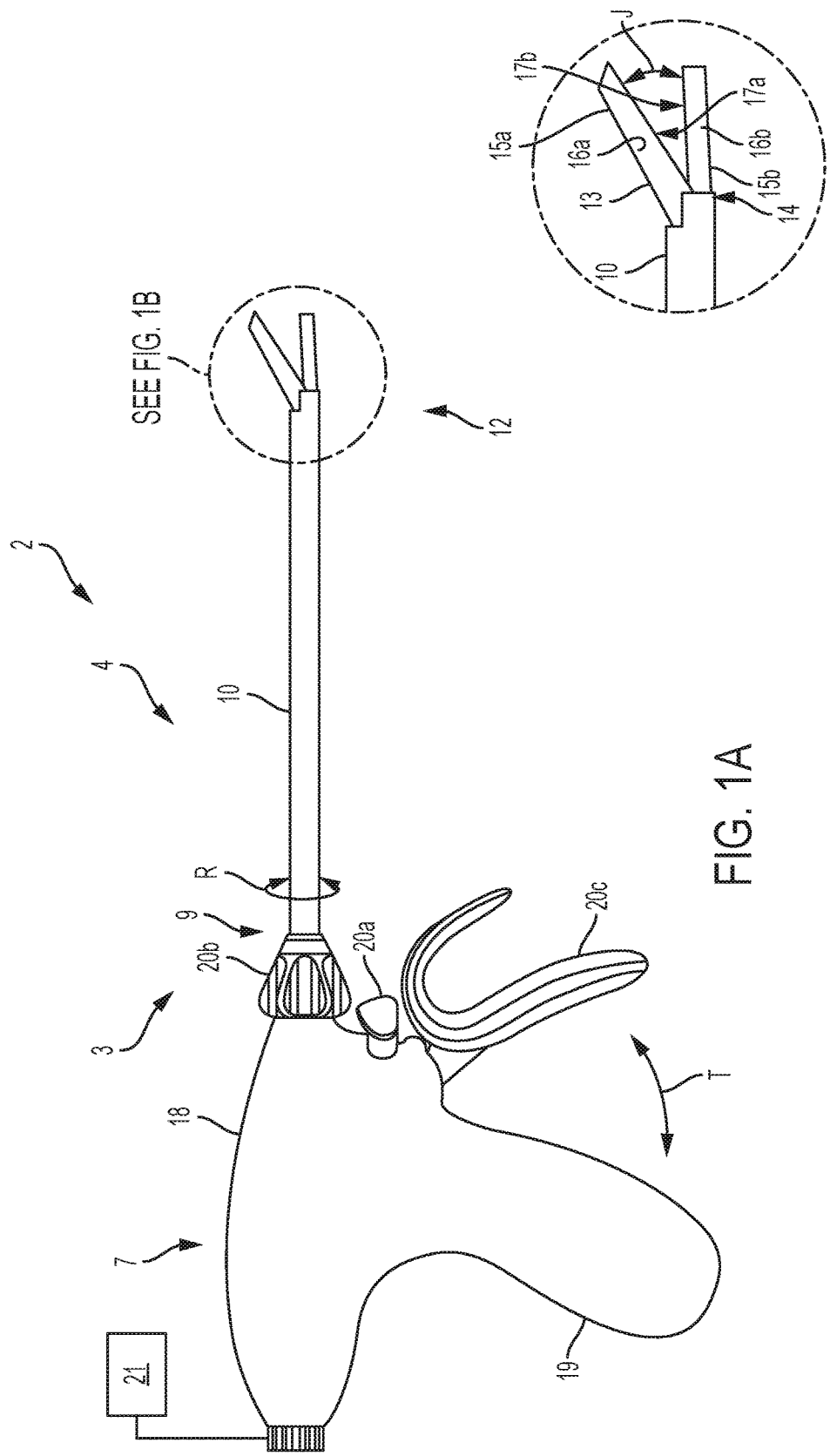

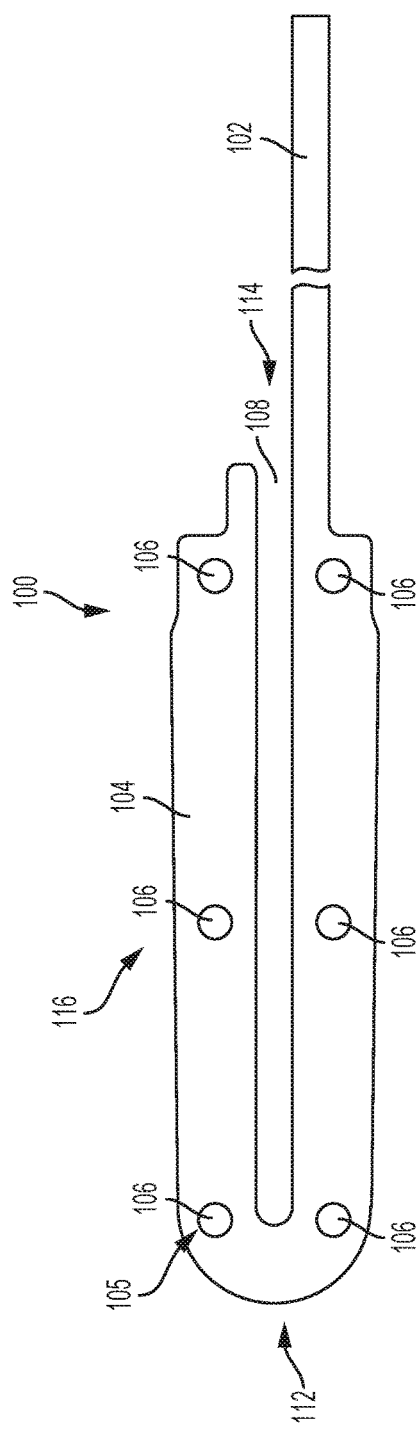
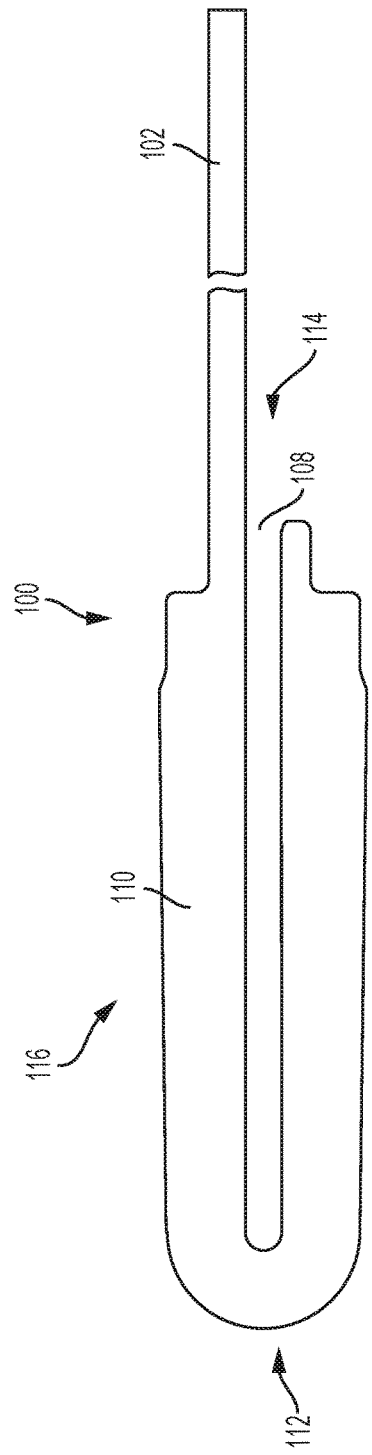

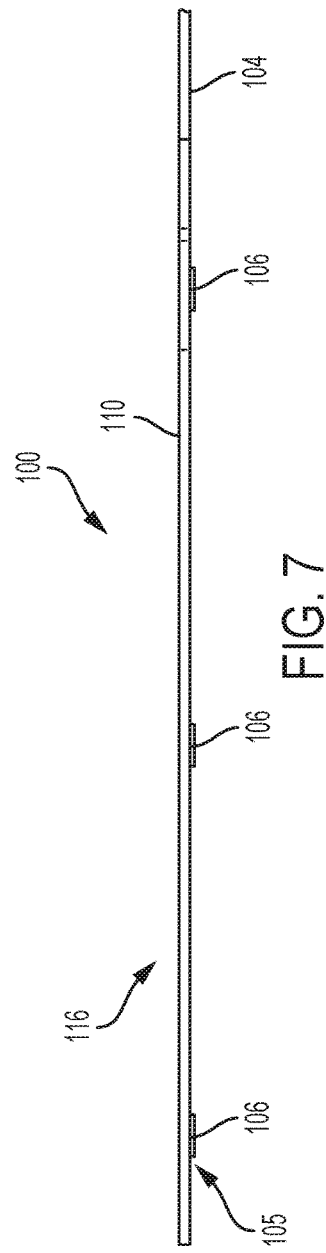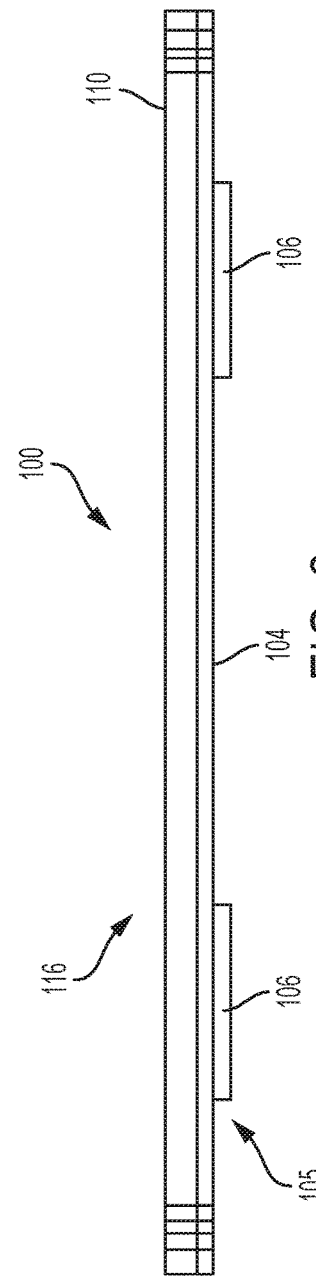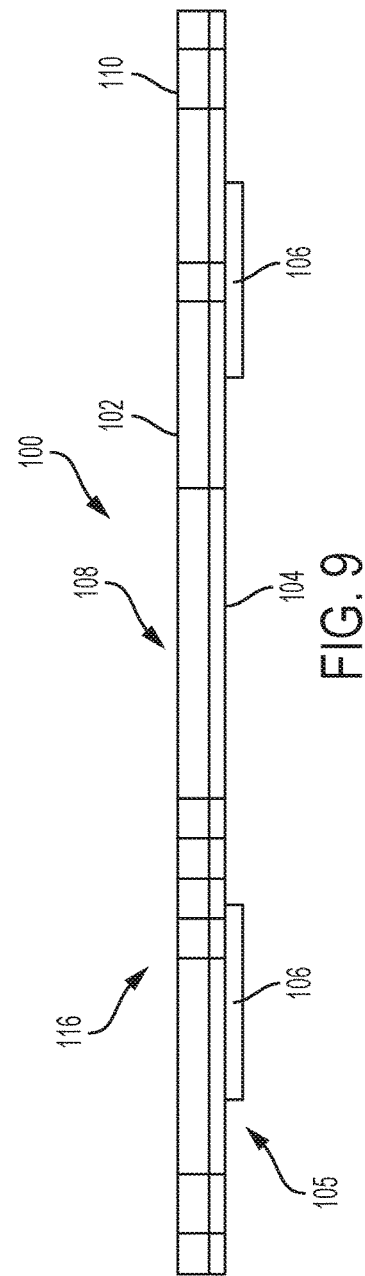

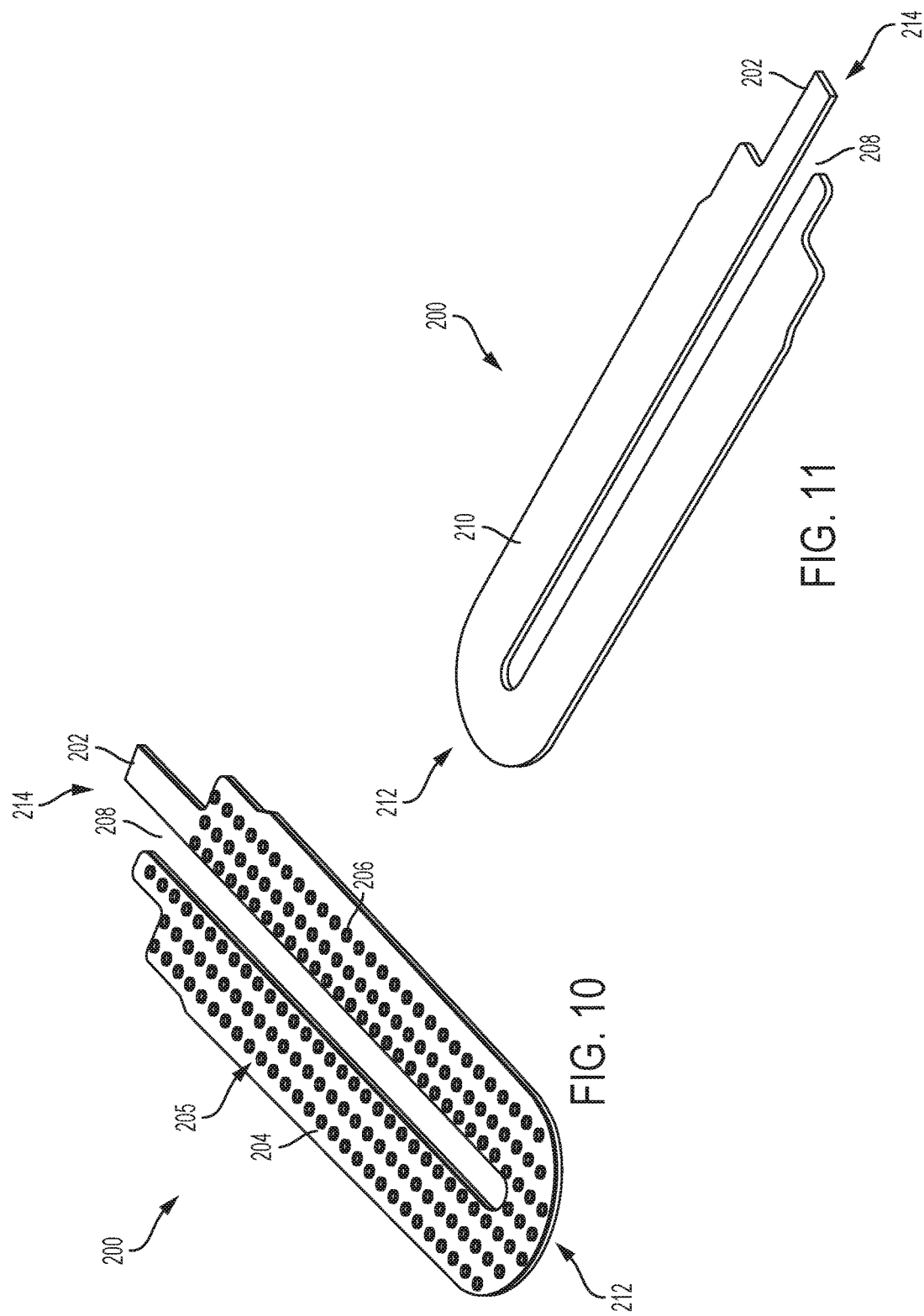

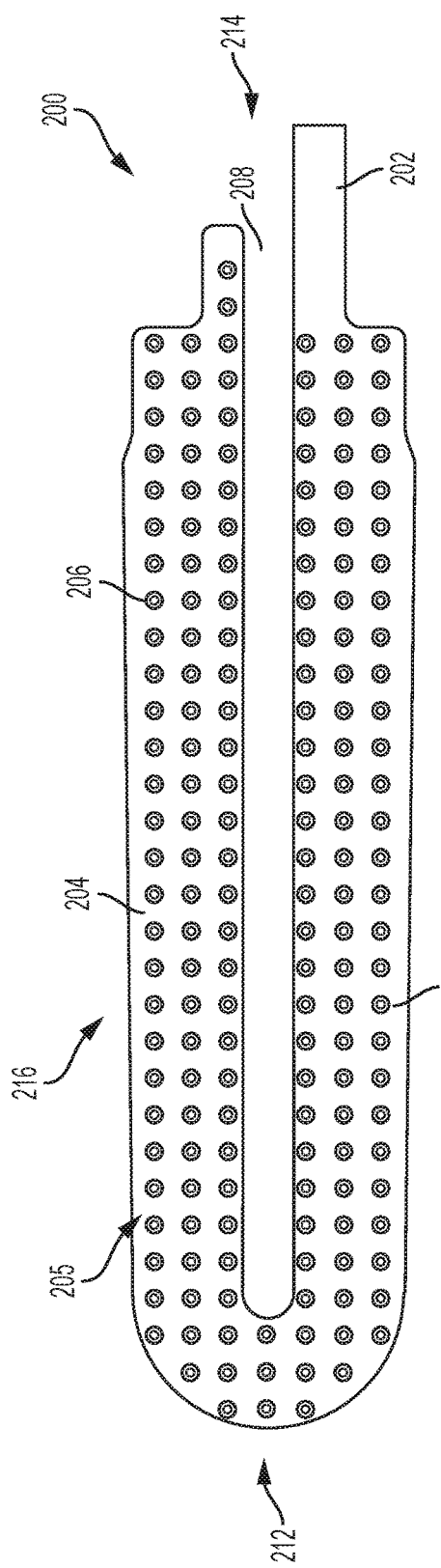
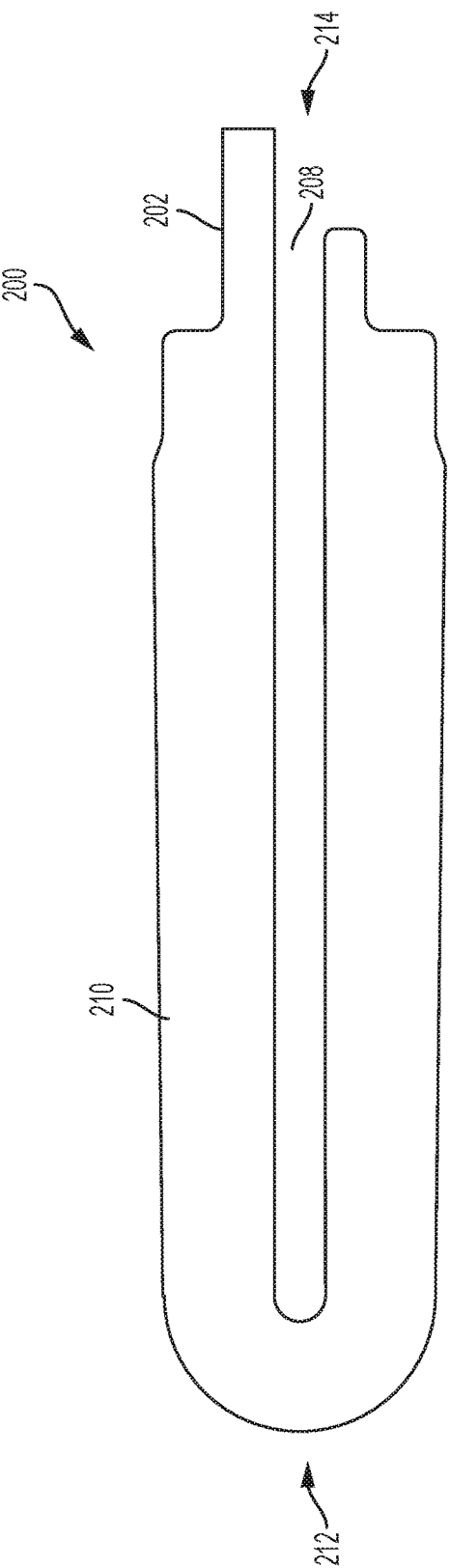
FIG. 12
FIG. 13

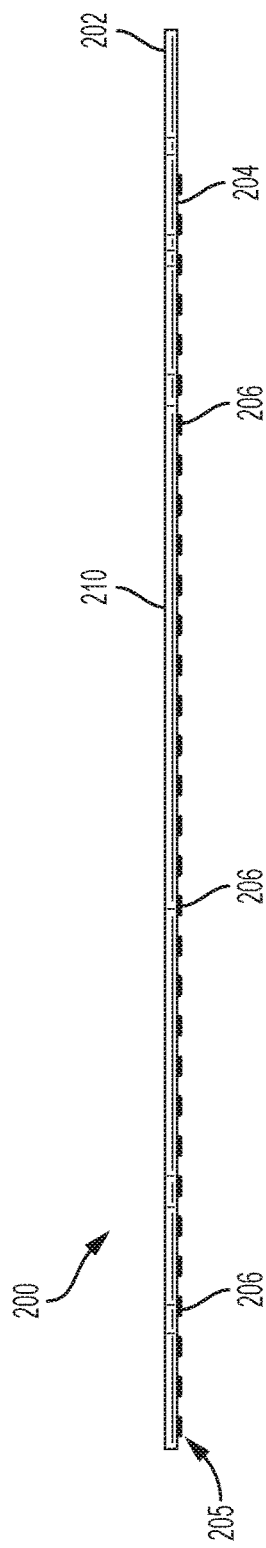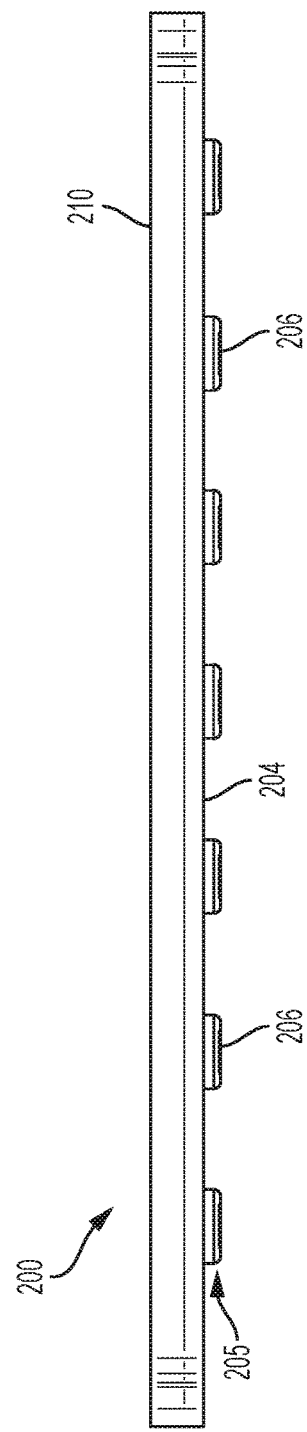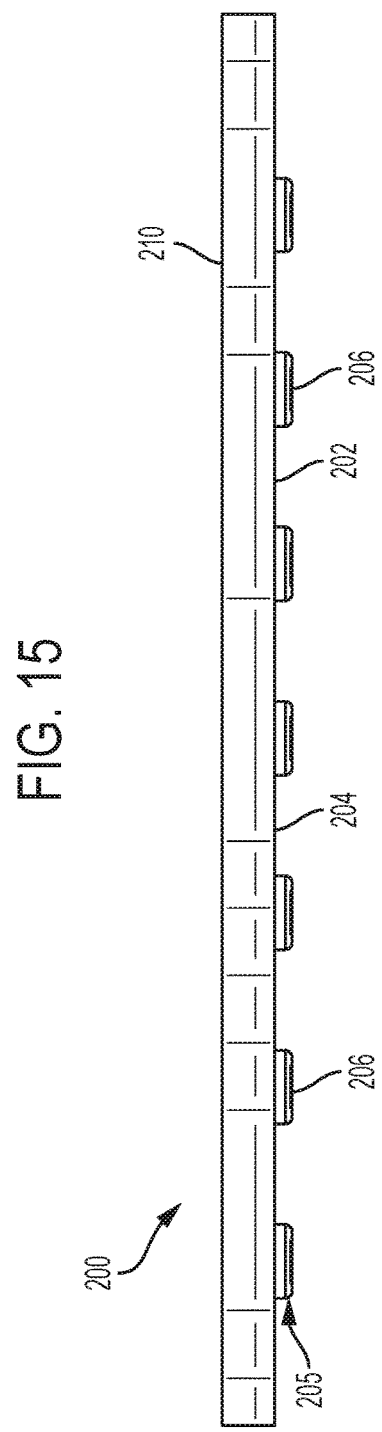

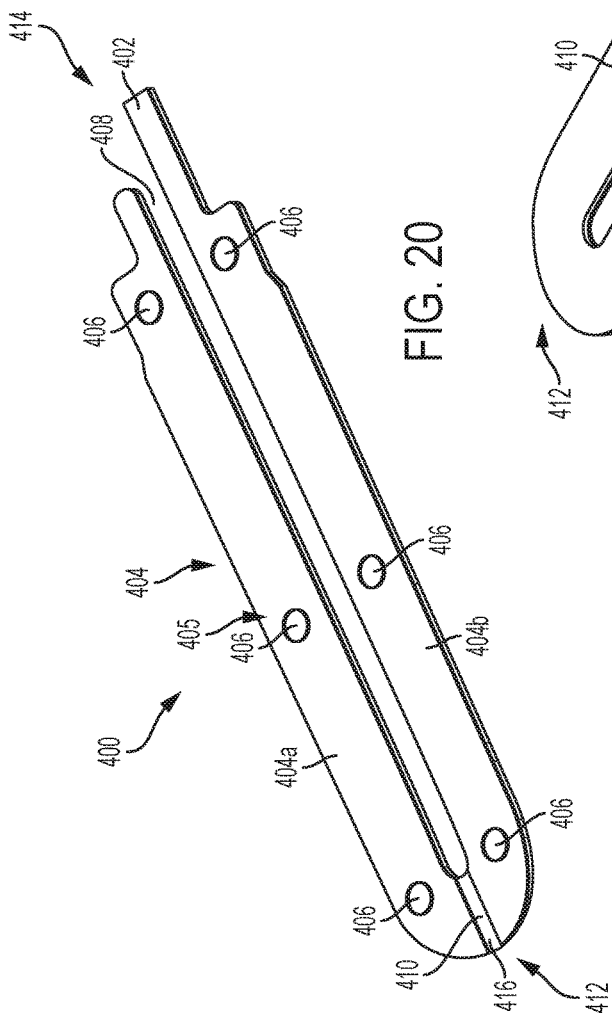
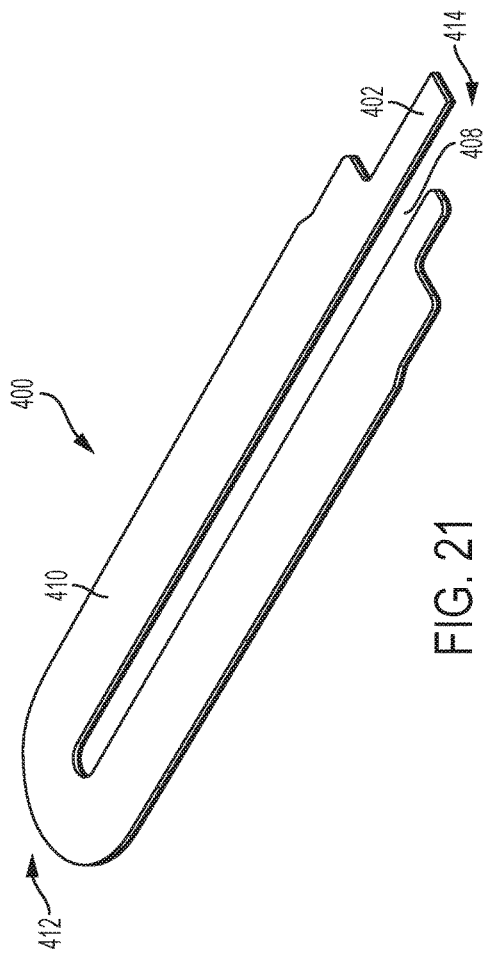

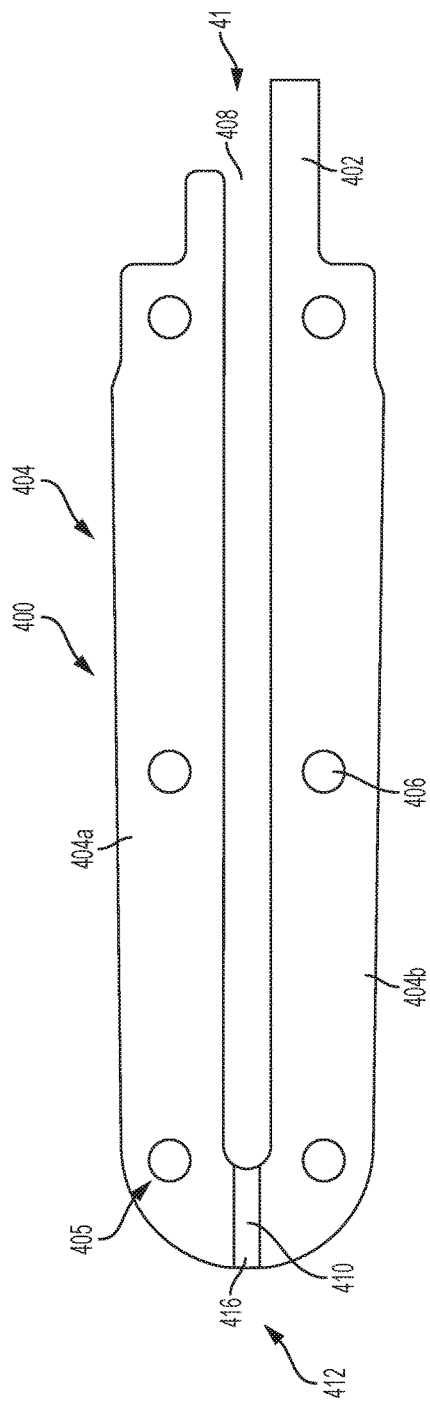
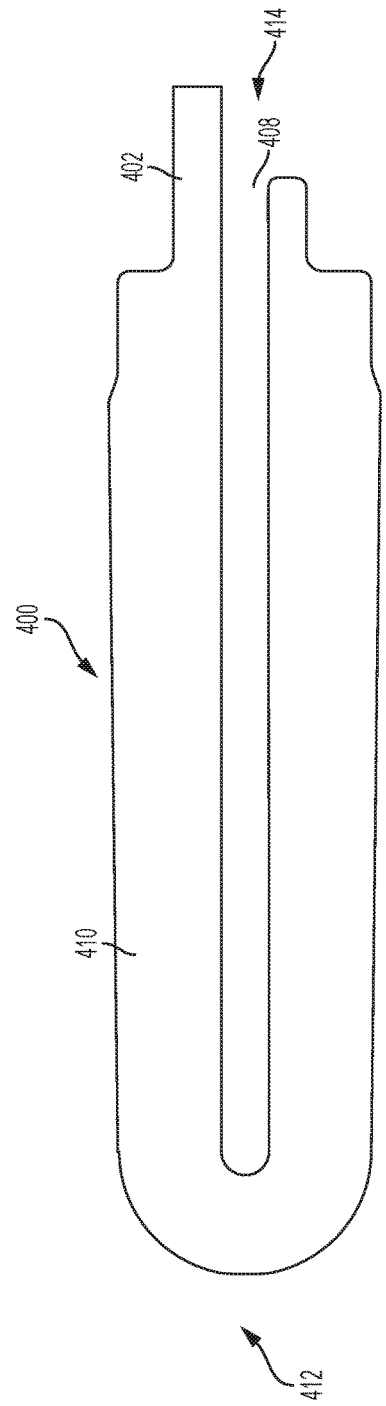

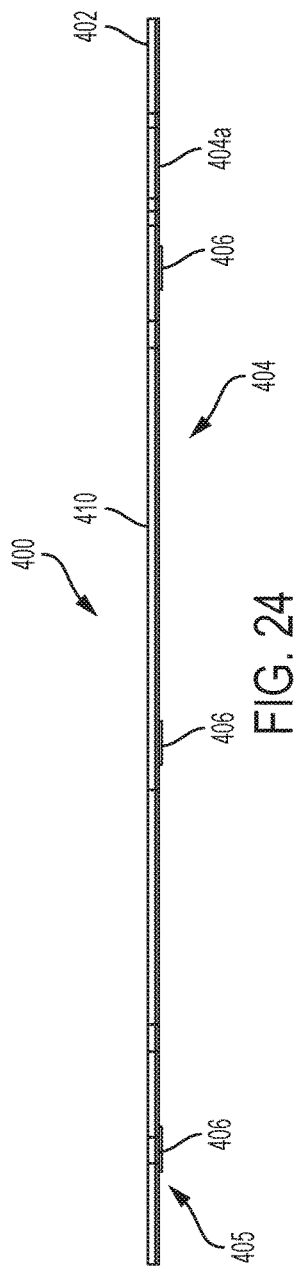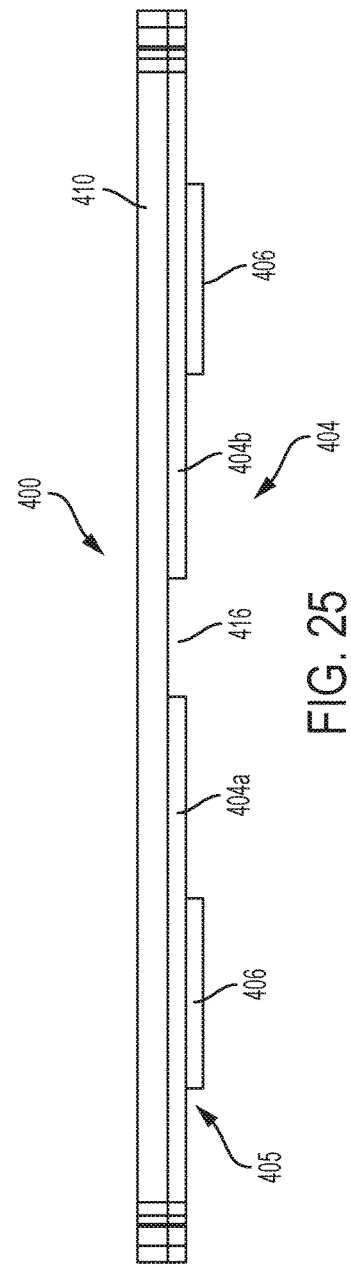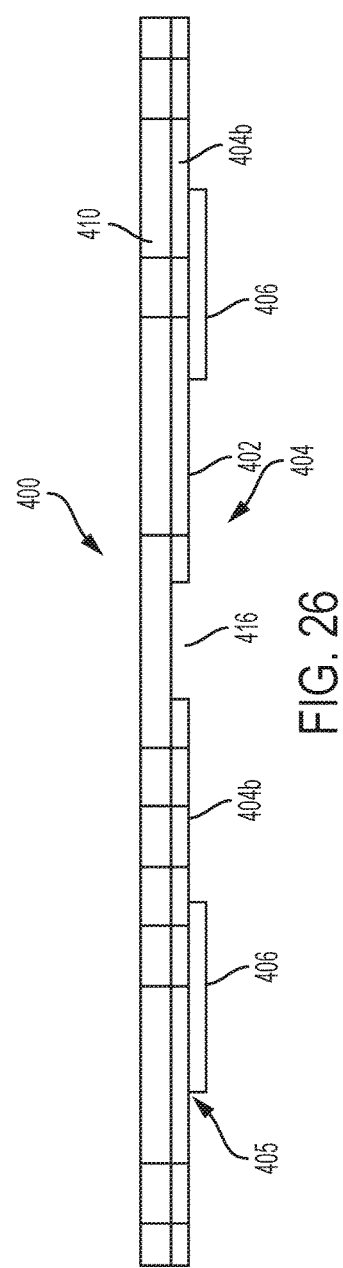

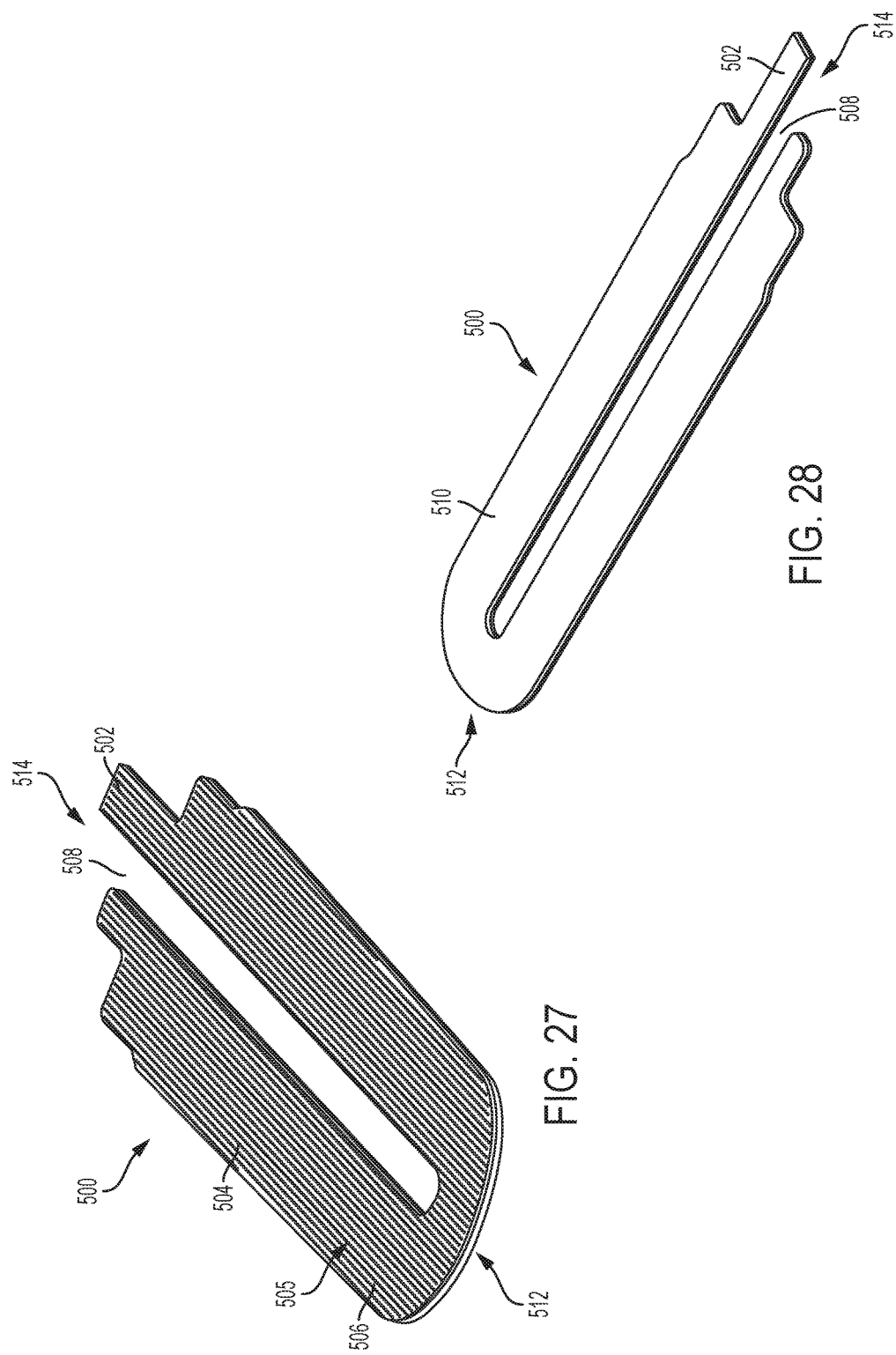

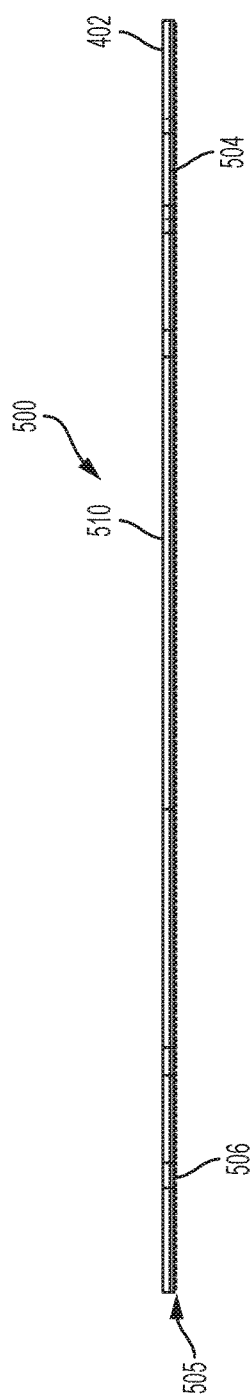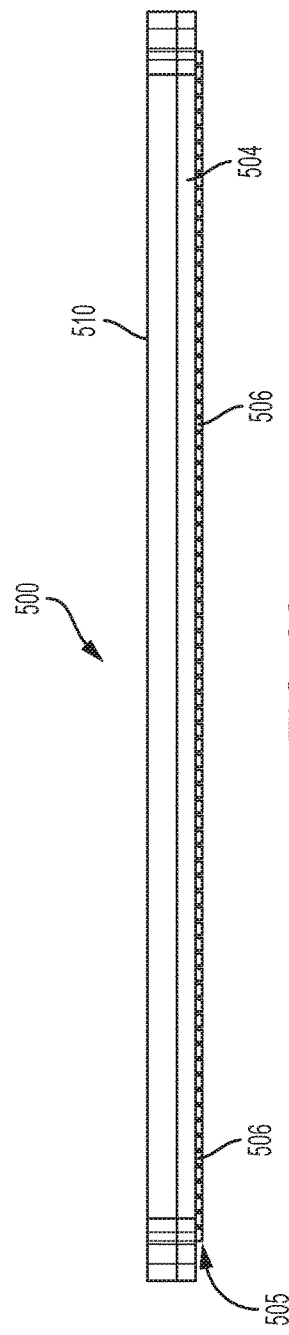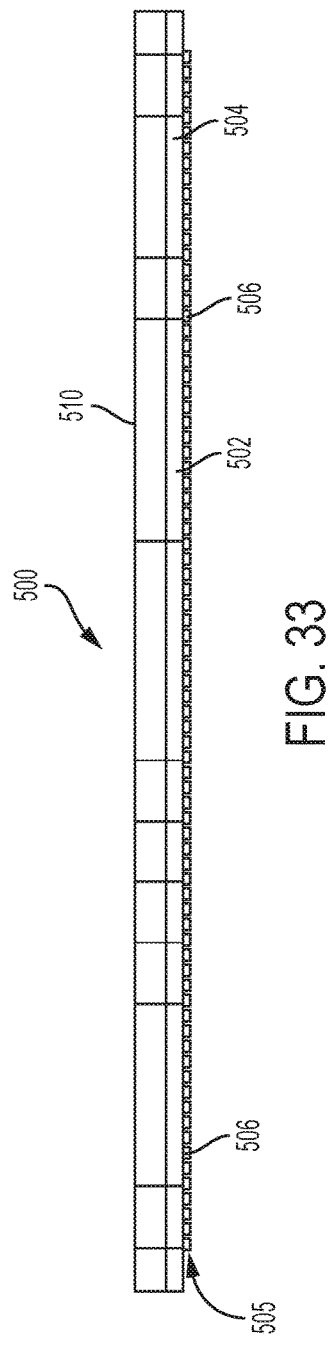

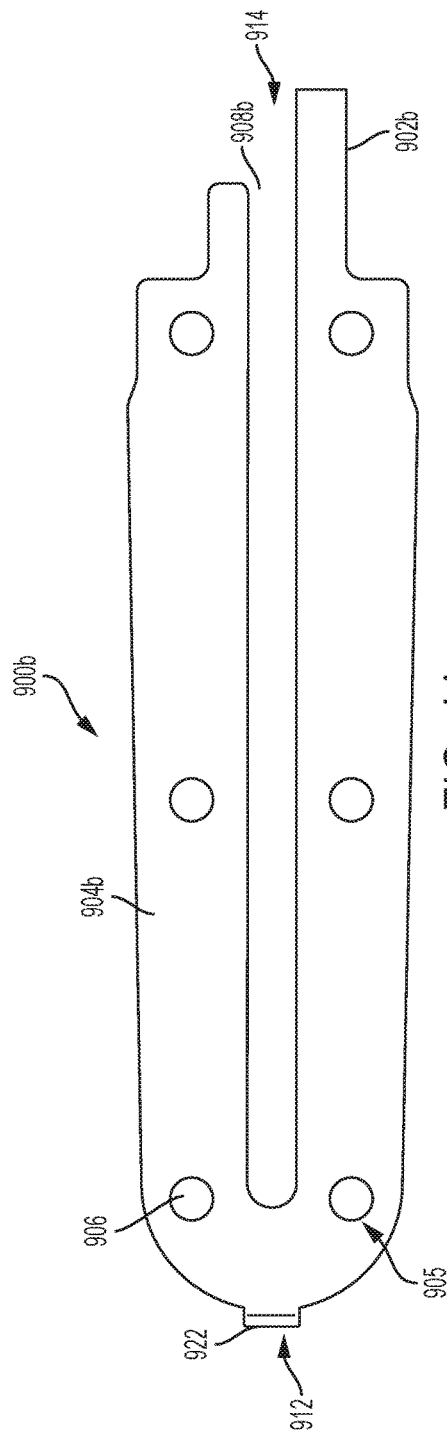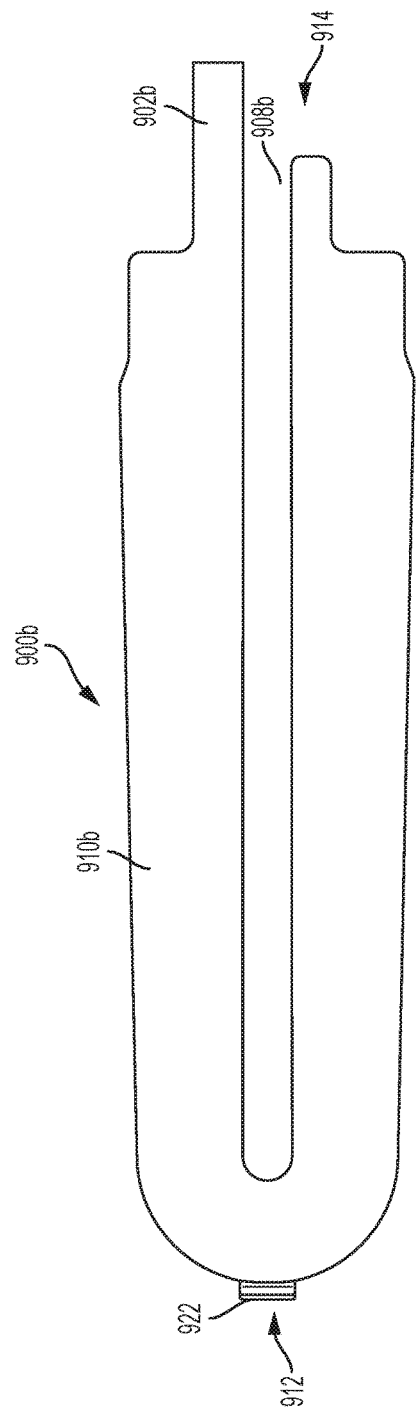

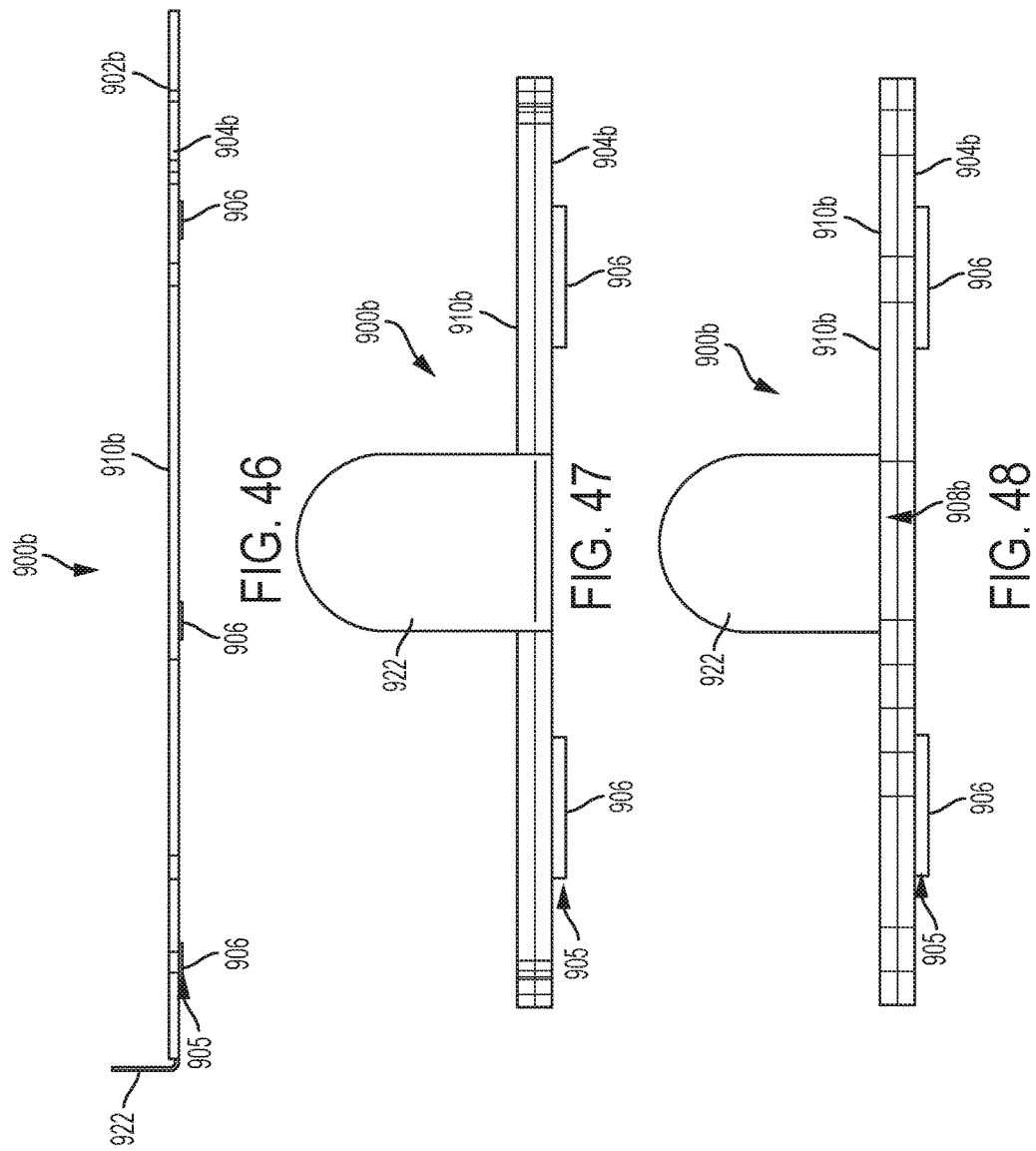

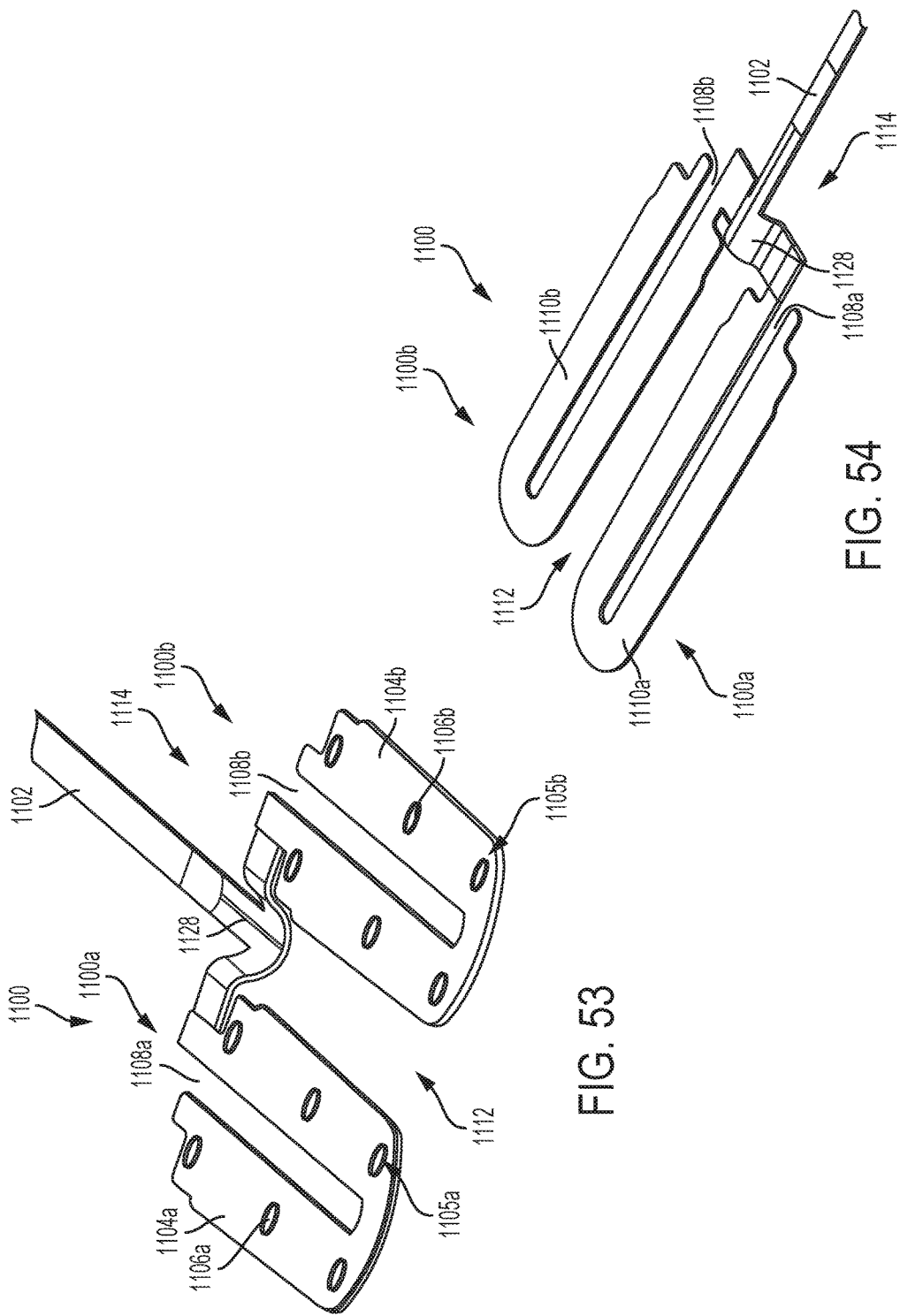

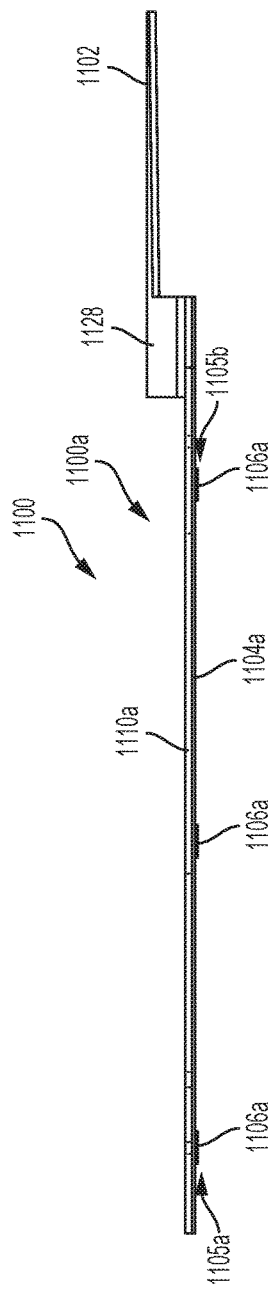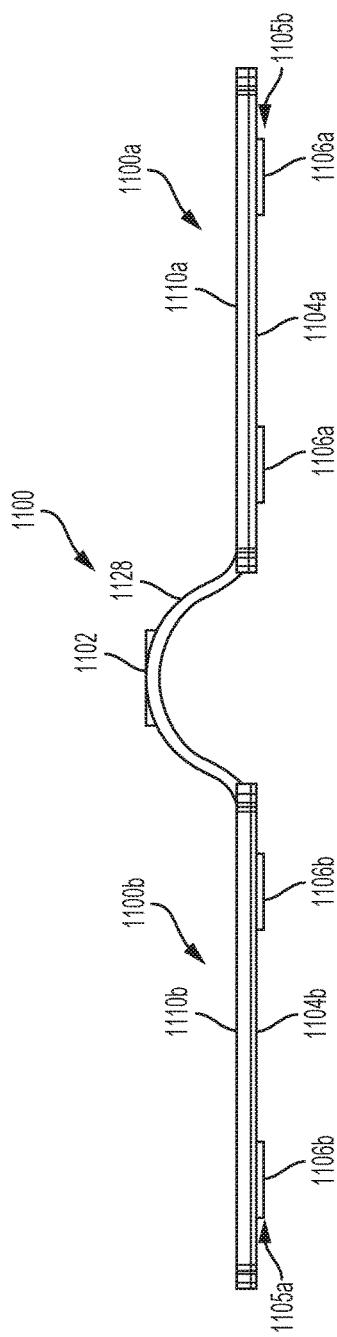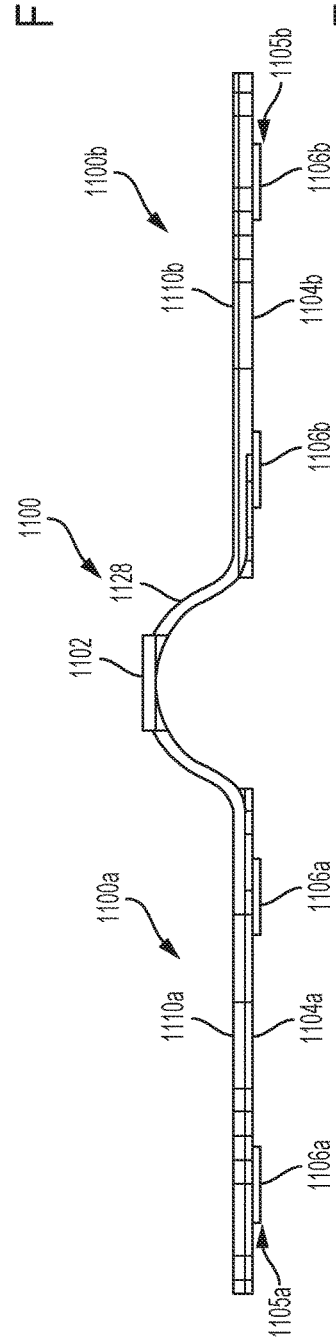

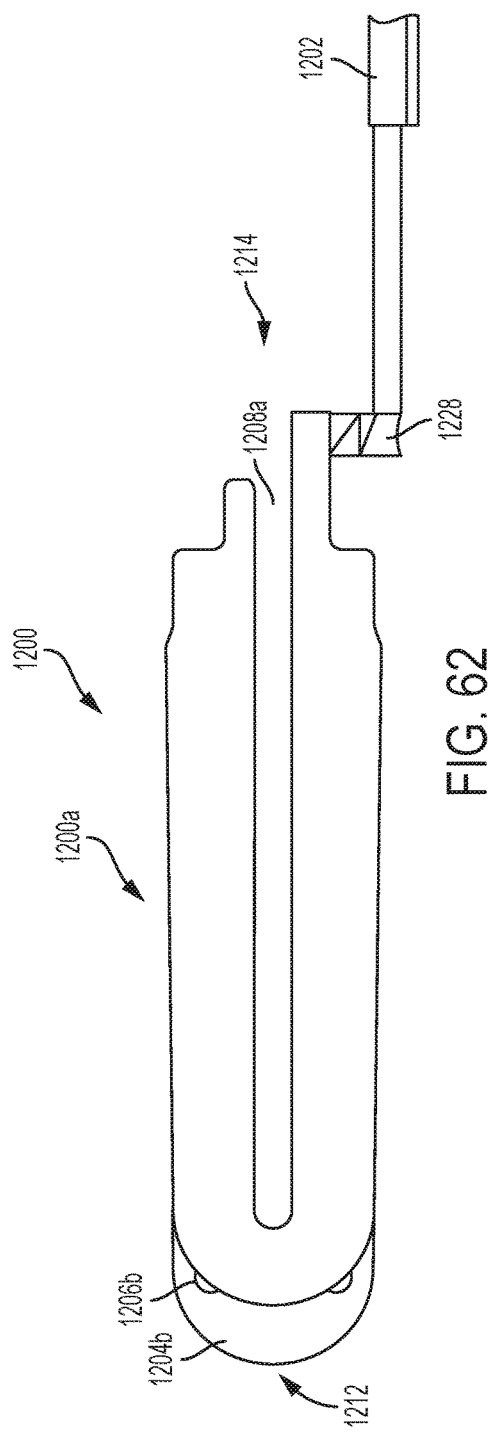
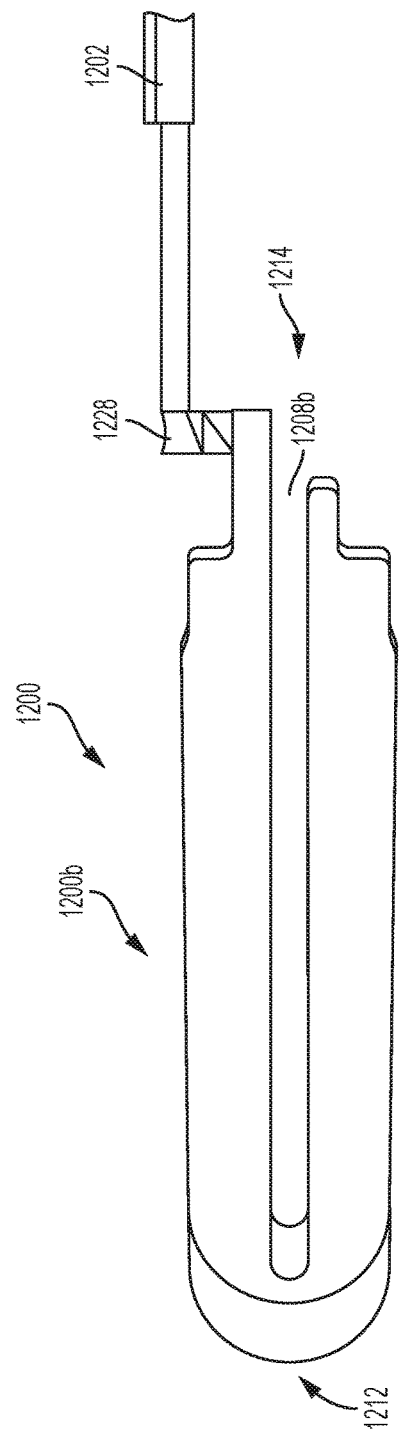

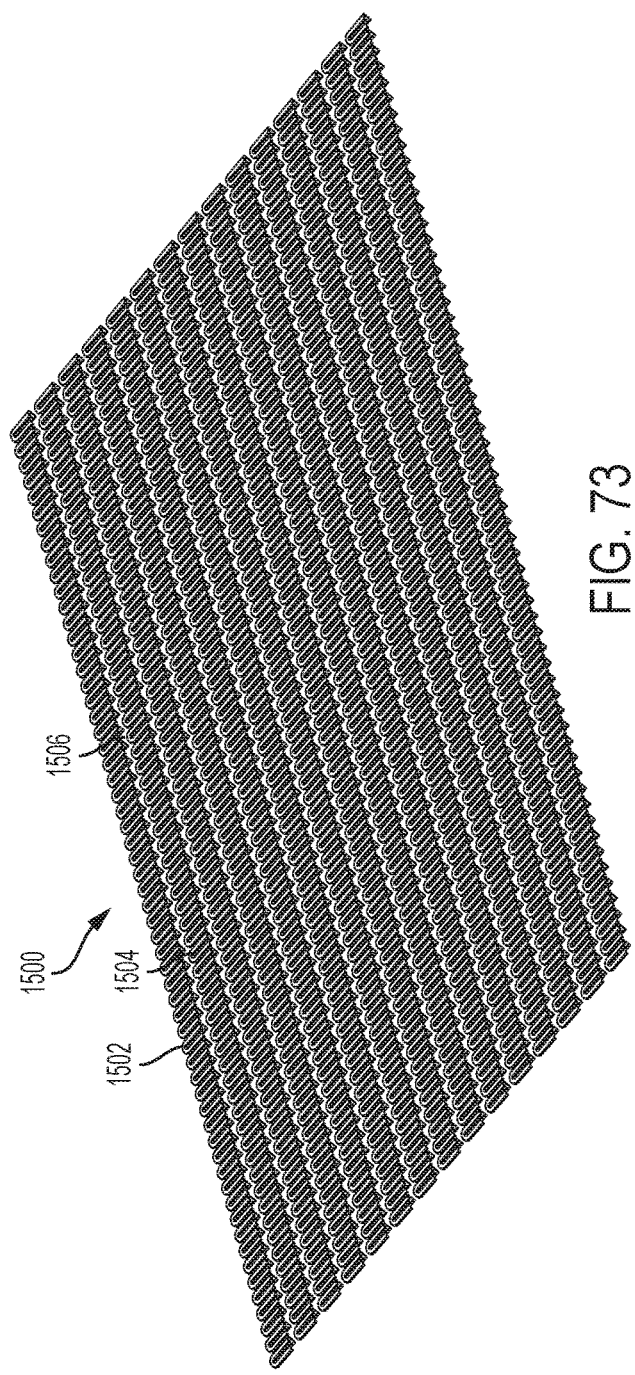
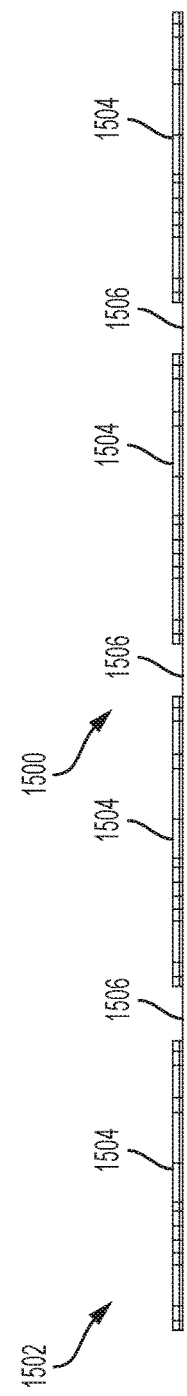

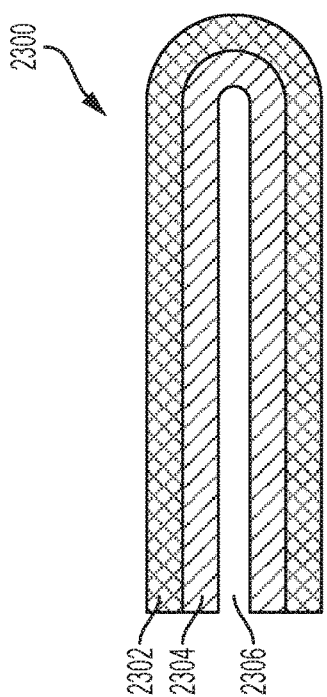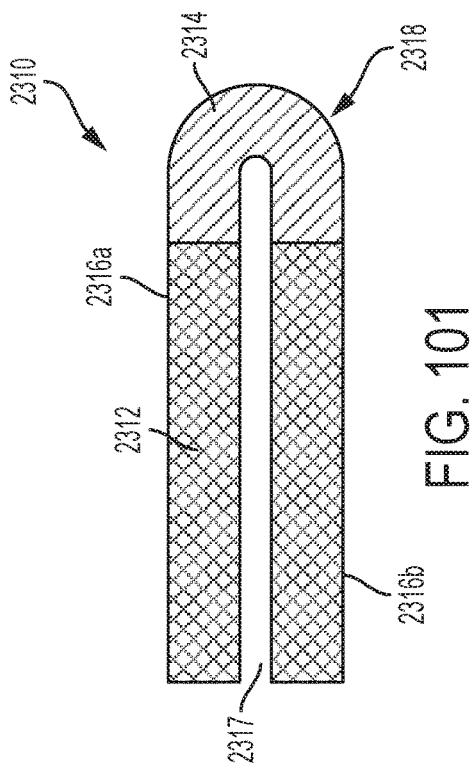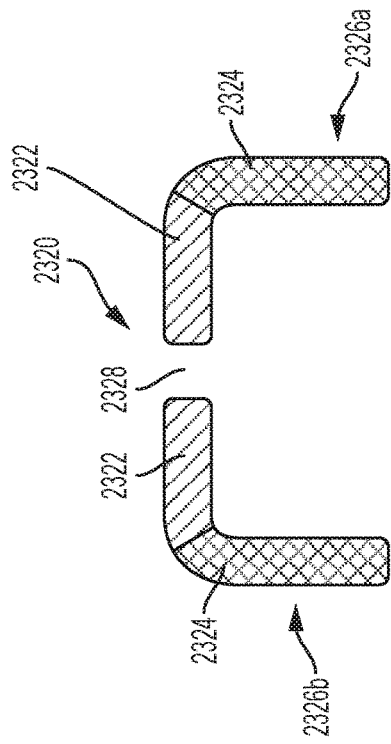

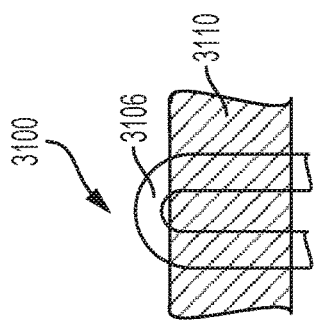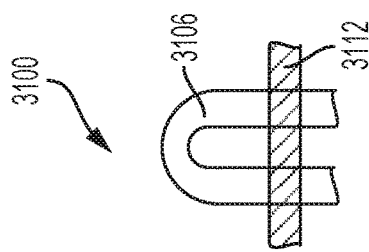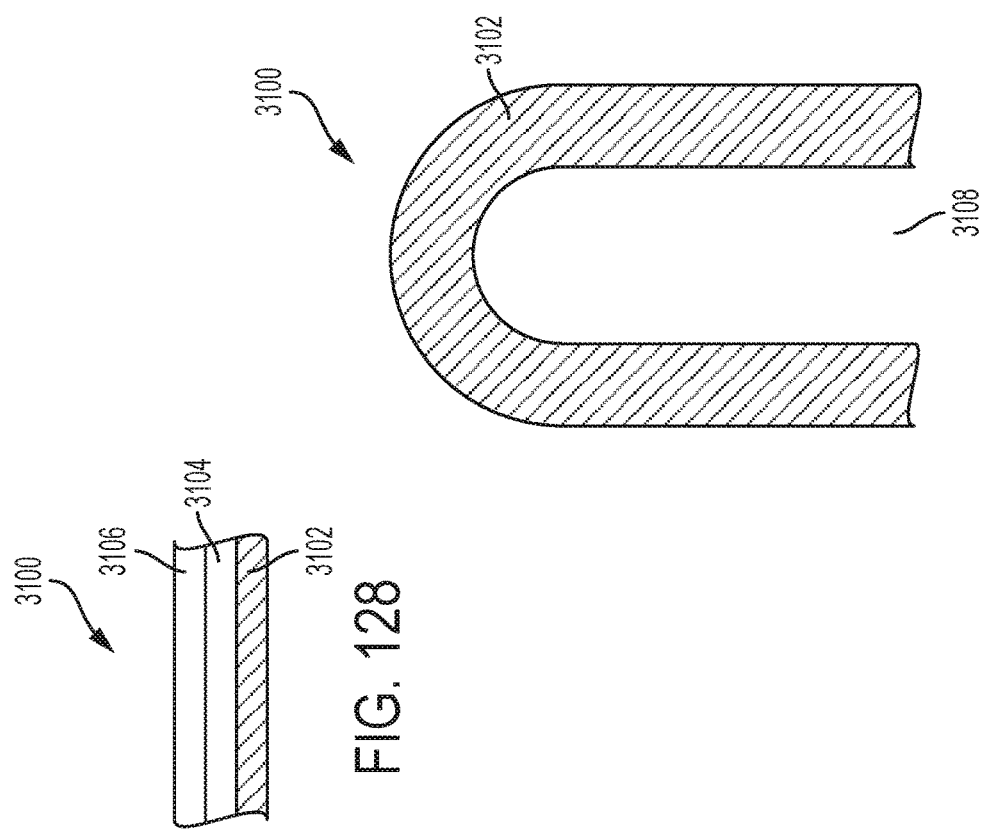

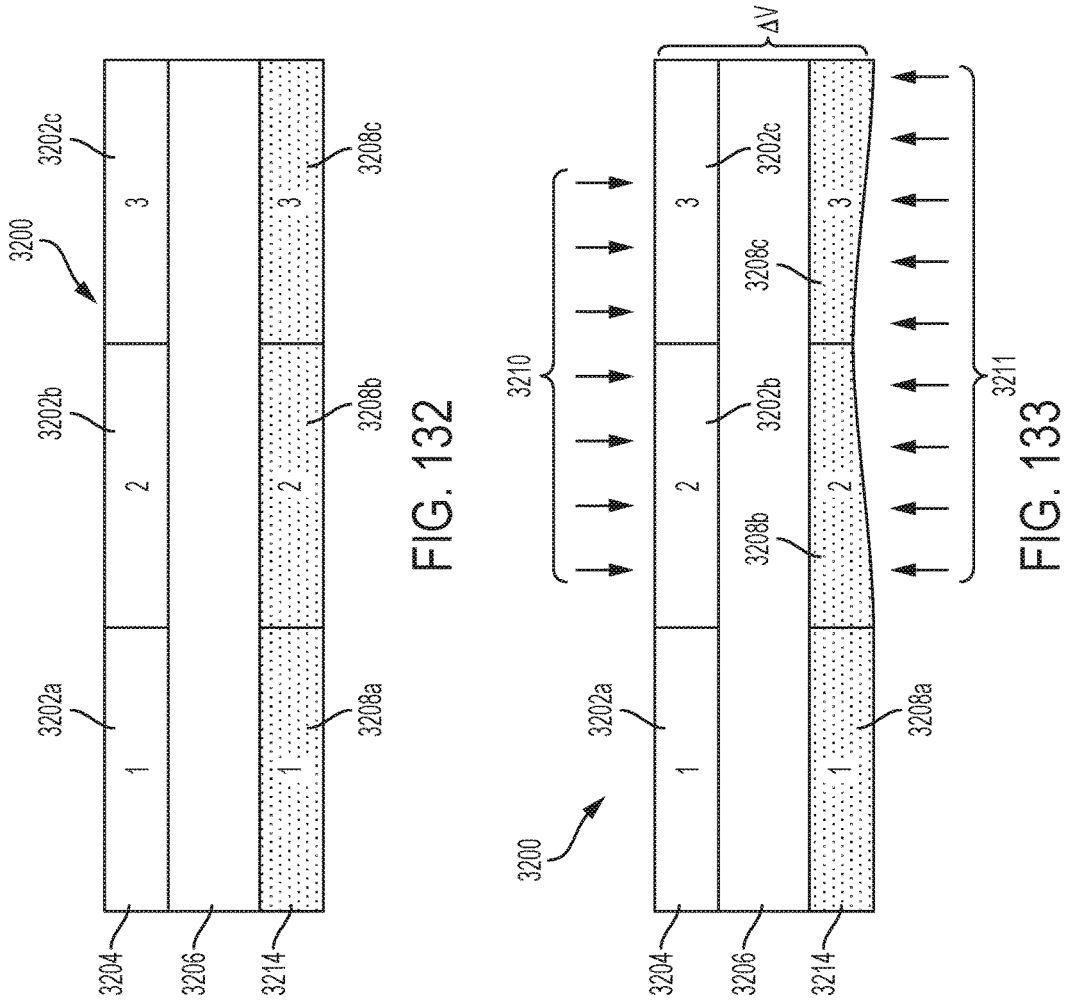
FIG. 132
FIG. 133
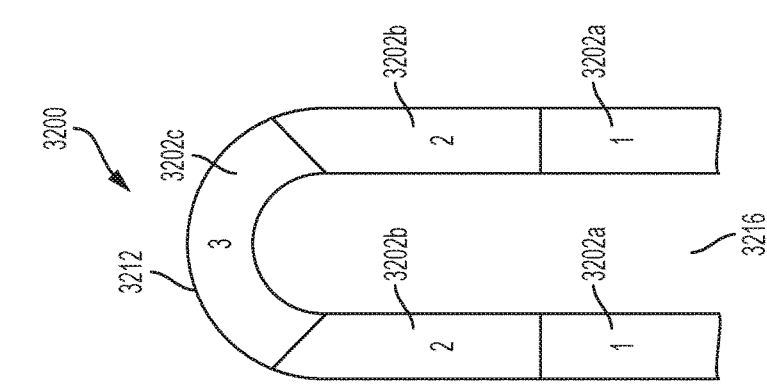
FIG. 131

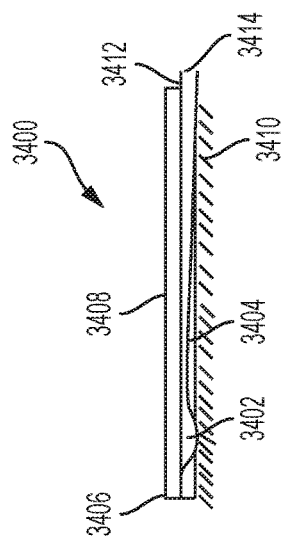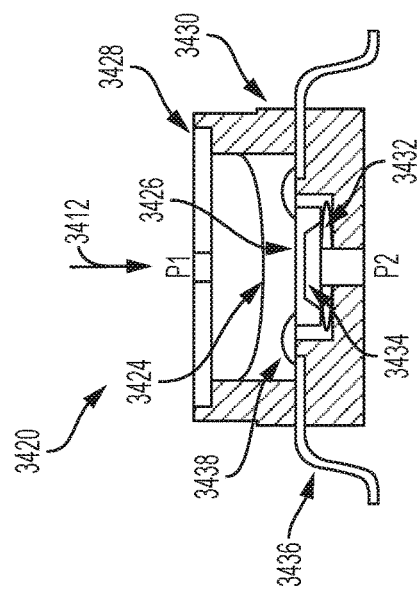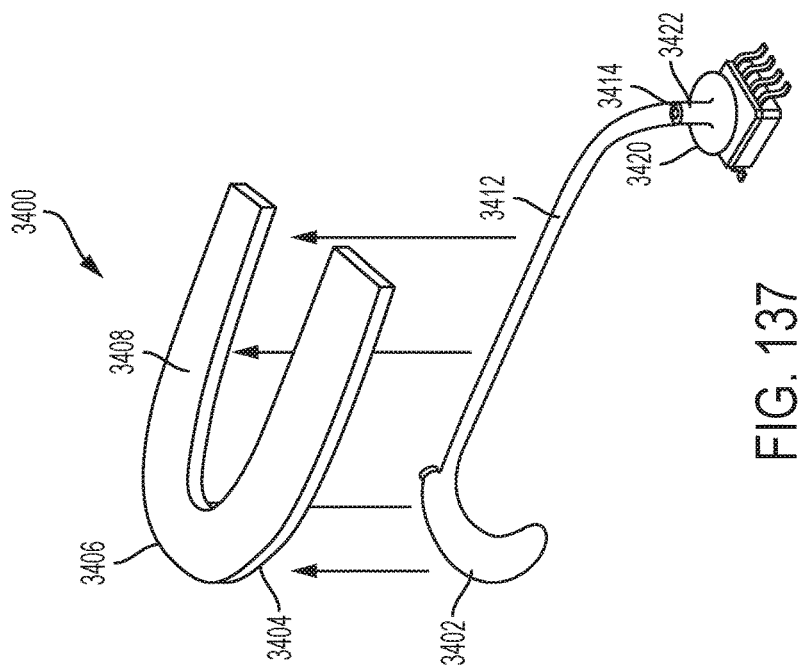

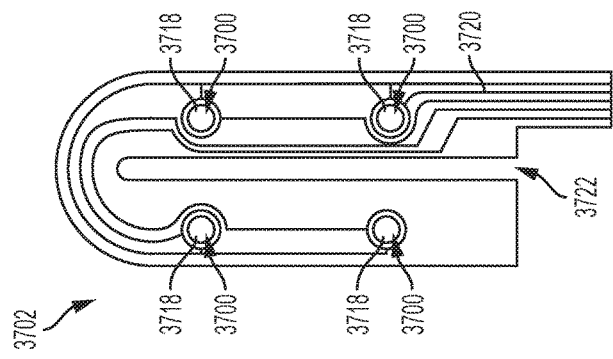
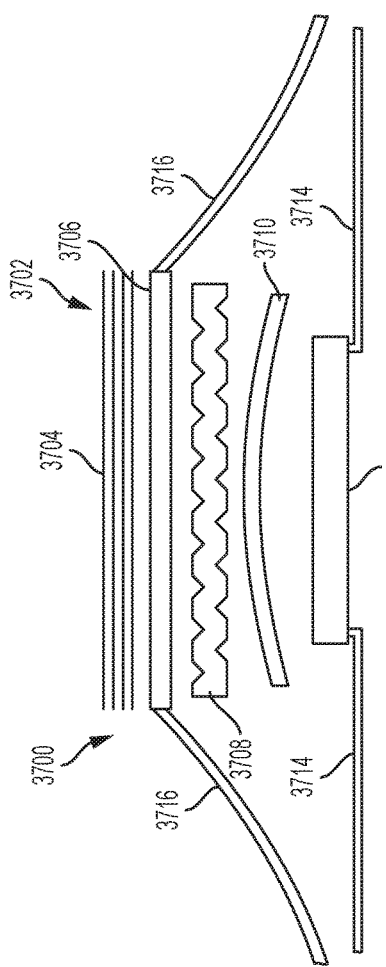
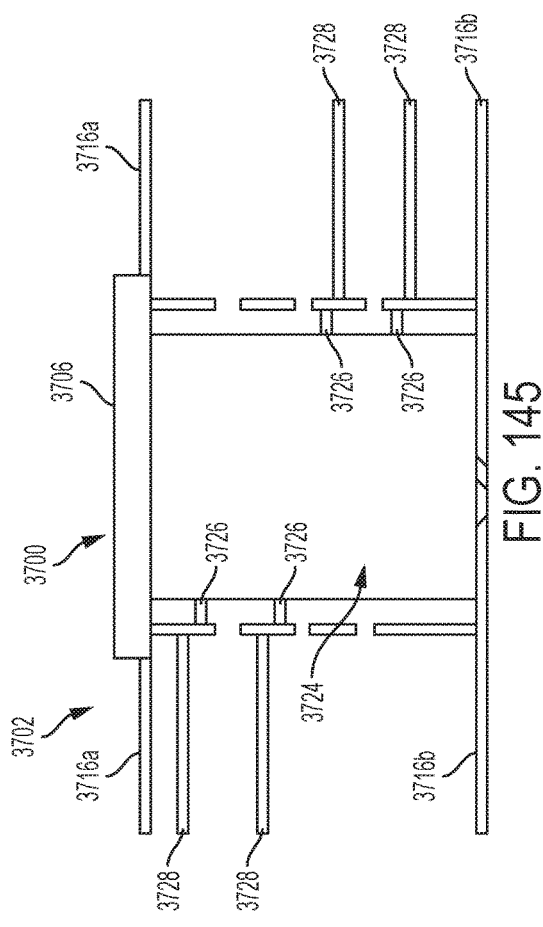

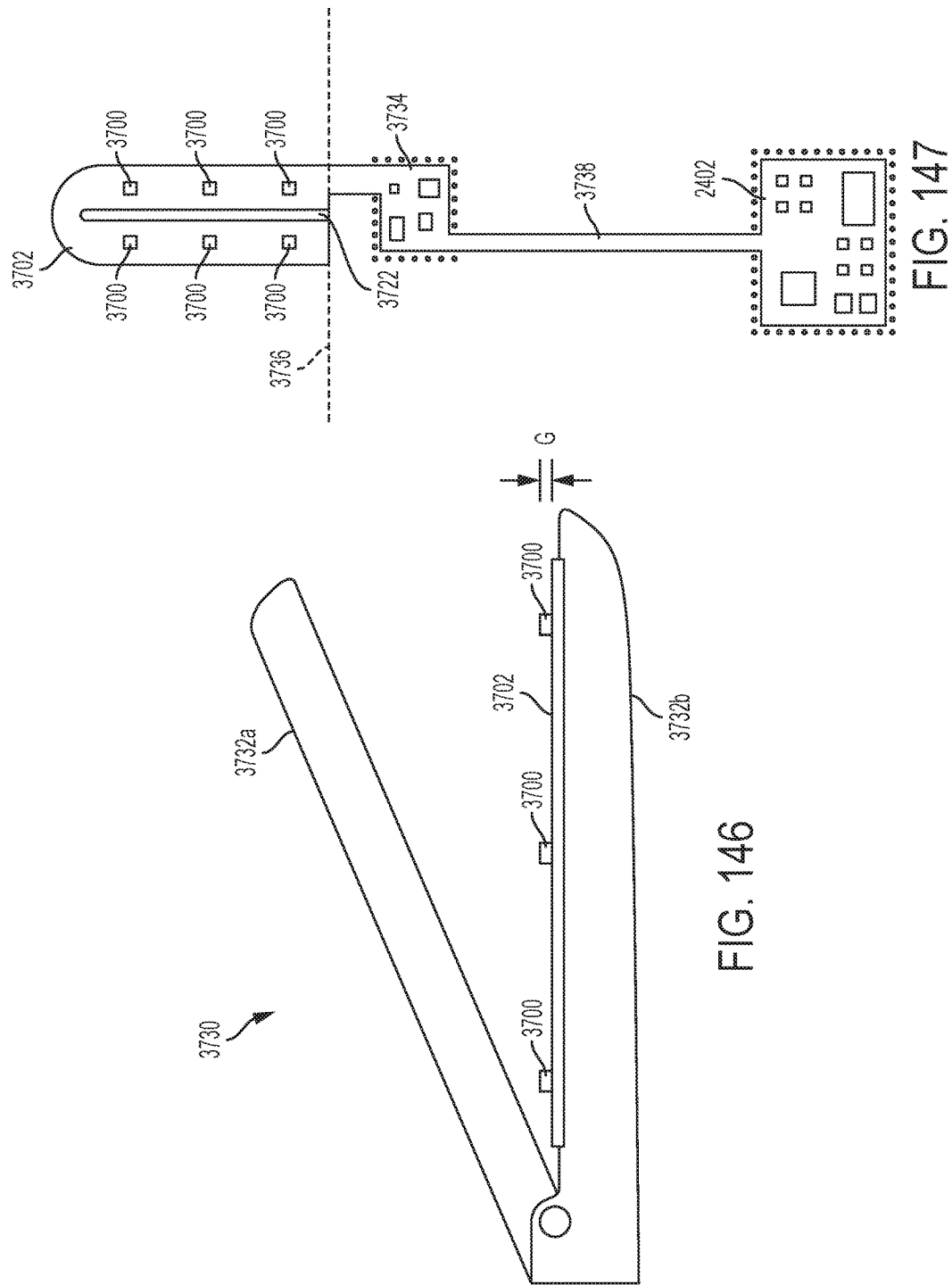

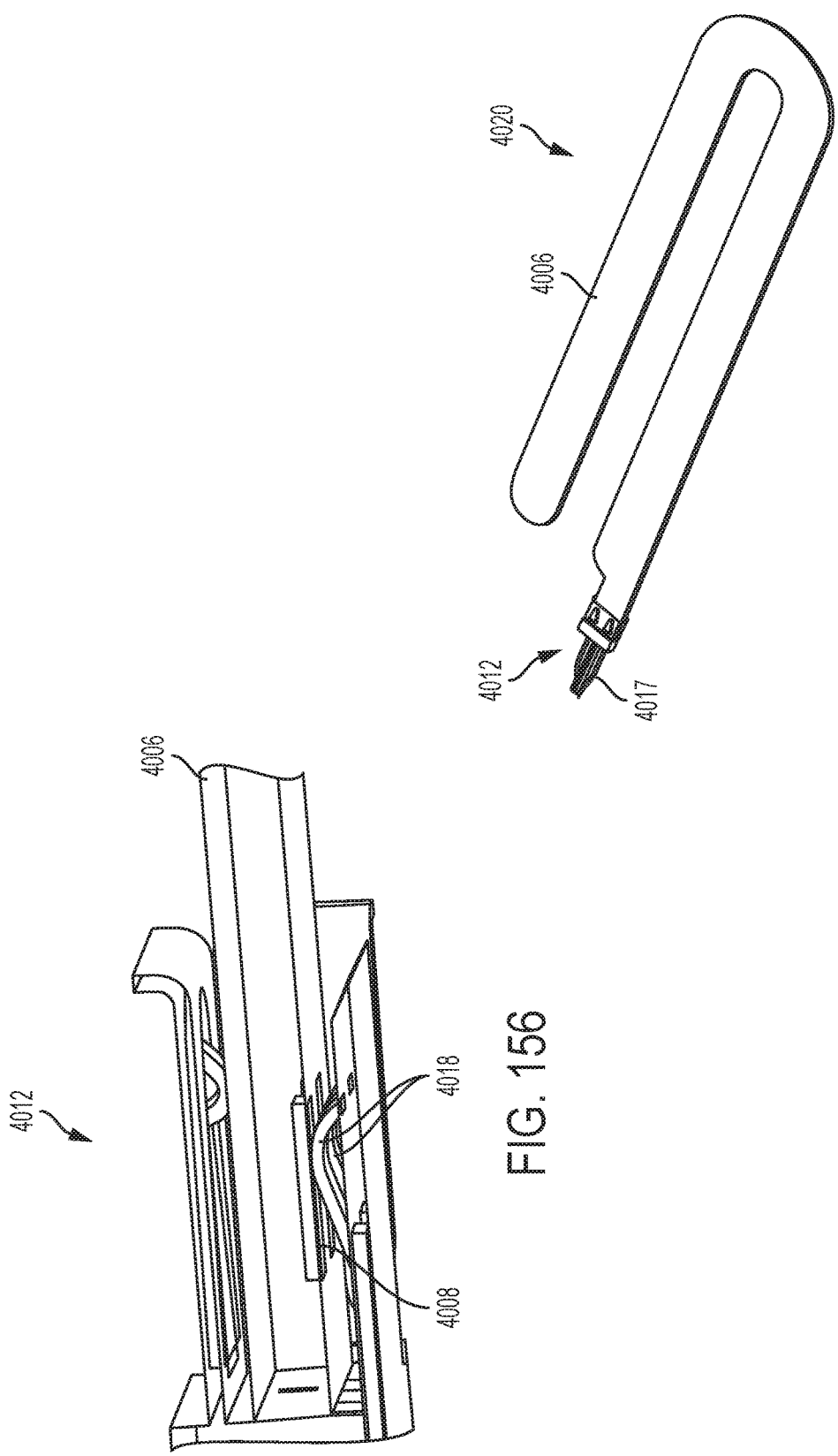

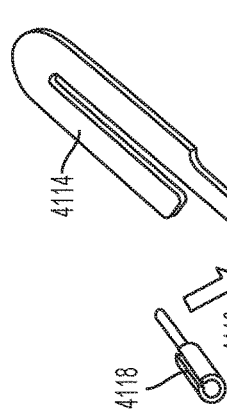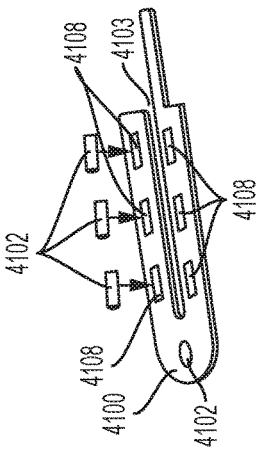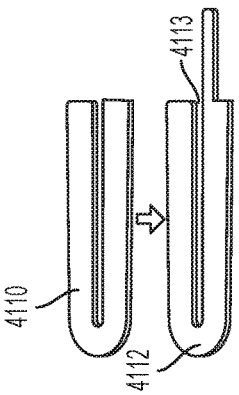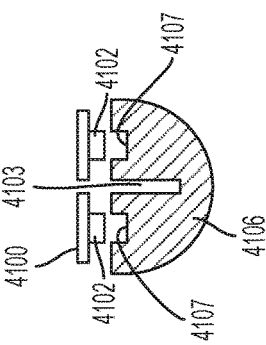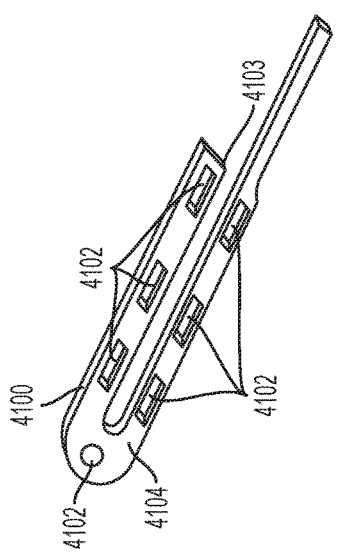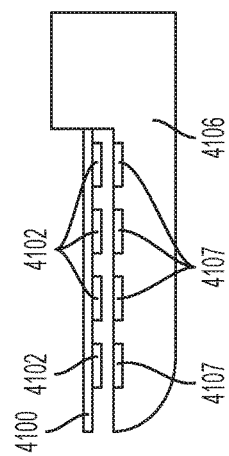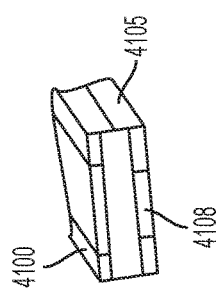

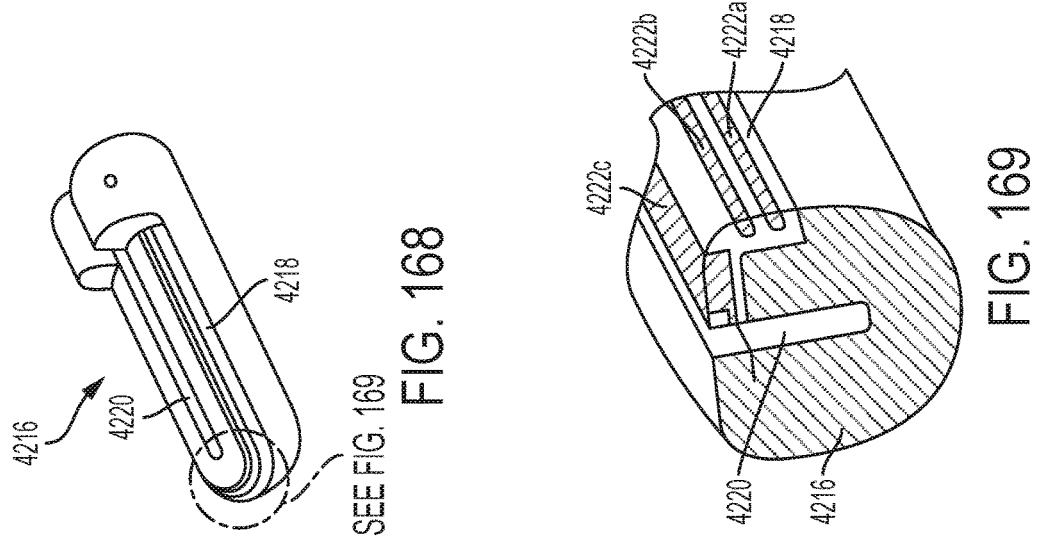
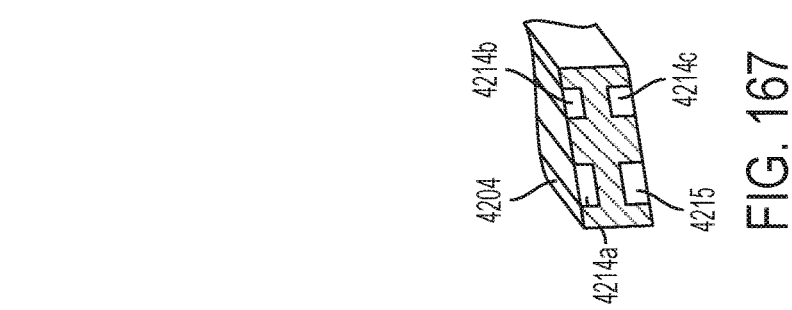
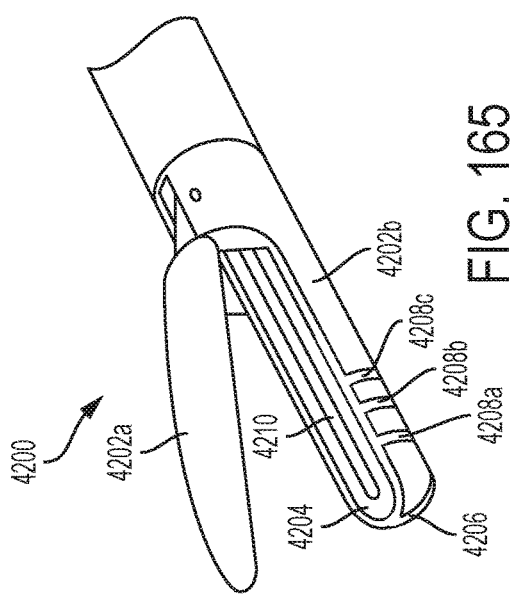
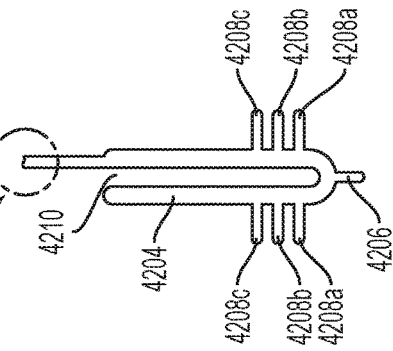

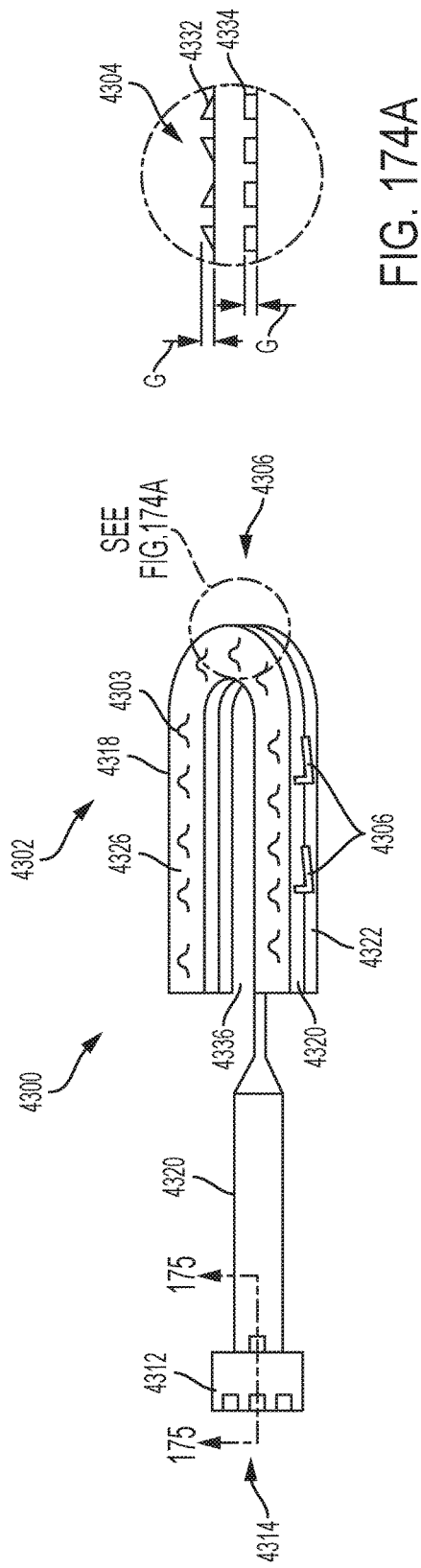
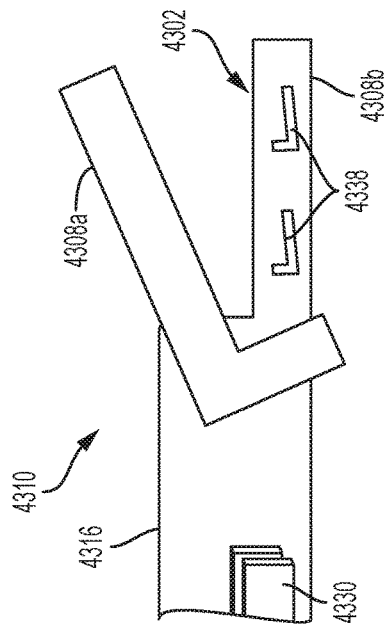
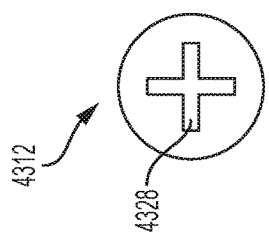
FIG. 174A
FIG. 174
FIG. 175
FIG. 176

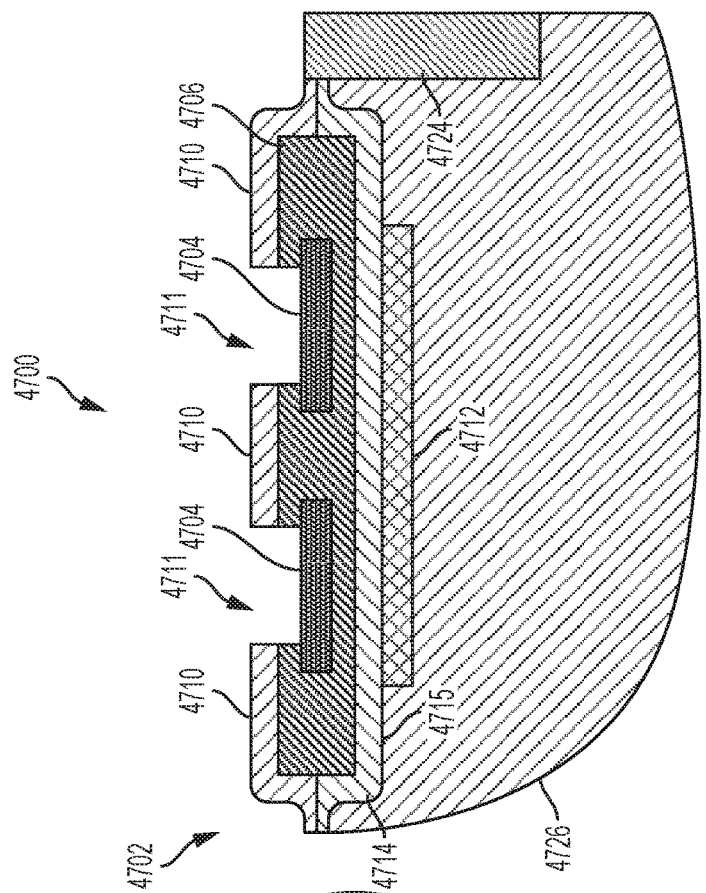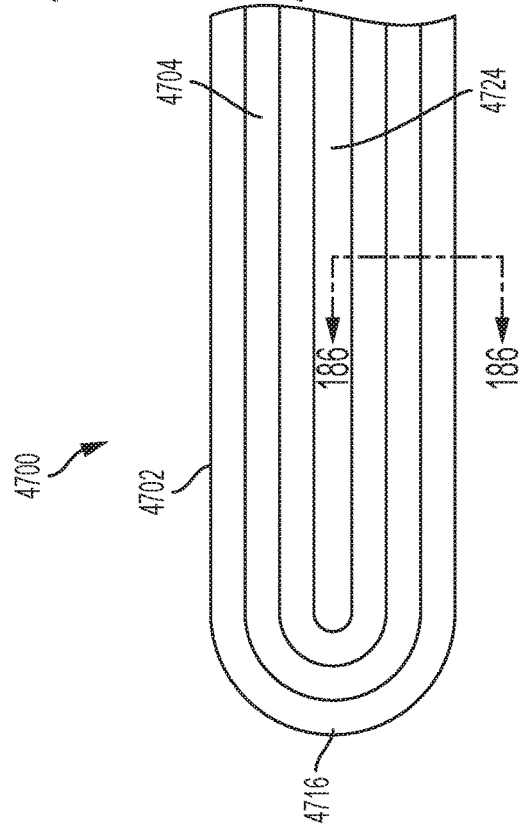

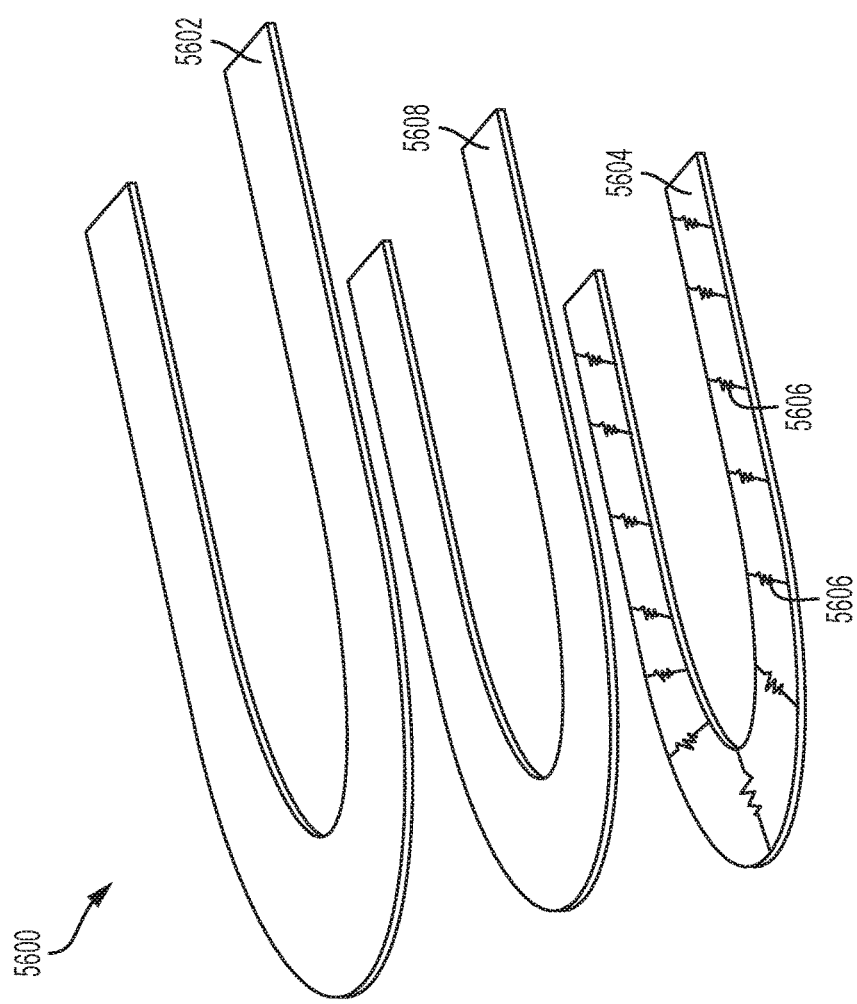

FLEXIBLE CIRCUITS FOR ELECTROSURGICAL INSTRUMENT

TECHNICAL FIELD

The present disclosure is related generally to medical devices having various mechanisms for grasping and sealing tissue. In particular, the present disclosure is related to medical devices having grasping instruments that perform sealing procedures by applying electrical energy via one or more flexible circuit electrodes.

BACKGROUND

In many surgeries, multiple devices are used to perform grasping of tissue, sealing of the tissue using electrical energy or in other cases ultrasonic energy. Conductive elements are use to delivering electrical energy from an energy source to the energy delivery location. The conductive elements can be bulky and awkward to route though the limited space available in the surgical instrument. While several devices have been made and used, it is believed that no one prior to the inventors has made or used the devices described in the appended claims.

SUMMARY

In some aspects, a method of manufacturing a flexible circuit electrode assembly or a flexible circuit electrode assembly manufactured by the following method is provided:

1. A method of manufacturing a flexible circuit electrode, the method comprising: laminating a flexible electrically conductive sheet to a flexible electrically insulative sheet with an adhesive therebetween to produce a flexible laminate; forming at least one electrode on the flexible electrically conductive sheet; forming at least one electrically insulative layer on a tissue contacting surface of the least one electrode; and separating the at least one electrode from the flexible laminate.

2. The method of example 1, wherein the flexible electrically conductive sheet is selected from any one of copper, gold plated copper, silver, platinum, stainless steel, or aluminum, or alloys thereof.

3. The method of example 1, wherein the flexible electrically insulative sheet is selected from any one of polyimide, polyester, fluorocarbon, or any polymeric material, or any combinations thereof.

4. The method of example 1, wherein forming the at least one electrode on the flexible electrically conductive sheet comprises etching at least one electrode on the flexible electrically conductive sheet.

5. The method of example 4, wherein etching comprises: screen printing a protective barrier on the flexible electrically conductive sheet; and photoetching away any remaining material which does not make up a final shape of the at least one electrode.

6. The method of any one of examples 1-5, wherein the at least one electrically insulative layer further defines the at least one electrode.

7. The method of example 1, wherein the at least one electrically insulative layer defines at least one electrically insulative element.

8. The method of example 7, wherein the at least one electrically insulative element is configured as a spacer.

9. The method of example 1, wherein forming the at least one electrically insulative layer comprises printing a dielectric material on the tissue contacting surface of the at least one electrode.

10. The method of example 1, wherein forming the at least one electrically insulative layer comprises bonding a dielectric cover film on the tissue contacting surface of the at least one electrode.

11. The method of any one of examples 1-10, further comprising forming a spacer by etching the dielectric cover film bonded to the tissue contacting surface of the at least one electrode.

12. The method of example 1, wherein forming the at least one electrically insulative element comprises printing at least one dielectric nonstick element on a tissue contacting surface of the at least one electrode.

13. The method of example 12, wherein printing the least one dielectric nonstick element comprises printing an annular wall on the tissue contacting surface of the at least one electrode, wherein the annular wall defines a cavity.

14. The method of example 1, wherein forming the at least one electrically insulative layer comprises printing at least one dielectric nonstick element on a tissue contacting surface of the at least one electrode.

15. The method of example 1, wherein forming the at least one electrically insulative layer on the tissue contacting surface of the at least one electrode comprises printing at least one electrically insulative element sized and configured to define a predetermined gap between opposing jaw members of a clamp jaw assembly.

16. The method of example 1, wherein forming the at least one electrically insulative layer on the tissue contacting surface of the at least one electrode comprises printing at least one electrically insulative pattern of electrically insulative elements on the tissue contacting surface of the at least one electrode.

17. The method of example 1, wherein separating the at least one electrode comprises die cutting the at least one electrode from the flexible laminate.

18. The method of example 1, wherein forming the at least one electrode comprises forming a distal electrode element on a distal end of the at least one electrode.

19. The method of example 18, wherein forming the distal electrode element comprises forming a distal electrode element that is electrically coupled to the at least one electrode.

20. The method of example 18, wherein forming the distal electrode element comprises forming a distal electrode element that is electrically isolated from the at least one electrode.

21. The method of example 1, wherein forming the at least one electrode comprises forming at least two electrode segments electrically isolated from each other by a gap.

22. The method of example 1, wherein forming the at least one electrode comprises forming at least two electrode segments connected by a flexure bearing.

23. The method of example 22, wherein forming the least two electrode segments connected by the flexure bearing comprises forming the at least two electrode segments spaced apart laterally relative to the flexure bearing on the at least one electrode.

24. The method of example 22, wherein forming the least two electrode segments connected by a flexure bearing comprises forming the at least two electrode segments are spaced apart longitudinally relative to the flexure bearing on the at least one electrode.

25. The method of example 1, wherein: forming at least one electrode on the flexible electrically conductive sheet comprises forming a plurality of electrodes on the flexible electrically conductive sheet; and forming at least one electrically insulative layer on a tissue contacting surface of the least one electrode comprises forming the at least one electrically insulative layer on a tissue contacting surface of each of the plurality of electrodes.

26. A flexible circuit electrode formed by a process, comprising: laminating a flexible electrically conductive sheet to a flexible electrically insulative sheet with adhesive therebetween to produce a flexible laminate; forming at least one electrode on the flexible electrically conductive sheet; forming at least one electrically insulative layer on a tissue contacting surface of the least one electrode; and separating the at least one electrode from the flexible laminate.

27. The flexible circuit electrode of example 26, wherein the flexible electrically conductive sheet is selected from any one of copper, gold plated copper, silver, platinum, stainless steel, or aluminum, or alloys thereof.

28. The flexible circuit electrode of example 26, wherein the flexible electrically insulative sheet is selected from any one of polyimide, polyester, fluorocarbon, or any polymeric material, or any combinations thereof.

29. The flexible circuit electrode of example 26, wherein forming the at least one electrode on the flexible electrically conductive sheet comprises etching at least one electrode on the flexible electrically conductive sheet.

30. The flexible circuit electrode of example 29, wherein etching comprises: screen printing a protective barrier on the flexible electrically conductive sheet; and photoetching away any remaining material which does not make up a final shape of the at least one electrode.

31. The flexible circuit electrode of example 30, wherein the at least one electrically insulative layer further defines the at least one electrode.

32. The flexible circuit electrode of example 26, wherein the at least one electrically insulative layer defines at least one electrically insulative element.

33. The flexible circuit electrode of example 32, wherein the at least one electrically insulative element is configured as a spacer.

34. The flexible circuit electrode of example 26, wherein forming the at least one electrically insulative layer comprises printing a dielectric material on the tissue contacting surface of the at least one electrode.

35. The flexible circuit electrode of example 26, wherein forming the at least one electrically insulative layer comprises bonding a dielectric cover film on the tissue contacting surface of the at least one electrode.

36. The flexible circuit electrode of any one of examples 26-35, further comprising forming a spacer by etching dielectric cover film bonded to the tissue contacting surface of the at least one electrode.

37. The flexible circuit electrode of example 26, wherein forming the at least one electrically insulative layer comprises printing at least one dielectric nonstick element on a tissue contacting surface of the at least one electrode.

38. The flexible circuit electrode of example 37, wherein the at least one dielectric nonstick element comprises printing an annular wall on the tissue contacting surface of the at least one electrode, wherein the annular wall defines a cavity.

39. The flexible circuit electrode of example 26, wherein forming the at least one electrically insulative element comprises printing at least one dielectric nonstick element on a tissue contacting surface of the at least one electrode.

40. The flexible circuit electrode of example 26, wherein forming the at least one electrically insulative layer on the tissue contacting surface of the at least one electrode comprises printing at least one electrically insulative element sized and configured to define a predetermined gap between opposing jaw members of a clamp jaw assembly.

41. The flexible circuit electrode of example 26, wherein forming the at least one electrically insulative layer on the tissue contacting surface of the at least one electrode comprises printing at least one electrically insulative pattern of electrically insulative elements on the tissue contacting surface of the at least one electrode.

42. The flexible circuit electrode of example 26, wherein separating the at least one electrode comprises die cutting the at least one electrode from the flexible laminate.

43. The flexible circuit electrode of example 26, wherein forming the at least one electrode comprises forming a distal electrode element on a distal end of the at least one electrode.

44. The flexible circuit electrode of example 43, wherein forming the distal electrode element comprises forming a distal electrode element that is electrically coupled to the at least one electrode.

45. The flexible circuit electrode of example 43, wherein forming the distal electrode element comprises forming a distal electrode element that is electrically isolated from the at least one electrode.

46. The flexible circuit electrode of example 26, wherein forming the at least one electrode comprises forming at least two electrode segments electrically isolated from each other by a gap.

47. The flexible circuit electrode of example 26, wherein forming the at least one electrode comprises forming at least two electrode segments connected by a flexure bearing.

48. The flexible circuit electrode of example 47, wherein forming the least two electrode segments connected by the flexure bearing comprises forming the at least two electrode segments spaced apart laterally relative to the flexure bearing on the at least one electrode.

49. The flexible circuit electrode of example 47, wherein forming the least two electrode segments connected by a flexure bearing comprises forming the at least two electrode segments are spaced apart longitudinally relative to the flexure bearing on the at least one electrode.

50. The flexible circuit electrode of example 26, wherein: forming at least one electrode on the flexible electrically conductive sheet comprises forming a plurality of electrodes on the flexible electrically conductive sheet; and forming at least one electrically insulative layer on a tissue contacting surface of the least one electrode comprises forming the at least one electrically insulative layer on a tissue contacting surface of each of the plurality of electrodes.

51. A method of manufacturing a flexible circuit electrode assembly, the method comprising: vacuum forming a flexible circuit; trimming the vacuum formed flexible circuit; and attaching the trimmed vacuum formed flexible circuit to a jaw member of a clamp jaw assembly.

52. The method of example 51, further comprising: placing the vacuum formed flexible circuit in a molding tool; and molding a substrate to support a profile of the vacuum formed flexible circuit.

53. The method of example 52, wherein attaching the trimmed vacuum formed flexible circuit to the jaw member of the clamp jaw assembly comprises molding the trimmed vacuum formed flexible circuit over the jaw member.

54. The method of example 51, wherein attaching the trimmed vacuum formed flexible circuit to the jaw member of the clamp jaw assembly comprises adhering the trimmed vacuum formed flexible circuit to the jaw member with adhesive.

The foregoing summary is illustrative only and is not intended to be in any way limiting. In addition to the illustrative aspects, aspects, and features described above, further aspects, aspects, and features will become apparent by reference to the drawings and the following detailed description.

BRIEF DESCRIPTION OF THE DRAWINGS

The novel features of the aspects described herein are set forth with particularity in the appended claims. The aspects, however, both as to organization and methods of operation may be better understood by reference to the following description, taken in conjunction with the accompanying drawings as follows.

FIG. 1A shows a surgical instrument in electrical communication with an energy source, according to one aspect of the present disclosure.

FIG. 1B is a detailed view of the end effector of the surgical instrument shown in FIG. 1A, according to one aspect of the present disclosure.

FIGS. 4-9 illustrate a flexible circuit electrode comprising an extended lead, according to one aspect of the present disclosure, where:

FIG. 4 is a perspective view of a flexible circuit electrode comprising an extended lead, according to one aspect of the present disclosure;

FIG. 5 is a plan view of the electrically conductive element side of the flexible circuit electrode shown in FIG. 4, according to one aspect of the present disclosure;

FIG. 6 is a plan view of the electrically insulative element side of the electrically conductive element of the flexible circuit electrode shown in FIG. 5, according to one aspect of the present disclosure;

FIG. 7 is a side elevation view of the flexible circuit electrode shown in FIG. 4, according to one aspect of the present disclosure;

FIG. 8 is an elevation view of the flexible circuit electrode shown in FIG. 4 taken from a distal end, according to one aspect of the present disclosure; and FIG. 9 is an elevation view of the flexible circuit electrode shown in FIG. 4 taken from a proximal end, according to one aspect of the present disclosure.

FIGS. 10-17 illustrate a flexible circuit electrode 200 comprising electrically insulative elements, according to one aspect of the present disclosure, where:

FIG. 10 is a perspective view of the electrically conductive side of a flexible circuit electrode comprising at least one electrically conductive element and at least one electrically insulative element, according to one aspect of the present disclosure;

FIG. 11 is a perspective view of the flexible circuit electrode shown in FIG. 10 showing the electrically insulative element of the electrically conductive element, according to one aspect of the present disclosure;

FIG. 12 is a plan view of the electrically conductive element side of the flexible circuit electrode shown in FIG. 10, according to one aspect of the present disclosure;

FIG. 13 is a plan view of the electrically insulative element side of the electrically conductive element of the flexible circuit electrode shown in FIG. 10, according to one aspect of the present disclosure;

FIG. 14 is a side elevation view of the flexible circuit electrode shown in FIG. 10, according to one aspect of the present disclosure;

FIG. 15 is an elevation view of the flexible circuit electrode shown in FIG. 10 taken from a distal end, according to one aspect of the present disclosure;

FIG. 16 is an elevation view of the flexible circuit electrode shown in FIG. 10 taken from a proximal end, according to one aspect of the present disclosure; and FIG. 17 is a detail view of the flexible circuit electrode shown in FIG. 10, according to one aspect of the present disclosure.

FIGS. 20-26 illustrate a segmented offset flexible circuit electrode, according to one aspect of the present disclosure, where:

FIG. 20 is a perspective view of a segmented offset flexible circuit electrode comprising two electrode segments of the electrically conductive element side, according to one aspect of the present disclosure;

FIG. 21 is a perspective view of the electrically insulative element side of the segmented offset flexible circuit electrode shown in FIG. 20, according to one aspect of the present disclosure;

FIG. 22 is a plan view of the electrically conductive element side of the segmented offset flexible circuit electrode shown in FIG. 20, according to one aspect of the present disclosure;

FIG. 23 illustrates a plan view of the electrically insulative element side of the segmented offset electrically conductive element of the flexible circuit electrode shown in FIG. 20, according to one aspect of the present disclosure;

FIG. 24 is a side elevation view of the segmented offset flexible circuit electrode shown in FIG. 20, according to one aspect of the present disclosure;

FIG. 25 is an elevation view of the segmented offset flexible circuit electrode shown in FIG. 20 taken from a distal end, according to one aspect of the present disclosure; and FIG. 26 is an elevation view of the segmented offset flexible circuit electrode shown in FIG. 20 taken from a proximal end, according to one aspect of the present disclosure.

FIGS. 27-33 illustrate a flexible circuit electrode comprising electrically insulative elements, according to one aspect of the present disclosure, where:

FIG. 27 is a perspective view of a flexible circuit electrode comprising an array of electrically insulative elements showing the electrically conductive element, according to one aspect of the present disclosure;

FIG. 28 is a perspective view of the electrically insulative element side of the electrically conductive element of the flexible circuit electrode shown in FIG. 27, according to one aspect of the present disclosure;

FIG. 29 is a plan view of the electrically conductive element side of the flexible circuit electrode shown in FIG. 27, according to one aspect of the present disclosure;

FIG. 30 is a plan view of the electrically insulative element of the electrically conductive element of the flexible circuit electrode shown in FIG. 27, according to one aspect of the present disclosure;

FIG. 31 is a side elevation view of the flexible circuit electrode shown in FIG. 27, according to one aspect of the present disclosure;

FIG. 32 is an elevation view of the flexible circuit electrode shown in FIG. 27 taken from a distal end, according to one aspect of the present disclosure; and FIG. 33 is an elevation view of the flexible circuit electrode shown in FIG. 27 taken from a proximal end, according to one aspect of the present disclosure.

FIG. 34 is a perspective view of an integrated flexible circuit electrode comprising electrically insulative elements showing the electrically conductive element side of the integrated flexible circuit electrode, according to one aspect of the present disclosure; and FIG. 35 is a section view of the integrated flexible circuit electrode shown in FIG. 34 taken through one of the electrically insulative elements, according to one aspect of the present disclosure.

FIGS. 42-48 illustrate a flexible circuit electrode comprising a distal electrode element and electrically insulative elements, according to one aspect of the present disclosure, where:

FIG. 42 is a perspective view of a flexible circuit electrode comprising a distal electrode element and electrically insu-lative elements showing the electrically conductive element, according to one aspect of the present disclosure.

FIG. 43 is a perspective view of the electrically insulative element of the of the flexible circuit electrode shown in FIG. 42, according to one aspect of the present disclosure;

FIG. 44 is a plan view of the electrically conductive element side of the flexible circuit electrode shown in FIG. 42, according to one aspect of the present disclosure;

FIG. 45 is a plan view of the electrically insulative element of the flexible circuit electrode shown in FIG. 42, according to one aspect of the present disclosure;

FIG. 46 is a side elevation view of the flexible circuit electrode shown in FIG. 42, according to one aspect of the present disclosure;

FIG. 47 is an elevation view of the flexible circuit electrode shown in FIG. 42 taken from a distal end, according to one aspect of the present disclosure; and FIG. 48 is an elevation view of the flexible circuit electrode shown in FIG. 42 taken from a proximal end, according to one aspect of the present disclosure.

FIG. 49 is a perspective view of a electrode comprising a non-isolated distal electrode element and electrically insulative elements, according to one aspect of the present disclosure;

FIG. 50 is a perspective view of the end effector shown in FIG. 49, according to one aspect of the present disclosure; and FIG. 51 is an elevation view of the end effector shown in FIG. 49 taken from a distal end, according to one aspect of the present disclosure.

FIGS. 53-59 illustrate a flat flexible circuit electrode comprising an upper electrode and a lower electrode, according to one aspect of the present disclosure, where:

FIG. 53 is a perspective view of the flat flexible circuit electrode comprising an upper electrode and a lower electrode coupled by a flexure bearing showing the electrically conductive elements side, which define the electrodes tissue sealing surfaces, according to one aspect of the present disclosure;

FIG. 54 is a perspective view showing the electrically insulative element side of the upper and lower flat flexible circuit electrodes shown in FIG. 53, according to one aspect of the present disclosure;

FIG. 55 is a plan view of the electrically conductive elements side of the upper and lower flat flexible circuit electrodes shown in FIG. 53, according to one aspect of the present disclosure;

FIG. 56 is a plan view of the electrically insulative element side of the upper and lower flat flexible circuit electrodes shown in FIG. 53, according to one aspect of the present disclosure;

FIG. 57 is a side elevation view of the upper and lower flat flexible circuit electrodes shown in FIG. 53, according to one aspect of the present disclosure;

FIG. 58 is an elevation view of the upper and lower flat flexible circuit electrodes shown in FIG. 53 taken from a distal end, according to one aspect of the present disclosure; and FIG. 59 is an elevation view of the upper and lower flat flexible circuit electrodes shown in FIG. 53 taken from a proximal end, according to one aspect of the present disclosure.

FIGS. 60-66 illustrate a flexible circuit electrode comprising a flexure bearing, according to one aspect of the present disclosure, where:

FIG. 60 is a perspective view of a flexible circuit electrode comprising upper and lower electrodes coupled by a flexure bearing and in an open configuration, according to one aspect of the present disclosure;

FIG. 61 is another perspective view of the flexible circuit electrode shown in FIG. 60, according to one aspect of the present disclosure;

FIG. 62 is a plan view of the flexible circuit electrode shown in FIG. 60, according to one aspect of the present disclosure;

FIG. 63 is a plan view of the flexible circuit electrode shown in FIG. 60, according to one aspect of the present disclosure;

FIG. 64 is a side elevation view of the flexible circuit electrode shown in FIG. 60, according to one aspect of the present disclosure;

FIG. 65 is an elevation view of the flexible circuit electrode shown in FIG. 60 taken from a distal end, according to one aspect of the present disclosure; and FIG. 66 is an elevation view of the flexible circuit electrode shown in FIG. 60 taken from a proximal end, according to one aspect of the present disclosure.

FIG. 67 is a perspective view of an end effector comprising a vacuum formed flexible circuit electrode, according to one aspect of the present disclosure;

FIG. 68 is a vacuum formed flexible circuit electrode that can be inserted in an injection molding tool, according to one aspect of the present disclosure;

FIG. 69 is a vacuum formed flexible circuit electrode that can be adhered directly to a jaw of the end effector jaw assembly shown in FIG. 67, according to one aspect of the present disclosure.

FIG. 70 illustrates a flexible circuit electrode, according to one aspect of the present disclosure;

FIG. 71 illustrates a flat conductive trace for a flexible circuit electrode, according to one aspect of the present disclosure; and FIG. 72 is a comparison of a conventional stainless steel electrode versus a thin copper flexible circuit electrode, according to one aspect of the present disclosure.

FIGS. 73-80 illustrate mass produced a cost effective flexile circuit electrode sub-assembly with insulative barrier along with non-conductive stand-offs, according to one aspect of the present disclosure, where:

FIG. 73 is a perspective view of an assembly comprising an array of flexible circuit electrodes, according to one aspect of the present disclosure;

FIG. 74 is an elevation view of the assembly shown in FIG. 73, according to one aspect of the present disclosure; and FIG. 75 is a detail plan view of the assembly shown in FIG. 73 showing individual flexible circuit electrodes fixed in a carrier web prior to die cutting, according to one aspect of the present disclosure.

FIG. 76 is a perspective view of an assembly comprising an array of flexible circuit electrodes in a carrier web, according to one aspect of the present disclosure;

FIG. 77 is a detail view of the array of flexible circuit electrodes in a carrier web shown in FIG. 76, according to one aspect of the present disclosure;

FIG. 78 is an individual flexible circuit electrode sub-assembly in a carrier web prior to die-cutting, according to one aspect of the present disclosure;

FIG. 79 is a detail view of the individual flexible circuit electrode sub-assembly in a carrier web shown in FIG. 78, according to one aspect of the present disclosure; and FIG. 80 is an individual flexible circuit electrode sub-assembly shown in FIG. 78 after die cutting and ready to be bonded to a jaw of an end effector, according to one aspect of the present disclosure.

FIG. 82 is a perspective view of an end effector jaw assembly comprising an electrode and a thermal assist heater, according to one aspect of the present disclosure;

FIG. 83 is a graphical depiction of power, voltage, and current versus impedance, according to one aspect of the present disclosure;

FIG. 84 is a schematic of a circuit of an RF drive source with a low impedance load between two electrodes, according to one aspect of the present disclosure;

FIG. 85 is a schematic of a circuit comprising an RF drive source with a low impedance load between the electrodes, a heater, and a thermal assist control circuit, according to one aspect of the present disclosure.

FIG. 86 is a graphical depiction of impedance (14 and power (P) versus time (t), according to one aspect of the present disclosure.

FIG. 87 is logic flow depicting a process for operating the thermal assist control circuit shown in FIG. 85, according to one aspect of the present disclosure.

FIG. 88 is an optical force sensor in a relaxed state, according to one aspect of the present disclosure;

FIG. 89 is a cross section of the optical force sensor shown in FIG. 88 in a relaxed state, according to one aspect of the present disclosure;

FIG. 90 is a cross section of the optical force sensor shown in FIG. 88 in a compressed state, according to one aspect of the present disclosure; and FIG. 91 is a simplified schematic diagram of the optical force sensor shown in FIG. 88, according to one aspect of the present disclosure.

FIG. 92 is a section view of a lower jaw of an end effector comprising a polymer optical fiber (POF) based force sensor, according to one aspect of the present disclosure; and FIG. 93 is a section view of the end effector shown in FIG. 92 with tissue disposed on the polymer optical fiber (POF) based force sensor, according to one aspect of the present disclosure.

FIG. 94 is a flat patterned flexible circuit electrode in a flat state where upper and lower jaw electrode elements are in transverse orientation relative to a longitudinal element, according to one aspect of the present disclosure; and FIG. 95 illustrates the flat patterned flexible circuit electrode shown in FIG. 94 in a folded state where the upper and lower jaw electrode elements create a flexure bearing, according to one aspect of the present disclosure.

FIG. 96 is a flat patterned flexible circuit electrode in a flat state where upper and lower jaw electrode elements are in parallel orientation relative to a longitudinal element, according to one aspect of the present disclosure; and FIG. 97 illustrates the flat patterned flexible circuit electrode shown in FIG. 96 in a folded state where the upper and lower jaw electrode elements create a flexure bearing, according to one aspect of the present disclosure.

FIG. 98 is a side elevation view of a flexible circuit electrode comprising an integrated slider switch, according to one aspect of the present disclosure; and FIG. 99 is a plan view of the flexible circuit electrode shown in FIG. 98 showing the integrated slider switch, according to one aspect of the present disclosure.

FIGS. 100-102 illustrate various flexible circuit electrode configurations with a controlled switching area to control various switching modes enabling a flexible circuit to be turned on and off in different areas, according to one aspect of the present disclosure, where:

FIG. 100 is a planar view of a flexible circuit electrode configured to enable inner and outer portions of the electrode to be controlled separately and independently, according to one aspect of the present disclosure;

FIG. 101 is a planar view of a flexible circuit electrode configured to enable separate and independent control of the distal tip of the electrode, according to one aspect of the present disclosure; and FIG. 102 is a section view of a flexible circuit electrode configured to enable separate and independent control of the outer edges of the electrode, according to one aspect of the present disclosure.

FIG. 103 is a diagram illustrating the components and interconnections of a system of an electrosurgical instrument for switching and controlling a radio frequency (RF) flexible circuit electrode, according to one aspect of the present disclosure;

FIG. 104 is diagram of the system for switching and controlling a radio frequency (RF) flexible circuit electrode shown in FIG. 103 where an application specific integrated circuit (ASIC) is employed for the control circuit, according to one aspect of the present disclosure;

FIG. 105 is an electrical schematic of the system for switching and controlling a radio frequency (RF) flexible circuit electrode shown in FIGS. 103 and 104, according to one aspect of the present disclosure;

FIG. 106 is a diagram of a serial communication circuit that may be employed by the system shown in FIG. 102, according to one aspect of the present disclosure;

FIG. 107 is a waveform generator circuit configured to generate up to 4 synchronous arbitrary digital waveforms that may be employed by the system shown in FIG. 102, according to one aspect of the present disclosure;

FIG. 108 is a stepper motor control circuit configured to drive a stepper motor that may be employed by the system shown in FIG. 102, according to one aspect of the present disclosure;

FIG. 109 is a quadrature encoder for sensing the position of a rotating disk that may be employed by the system shown in FIG. 102, according to one aspect of the present disclosure;

FIG. 110 is a schematic diagram of the quadrature encoder shown in FIG. 109, according to the present disclosure;

FIG. 111 is a section view of a flexible circuit electrode comprising a sensing layer disposed below a polyimide layer, which is disposed below an electrically conductive layer, according to one aspect of the present disclosure;

FIG. 112 is a plan view of a segmented flexible circuit electrode comprising four segments, according to one aspect of the present disclosure; and FIG. 113 is a logic diagram for controlling a segmented flexible circuit electrode that may be employed by the system shown in FIGS. 103 and 104, according to one aspect of the present disclosure.

FIG. 114 is a cross section view of a multilayer flexible circuit electrode comprising a mechanical switch in the form of a dome disposed on the lowest layer of the multilayer flexible circuit electrode in a non-contact state, according to one aspect of the present disclosure;

FIG. 115 is a lower plan view of the multilayer flexible circuit electrode shown in FIG. 114, according to one aspect of the present disclosure;

FIG. 116 is an upper plan view of the multilayer flexible circuit electrode shown in FIG. 114, according to one aspect of the present disclosure;

Figure 117:
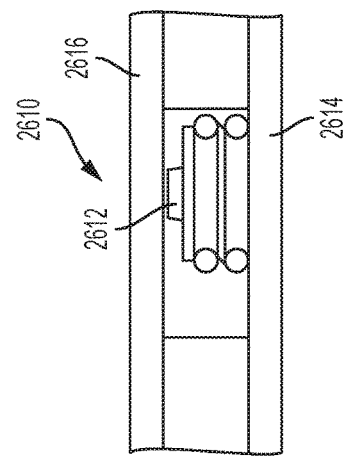
Figure 118:
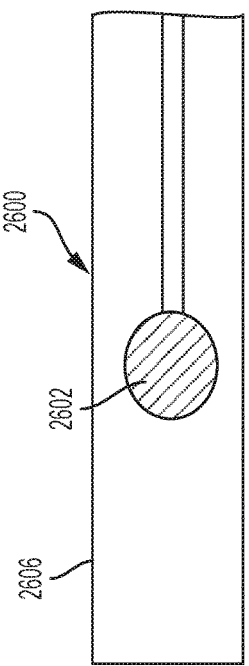
Figure 119:
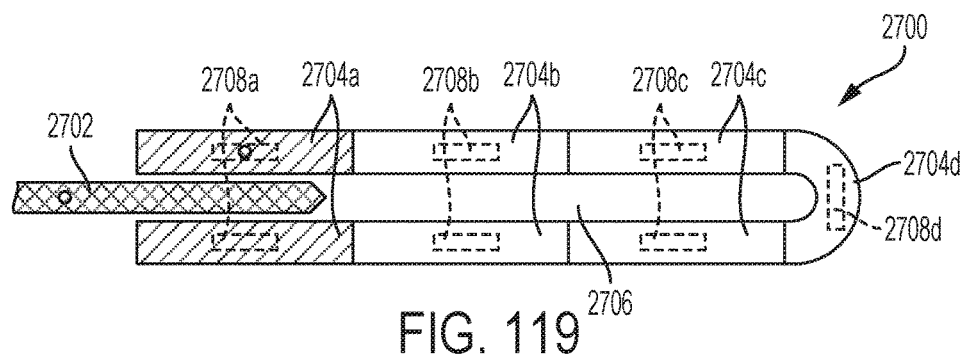
Figure 120:
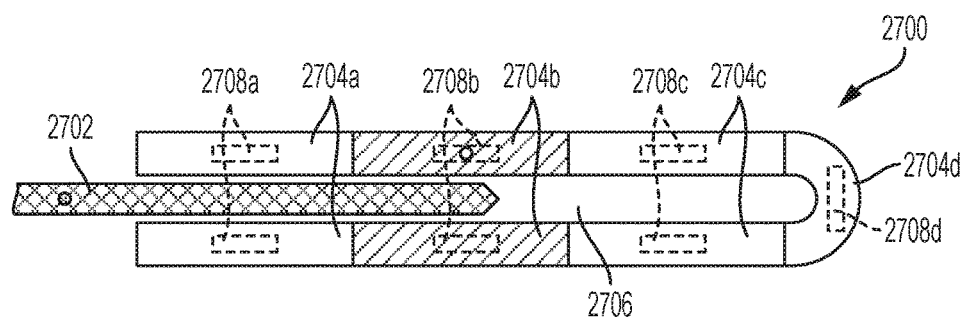
Figure 121:
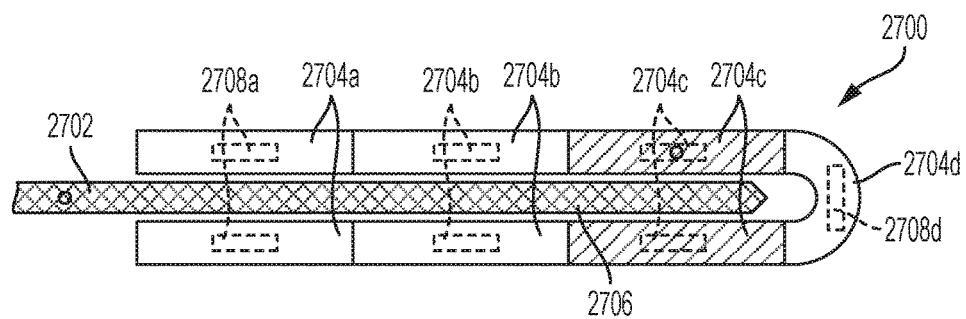

FIG. 117 is a cross section view of the multilayer flexible circuit electrode showing the dome formed on the lowest layer of the multilayer flexible circuit electrode in an electrical contact state, according to one aspect of the present disclosure; and FIG. 118 is a cross section view of a multilayer flexible circuit electrode comprising a mechanical switch in the form of a spring disposed on the lowest layer of the multilayer flexible circuit electrode in a non-contact state, according to one aspect of the present disclosure;

FIGS. 119-121 illustrate a segmented flexible circuit electrode including a sensor configured to provide feedback to a motorized knife control circuit for controlling the position of the motorized knife, according to one aspect of the present disclosure, where, FIG. 119 illustrates the segmented flexible circuit electrode where only the proximal electrode segment is activated, according to one aspect of the present disclosure;

FIG. 120 illustrates a segmented flexible circuit electrode where only the intermediate electrode segment is activated, according to one aspect of the present disclosure; and FIG. 121 illustrates a segmented flexible circuit electrode where only the distal electrode segment is activated, according to one aspect of the present disclosure.

Figure 122:
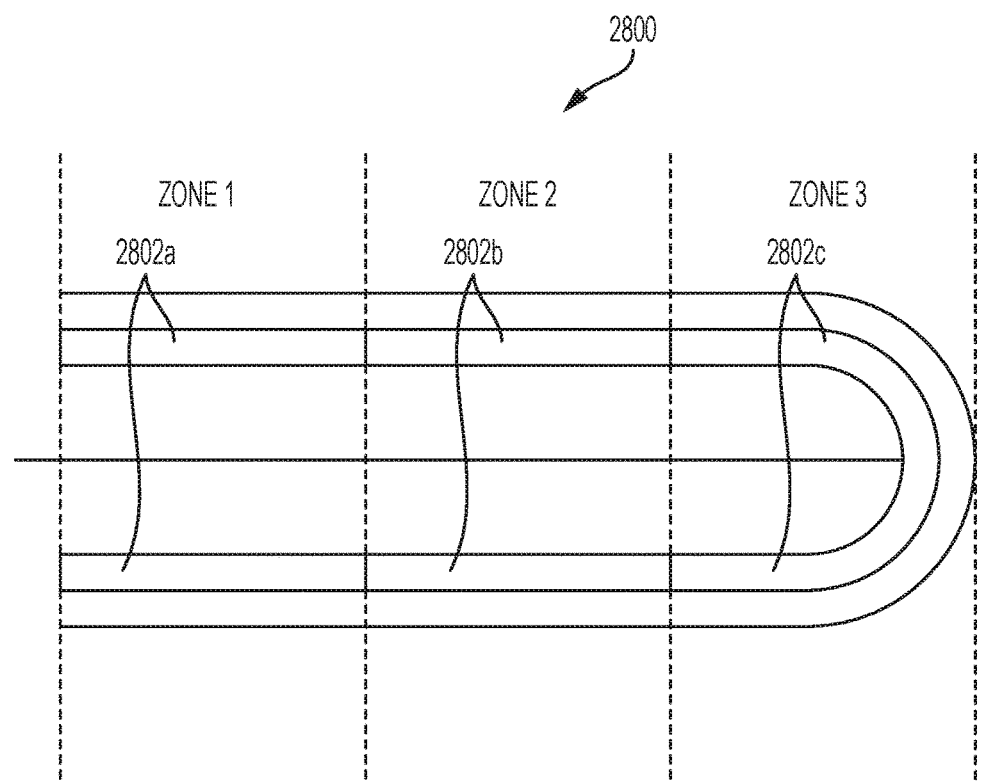

FIG. 122 illustrates a multi-zone segmented flexible circuit electrode configured to output different algorithms for each zone and treat tissue in each zone independently, according to one aspect of the present disclosure.

Figure 123:
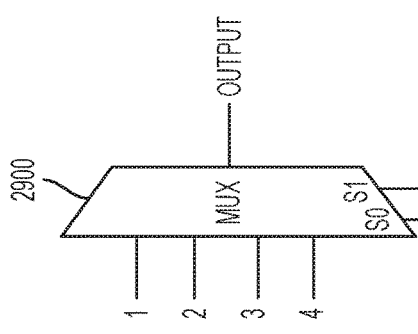
Figure 124:
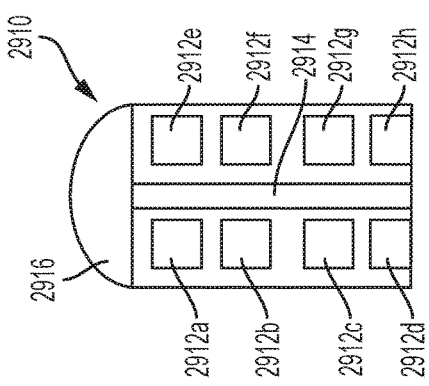

FIGS. 123-124 illustrate a technique for implementing a multiplexer with flexible electronic circuits to provide improved control methods, according to one aspect of the present disclosure, where:

FIG. 123 illustrates a two line multiplexer implemented with flexible electronic circuits, according to one aspect of the present disclosure; and FIG. 124 illustrates a jaw configuration with independently actuatable electrodes, according to one aspect of the present disclosure.

Figure 125:
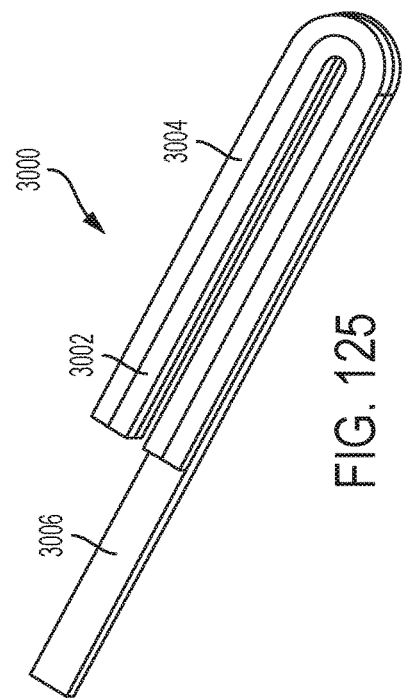

FIG. 125 illustrates a flexible circuit segmented electrode comprising an inner electrode and an outer electrode that have different thermal conductivity properties for altering tissue effects, according to one aspect of the present disclosure.

Figure 126:
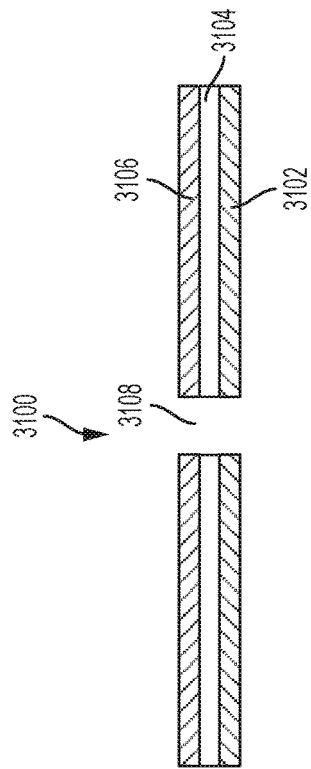

FIGS. 126-130 illustrates an integrated thin flexible circuit electrode shown in FIG. 126 comprising a pressure sensor integrated with the flexible circuit electrode, according to one aspect of the present disclosure, where:

FIG. 126 is a elevation section view of a thin and flexible circuit electrode comprising a switching pressure sensor, according to one aspect of the present disclosure;

FIG. 127 is a lower plan view of the flexible circuit electrode shown in FIG. 126 showing the pressure sensor, according to one aspect of the present disclosure;

FIG. 128 is a side view of the flexible circuit electrode shown in FIG. 126 with an embedded pressure sensor, according to one aspect of the present disclosure;

FIG. 129 is a plan view of the flexible circuit electrode shown in FIG. 126 with a tissue bundle present thereon, according to one aspect of the present disclosure; and FIG. 130 is a plan view of the flexible circuit electrode shown in FIG. 126 with a vessel present, according to one aspect of the present disclosure.

FIGS. 131-133 illustrate a flexible circuit electrode comprising selective electrode zone activation employing piezoelectric pressure detection, according to tone aspect of the present disclosure, where:

FIG. 131 illustrates a segmented flexible circuit electrode divided into three activation segments, according to one aspect of the present disclosure;

FIG. 132 is a section view of the segmented flexible circuit electrode shown in FIG. 131 showing an electrode, a circuit, a piezoelectric sensor, and a knife slot according to one aspect of the present disclosure; and FIG. 133 schematically illustrates a load pressure from tissue being applied to electrode segments (sections 2-3) and a reaction pressure applied to underlying ceramic piezoelectric sensors, according to one aspect of the present disclosure.

Figure 136:
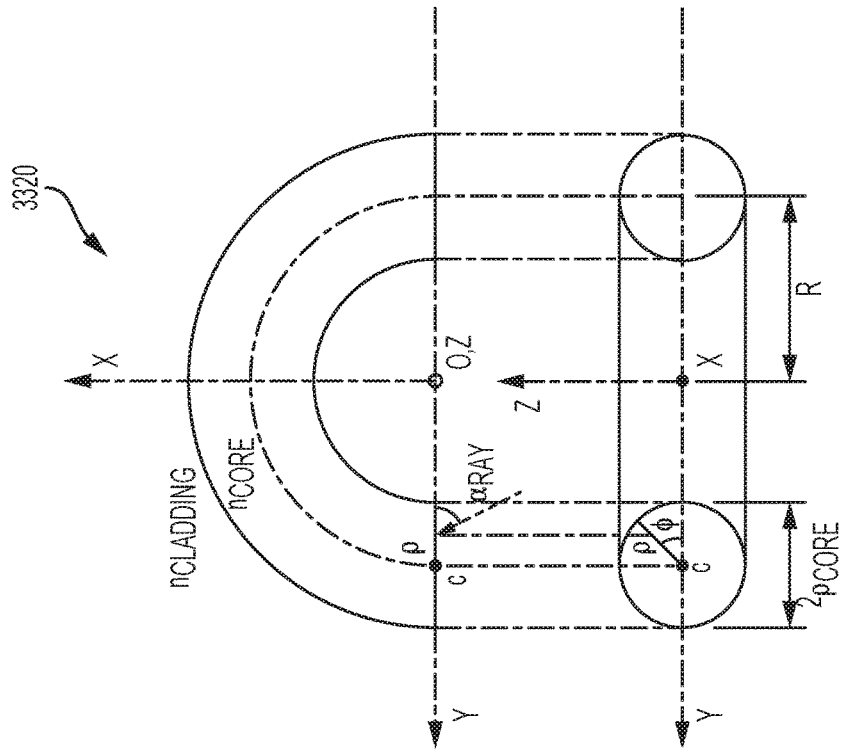
Figure 134:
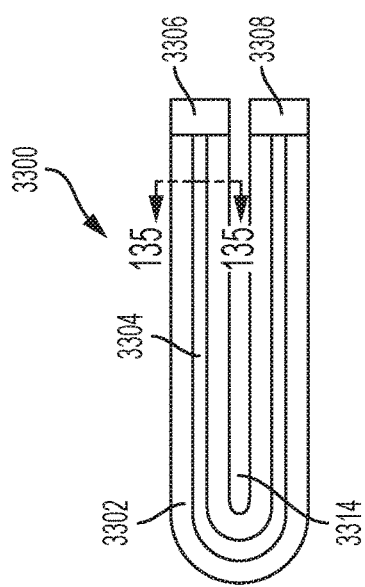
Figure 135:
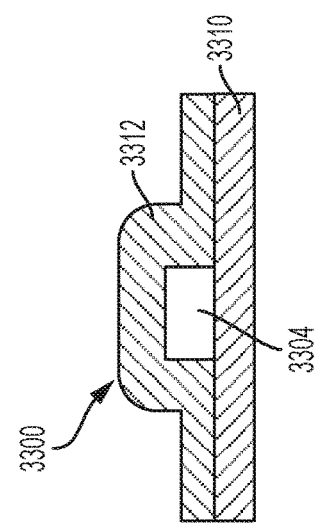

FIGS. 134-136 illustrate an optical temperature sensor embedded in a flexible circuit electrode, according to one aspect of the present disclosure, where:

FIG. 134 is a plan view of an optical temperature sensor embedded in a flexible circuit electrode, according to one aspect of the present disclosure;

FIG. 135 is as section view of the optical temperature sensor embedded in a flexible circuit electrode taken along section line 135-135 as shown in FIG. 134, according to one aspect of the present disclosure; and FIG. 136 is a schematic of a bent fiber section curved with a radius of curvature R, according to one aspect of the present disclosure.

FIGS. 137-138 illustrate a flexible circuit bladder sensor for sensing pressure and temperature, according to one aspect of the present disclosure, where:

FIG. 137 is an exploded view of the flexible circuit bladder sensor, according to one aspect of the present disclosure;

FIG. 138 is an elevation view of the flexible circuit bladder sensor attached to a jaw member of an end effector, according to one aspect of the present disclosure; and FIG. 138A is a section view of the pressure sensing integrated circuit, according to one aspect of the present disclosure.

Figure 139:
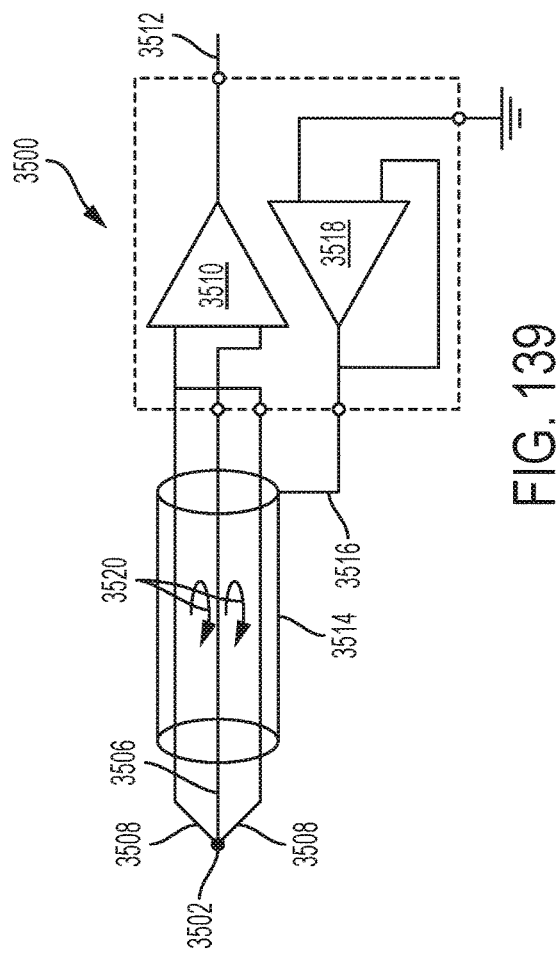
Figure 140:
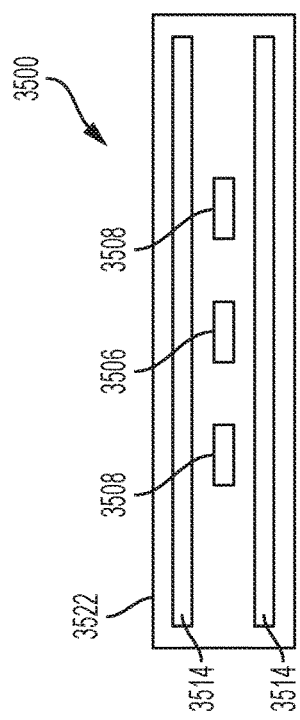

FIGS. 139-140 illustrate a flexible circuit thermocouple sensor, according to one aspect of the present disclosure, where:

FIG. 139 is a schematic diagram of the flexible circuit thermocouple sensor, according to one aspect of the present disclosure; and FIG. 140 is a section view of the flexible circuit thermocouple sensor, according to one aspect of the present disclosure.

Figure 141:
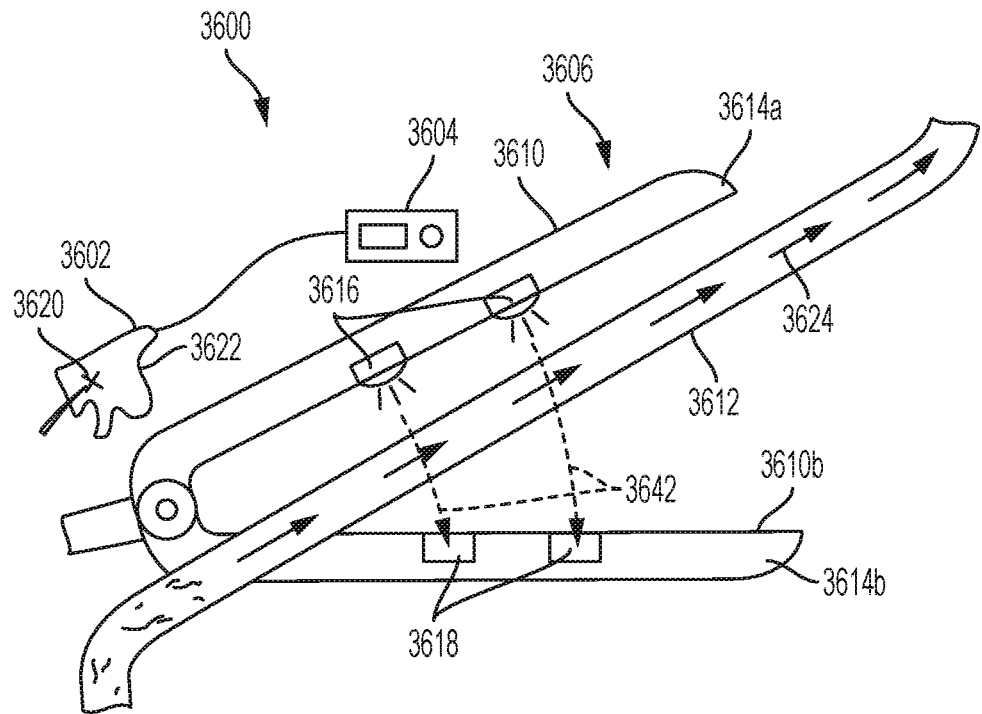
Figure 142:
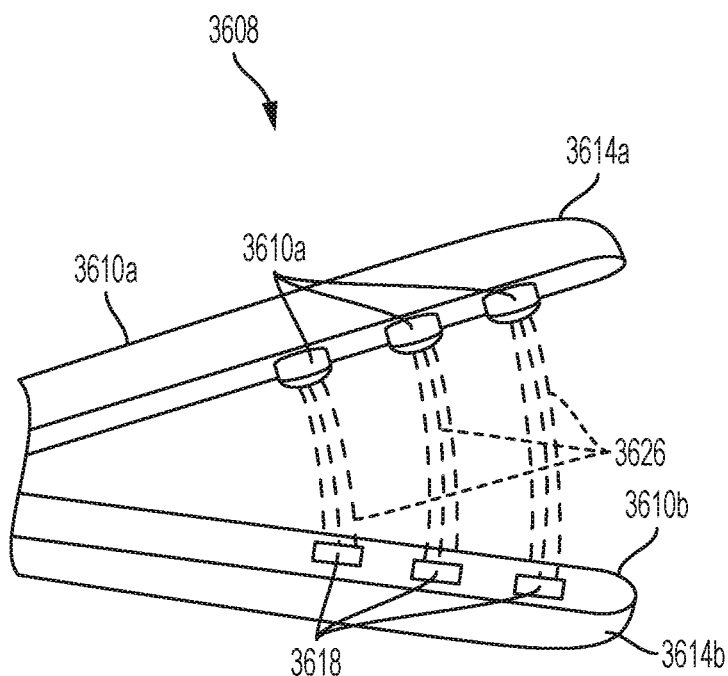

FIGS. 141-142 illustrate a pulse-oximeter and/or an i-watch sensor integrated in a flexible circuit electrode for identifying blood flow in tissue located between the jaws prior to clamping and cutting, according to one aspect of the present disclosure, where:

FIG. 141 illustrates a system 3600 comprising an electrosurgical instrument 3602 coupled to a generator 3604, according to one aspect of the present disclosure; and FIG. 142 is a detail view of the end effector shown in FIG. 141 comprising a pulse-oximeter sensor integrated in the flexible circuit electrodes, according to one aspect of the present disclosure.

FIGS. 143-147 illustrate electro optical sensors integrated with a flexible circuit for sensing tissue properties, according to one aspect of the present disclosure, where:

FIG. 143 illustrates an exploded view of an electro optical sensor for sensing of tissue properties integrated with a flexible circuit electrode, according to one aspect of the present disclosure;

FIG. 144 is a plan view of the flexible circuit electrode comprising an electro optical sensor for sensing of tissue properties shown in FIG. 143 integrated in a via of the flexible circuit electrode 3702, according to one aspect of the present disclosure;

FIG. 145 is a section view of the electro optical sensor integrated in a via of a flexible circuit electrode for sensing of tissue properties, according to one aspect of the present disclosure;

FIG. 146 is an elevation view of an end effector with a flexible circuit electrode comprising an electro optical sensor integrated therewith, according to one aspect of the present disclosure; and FIG. 147 is a plan view of a flexible circuit electrode comprising a plurality of electro optical sensors integrated with, according to one aspect of the present disclosure.

Figure 148:
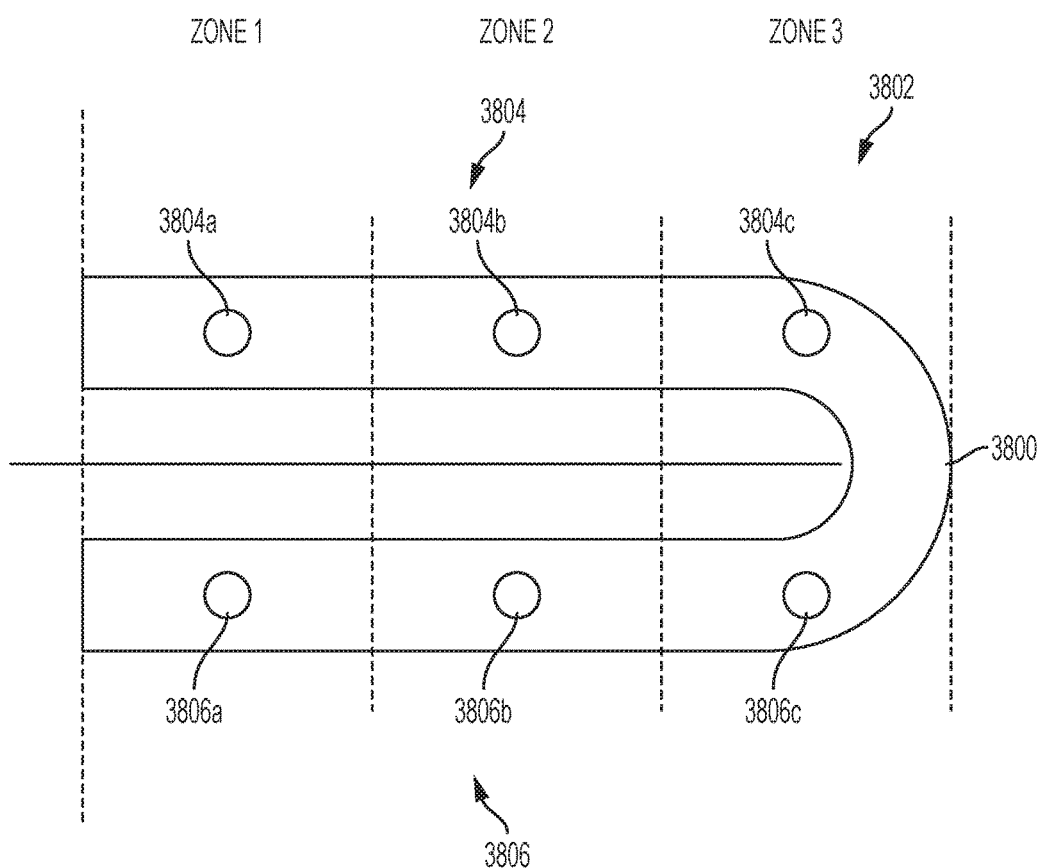

FIG. 148 illustrates a flexible circuit electrode comprising a vascular sensor comprising a LED and photodiode arrangement integrated therewith for sensing vascularity, according to one aspect of the present disclosure.

Figure 150:
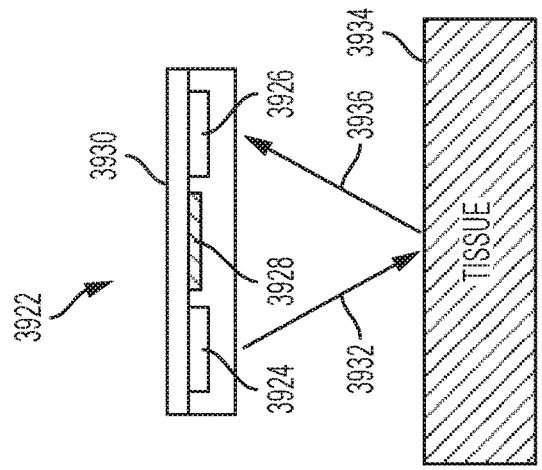
Figure 149:
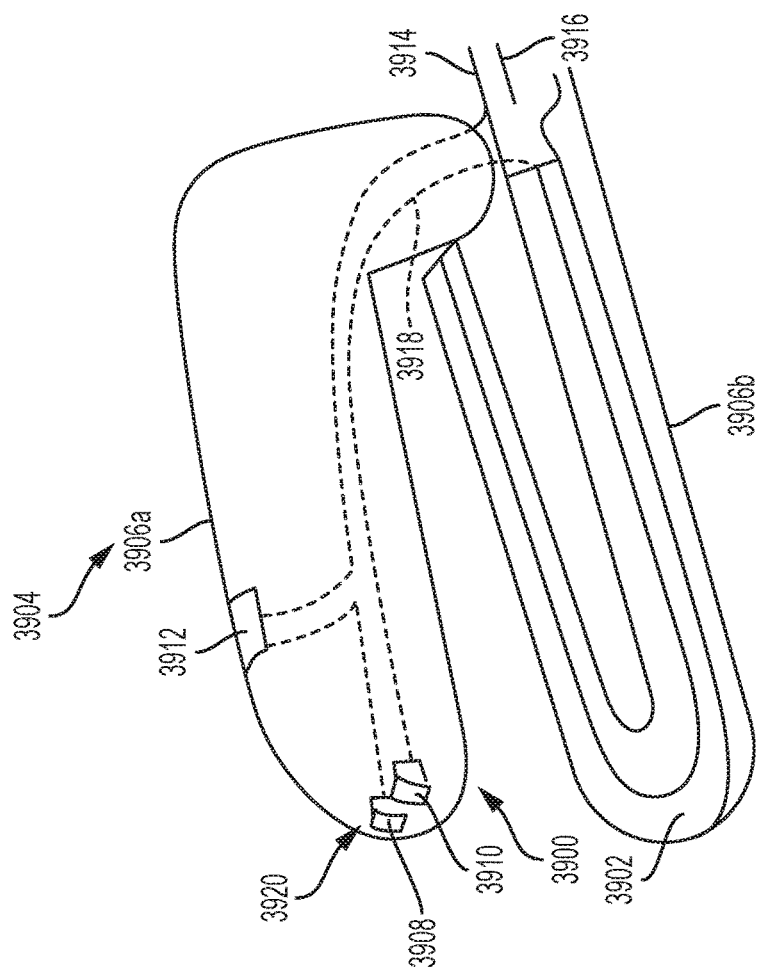

FIGS. 149-150 illustrate a vascular tissue sensor integrated with an flexible circuit electrode, according to one aspect of the present disclosure, where:

FIG. 149 is an end effector comprising upper and lower jaw members and a vascular tissue sensor integrated with a flexible circuit electrode, according to one aspect of the present disclosure; and FIG. 150 is a schematic diagram of a sensor for mobile heart rate monitoring, according to one aspect of the present disclosure.

Figure 151:
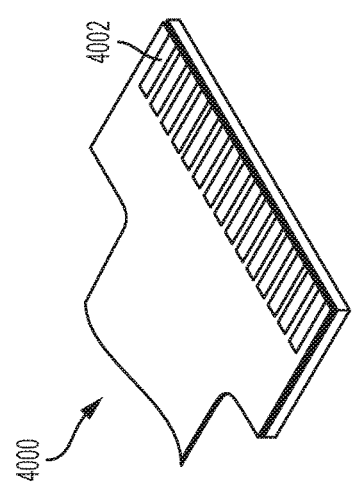
Figure 152:
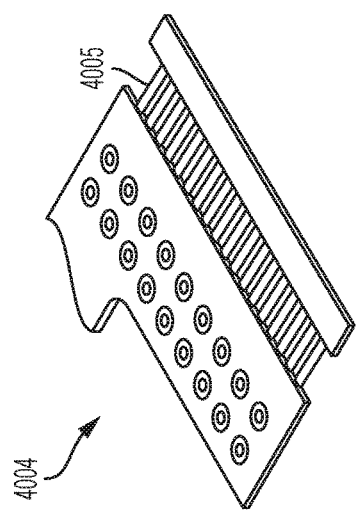
Figure 154:
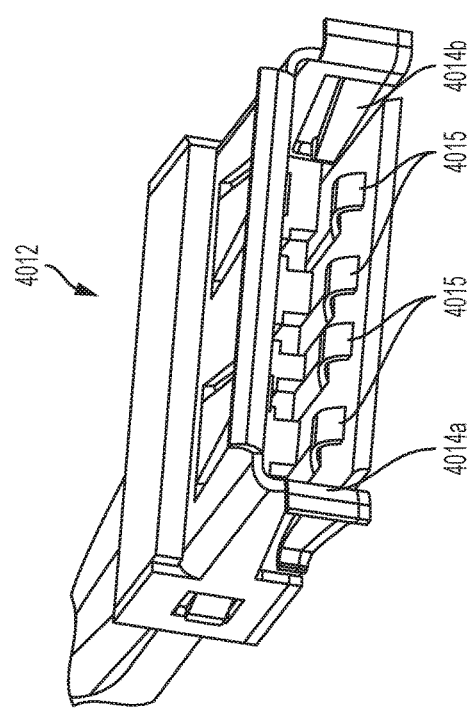
Figure 155:
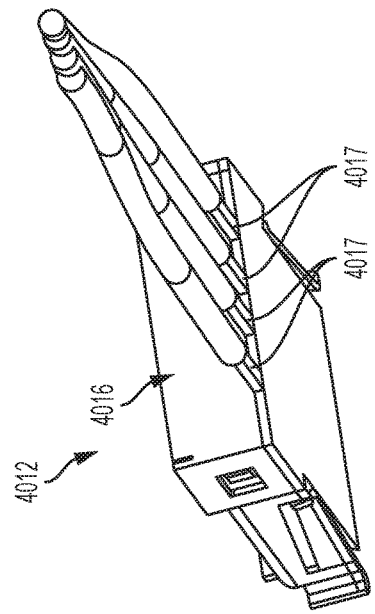
Figure 153:
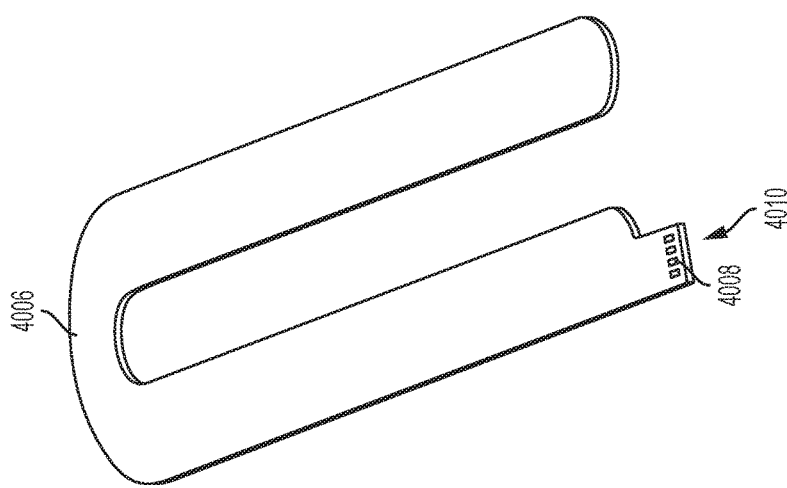

FIGS. 151-157 illustrate various attachment techniques to connect and disconnect flexible circuits to wiring on reusable instrument connections, according to one aspect of the present disclosure, where:

FIG. 151 illustrates a flexible circuit termination comprising supported fingers, according to one aspect of the present disclosure;

FIG. 152 illustrates a flexible circuit termination comprising unsupported fingers, according to one aspect of the present disclosure;

FIG. 153 illustrates an example flexible circuit electrode with four supported fingers exposed on the proximal end, according to one aspect of the present disclosure;

FIG. 154 is the frontside of a female electrical connector configures to receive a flexible circuit electrode, according to one aspect of the present disclosure;

FIG. 155 illustrates the backside of the electrical connector shown in FIG. 154, according to one aspect of the present disclosure;

FIG. 156 is an internal section view of biased contacts connected to supported finger shown in FIG. 153, according to one aspect of the present disclosure; and FIG. 157 is a full flexible circuit electrode assembly comprising a flexible circuit electrode connected to a connector, according to one aspect of the present disclosure.

FIGS. 158-164 illustrate flexible circuit electrode attachment features for connection and mechanical attachment, according to one aspect of the present disclosure to processing circuits and energy sources, where:

FIG. 158 is a perspective view of a flexible circuit electrode with attachment/alignment features provided on a surface thereon, according to one aspect of the present disclosure;

FIG. 159 is a section elevation view of a lower jaw member with the flexible circuit electrode shown in FIG. 158 with attachment/alignment features shown in FIG. 158 prior to being disposed thereon, according to aspect of the present disclosure;

FIG. 160 is a section view of the lower jaw member shown in FIG. 159 with the flexible circuit electrode with attachment/alignment features shown in FIG. 159 prior to being disposed thereon, according to aspect of the present disclosure;

FIG. 161 is a partial perspective view of the flexible circuit electrode shown in FIG. 158 disposed on an insulative flexible substrate with a solder point for connecting an attachment/alignment feature shown in FIG. 158 to the flexible circuit electrode, according to one aspect of the present disclosure;

FIG. 162 is an exploded view of the flexible circuit electrode show in FIG. 158 with multiple attachment/alignment features shown removed from the flexible circuit electrode, according to aspect of the present disclosure;

FIG. 163 is an exploded view of lower a flexible circuit electrode with a single attachment/alignment feature shown removed from the flexible circuit electrode, according to aspect of the present disclosure; and FIG. 164 is a perspective view of a flexible circuit electrode comprising an attachment feature for a wire/cable connector, according to one aspect of the present disclosure.

Figure 172:
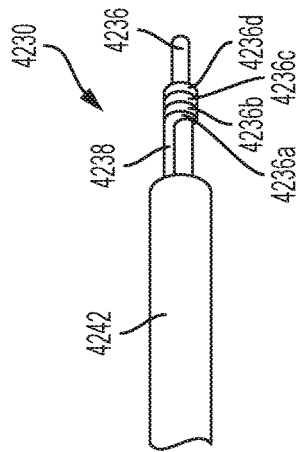
Figure 173:
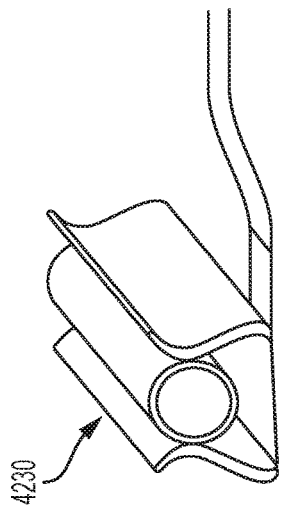
Figure 170:
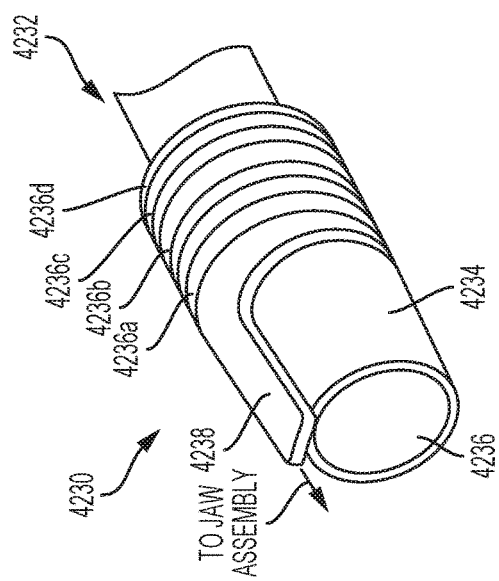
Figure 171:
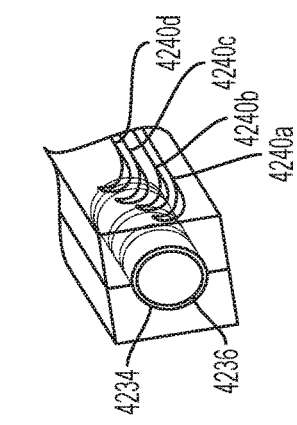

FIGS. 165-173 illustrate a flexible circuit electrode including alternate contacts for routing and wiring multiple electrode paths to monopolar or bipolar instruments for spot coagulation, according to one aspect of the present disclosure, where:

FIG. 165 is a perspective view of an end effector comprising an upper and lower jaw member comprising a flexible circuit electrode with a distal monopolar electrode and lateral bipolar electrodes, according to one aspect of the present disclosure;

FIG. 166 is a plan view of the flexible circuit electrode shown in FIG. 165, according to one aspect of the present disclosure;

FIG. 167 is a detail section view of the proximal end of the flexible circuit electrode shown in FIG. 166 showing the electrically conductive traces for the distal monopolar electrode and the lateral bipolar electrodes, according to one aspect of the present disclosure;

FIG. 168 is a perspective view of a lower jaw member of a jaw assembly comprising a fold over flexible circuit electrode, according to one aspect of the present disclosure;

FIG. 169 is a detail view of the fold over flexible circuit electrode shown in FIG. 166, according to one aspect of the present disclosure;

FIG. 170 is a perspective view of a rotating contact assembly disposed about the outer surface of an inner tube of a shaft component of the electrosurgical instrument, according to one aspect of the present disclosure;

FIG. 171 is a detail section view of electrical contact wipers electrically and rotatably coupled to the plurality of rotating contacts of the rotating contact assembly disposed about the outer surface of the inner tube, according to one aspect of the present disclosure;

FIG. 172 is a perspective view of the rotating contact assembly, according to one aspect of the present disclosure; and FIG. 173 is a perspective view of the rotating contact assembly comprising an outer tube, an inner tube, and a plurality of rotating contacts formed on a flexible circuit electrode and disposed about the inner tube, according to one aspect of the present disclosure.

FIGS. 174-176 illustrate flexible circuit comprising a snap in electrode assembly and grasping/gap setting elements at a distal end, the elements having various geometries to aid in grasping and setting the gap between the upper jaw and the lower jaw members of a clamp jaw assembly, and a connecting scheme to couple the snap in electrode assembly to the clamp jaw assembly, according to one aspect of the present disclosure, where:

FIG. 174 is a perspective view of a flexible circuit comprising a snap in electrode assembly at a distal end and an edge connector that contains an identification card at a proximal end, according to one aspect of the present disclosure;

FIG. 174A is a detail view of two types of elements, according to various aspects of the present disclosure;

FIG. 175 is a section view of the proximal end of the flexible circuit taken along section line 175-175, as shown in FIG. 174, showing a T-slot configuration for alignment of the flexible circuit with the shaft; and FIG. 176 is an elevation view of a clamp jaw assembly showing the female end of an edge connector and snap fit feature for electrically and mechanically coupling the connector portion of the flexible circuit electrode in to the clamp jaw assembly as shown in FIG. 174 to a control circuit and/or a generator, according to one aspect of the present disclosure.

Figure 178:
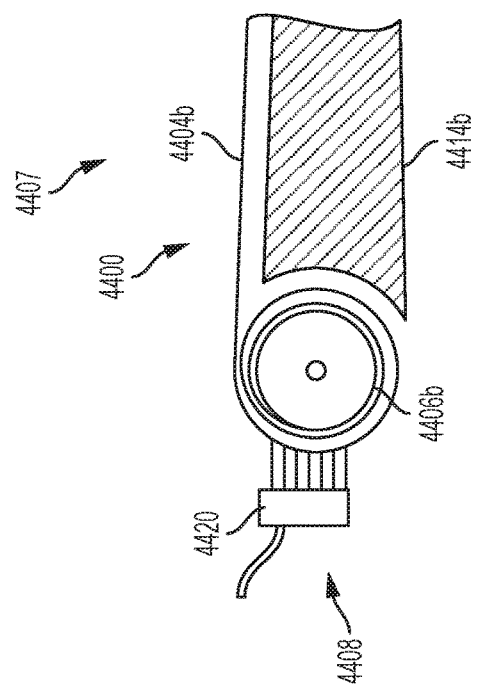
Figure 177:
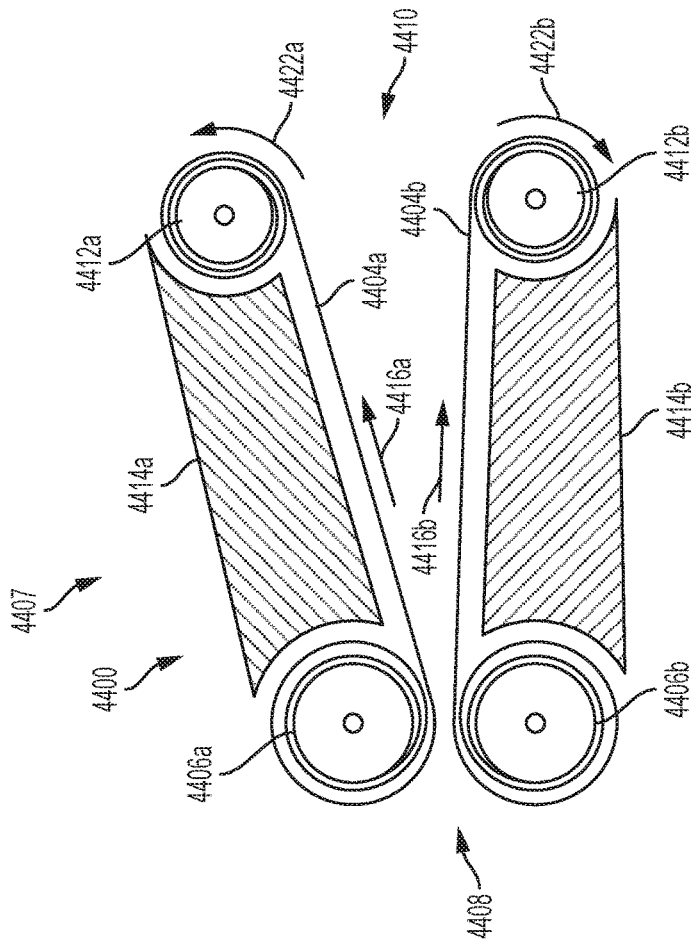

FIGS. 177-178 illustrate an automatic electrode renewal system for flexible circuit electrodes, such as spools of flexible circuit electrodes, according to one aspect of the present disclosure, where:

FIG. 177 is an elevation view of a clamp jaw assembly comprising an upper jaw element and a lower jaw element and a renewable flexible circuit electrode system for unwinding and advancing clean flexible circuit electrodes from a proximal end pair of upper and lower rollers and winding used flexible circuit electrodes about a distal end pair of upper and lower spools in a distal direction, according to aspect of the present disclosure; and FIG. 178 is an elevation view of the automatic electrode renewal system shown in FIG. 177 comprising an electrical brush contact to electrically couple to a flexible circuit electrode disposed about the lower roller at the proximal end, according to one aspect of the present disclosure.

Figure 179:
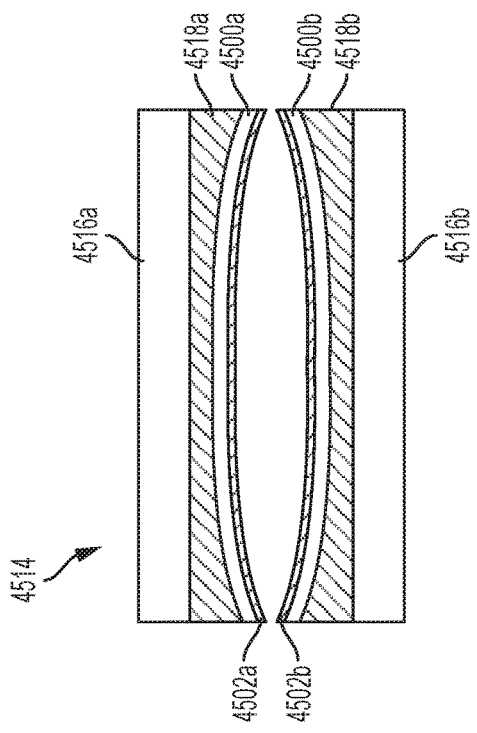
Figure 180:
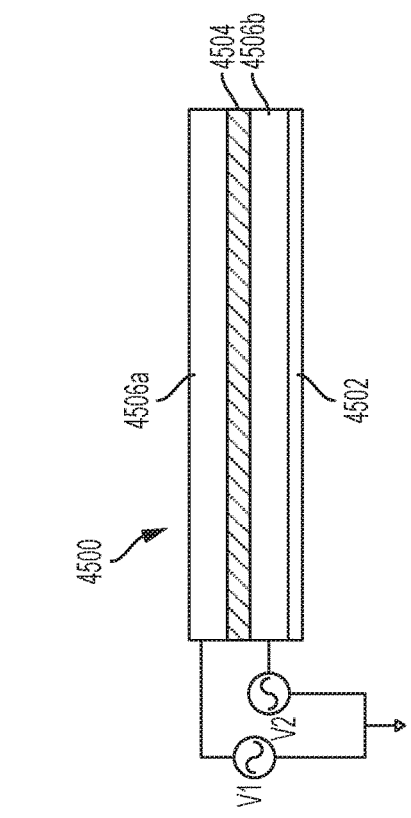
Figure 181:
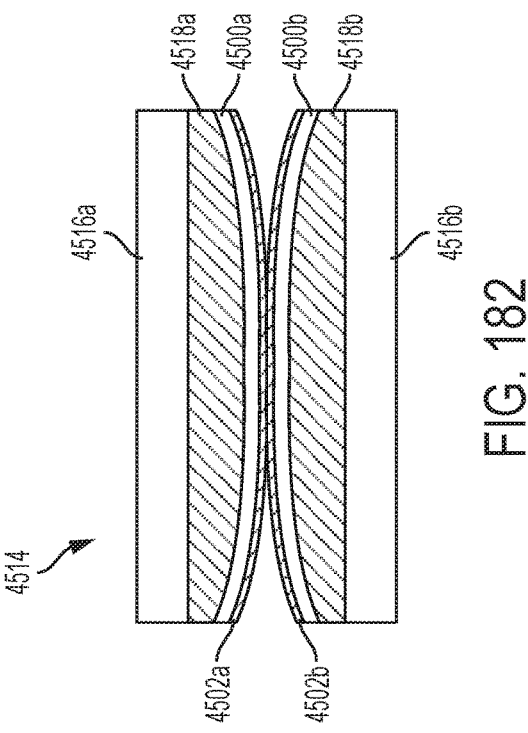
Figure 182:
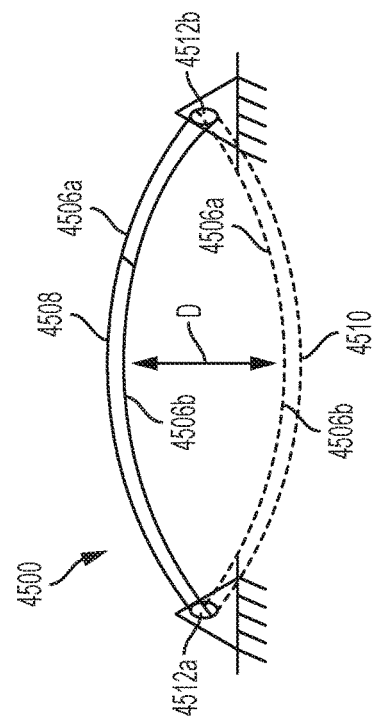
Figure 184:
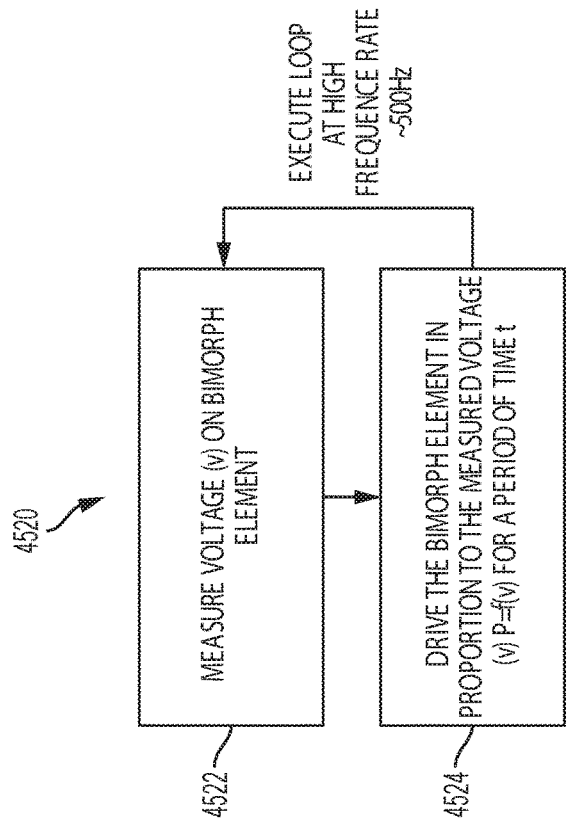
Figure 183:
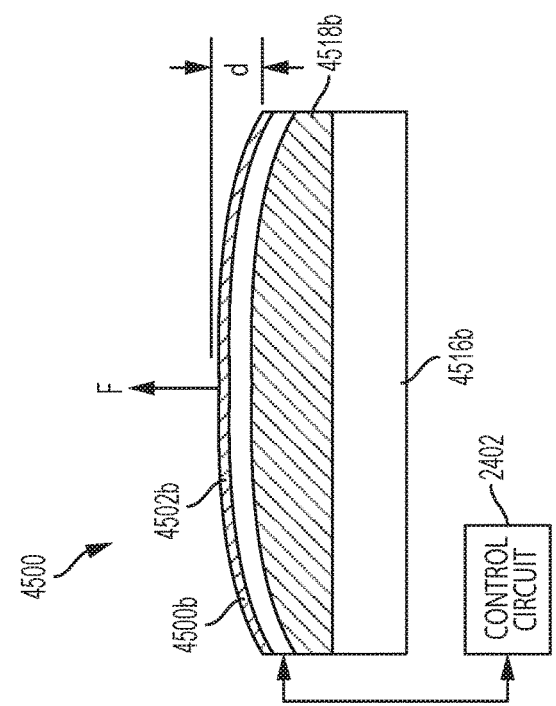

FIGS. 179-184 illustrate a flexible circuit comprising an electrode and a vibratory element to mitigate tissue sticking to the clamp jaw members, according to one aspect of the present disclosure, where:

FIG. 179 is a section view of a piezoelectric bimorph transducer attached to a flexible circuit electrode, according to one aspect of the present disclosure;

FIG. 180 is a schematic illustration of the displacement of the piezoelectric bimorph transducer shown in FIG. 179, where a first mode of deflection is shown in solid line and a second mode of deflection is shown in dashed line, according to one aspect of the present disclosure;

FIG. 181 is a section view of a clamp jaw assembly comprising upper and lower bimorph transducers located in respective upper and lower jaw members, according to one aspect of the present disclosure;

FIG. 182 is a section view of the clamp jaw assembly shown in FIG. 181, where the bimorph transducers located in the respective upper and lower jaw members are in the second mode of maximum deflection (FIG. 180), according to one aspect of the present disclosure;

FIG. 183 is a section view of the lower bimorph transducer located on a lower jaw member of the clamp jaw assembly configured in sensor mode to measure the adhesion force "F" of tissue sticking to the lower jaw member, according to one aspect of the present disclosure; and FIG. 184 is a logic flow diagram of a technique for operating a bimorph transducer by switching between a force measuring bimorph sensor to a driving bimorph transducer resulting in vibrations proportional to the adhesion force, according to one aspect of the present disclosure.

Figure 187:
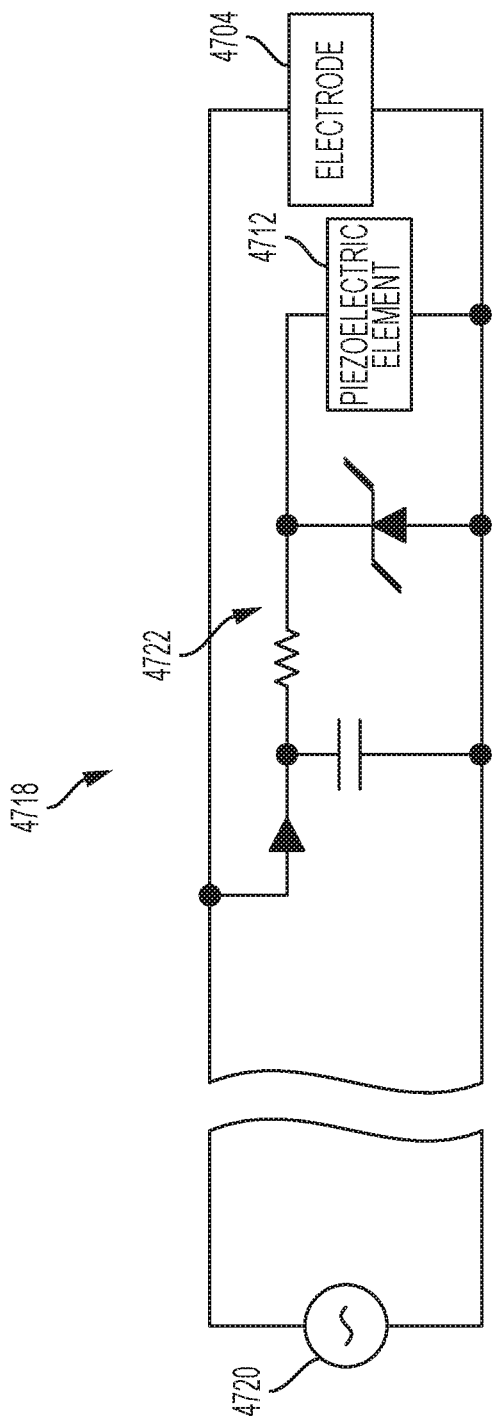

FIGS. 185-186 illustrate a jaw member comprising a flexible circuit electrode assembly comprising a vibratory element configured to vibrate to reduce tissue adhesion on an electrode or remove tissue adhered to the electrode, according to one aspect of the present disclosure, where:

FIG. 185 is a plan view of a vibrating jaw member comprising a flexible circuit electrode assembly configured to vibrate to reduce tissue adhesion to the electrode or remove tissue adhered to the electrode, according to one aspect of the present disclosure; and FIG. 186 is a section view of the vibrating jaw comprising a flexible circuit electrode shown in FIG. 186 taken along section 186-186, according to one aspect of the present disclosure;

FIG. 187 is a schematic diagram of a circuit configured to activate the flexible circuit electrode assembly (FIGS. 185-186) and the piezoelectric element (FIG. 186) simultaneously, according to one aspect of the present disclosure.

Figure 189:
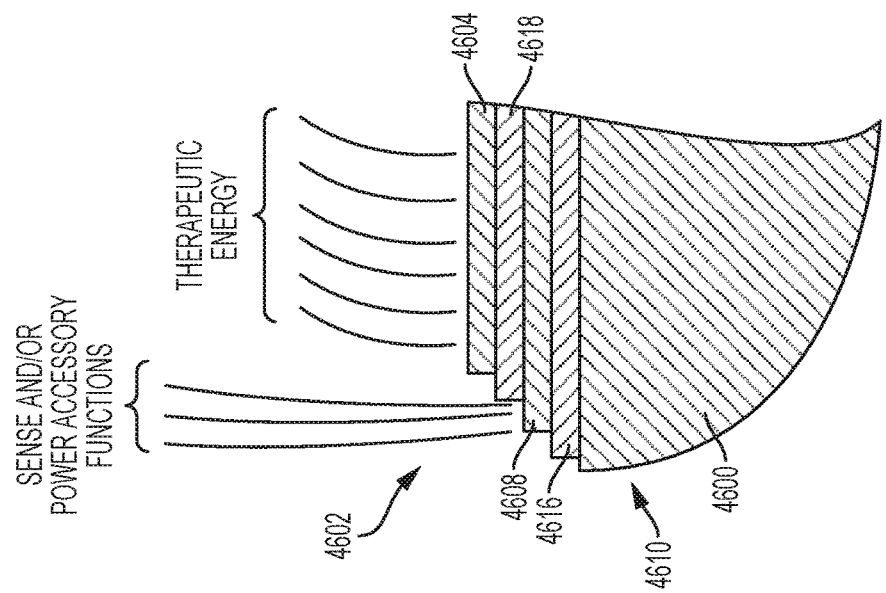
Figure 188:
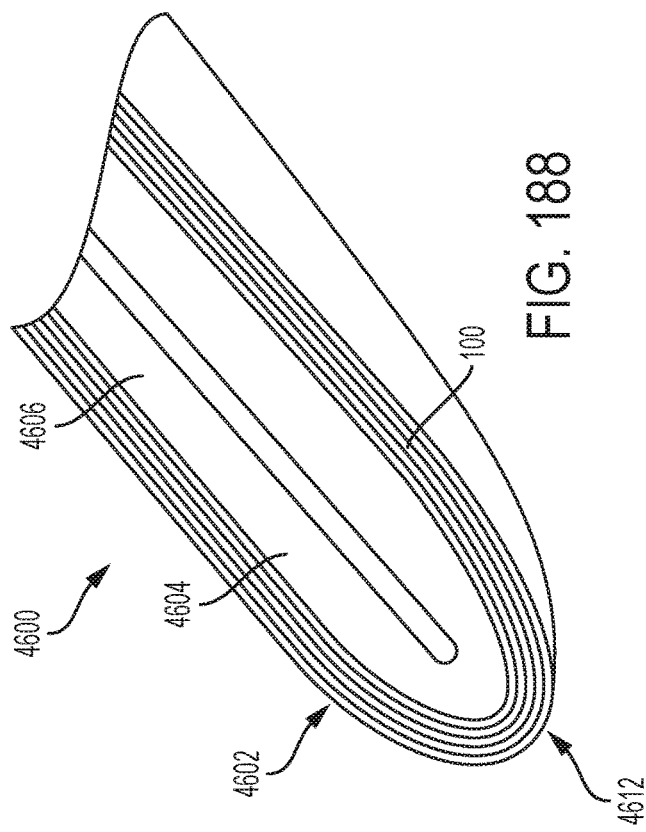

FIGS. 188-189 illustrate a jaw member 4600 of clamp jaw assembly comprising a flexible circuit 4602 comprising an inner electrode 4604 for applying therapy to tissue and an outer electrode 4608 for sensing, powering accessory functions, and proximity detection among other functions, according to one aspect of the present disclosure, where:

FIG. 188 is a perspective view of a jaw member comprising a flexible circuit comprising an inner electrode and an outer electrode, according to one aspect of the present disclosure; and FIG. 189 is a detail view of the jaw member shown in FIG. 188, according to one aspect of the present disclosure.

Figure 190:
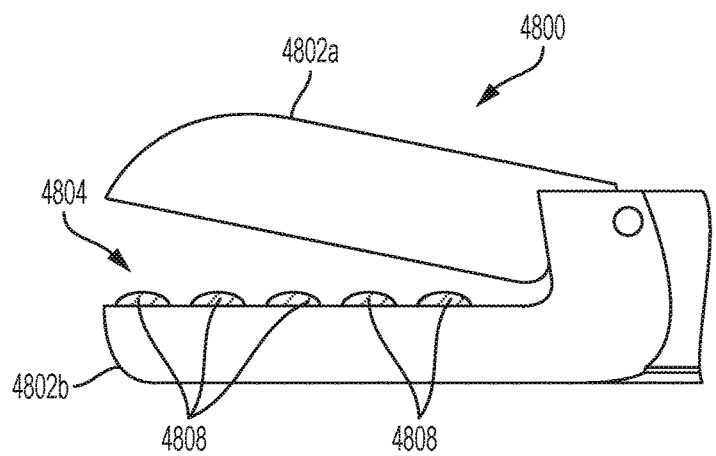
Figure 191:
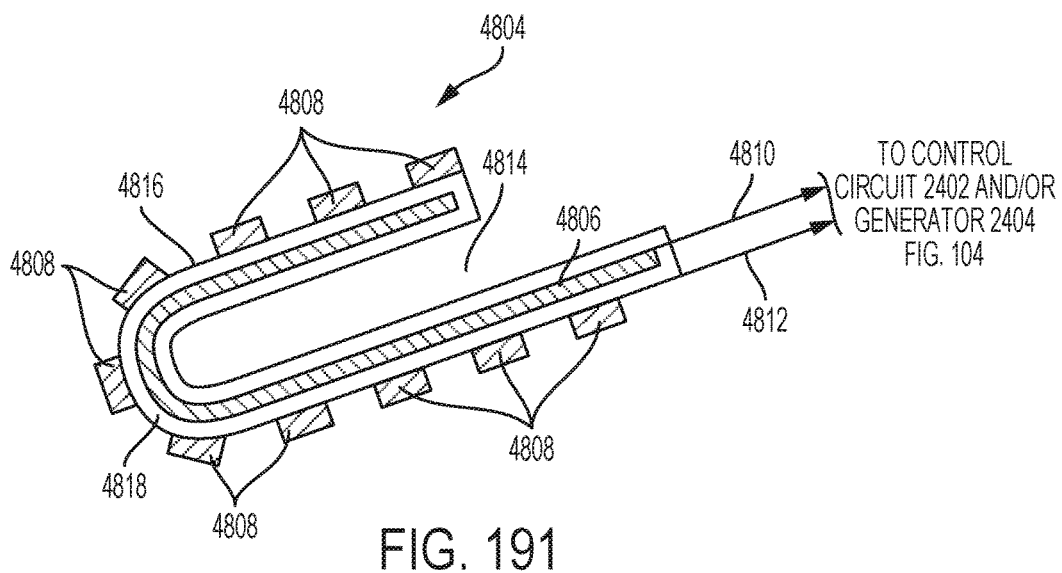
Figure 192:
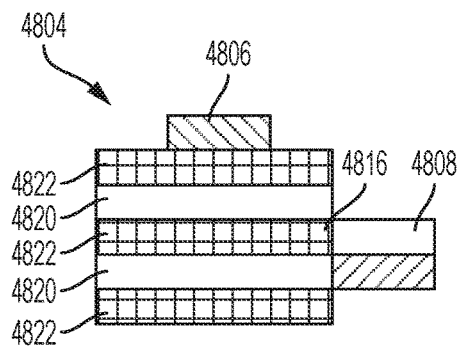

FIGS. 190-192 illustrate a flexible circuit electrode assembly comprising electrodes for tissue treatment and LEDs for illuminating tissue, according to one aspect of the present disclosure, where:

FIG. 190 is an elevation view of a clamp jaw assembly comprising an upper jaw member and a lower jaw member comprising a flexible circuit electrode assembly in the lower jaw member, according to one aspect of the present disclosure;

FIG. 191 is a plan view of the flexible circuit electrode assembly comprising the electrode and the plurality of LEDs positioned around the periphery of the lower jaw member, according to one aspect of the present disclosure; and FIG. 192 is a section view of the flexible circuit electrode assembly taken along section line 192-192 as shown in FIG. 191, according to one aspect of the present disclosure.

Figure 194:
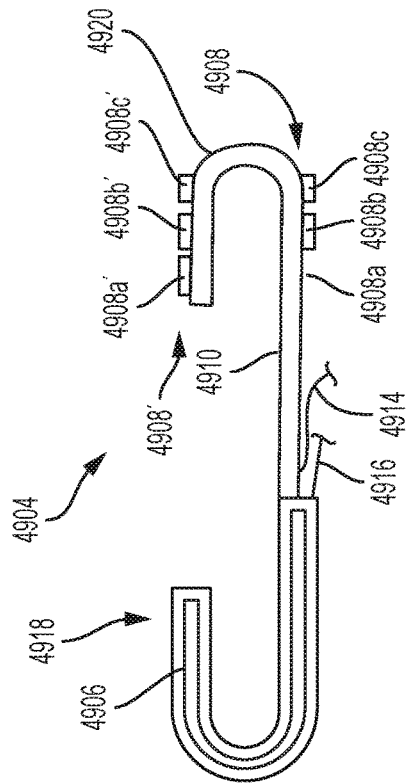
Figure 193:
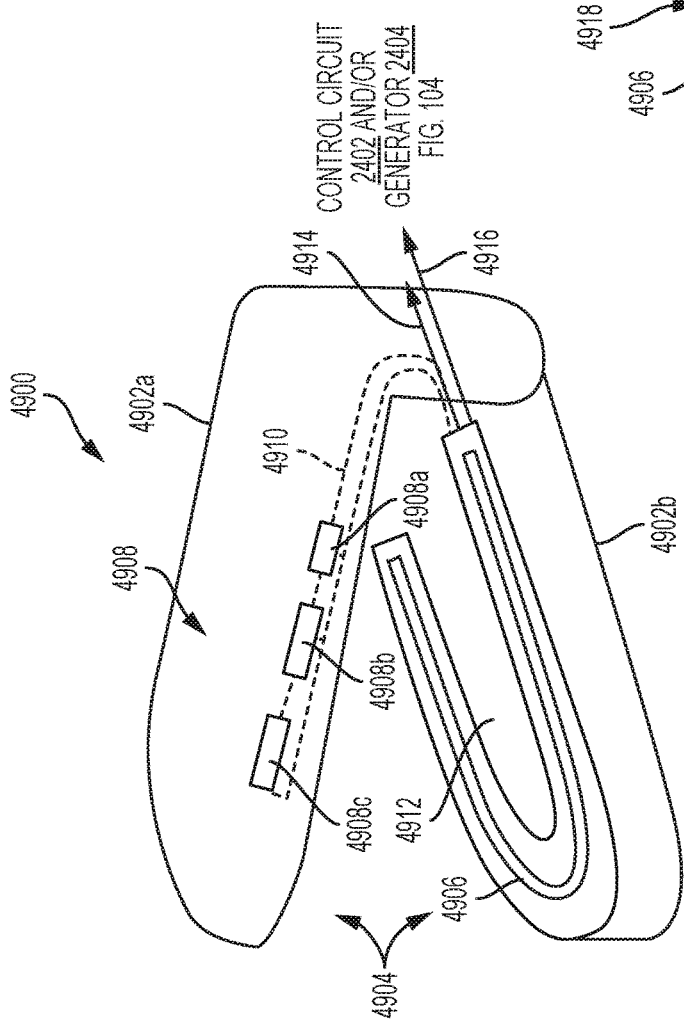

FIGS. 193-194 illustrate a flexible circuit electrode assembly comprising an electrode and an LED for signaling status, according to one aspect of the present disclosure, where:

FIG. 193 is a perspective view of a clamp jaw assembly comprising an upper jaw member and a lower jaw member and a flexible circuit electrode assembly, according to one aspect of the present disclosure; and FIG. 194 is a plan view of the flexible circuit electrode assembly 4904 shown in FIG. 193, according to one aspect of the present disclosure.

Figure 196:
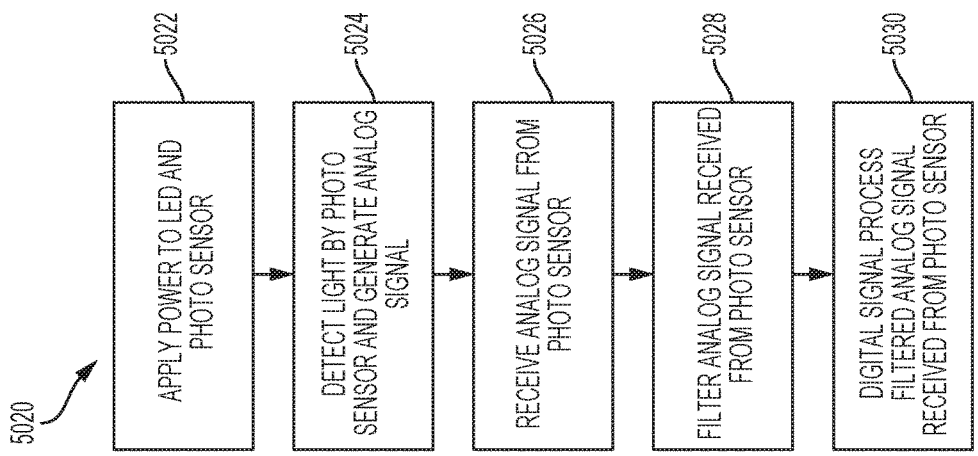
Figure 195:
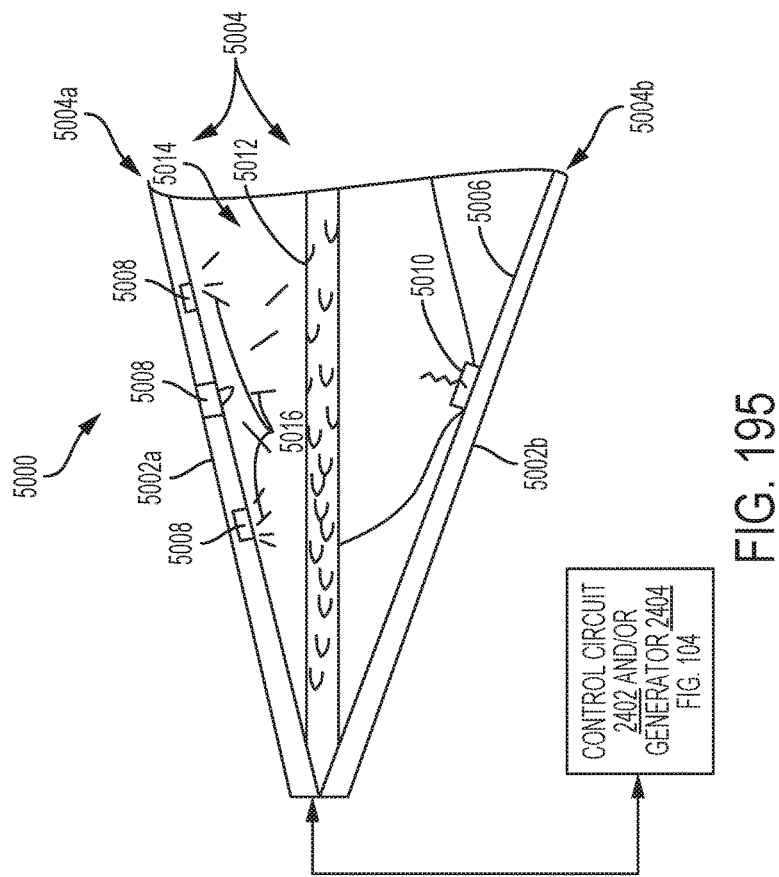

FIGS. 195-196 illustrate a flexible circuit electrode assembly comprising an optical sensing system comprising at least one light emitting diode (LED) and photo sensor to provide an indication of tissue status and visualization of the surgical site, according to one aspect, where:

FIG. 195 is an elevation view of a clamp jaw assembly comprising an upper jaw member and a lower jaw member and a flexible circuit electrode assembly, according to one aspect of the present disclosure; and FIG. 196 is a logic diagram of operating the optical sensing system described in connection with FIG. 195, according to one aspect of the present disclosure.

Figure 197:
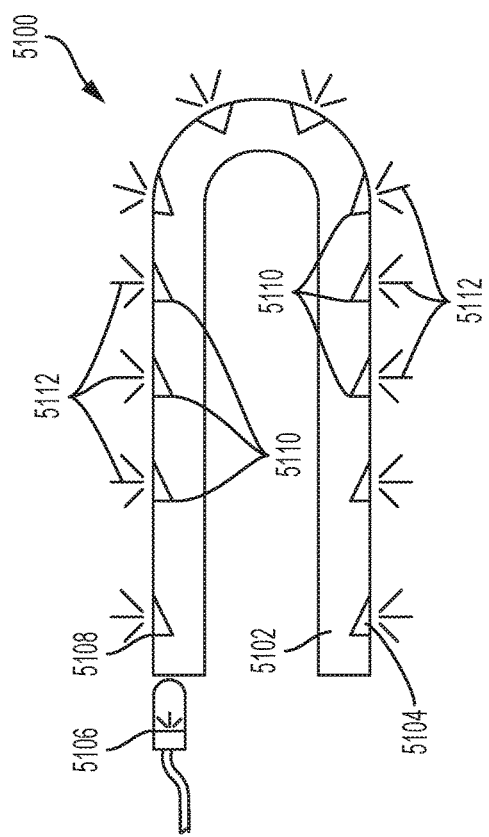

FIG. 197 illustrates a flexible circuit electrode assembly comprising an electrode and a light pipe, according to one aspect of the present disclosure.

Figure 198:
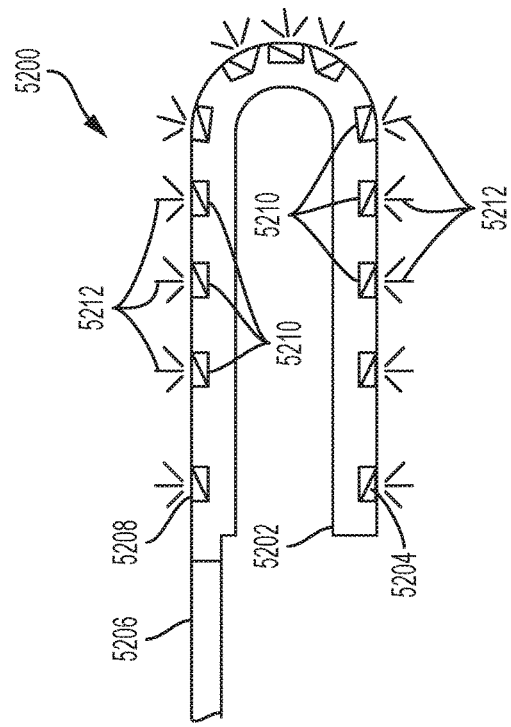

FIG. 198 illustrates a flexible circuit electrode assembly comprising an electrode and a light pipe, according to one aspect of the present disclosure.

Figure 199:
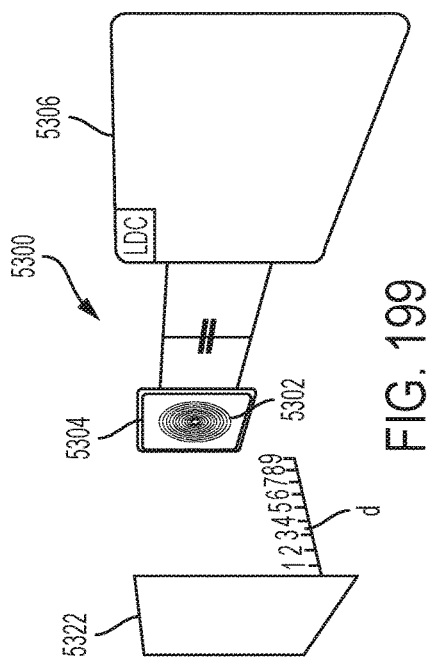
Figure 200:
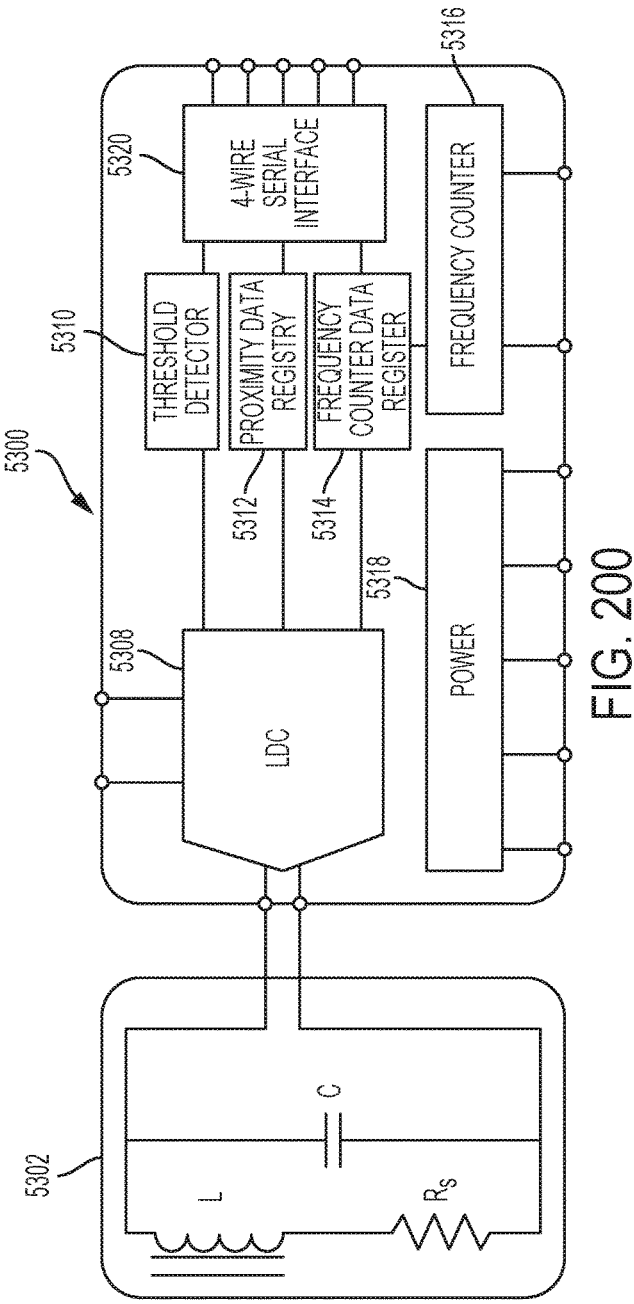
Figure 201:
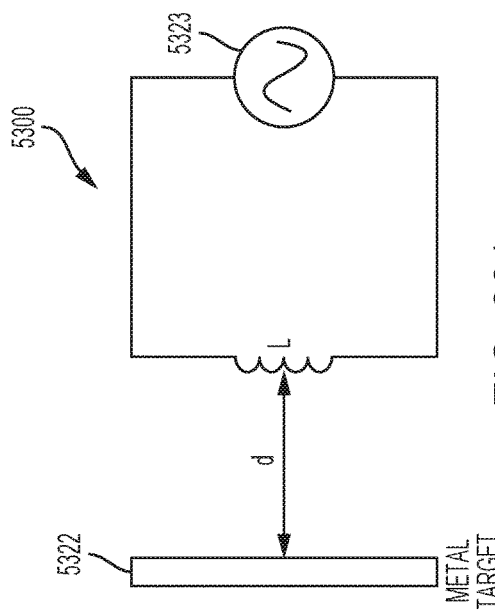
Figure 202:
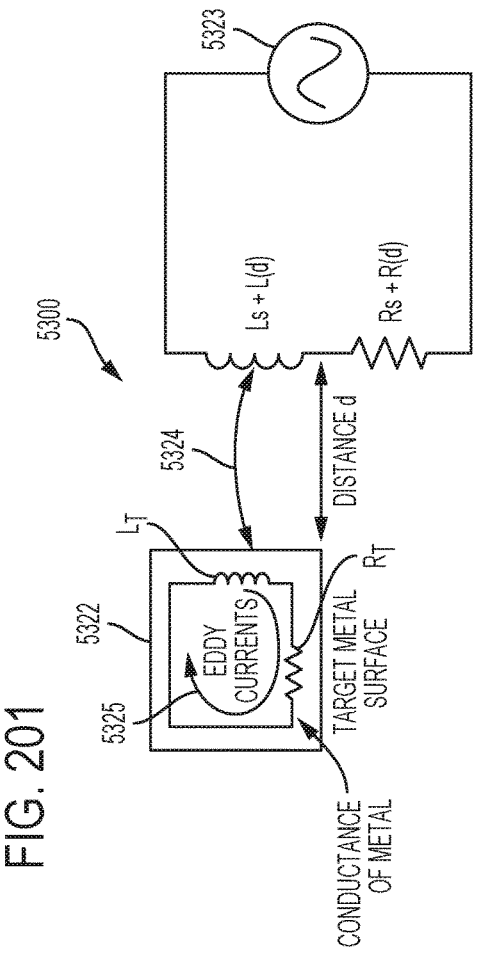
Figure 204:
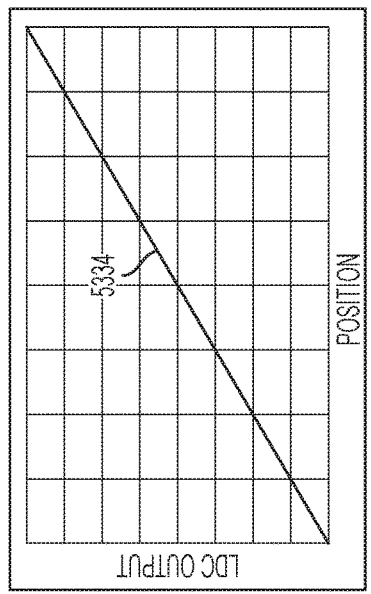
Figure 206:
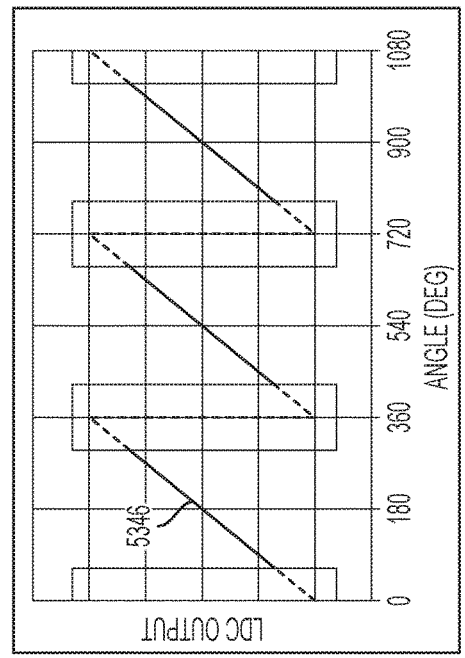
Figure 203:
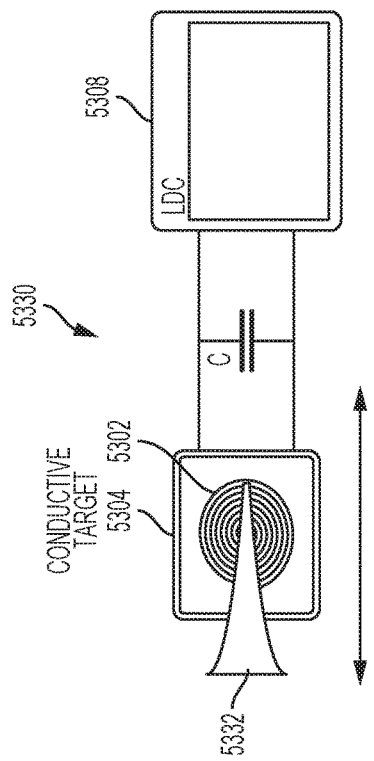
Figure 205:
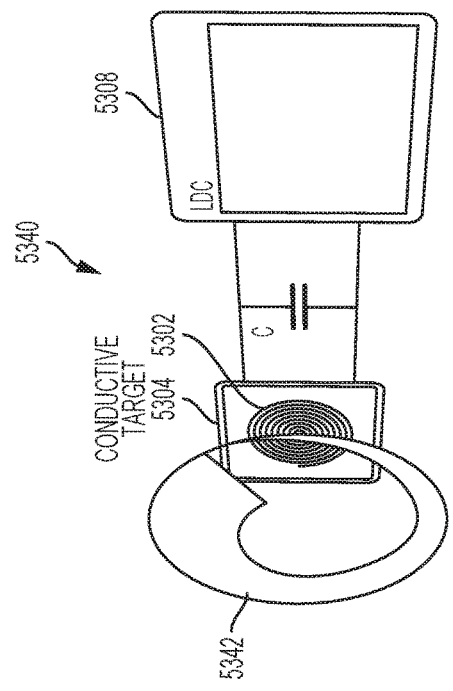
Figure 207:
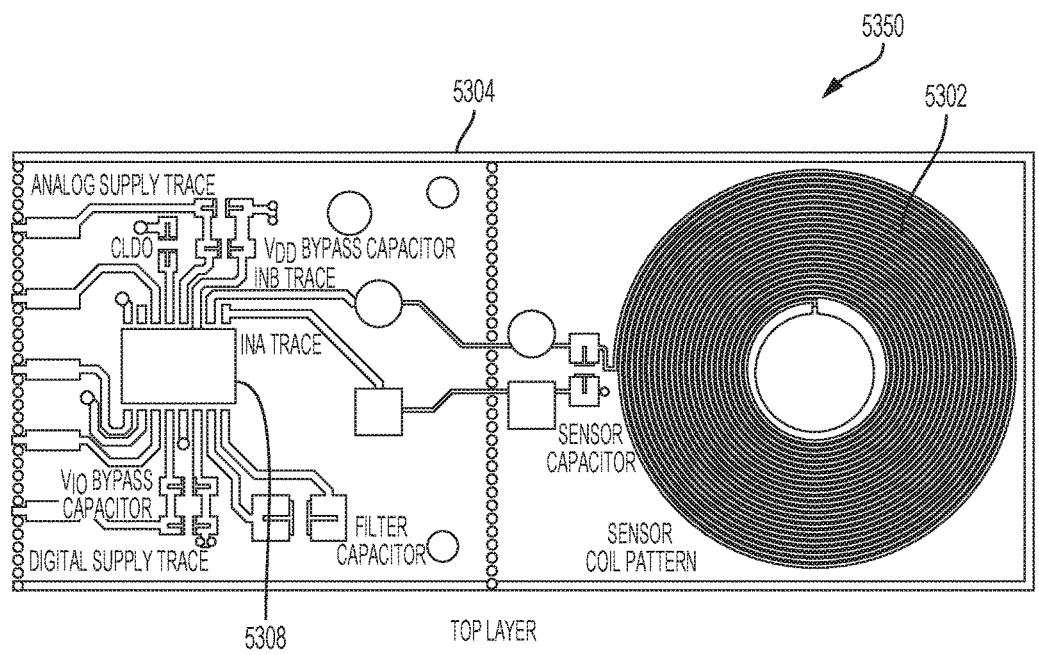
Figure 208:
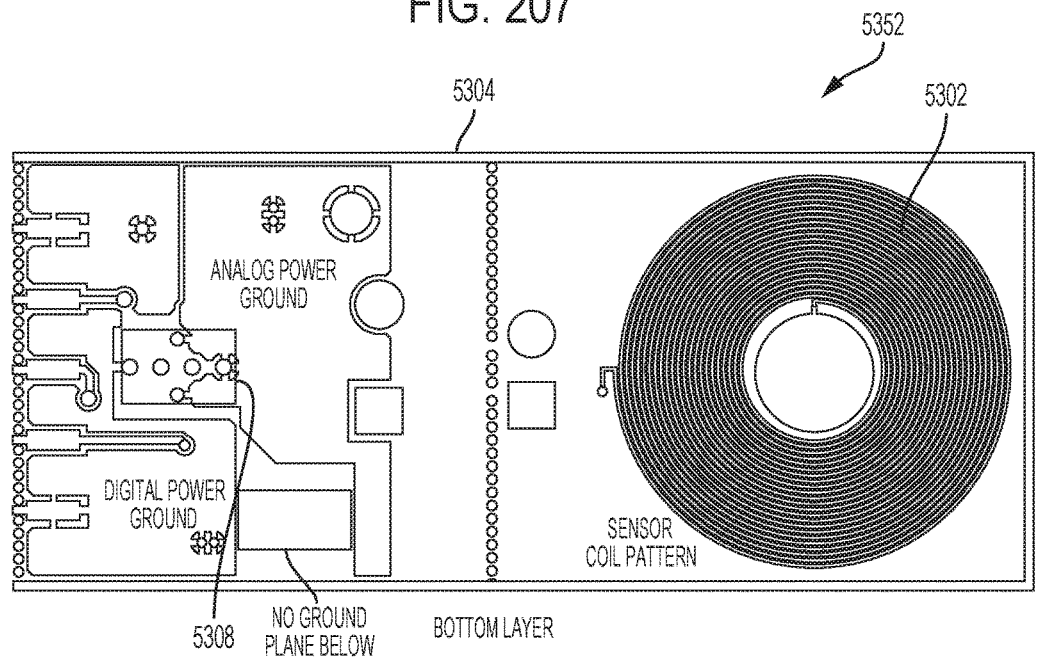

FIGS. 199-208 illustrate a flexible circuit inductive sensor inductance-to-digital converter circuit and operation thereof, according to one aspect of the present disclosure, where:

FIG. 199 illustrate a proximity sensor system comprising an inductive element formed on a flexible circuit, according to one aspect;

FIG. 200 is a functional block diagram of the proximity sensor system, according to one aspect;

FIG. 201 is a simplified circuit model of the proximity sensor system and a proximal metal target, according to one aspect of the present disclosure;

FIG. 202 is a simplified circuit model of a metal target modeled as L and R with circulating eddy currents, according to one aspect of the present disclosure;

FIG. 203 is a schematic diagram of a linear position sensing system comprising a flexible circuit inductive element and an inductance-to-digital converter circuit, according to one aspect of the present disclosure;

FIG. 204 is a graphical representation of the linear position sensing system shown in FIG. 203, according to one aspect of the present disclosure;

FIG. 205 is a schematic diagram of an angular position sensing system comprising a flexible circuit inductive element, according to one aspect of the present disclosure;

FIG. 206 is a graphical representation of the angular position sensing system shown in FIG. 203, according to one aspect of the present disclosure;

FIG. 207 is an upper layer layout of the flexible circuit inductive element and inductance-to-digital converter circuit; and FIG. 208 is a lower layer layout of the flexible circuit inductive element and inductance-to-digital converter circuit.

Figure 210:
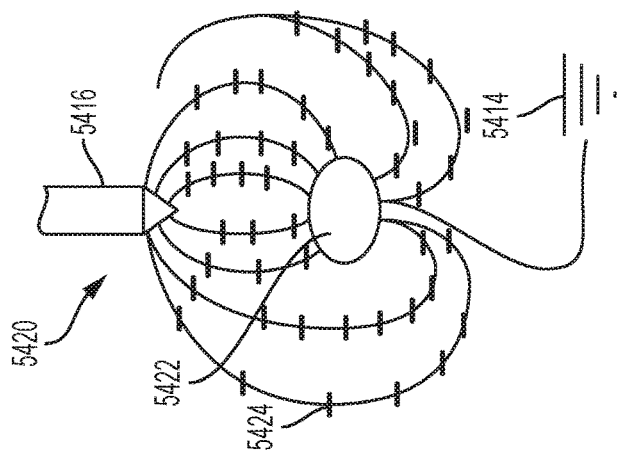
Figure 209:
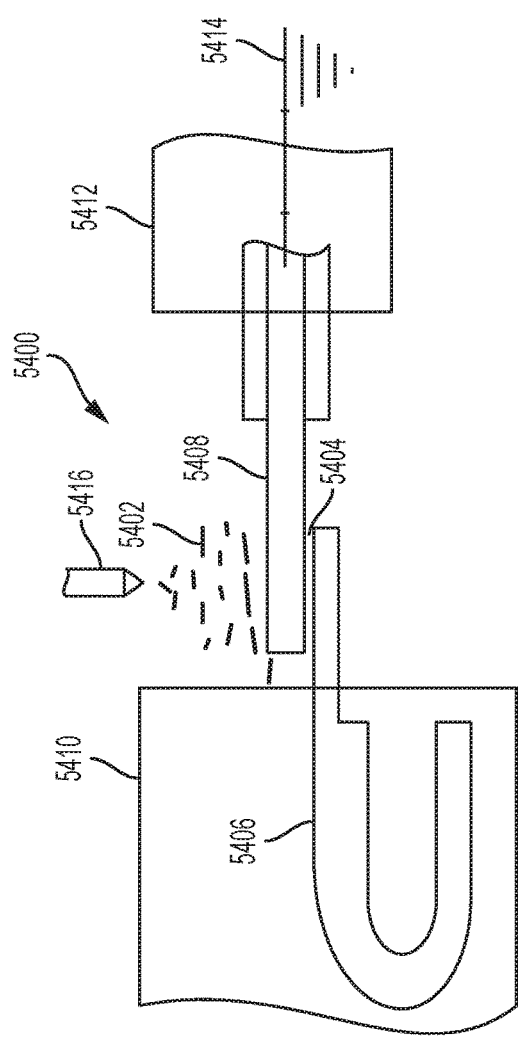

FIGS. 209-210 illustrate examples of flexible circuit electrodes coated with ultraviolet (U.V.) cured paint insulation systems, according to one aspect of the present disclosure, where:

FIG. 209 illustrates an electrical connection or joint of a flexible circuit electrode assembly in the process of being coated by electro spraying a dielectric material thereon, according to one aspect of the present disclosure.

FIG. 210 is an electrical schematic diagram of the electrospray process, according to one aspect of the present disclosure.

Figure 211:
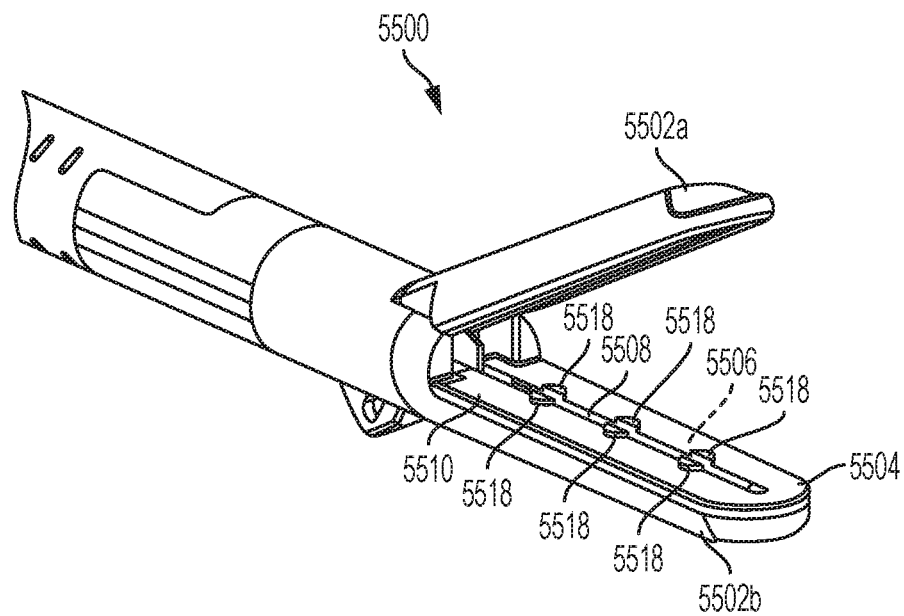
Figure 212:
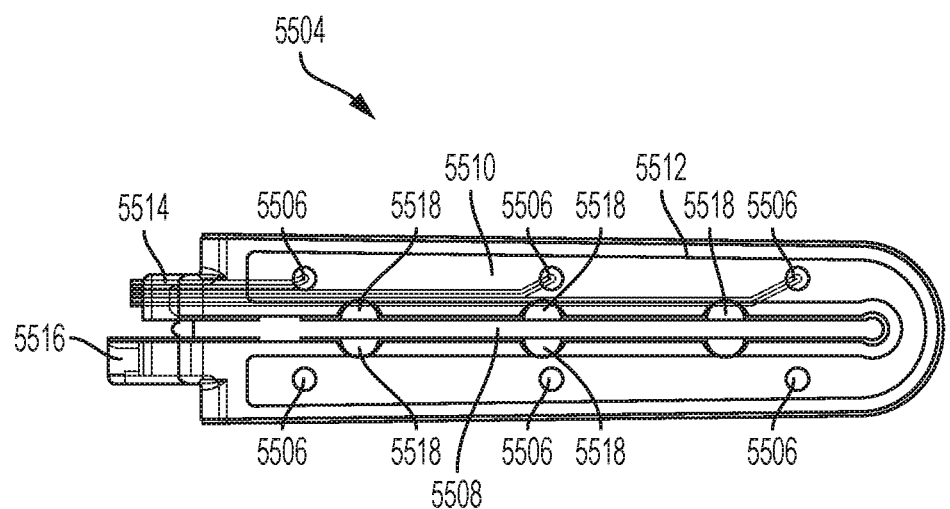
Figure 213:
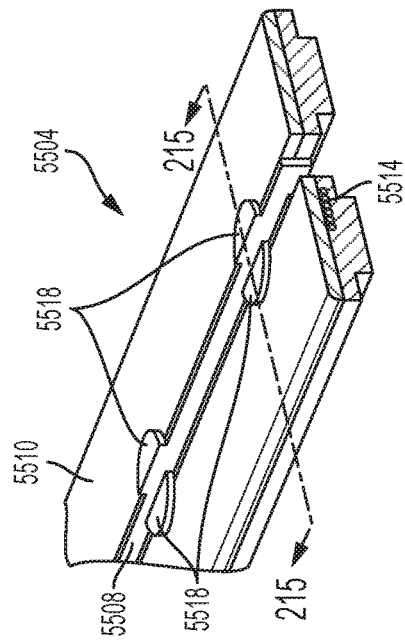
Figure 214:
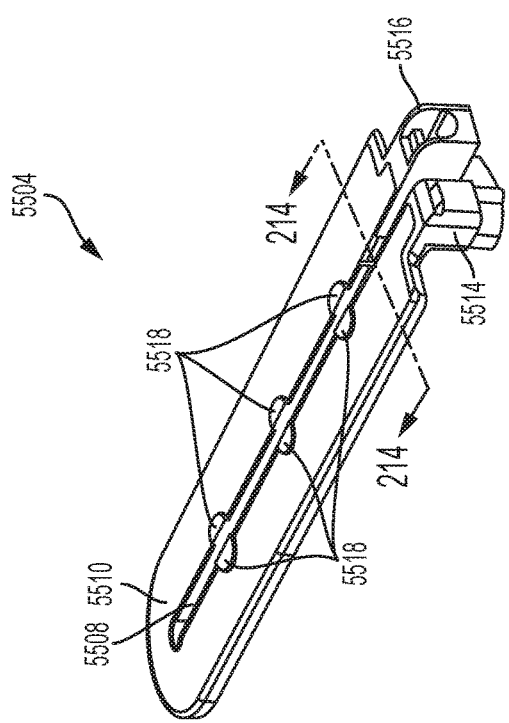
Figure 215:
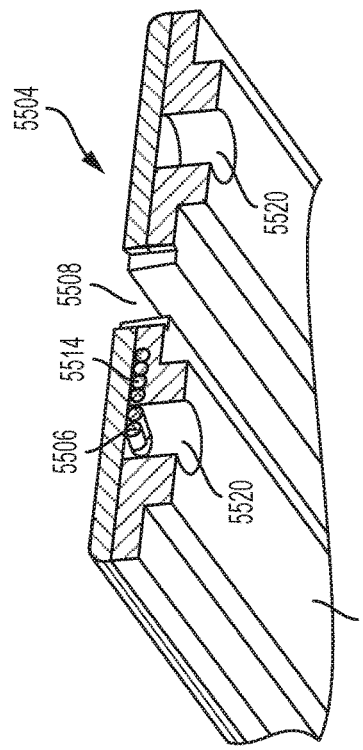

FIGS. 211-215 illustrate temperature sensor overmolded with a flexible circuit electrode assembly located in a jaw member to provide a biocompatible clamp jaw assembly, according to one aspect of the present disclosure, where:

FIG. 211 is a perspective view of a clamp jaw assembly configured for an electrosurgical instrument tissue sealer comprising an embedded temperature sensor 5506, according to one aspect of the present disclosure;

FIG. 212 is a plan view of the flexible circuit electrode assembly comprising an embedded temperature sensor overmolded therewith, according to pone aspect of the present disclosure;

FIG. 213 is a perspective view from the proximal end of the flexible circuit electrode assembly with a temperature sensor overmolded therewith, according to one aspect of the present disclosure;

FIG. 214 is a section view of the flexible circuit electrode assembly with a temperature sensor overmolded therewith taken along section line 214-214 as shown in FIG. 213, according to one aspect of the present disclosure; and FIG. 215 is a section view of the flexible circuit electrode assembly with a temperature sensor overmolded therewith taken along section line 215-215 as shown in FIG. 213, according to one aspect of the present disclosure.

Figure 219:
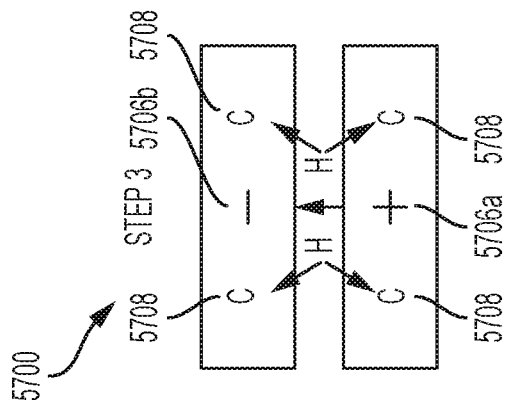
Figure 218:
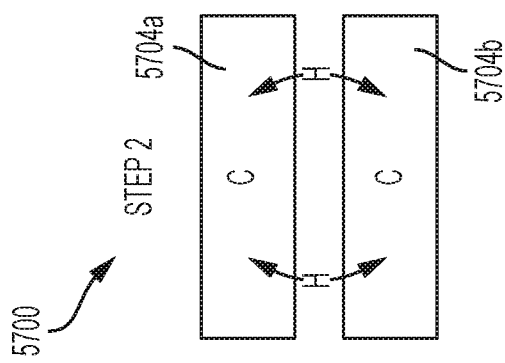
Figure 217:
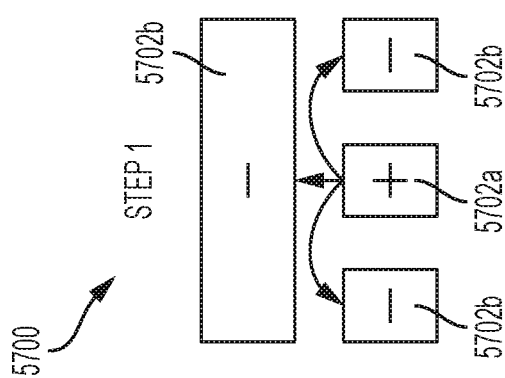

FIG. 216 illustrates a flexible circuit electrode assembly comprising dual electrode heater elements, according to one aspect of the present disclosure FIGS. 217-219 illustrate flexible circuit electrode assemblies comprising electric knife and cooling cells, such as superconducting heat and/or MEMS cooling cells, according to one aspect of the present disclosure, where:

FIGS. 217-219 illustrate a process of sealing, cooling, and cutting tissue while cooling, according to one aspect of the present disclosure.

FIG. 217 is a section view of a clamp jaw assembly in the process of performing a first step of sealing tissue disposed in the clamp jaw assembly, according to one aspect of the present disclosure;

FIG. 218 is a section view of the clamp jaw assembly shown in FIG. 217 in the process of performing a second step of cooling the tissue disposed in the clamp jaw assembly, according to one aspect of the present disclosure; and FIG. 219 is a section view of the clamp jaw assembly 5700 shown in FIG. 217 in the process of performing a third step of cooling and cutting the tissue disposed in the clamp jaw assembly, according to one aspect of the present disclosure.

DETAILED DESCRIPTION

In the following detailed description, reference is made to the accompanying drawings, which form a part hereof. In the drawings, similar symbols and reference characters typically identify similar components throughout the several views, unless context dictates otherwise. The illustrative aspects described in the detailed description, drawings, and claims are not meant to be limiting. Other aspects may be utilized, and other changes may be made, without departing from the scope of the subject matter presented here.

The following description of certain examples of the technology should not be used to limit its scope. Other examples, features, aspects, aspects, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, aspects, examples, etc. described herein may be combined with any one or more of the other teachings, expressions, aspects, examples, etc. that are described herein. The following-described teachings, expressions, aspects, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Also, in the following description, it is to be understood that terms such as front, back, inside, outside, upper, lower and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings. Throughout this disclosure, the term "proximal" is used to describe the side of a component, e.g., a shaft, a handle assembly, etc., closer to a user operating the surgical instrument, e.g., a surgeon, and the term "distal" is used to describe the side of the component further from the user operating the surgical instrument.

Aspects of the present disclosure are presented for a single surgical instrument configured for grasping tissue, performing sealing procedures using electrical or ultrasonic energy. An end effector of the surgical instrument may include multiple members arranged in various configurations to collectively perform the aforementioned functions. As used herein, an end effector may be referred to as a jaw assembly or clamp jaw assembly comprising an upper jaw member and a lower jaw member where the upper jaw member is movable relative to the lower jaw member. In some aspects one or both jaw members are movable relative to each other.

In some aspects, an end effector of a surgical instrument includes a pair of jaws for grasping and applying electrical energy to tissue at the surgical site. In some aspects, an end effector of a surgical instrument includes an ultrasonic member. The ultrasonic member may be implemented in various different shapes, such as in a spoon shape, a hook shape, a wedge shape, or in a shape configured to grab or grasp tissue. The ultrasonic member may be configured to deliver ultrasonic energy through being vibrated at an ultrasonic frequency. In some aspects, the ultrasonic member may be retracted into a closure tube to allow for focused use of one or the other members.

In some aspects, any of the mentioned examples also may be configured to articulate along at least one axis through various means, including, for example, a series of joints, one or more hinges or flexure bearings, and one or more cam or pulley systems. Other various features may include cameras or lights coupled to one or more of the members of the end effector, and various energy options for the surgical instrument. The type of energy applied at the surgical site may take various forms and includes, without limitation, monopolar and/or bipolar radio frequency (RF) energy, microwave energy, reversible and/or irreversible electroporation energy, and/or ultrasonic energy, or any combination thereof.

Various features described herein may be incorporated in electrosurgical devices for applying electrical energy to tissue in order to treat and/or destroy the tissue are also finding increasingly widespread applications in surgical procedures. An electrosurgical instrument typically includes a hand piece, an instrument having a distally-mounted end effector (e.g., one or more electrodes). The end effector can be positioned against the tissue such that electrical current is introduced into the tissue. Electrosurgical instrument can be configured for bipolar or monopolar RF energy operation, and/or microwave energy, reversible and/or irreversible electroporation energy, and/or ultrasonic energy, or any combination thereof. During bipolar RF operation, electrical current is introduced into and returned from the tissue by active and return electrodes, respectively, of the end effector. During monopolar RF operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical device also may include a cutting member that is movable relative to the tissue and the electrodes to transect the tissue. Reversible and/or irreversible electroporation energy may be applied through the end effector in a similar manner. In instruments comprising an ultrasonic member, electrical current may be conducted through the ultrasonic member.

Electrical energy applied by an electrosurgical device can be transmitted to the instrument by a generator in communication with the hand piece. Electrical energy applied by an electrosurgical device can be transmitted to the instrument by a generator in communication with the hand piece. The electrical energy may be in the form of RF energy that may be in a frequency range described in EN 60601-2-2:2009+A11:2011, Definition 201.3.218—HIGH FREQUENCY. For example, the frequencies in monopolar RF applications are typically restricted to less than 5 MHz. However, in bipolar RF applications, the frequency can be almost anything. Frequencies above 200 kHz can be typically used for MONOPOLAR applications in order to avoid the unwanted stimulation of nerves and muscles which would result from the use of low frequency current. Lower frequencies may be used for BIPOLAR techniques if the RISK ANALYSIS shows the possibility of neuromuscular stimulation has been mitigated to an acceptable level. Normally, frequencies above 5 MHz are not used in order to minimize the problems associated with HIGH FREQUENCY LEAKAGE CURRENTS. However, higher frequencies may be used in the case of BIPOLAR techniques. It is generally recognized that 10 mA is the lower threshold of thermal effects on tissue.

In application, an electrosurgical device can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

FIG. 1A shows an electrosurgical instrument 2 in electrical communication with a generator 21, according to one aspect of the present disclosure. The surgical instrument 2 is configurable with a flexible circuit 3 according to various aspects. The surgical instrument 2 comprises an elongate member 4, such as a shaft, having a proximal portion 9 coupled to a handle assembly 7. A distal portion 12 of the elongate member 4 comprises an end effector 14 (see FIG. 1B) coupled to a distal end of the shaft 10. In some aspects, the end effector 14 comprises a first jaw 15a and a second jaw 15b, each having an outer portion or surface 16a, 16b. At least one of the first jaw 15a and the second jaw 15b is rotatably movable relative to the other along a path shown by arrow J to transition the first and second jaws 15a, 15b between open and closed positions. In operation, the first and second jaws 15a, 15b may be transitioned from the open position to a closed position to capture tissue therebetween. Captured tissue may contact one or more working portions of the jaw set, indicated generally as 17a, 17b, configured to apply energy to treat target tissue located at or near the end effector 14. The type of energy may take various forms and includes, without limitation, monopolar and/or bipolar radio frequency (RF) energy, microwave energy, reversible and/or irreversible electroporation energy, and/or ultrasonic energy, or any combination thereof.

The handle assembly 7 comprises a housing 18 defining a grip 19. In various aspects, the handle includes one or more control interfaces 20a-c, e.g., a button or switch 20a, rotation knob 20b rotatable along arrow R, and a trigger 20c movable relative to the grip 19 along arrow T, configured to provide operation instructions to the end effector 13. Multiple buttons, knobs, or triggers described also may be included as part of the housing 18 in order to manipulate one or more of the functioning members at the end effector 14. In some aspects, the handle assembly 7 is further configured to electrically couple to a generator 21 to supply the surgical instrument 2 with energy. While the generator 21 is illustrated as generally coupled to the handle assembly 7, e.g., with a cord, it is to be understood that in some aspects the generator 21 may be positioned within the elongate member 4. For example, in one aspect, the generator 21 comprises one or more direct current batteries positioned in the handle assembly 7, shaft 10, or a portion thereof.

Figure 1C:
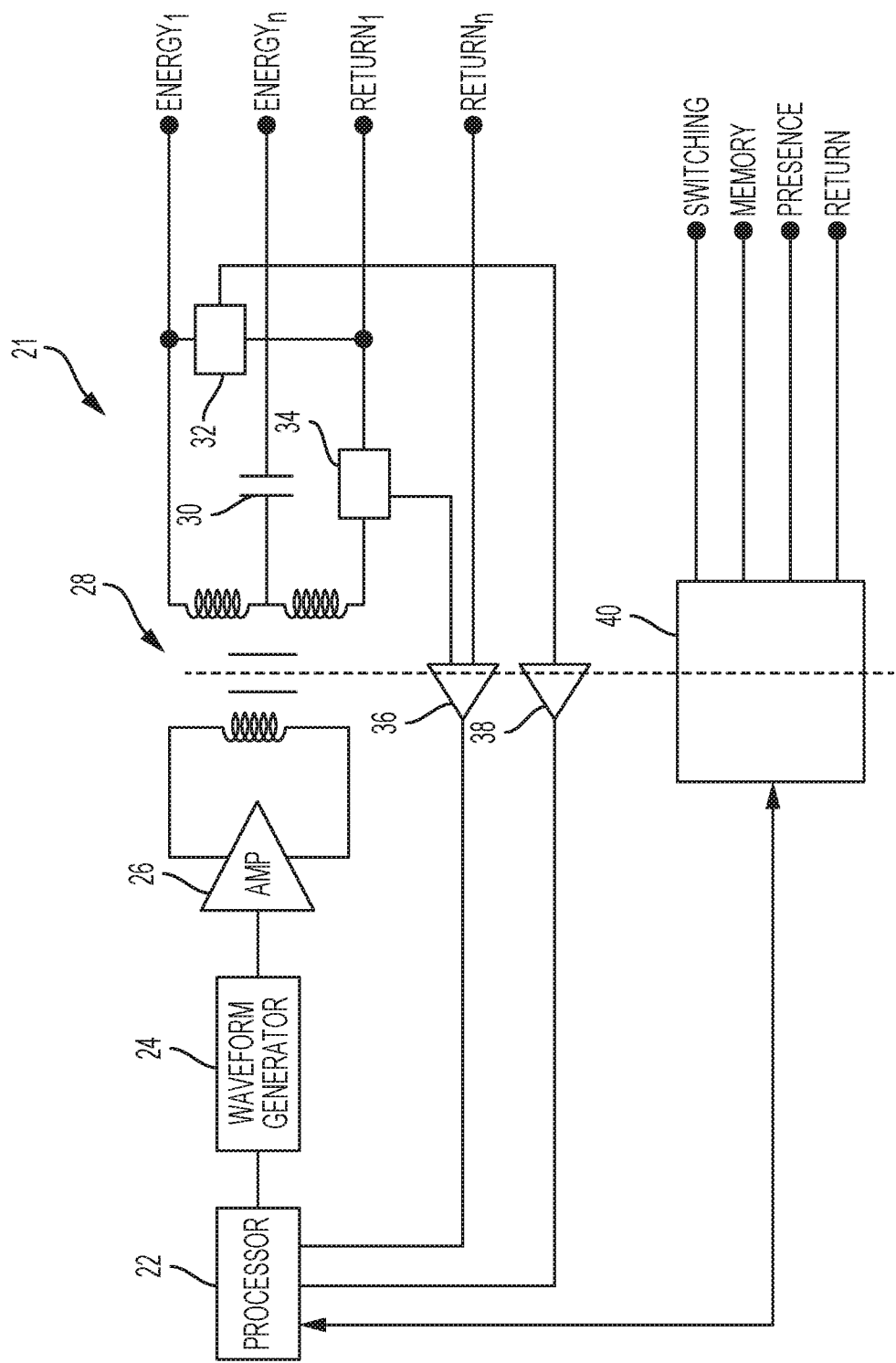
FIG. 1C illustrates an example of a generator for delivering multiple energy modalities to the surgical instrument of FIG. 1A, according to one aspect of the present disclosure.

FIG. 1C illustrates an example of a generator 21 for delivering multiple energy modalities to a surgical instrument. As noted above, at least one generator output can deliver multiple energy modalities (e.g., ultrasonic, bipolar or monopolar RF, irreversible and/or reversible electroporation, and/or microwave energy, among others) through a single port and these signals can be delivered separately or simultaneously to the end effector to treat tissue. FIG. 10 illustrates an example of a generator 21 for delivering multiple energy modalities to a surgical instrument. The generator 21 comprises a processor 22 coupled to a waveform generator 24. The processor 22 and waveform generator 24 are configured to generate a variety of signal waveforms based on information stored in a memory coupled to the processor 22, not shown for clarity of disclosure. The digitally information associated with a waveform is provided to the waveform generator 24 which includes one or more digital-to-analog (DAC) converters to convert the digital input into an analog output. The analog output is fed to an amplifier 26 for signal conditioning and amplification. The conditioned and amplified output of the amplifier 26 is coupled to a power transformer 28. The signals are coupled across the power transformer 28 to the secondary side, which is in the patient isolation side. A first signal of a first energy modality is provided to the surgical instrument between the terminals labeled $ENERGY_1$ and $RETURN_1$. A second signal of a second energy modality is coupled across a capacitor 30 and is provided to the surgical instrument between the terminals labeled $ENERGY_n$ and $RETURN_n$. The subscript n is used to indicate that up to n ENERGY/RETURN terminals may be provided, where n is a positive integer greater than 1. As an example, the first energy modality may be ultrasonic energy and the second energy modality may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 10 shows separate return paths $RETURN_1$ and $RETURN_n$, it will be appreciated that at least one common return path may be provided for two or more energy modalities.

A voltage sensing circuit 32 is coupled across the terminals labeled $ENERGY_1$ and $RETURN_1$ to measure the output voltage. A current sensing circuit 34 is disposed in series with the $RETURN_1$ leg of the secondary side of the power transformer 28 as shown to measure the output current. The outputs of the voltage sensing circuit 32 is provided to an isolation transformer and analog-to-digital converter (ADC) 36 and the output of the current sensing circuit 34 is provided to another isolation transformer and ADC 38. The digital version of the output voltage and output current are fed back to the processor 22. The output voltage and output current information can be employed to adjust the output voltage and current provided to the instrument and to compute output impedance, among other parameters. Input/output communications between the processor 22 and patient isolated circuits is provided through an interface circuit 40. It will be appreciated that a similar voltage sensing circuit may be provided across the $ENERGY_n$ and $RETURN_n$ terminals and a similar current sensing circuit may be disposed in series with the $RETURN_n$ leg.

As shown in FIG. 10, the generator 21 comprises at least one output port can include a power transformer 28 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 21 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 21 can be steered, switched, or filtered to provide the frequency to the end effector of the surgical instrument. The connection of a transducer to the generator 21 output would be preferably located between the output labeled ENERGY1 and $RETURN_1$ as shown in FIG. 10. In one example, a connection of RF bipolar electrodes to the generator 21 output would be preferably located between the output labeled $ENERGY_n$ and $RETURN_n$. In the case of monopolar output, the preferred connections would be active electrode (e.g., pencil or other probe) to the $ENERGY_n$ output and a suitable return pad connected to the $RETURN_n$ output.

The following descriptions and related figures provide examples of more detailed designs of the end effector 14, including one or more members for grasping and applying sealing energy, and one or more members with a fluid path for suction and irrigation. The following are merely examples, and it may be apparent to those with skill in the art how the various examples may be combined or interchanged to be included in various other aspects, and aspects are not so limited.

I. Flexible Circuit Electrode Configurations

A. Bipolar Flexible Circuit Electrode Assembly

Figure 2:
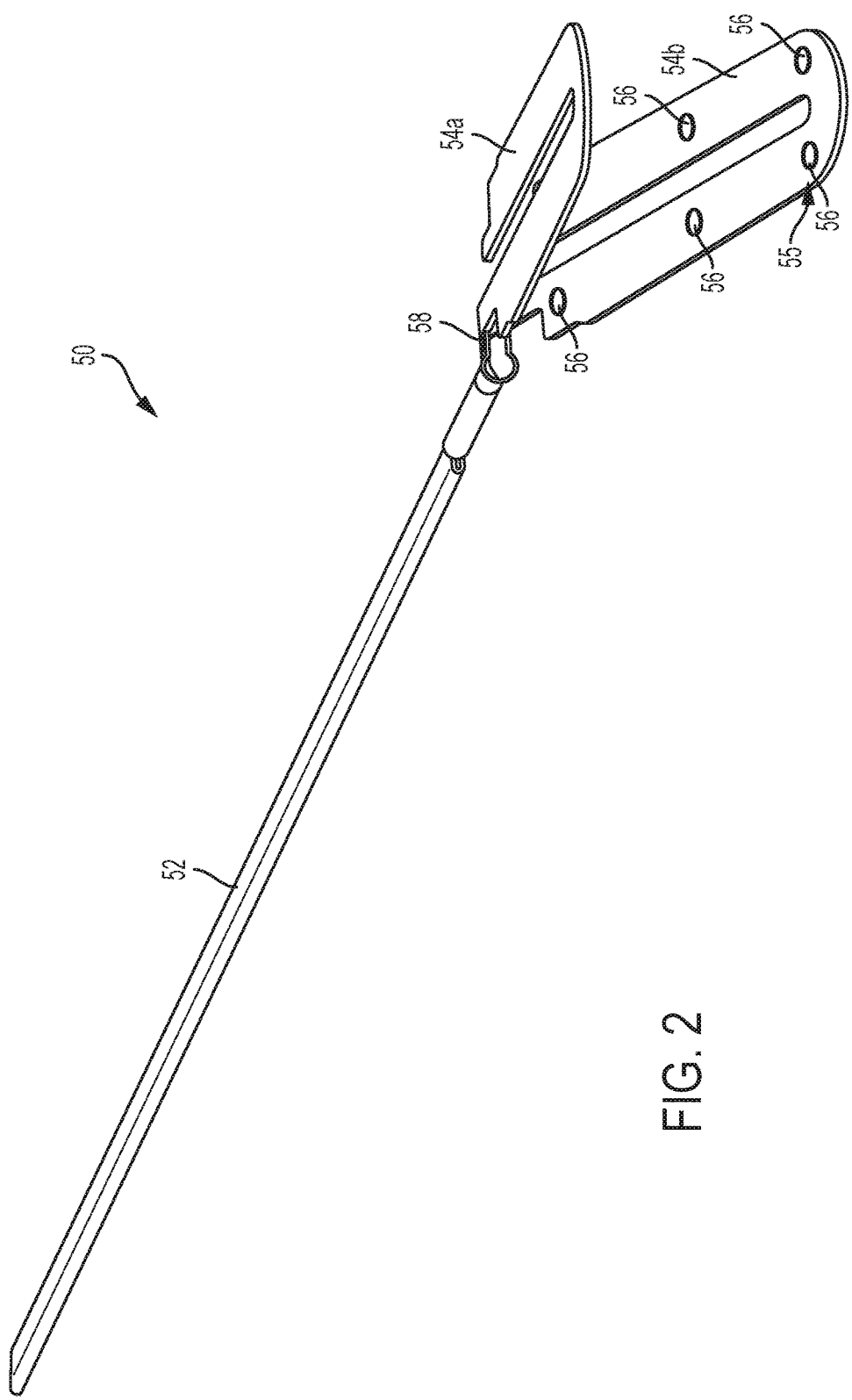
FIG. 2 illustrates a bipolar flexible circuit electrode assembly that utilizes the flexible nature of flexible circuit electrode manufacturing process to incorporate a variety of lead lengths and active/passive components in the electrode circuit, according to one aspect of the present disclosure.

FIG. 2 illustrates a bipolar flexible circuit electrode assembly 50 that utilizes the flexible nature of flexible circuit electrode manufacturing process to incorporate a variety of lead 52 lengths and active/passive components in the electrode circuit, according to one aspect of the present disclosure. The bipolar flexible circuit electrode assembly 50 comprises an upper jaw flexible circuit electrode 54a and a lower jaw flexible circuit electrode 54b. A flexure bearing 58 connects the upper and lower jaw electrodes 54a, 54b. As used herein, the flexure bearing is made from the same material as the two flexible circuit electrodes it connects, and may be referred to as a living hinge or living bearing. The upper and lower jaw flexible electrodes 54a, 54b are configured to mount to a clamp jaw assembly, such as, for example, the end effector 14 shown in FIG. 1C, of the electrosurgical device such as, for example, the surgical instrument 2 shown in FIG. 1A. The upper and lower jaw flexible electrodes 54a, 54b are electrically coupled to an generator 21 at the handle assembly 7 of the electrosurgical instrument 2, all shown in FIG. 1A. The lead 52 is disposed within the shaft 10 of the electrosurgical instrument 2, as shown in FIGS. 1A, 1B. The lower jaw electrode 54b comprises an electrically insulative layer 55 defining a plurality of electrically insulative elements 56 to prevent the upper and lower jaw electrodes 54a, 54b from shorting when the jaws are in a closed configuration. The electrically insulative elements 56 define a gap between the upper and lower jaw electrodes 54a, 54b when they are in a closed configuration and also improve tissue grasping between the jaw electrodes 54a, 54b.

In one aspect, the electrically insulative elements 56 can be provided on the upper jaw electrode 54a and in other aspects the electrically insulative elements 56 can be provided on both the upper and lower jaw electrodes 54a, 54b. The electrically insulative elements 56 can be formed of a dielectric material which can be printed on the flexible circuit electrodes 54a, 54b as described in further detail herein. In yet another aspect, the insulative layer 55 may be configured as an electrically insulative cover that further defines the electrically conductive lower jaw electrode 54b and can act as a spacer element. In one aspect, the electrically insulative elements 56 may comprise a nonstick coating or may be formed of a nonstick material such as polytetrafluoroethylene (PTFE), which is a synthetic fluoropolymer of tetrafluoroethylene that has numerous applications. The best known brand name of PTFE-based formulas is TEFLON by DuPont Co., for example. In one aspect, the electrically insulative elements 56 may be formed of a dielectric material.

In one aspect, the electrically insulative layer 55 may be formed by bonding a dielectric cover film on the tissue contacting surface of the flexible circuit electrodes 54a, 54b. In one aspect, the electrically insulative elements 56 may be formed by etching the dielectric cover film bonded to the tissue contacting surface of the electrode 54a, 54b. In one aspect, at least one of the electrically insulative elements 56 may be configured as a spacer to provide a predetermined gap between upper and lower electrodes.

As used throughout this description, the term element is used to refer a piece of material used to create or maintain a space between two things, such as jaw members of an end effector. The pacers may be electrically conductive or nonconductive and in various aspects are formed of a dielectric material. In one aspect, the elements can be made of a Positive Thermal Coefficient (PTC) ceramic, e.g., barium titanate or lead titanate composites. The elements can alternatively be made of exotic materials, including platinum, molybdenum disilicide, and silicon carbide. These are just a few examples, which are not meant to be limiting. In an electrically conductive configuration, the elements may be employed to set a uniform or non-uniform predetermined gap between tissue contacting surfaces of the upper and lower jaw members. In an electrically nonconductive configuration, the elements may be employed to set a uniform or non-uniform predetermined gap between tissue contacting surfaces of the upper and lower jaw members and prevent the electrodes in the upper and lower jaw members from electrically shorting.

Figure 3:
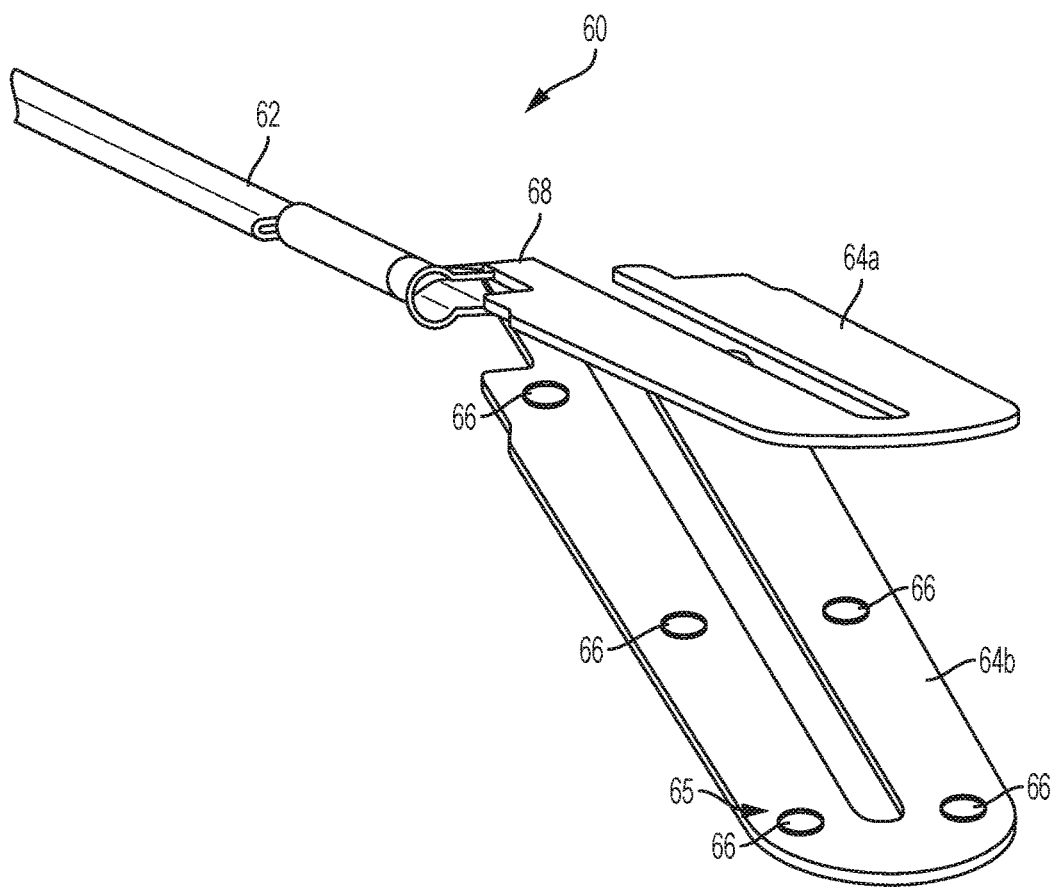
FIG. 3 illustrates a detail view of a bipolar flexible circuit electrode assembly comprising a short lead length, according to one aspect of the present disclosure.

FIG. 3 illustrates a detail view of a bipolar flexible circuit electrode assembly 60 comprising a short lead 62 length, according to one aspect of the present disclosure. The bipolar flexible circuit electrode assembly 60 comprises an upper jaw flexible circuit electrode 64a and a lower jaw flexible circuit electrode 64b. A flexure bearing 68 connects the upper and lower jaw electrodes 64a, 64b. The upper and lower jaw flexible electrodes 64a, 64b are configured to mount to a clamp jaw assembly, such as, for example, the end effector 14 shown in FIG. 1C, of the electrosurgical device such as, for example, the surgical instrument 2 shown in FIG. 1A. The upper and lower jaw flexible electrodes 64a, 64b are electrically coupled to a generator 21 at the handle assembly 7 of the electrosurgical instrument 2, all shown in FIG. 1A. The short lead 62 provides for replaceable electrodes 64a, 64b or a replaceable jaw assembly of the end effector 14.

The lower jaw electrode 64b comprises an electrically insulative layer 65 defining a plurality of electrically insulative elements 66 to prevent the upper and lower jaw electrodes 64a, 64b from shorting when the jaws are in a closed configuration. The electrically insulative elements 66 also define a gap between the upper and lower jaw electrodes 64a, 64b when they are in a closed configuration and also improve tissue grasping between the jaw electrodes 64a, 64b. In one aspect, the electrically insulative elements 66 can be provided on the upper jaw electrode 64a and in other aspects the electrically insulative elements 66 can be provided on both the upper and lower jaw electrodes 64a, 64b. The electrically insulative elements 66 can be formed of a dielectric material which can be printed on the flexible circuit electrodes 64a, 64b as described in further detail herein. In yet another aspect, the electrically insulative layer 65 may be configured as an electrically insulative cover that further defines the electrically conductive lower jaw electrode 64b and can act as a spacer element.

The electrically insulative element 66 may be defined by the electrically insulative layer 65 and can be configured as an electrically insulative barrier between the jaw electrodes, provide a predetermined gap between the jaw electrodes, and/or assist tissue grasping between the jaw electrodes. In one aspect, the electrically insulative elements 66 may comprise a nonstick coating or may be formed of a nonstick material such as TEFLON to prevent tissue from sticking thereto. In one aspect, the electrically insulative elements 66 may be formed of a dielectric material.

In one aspect, the electrically insulative layer 65 may be formed by bonding a dielectric cover film on the tissue contacting surface of the flexible circuit electrodes 64a, 64b. In one aspect, the electrically insulative elements 66 may be formed by etching the dielectric cover film bonded to the tissue contacting surface of the electrode 64a, 64b. In one aspect, at least one of the electrically insulative elements 66 may be configured as a spacer to provide a predetermined gap between upper and lower electrodes.

With reference now to FIGS. 2 and 3, in various aspects the bipolar flexible circuit electrode assemblies 50, 60 utilize the flexible nature of the flexible circuit electrode manufacturing process to incorporate a variety of lead lengths and active/passive components can be provided in the electrode circuit. The bipolar flexible circuit electrode assemblies 50, 60 can be configured in a variety of ways. For example, as shown in FIG. 2, the length of the lead 52 may be, to enable moving the electrical termination point to the handle assembly 7 (FIG. 1A), reducing part count, electrical connection points and enabling the inclusion of additional active components such as switches, electrically erasable programmable read only memory (EEPROM), etc., intimately associated with the electrodes. Alternatively, as shown in FIG. 3, the length of the short lead 62 can be short as shown in FIG. 3, i.e., near the flexure bearing 68 connecting the upper and lower jaw electrodes 64a, 64b, which can enable replaceable electrodes 64a, 64b or jaws.

B. Bipolar Flexible Circuit Electrode Assembly Including Extended Leads

Figure 4:
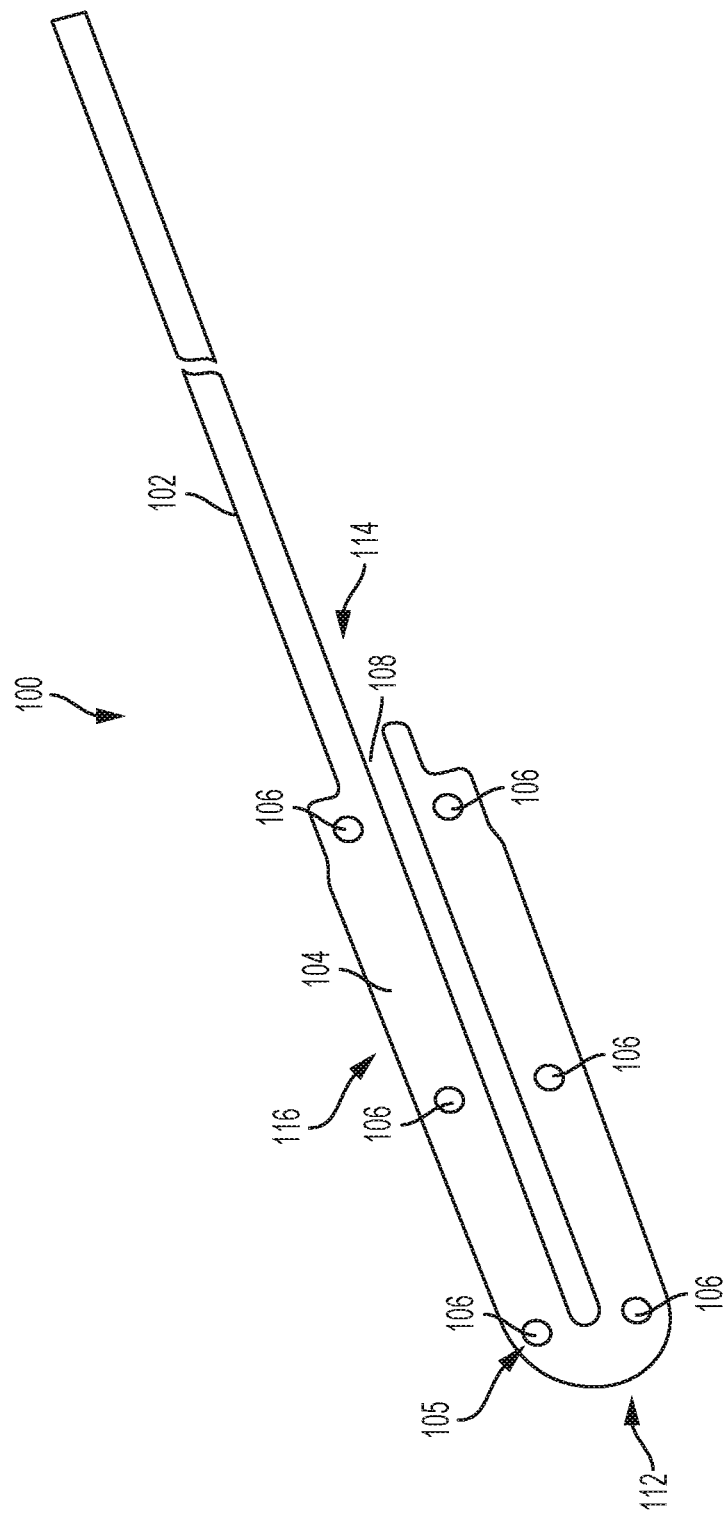

FIGS. 4-9 illustrate a flexible circuit electrode 100 comprising an extended lead 102, according to one aspect of the present disclosure. FIG. 4 is a perspective view of a flexible circuit electrode 100 comprising an extended lead 102, according to one aspect of the present disclosure.

FIG. 5 is a plan view of the electrically conductive element 104 side of the flexible circuit electrode 100 shown in FIG. 4, according to one aspect of the present disclosure. FIG. 6 is a plan view of the electrically insulative element 110 side of the flexible circuit electrode 100 shown in FIG. 5, according to one aspect of the present disclosure.

FIG. 7 is a side elevation view of the flexible circuit electrode 100 shown in FIG. 4, according to one aspect of the present disclosure. FIG. 8 is an elevation view of the flexible circuit electrode 100 shown in FIG. 4 taken from a distal end 112, according to one aspect of the present disclosure. FIG. 9 is an elevation view of the flexible circuit electrode shown in FIG. 4 taken from a proximal end 114, according to one aspect of the present disclosure.

With reference now to FIGS. 4-9, the flexible circuit electrode 100 comprises a lead 102 for connecting the electrode 100 to an energy source, such, for example, a radio frequency (RF) generator that outputs enough power to seal tissue. The lead 102 enables the electrode 100 to be connected to the energy source at the handle portion of the electrosurgical device. The electrode 100 comprises a jaw member portion 116 that can be attached either to the upper jaw member, the lower jaw member, or both, of a clamp jaw assembly of the electrosurgical instrument. The jaw member portion 116 comprises at least one electrically conductive element 104 and a knife slot 108. The knife portion of the electrosurgical instrument 2 (FIG. 1A) is slidably movable within the knife slot 108 to cut the tissue after it has been sealed using electrosurgical energy.

In one aspect, an electrically insulative layer 105 may be provided on the at least one electrically conductive element 104 to prevent electrically shorting the jaw member electrodes when they are in a closed configuration. In another aspect, the electrically insulative layer 105 defines at least one electrically insulative element 106 to establish a predetermined gap between the jaw electrodes of a bipolar electrosurgical instrument. In yet another aspect, the electrically insulative layer 105 may be configured as an electrically insulative cover that further defines the electrically conductive element 104 and can act as a spacer. The electrically insulative element 106 may be defined by the electrically insulative layer 105 and can be configured as an electrically insulative barrier between the jaw electrodes, provide a predetermined gap between the jaw electrodes, and/or assist tissue grasping between the jaw electrodes. In one aspect, the electrically insulative elements 106 may comprise a nonstick coating or may be formed of a nonstick material such as TEFLON to prevent tissue from sticking thereto. In one aspect, the electrically insulative elements 106 may be formed of a dielectric material.

In one aspect, the electrically insulative layer 105 may be formed by bonding a dielectric cover film on the electrically conductive element 104. In one aspect, at least one of the electrically insulative elements 106 may be formed by etching the dielectric cover film bonded to the electrically conductive element 104. In one aspect, at least one of the electrically insulative elements 106 may be configured as a spacer to provide a predetermined gap between upper and lower electrodes.

The electrically conductive element 104 comprises electrically conductive material such as copper, gold plated copper, silver, platinum, stainless steel, aluminum, or any suitable electrically conductive biocompatible material, for example. In one aspect, the electrically insulative layer 105 further defines the at least one electrically conductive element 104. One or more than one of the electrically conductive elements 104 may be configured and arranged to define a conductive electrode.

The jaw member portion 116 of the flexible circuit electrode 100 defines a knife slot 108 that extends along a length of the jaw member portion 116. Although generally speaking the knife slot 108 is laterally centered, this is not necessarily always the case, and in other aspects, the knife slot 108 may be laterally offset from center.

The electrically insulative element 110 portion of the electrically conductive element 104 of the flexible circuit electrode 100 is formed of electrically insulative material such as a polymer and more specifically can be a polyimide, polyester, fluorocarbon, or any polymeric material, or any combinations thereof. The electrically insulative element 110 of the electrically conductive element 104 is generally attached to the tissue contacting side of the upper or lower jaw members of the clamp jaw assembly.

The flexible circuit electrode 100 can be mass produced for a bipolar medical device, generally referred to as an electrosurgical device. A flexible electrically conductive sheet (e.g., Cu) is bonded to an electrically insulative backing sheet (e.g., polyimide backing) and the electrically elements 106 are printed at two or more locations on the electrically conductive element 104 of the electrode 100. The elements 106 serve to prevent the electrode 100 from shorting within the opposing jaws, create a defined gap between the jaws, and/or assist tissue grasping. After the elements 106 are printed on the electrically conductive element 104 of the electrically conductive sheet.

In one aspect, the electrode 100 can be produced by laminating the metallic sheet to an electrically insulative film made of polyimide, polyester, fluorocarbon, or any polymeric material, or any combinations thereof. The electrically insulative layer 105 as well as the elements 106 may be screen printed on the conductive face of the electrically conductive element 104 of the electrode 100. The shape of the electrode 100 is formed by screen printing a protective barrier to the metallic film. This protective barrier allows the shape of the electrode 100 to be formed by photoetching away the remaining material which does not make up the final shape of the electrode 100. Finally the individual electrode 100 is die-cut out leaving an electrode subassembly that can be bonded to the jaws.

The electrically insulative element 110 can have an adhesive or a braze-able surface on the back side to attach the flexible circuit electrode 100 to the lower or upper jaw of the end effector depending on the jaw construction of the surgical instrument.

Figure 66:
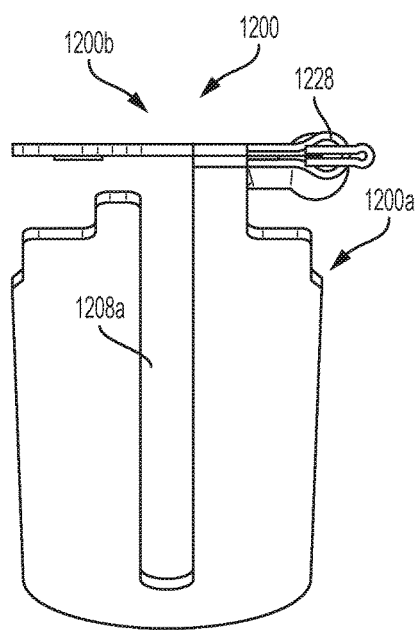

The various types of flexible circuit electrodes described in connection with FIGS. 2-66 can be manufactured in a manner similar to that described in the preceding paragraphs and for conciseness and clarity of disclosure will not be repeated in the description of such figures. Furthermore, a detailed process of manufacturing flexible circuit electrodes is discussed in connection with FIGS. 73-81. The description now turns to another type of flexible circuit electrode comprising a dielectric layer, which in one aspect comprises at least one nonstick element and in a further aspect defines an annular configuration.

Further, any of the electrodes described in connection with FIGS. 2-66, may be formed of the following materials having the indicated thicknesses. Potential materials and combination of materials for the electrically conductive portion of the electrodes include copper, gold plated copper, silver, platinum, stainless steel, aluminum, or any suitable electrically conductive biocompatible material, for example, among other electrically conductive metals and/or alloys. In one example, the flexible circuit electrode as described herein can include an electrically conductive metal layer (e.g., copper, gold plated copper, silver, platinum, stainless steel, aluminum, or any suitable electrically conductive biocompatible material, for example, among other electrically conductive metals and/or alloys), an electrically insulative film (e.g., polyimide, polyester, fluorocarbon, or any polymeric material, or any combinations thereof) bonded to the electrically conductive metal layer, and an adhesive used to bond the electrically conductive metal layer to the electrically insulative film.

In one example, the flexible circuit electrode 100 comprises an acrylic-based copper clad laminate known under the trade name Pyralux LF9250 supplied by DuPont, the copper clad laminate comprising a coverlay, a bondply, and a sheet adhesive. A coverlay is a material laminated to the outside layers of the flexible circuit to insulate the copper conductor and a bondply is an unreinforced, thermoset based thin film available in various thicknesses adhesive system intended for use in high performance, high reliability multi-layer flexible circuit constructions. In one aspect, the components of the flexible circuit electrode 100 may comprise a copper layer having a thickness of ~0.0028", a polyimide film layer having a thickness of ~0.005", and an adhesive layer having a thickness of ~0.001" for a total thickness of ~0.0088". In another example, the flexible circuit electrode 100 comprises an acrylic-based copper clad laminate known under the trade name Pyralux LF9230 supplied by DuPont, the copper clad laminate comprising a coverlay, a bondply, and a sheet adhesive. In one aspect, the components of the flexible circuit electrode 100 may comprise a copper layer having a thickness of ~0.0028", a polyimide film layer having a thickness of ~0.003", and an adhesive layer having a thickness of ~0.001" for a total thickness of ~0.0068". It will be appreciated that the thicknesses of the individual layers ad the total thickness may vary based on the particular implementation details.

II. Flexible Circuit Electrode Including Dielectric and/or Nonstick and/or Annular Elements Flexible Circuit Electrode Including Electrically Conductive and Insulative Elements FIGS. 10-17 illustrate a flexible circuit electrode 200 comprising at least one electrically conductive element 204 and at least one electrically insulative element 206, according to one aspect of the present disclosure. The at least one electrically insulative element 206 may be configured to establish a desired gap between electrodes in bipolar electrosurgical instruments, to prevent the electrodes from shorting, to prevent tissue from sticking to the element, and/or to assist tissue grasping.

FIG. 10 is a perspective view of the electrically conductive side of a flexible circuit electrode 200 comprising at least one electrically conductive element 204 and at least one electrically insulative element 206, according to one aspect of the present disclosure. In one aspect, a plurality of electrically insulative elements 206 may be disposed on the electrically conductive element 204. In one aspect, each of the electrically insulative elements 206 comprises an annular wall 216 formed on the tissue contacting surface of the electrically conductive element 204 and defines a cavity 218 within the annular wall 216. FIG. 11 is a perspective view of the flexible circuit electrode 200 shown in FIG. 10 showing the electrically insulative element 210 side of the flexible circuit electrode 200, according to one aspect of the present disclosure. In one aspect, the annular wall 216 and cavity 218 geometry of the electrically insulative elements 206 provide nonstick properties to prevent or minimize tissue sticking to thereto.

FIG. 12 is a plan view of the electrically conductive element 204 side of the flexible circuit electrode 200 shown in FIG. 10, according to one aspect of the present disclosure. FIG. 13 is a plan view of the electrically insulative element 210 side of the flexible circuit electrode 200 shown in FIG. 10, according to one aspect of the present disclosure.

Figure 17:
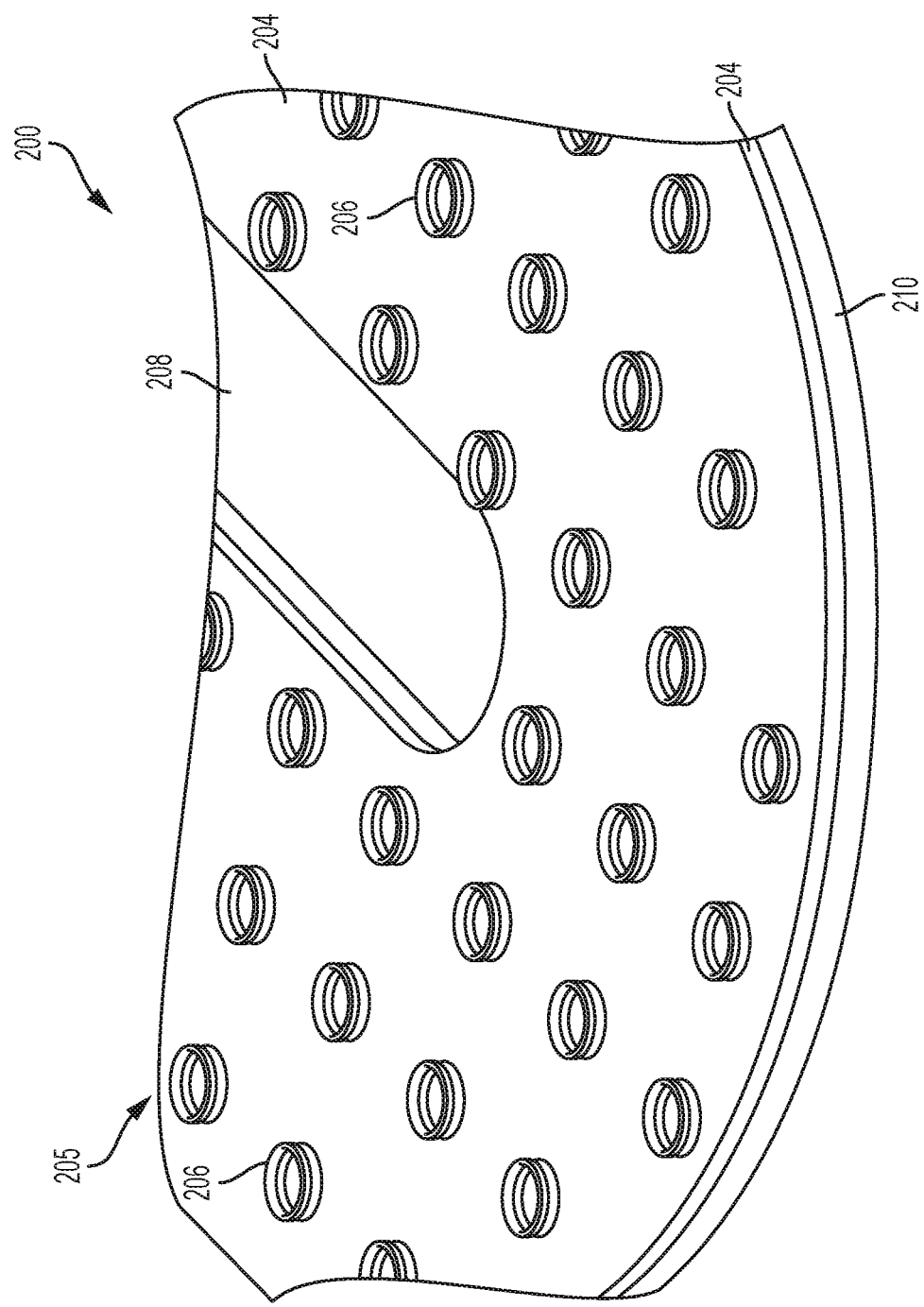

FIG. 14 is a side elevation view of the flexible circuit electrode 200 shown in FIG. 10, according to one aspect of the present disclosure. FIG. 15 is an elevation view of the flexible circuit electrode 200 shown in FIG. 10 taken from a distal end 212, according to one aspect of the present disclosure. FIG. 16 is an elevation view of the flexible circuit electrode 200 shown in FIG. 10 taken from a proximal end 214, according to one aspect of the present disclosure. FIG. 17 is a detail view of the flexible circuit electrode 200 shown in FIG. 10, according to one aspect of the present disclosure.

With reference now to FIGS. 10-17, the electrode 200 can be attached either to the upper jaw member, the lower jaw member, or both, of a clamp jaw assembly of the electrosurgical instrument. The electrode 200 comprises a lead 202 for connecting the electrode 200 to an energy source, such, for example, a radio frequency (RF) generator that outputs enough power to seal tissue. The short lead 202 enables the electrode 200 to be connected to the energy source near the distal end of the end effector. A longer lead may be provided where it is desirable to connect the electrode 200 to an energy source at the handle portion of the electrosurgical device.

In one aspect, an electrically insulative layer 205 may be provided on the at least one electrically conductive element 204 to prevent electrically shorting the jaw member electrodes when they are in a closed configuration. In another aspect, the electrically insulative layer 205 defines at least one electrically insulative element 206 to establish a predetermined gap between the jaw electrodes of a bipolar electrosurgical instrument. In yet another aspect, the electrically insulative layer 205 may be configured as an electrically insulative cover that further defines the electrically conductive element 204 and can act as a spacer. The electrically insulative element 206 may be defined by the electrically insulative layer 205 and can be configured as an electrically insulative barrier between the jaw electrodes, provide a predetermined gap between the jaw electrodes, and/or assist tissue grasping between the jaw electrodes. In one aspect, the electrically insulative elements 206 may comprise a nonstick coating or may be formed of a nonstick material such as TEFLON to prevent tissue from sticking thereto. In one aspect, the electrically insulative elements 206 may be formed of a dielectric material.

In one aspect, the electrically insulative layer 205 may be formed by bonding a dielectric cover film on the electrically conductive element 204. In one aspect, the electrically insulative elements 206 may be formed by etching the dielectric cover film bonded to the tissue contacting surface of the electrically conductive element 204. In one aspect, at least one of the electrically insulative elements 206 may be configured as a spacer to provide a predetermined gap between upper and lower electrodes.

The electrically conductive element 204 comprises electrically conductive material such as copper, gold plated copper, silver, platinum, stainless steel, aluminum, or any suitable electrically conductive biocompatible material, for example. In one aspect, the electrically insulative layer 205 further defines the at least one electrically conductive element 204. One or more than one of the electrically conductive elements 204 may be configured and arranged to define a conductive electrode.

The flexible circuit electrode 200 defines a knife slot 208 that extends along a length of the flexible circuit electrode 200. The knife portion of the electrosurgical instrument 2 (FIG. 1A) is slidably movable within the knife slot 208 to cut the tissue after it has been sealed using electrosurgical energy. Although generally speaking the knife slot 208 is located along the lateral center of the flexible circuit electrode 200, this is not necessarily always the case. Thus, in other aspects, the knife slot 208 may be offset from the center to either side of the flexible circuit electrode 200.

The electrically insulative element 210 of the flexible circuit electrode 200 is formed of electrically insulative material such as a polymer and more specifically can be an electrically insulative material (e.g., polyimide, polyester, fluorocarbon, or any polymeric material, or any combinations thereof). The electrically insulative element 210 is generally attached to the tissue contacting side of the upper or lower jaw members of the clamp jaw assembly.

In one aspect, the electrically insulative elements 206 may comprise a nonstick coating or may be formed of a nonstick material such as TEFLON. Any nonstick material or nonstick surface finish may be suitable to prevent tissue from sticking to the electrically conductive element 204 of the flexible circuit electrode 200. As illustrated most clearly in FIG. 17, dielectric nonstick annular elements 206 may be configured to define a ring like or donut like structure. Such a structure, however, should not be construed as limiting the dielectric nonstick annular elements 206 to the disclosed form.

III. Segmented Offset Flexible Circuit Electrode

Figure 18:
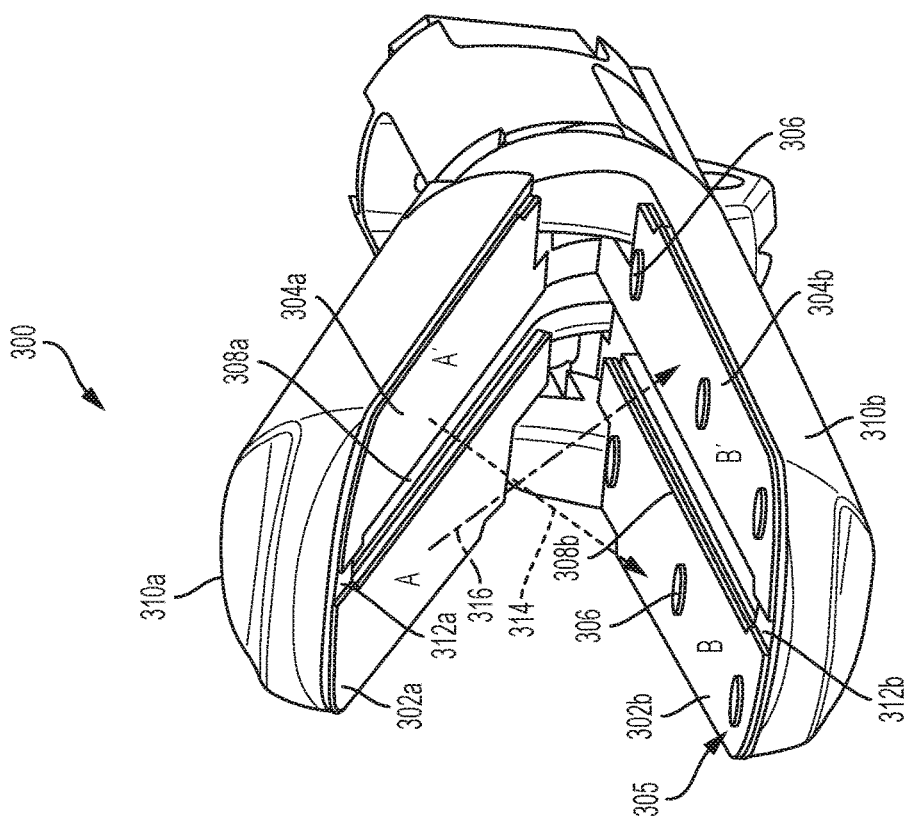
FIG. 18 illustrates an end effector comprising four flexible circuit electrodes that can be independently energized and configured to provide an offset current path according to one aspect of the present disclosure.

End Effector Including Independently Energizable Flexible Circuit Electrodes Configured to Provide Offset Current Paths FIG. 18 illustrates an end effector 300 comprising four flexible circuit electrodes 302a, 302b, 304a, 304b that can be independently energized and configured to provide an offset current path 314, 316 according to one aspect of the present disclosure. The end effector 300 comprises a clamp jaw assembly comprising an upper jaw 310a and a lower jaw 310b. The lower jaw 310b is fixed and the upper jaw 310a is pivotally movable relative to the lower jaw 310b from an open position to a closed position and vice versa. In other aspects, the upper jaw may be fixed and the lower jaw may be movable. In other aspects, both the upper and lower jaws may be movable.

Two of the flexible circuit electrodes 302a, 304a are attached to the upper jaw 310a and the other two flexible circuit electrodes 302b, 304b are attached to the lower jaw 310b. A first gap 312a is provided between the two upper jaw 310a electrodes 302a, 304a to electrically isolate them and provide two independent sections. Likewise, a second gap 312b is provided between the two lower jaw 310b electrodes 302b, 304b to electrically isolate them and provide two more independent sections. The four electrodes 302a, 302b, 304a, 304b can be independently energized to create a first independent offset current path 314 between the upper jaw 310a electrode 304a and the lower jaw 310b electrode 302b. A second offset current path 316 is created between the upper jaw 310a electrode 302a and the lower jaw 310b electrode 304b. Other current paths can be created by independently energizing and grounding the four electrodes 302a, 302b, 304a, 304b.

The lower jaw 310b electrodes 302b, 304b include an electrically insulative layer 305 that defines at least one electrically insulative element 306 (e.g., insulative elements to establish desired gaps between electrodes in bipolar electrosurgical instruments, assist tissue gripping, and electrically isolate the electrodes). In one aspect, multiple electrically insulative elements 306 may be defined by the electrically insulative layer 305 on the lower jaw 310b electrodes 302b, 304b may be configured as elements as discussed previously herein, which in one aspect may define an annular configuration. The tissue contacts the electrodes 302b, 304b in between the electrically insulative elements 306. Knife slots 308a is defined in the upper jaw 310a and electrode 304a and another knife slot 308b is defined in the lower jaw 310b and electrode 304b.

It will be appreciated that is some aspects, only the upper jaw electrodes can be isolated or the lower jaw electrodes can be isolated. Still in other aspects, the end effector 300 may be fitted with the electrode 100 shown in FIGS. 5-9 or the electrode 200 shown in FIGS. 10-17, in which case neither the upper nor the lower jaw electrodes include an isolation gap.

In one aspect, an electrically insulative layer 305 may be provided on at least one of the electrodes 302a, 302b, 304a, 304b to prevent electrically shorting the jaw member electrodes 302a, 302b, 304a, 304b when they are in a closed configuration. In another aspect, the electrically insulative layer 305 defines at least one electrically insulative element 306 to establish a predetermined gap between the jaw electrodes 302a, 302b, 304a, 304b of the bipolar electrosurgical instrument. In yet another aspect, the electrically insulative layer 305 may be configured as an electrically insulative cover that further defines the electrodes 302a, 302b, 304a, 304b and can act as a spacer. The electrically insulative element 306 may be defined by the electrically insulative layer 305 and can be configured as an electrically insulative barrier between the jaw electrodes, provide a predetermined gap between the jaw electrodes, and/or assist tissue grasping between the jaw electrodes. In one aspect, the electrically insulative elements 306 may comprise a nonstick coating or may be formed of a nonstick material such as TEFLON to prevent tissue from sticking thereto. In one aspect, the electrically insulative element may be formed of a dielectric material.

In one aspect, the electrically insulative layer 305 may be formed by bonding a dielectric cover film on the electrically conductive elements 304a, 304b. In one aspect, the electrically insulative elements 306 may be formed by etching the dielectric cover film bonded to the tissue contacting surface of the electrically conductive elements 304a, 304b. In one aspect, at least one of the electrically insulative elements 306 may be configured as a spacer to provide a predetermined gap between upper and lower electrodes.

The electrodes 302a, 302b, 304a, 304b comprise electrically conductive material such as copper, gold plated copper, silver, platinum, stainless steel, aluminum, or any suitable electrically conductive biocompatible material, for example. One or more than one of the electrically conductive electrodes 302a, 302b, 304a, 304b may be configured and arranged to define a conductive electrode.

Figure 19:
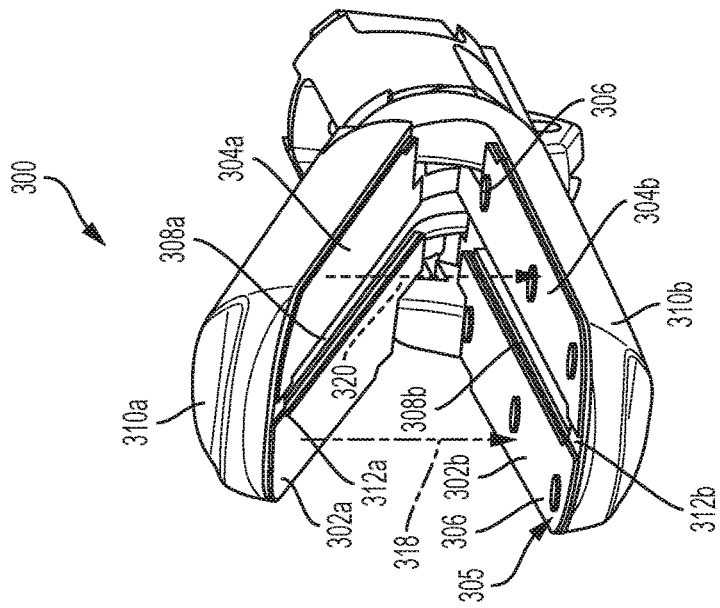
FIG. 19 illustrates the end effector shown in FIG. 18 comprising four flexible circuit electrodes that can be independently energized and configured to provide a direct current path, according to one aspect of the present disclosure.

FIG. 19 illustrates the end effector 300 shown in FIG. 18 comprising four flexible circuit electrodes 302a, 302b, 304a, 304b that can be independently energized and configured to provide a first and second direct current path 318, 320, according to one aspect of the present disclosure. In the example illustrate din FIG. 19, the electrodes 302a, 302b, 304a, 304b are configured to set up a first direct current path 318 between the upper electrode 302a and the lower electrode 302b and a second current path 320 between the upper electrode 304a and the lower electrode 304b. Knife slots 308a is defined in the upper jaw 310a and electrode 304a and another knife slot 308b is defined in the lower jaw 310b and electrode 304b.

With reference now to FIGS. 18 and 19, with the flexible circuit technology the segmented electrodes 302a, 302b, 304a, 304b can be cost effectively manufactured to provide control over independent sections of the electrodes 302a, 302b, 304a, 304b. This technique provides offset electrode functionality and tissue impedance sensing per section of the jaw with subsequent tailored control of the power applied to that section of tissue. The electrodes 302a, 302b, 304a, 304b can be cost effectively manufactured and provide multiple isolated zones independently controlled.

FIGS. 20-26 illustrate a segmented offset flexible circuit electrode 400, according to one aspect of the present disclosure. The segmented offset flexible circuit electrode 400 is configured to be attached to the end effector 300 shown in FIGS. 18 and 19. The electrode 400 can be attached either to the upper jaw member, the lower jaw member, or both, of a clamp jaw assembly of the electrosurgical instrument.

FIG. 20 is a perspective view of the electrically conductive elements 404 side of a segmented offset flexible circuit electrode 400 comprising two electrode segments 404a, 404b of the electrically conductive element 404, according to one aspect of the present disclosure. The two electrode segments 404a, 404b are electrically isolated from each other. FIG. 21 is a perspective view of the electrically insulative element 410 side of the segmented offset flexible circuit electrode 400 shown in FIG. 20, according to one aspect of the present disclosure.

FIG. 22 is a plan view of the electrically conductive element 404 side of the segmented offset flexible circuit electrode 400 shown in FIG. 20, according to one aspect of the present disclosure. FIG. 23 illustrates a plan view of the electrically insulative element 410 side of the segmented offset flexible circuit electrode 400 shown in FIG. 20, according to one aspect of the present disclosure.

FIG. 24 is a side elevation view of the segmented offset flexible circuit electrode 400 shown in FIG. 20, according to one aspect of the present disclosure. FIG. 25 is an elevation view of the segmented offset flexible circuit electrode 400 shown in FIG. 20 taken from a distal end 412, according to one aspect of the present disclosure. FIG. 26 is an elevation view of the segmented offset flexible circuit electrode 400 shown in FIG. 20 taken from a proximal end 414, according to one aspect of the present disclosure.

With reference now to FIGS. 20-26, the segmented offset flexible circuit electrode 400 comprises a lead 402 for connecting the flexible circuit electrode 400 to an energy source, such, for example, a radio frequency (RF) generator that outputs enough power to seal tissue. The short lead 402 enables the electrode 400 to be connected to the energy source near the distal end of the end effector. A longer lead may be provided where it is desirable to connect the electrode 400 to an energy source at the handle portion of the electrosurgical device.

The electrode 400 can be attached either to the upper jaw member, the lower jaw member, or both, of a clamp jaw assembly of the electrosurgical instrument, as shown in FIGS. 18 and 19, for example. The electrically conductive element 404 comprises two segments 404a, 404b. A gap 416 is provided between the segments 404a, 404b electrically isolated them from each other. The electrode 400 further comprises a knife slot 408. The knife portion of the electrosurgical instrument 2 (FIG. 1A) is slidably movable within the knife slot 408 to cut the tissue after it has been sealed using electrosurgical energy.

In one aspect, an electrically insulative layer 405 may be provided on the at least one electrically conductive elements 404a, 404b to prevent electrically shorting the jaw member electrodes when they are in a closed configuration. In another aspect, the electrically insulative layer 405 defines at least one electrically insulative element 406 to establish a predetermined gap between the jaw electrodes of a bipolar electrosurgical instrument. In yet another aspect, the electrically insulative layer 405 may be configured as an electrically insulative cover that further defines the electrically conductive elements 404a, 404b and can act as a spacer. The electrically insulative element 406 may be defined by the electrically insulative layer 405 and can be configured as an electrically insulative barrier between the jaw electrodes, provide a predetermined gap between the jaw electrodes, and/or assist tissue grasping between the jaw electrodes. In one aspect, the electrically insulative elements 406 may comprise a nonstick coating or may be formed of a nonstick material such as TEFLON to prevent tissue from sticking thereto. In one aspect, the electrically insulative elements 406 may be formed of a dielectric material.

In one aspect, the electrically insulative layer 405 may be formed by bonding a dielectric cover film on the electrically conductive element 404. In one aspect, the electrically insulative elements 406 may be formed by etching the dielectric cover film bonded to the electrically conductive element 404. In one aspect, at least one of the electrically insulative elements 406 is configured as a spacer to provide a predetermined gap between upper and lower electrodes.

The electrically conductive elements 404a, 404b comprise electrically conductive material such as copper, gold plated copper, silver, platinum, stainless steel, aluminum, or any suitable electrically conductive biocompatible material, for example. One or more than one of the electrically conductive elements 404 may be configured and arranged to define a conductive electrode.

The flexible circuit electrode 400 defines a knife slot 408 that extends along a length of the electrode 400. Although generally speaking the knife slot 408 is laterally centered, this is not necessarily always the case, and in other aspects, the knife slot 408 may be laterally offset from center.

The electrically insulative element 410 of the flexible circuit electrode 400 is formed of electrically insulative material such as a polymer and more specifically can be an electrically insulative material (e.g., polyimide, polyester, fluorocarbon, or any polymeric material, or any combinations thereof). The electrically insulative element 410 is generally attached to the tissue contacting side of the upper or lower jaw members of the clamp jaw assembly.

IV. Flexible Circuit Electrode Including Electrically Insulative Elements

A. Flexible Circuit Electrode Including Electrically Insulative Elements

FIGS. 27-33 illustrate a flexible circuit electrode 500 comprising electrically insulative elements 506 (e.g., insulative elements to establish desired gaps between electrodes in bipolar electrosurgical instruments), according to one aspect of the present disclosure.

FIG. 27 is a perspective view of a flexible circuit electrode 500 comprising an array of electrically insulative elements 506 showing the electrically conductive element 504 side, according to one aspect of the present disclosure. FIG. 28 is a perspective view of the electrically insulative element 510 side of the flexible circuit electrode 500 shown in FIG. 27, according to one aspect of the present disclosure.

Figure 29:
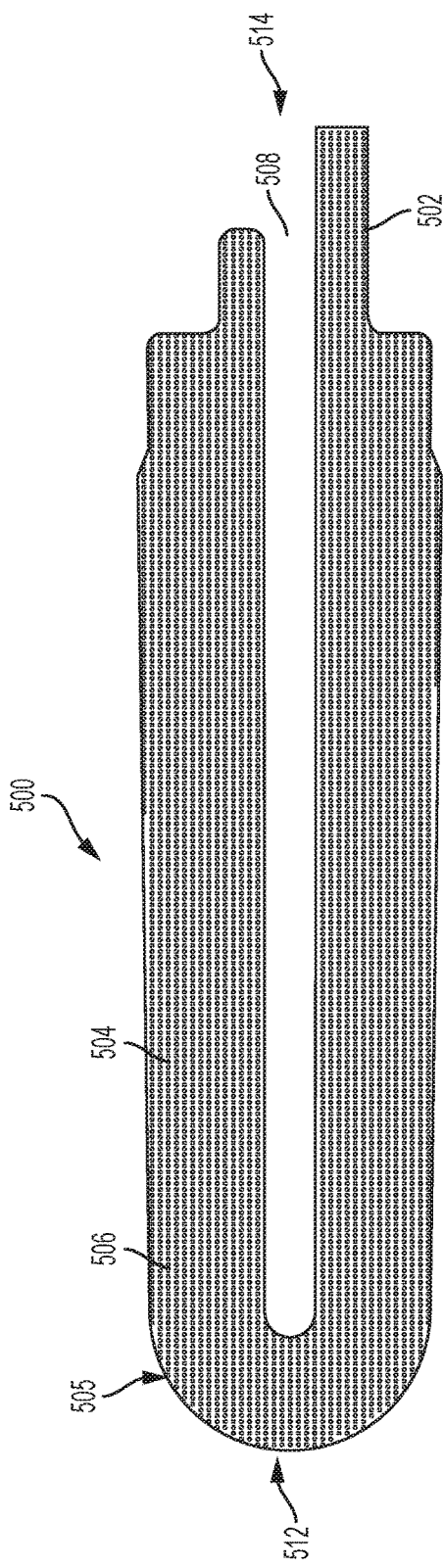
Figure 30:
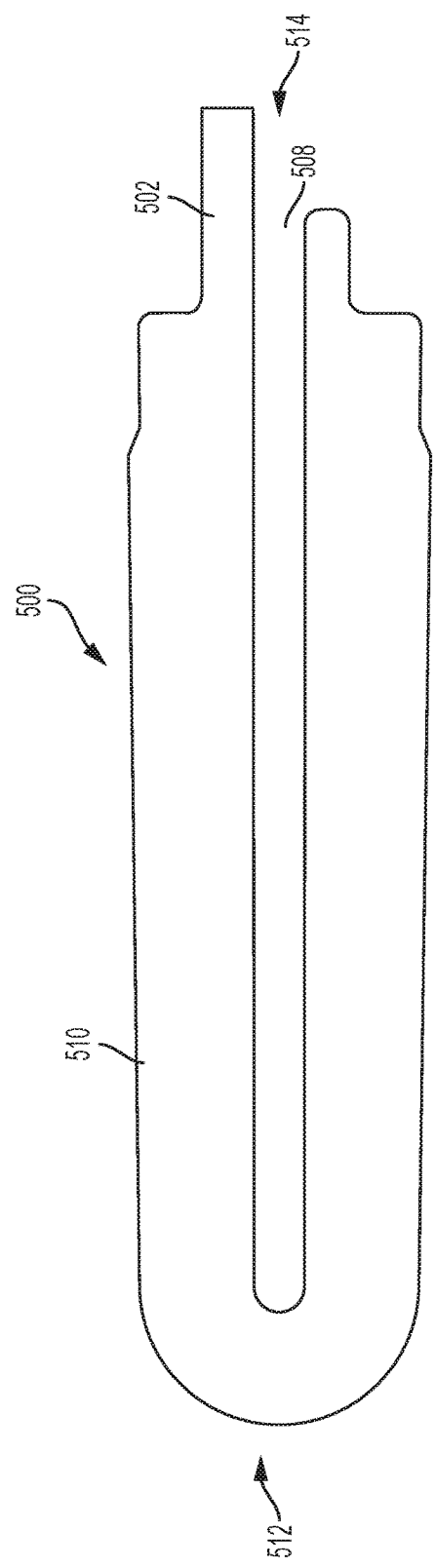

FIG. 29 is a plan view of the electrically conductive element 504 side of the flexible circuit electrode 500 shown in FIG. 27, according to one aspect of the present disclosure. FIG. 30 is a plan view of the electrically insulative element 510 side of the flexible circuit electrode 500 shown in FIG. 27, according to one aspect of the present disclosure.

FIG. 31 is a side elevation view of the flexible circuit electrode 500 shown in FIG. 27, according to one aspect of the present disclosure. FIG. 32 is an elevation view of the flexible circuit electrode 500 shown in FIG. 27 taken from a distal end 512, according to one aspect of the present disclosure. FIG. 33 is an elevation view of the flexible circuit electrode 500 shown in FIG. 27 taken from a proximal end 514, according to one aspect of the present disclosure.

With reference now to FIGS. 27-33, the electrode 500 can be attached either to the upper jaw member, the lower jaw member, or both, of a clamp jaw assembly of the electrosurgical instrument.

The electrode 500 comprises a lead 502 for connecting the electrode 500 to an energy source, such, for example, a radio frequency (RF) generator that outputs enough power to seal tissue. The short lead 502 enables the electrode 500 to be connected to the energy source near the distal end of the end effector. A longer lead may be provided where it is desirable to connect the electrode 500 to an energy source at the handle portion of the electrosurgical device.

In one aspect, an electrically insulative layer 505 may be provided on the at least one electrically conductive element 504 to prevent electrically shorting the jaw member electrodes when they are in a closed configuration. In another aspect, the electrically insulative layer 505 defines at least one electrically insulative element 506 to establish a predetermined gap between the jaw electrodes of a bipolar electrosurgical instrument. In yet another aspect, the electrically insulative layer 505 may be configured as an electrically insulative cover that further defines the electrically conductive element 504 and can act as a spacer. The electrically insulative element 506 may be defined by the electrically insulative layer 505 and can be configured as an electrically insulative barrier between the jaw electrodes, provide a predetermined gap between the jaw electrodes, and/or assist tissue grasping between the jaw electrodes. In one aspect, the electrically insulative elements 506 may comprise a nonstick coating or may be formed of a nonstick material such as TEFLON to prevent tissue from sticking thereto. In one aspect, the electrically insulative elements 506 may be formed of a dielectric material.

In one aspect, the electrically insulative layer 505 may be formed by bonding a dielectric cover film on the electrically conductive element 504. In one aspect, the electrically insulative elements 506 may be formed by etching the dielectric cover film bonded to the electrically conductive element 504. In one aspect, at least one of the electrically insulative elements 506 may be configured as a spacer to provide a predetermined gap between upper and lower electrodes.

The electrically conductive element 504 comprises electrically conductive material such as copper, gold plated copper, silver, platinum, stainless steel, aluminum, or any suitable electrically conductive biocompatible material, for example. One or more than one of the electrically conductive elements 504 may be configured and arranged to define a conductive electrode.

As shown in FIGS. 27 and 31, the array of electrically insulative elements 506 may be provided on a distal portion of the electrode 500. Nevertheless, the array of electrically insulative elements 506 can be provided along the full length of the conductive element 504 side of the electrode 500.

The flexible circuit electrode 500 defines a knife slot 508 that extends along a length of the flexible circuit electrode 500. Although generally speaking the knife slot 508 is located along the lateral center of the flexible circuit electrode 500, this is not necessarily always the case. Thus, in other aspects, the knife slot 508 may be offset from the center to either side of the flexible circuit electrode 500. The knife portion of the electrosurgical instrument 2 (FIG. 1A) is slidably movable within the knife slot 508 to cut the tissue after it has been sealed using electrosurgical energy.

The electrically insulative element 510 of the flexible circuit electrode 500 is formed of electrically insulative material such as a polymer and more specifically can be an electrically insulative material (e.g., polyimide, polyester, fluorocarbon, or any polymeric material, or any combinations thereof). The electrically insulative element 510 is generally attached to the tissue contacting side of the upper or lower jaw members of the clamp jaw assembly.

B. Integrated Flexible Circuit Electrode Including Electrically Insulative Elements FIGS. 34-35 illustrate an integrated flexible circuit electrode 600 comprising electrically insulative elements 606 (e.g., insulative elements to establish desired gaps between electrodes in bipolar electrosurgical instruments), according to one aspect of the present disclosure.

Figure 34:
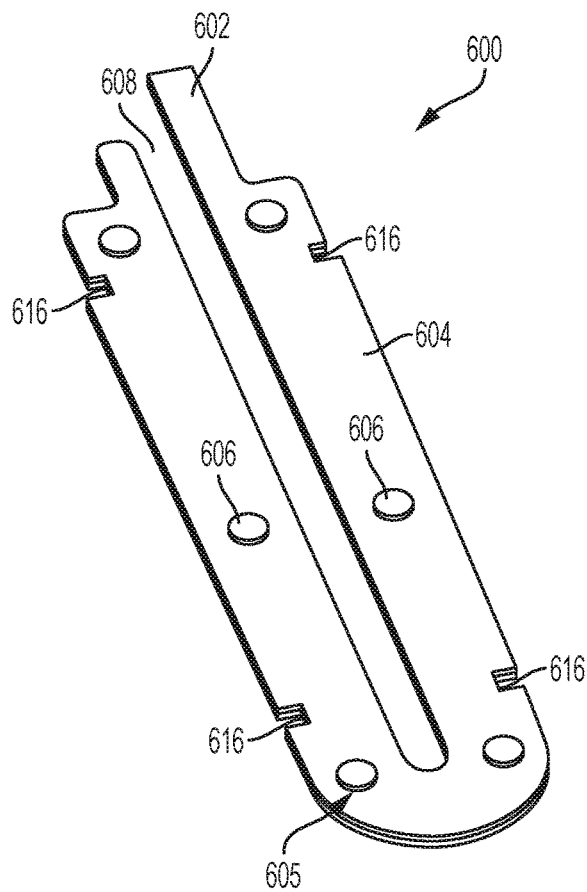
FIGS. 34-35 illustrate an integrated flexible circuit electrode comprising electrically insulative elements, according to one aspect of the present disclosure, where.

FIG. 34 is a perspective view of an integrated flexible circuit electrode 600 comprising electrically insulative elements 606 showing the electrically conductive element 604 side of the integrated flexible circuit electrode 600, according to one aspect of the present disclosure. FIG. 35 is a section view of the integrated flexible circuit electrode 600 shown in FIG. 34 taken through one of the electrically insulative elements 606, according to one aspect of the present disclosure.

Figure 35:
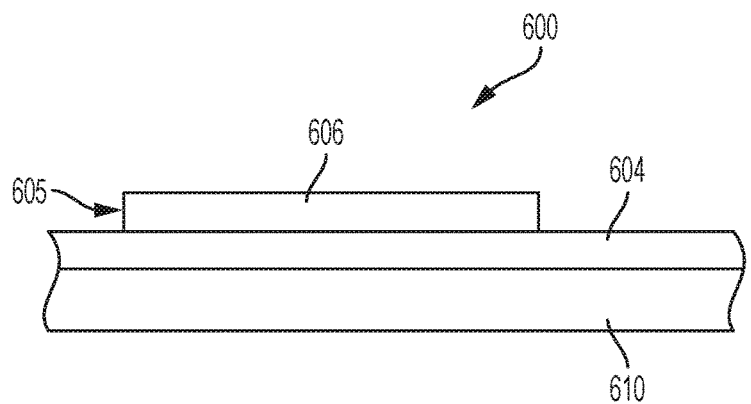

With reference now to FIGS. 34-35, the electrode 600 can be attached either to the upper jaw member, the lower jaw member, or both, of a clamp jaw assembly of the electrosurgical instrument. Attachment features 616 are provided on the electrode 600 to attach the electrode to the jaws of the end effector.

The electrode 600 comprises a lead 602 for connecting the electrode 600 to an energy source, such, for example, a radio frequency (RF) generator that outputs enough power to seal tissue. The short lead 602 enables the electrode 600 to be connected to the energy source near the distal end of the end effector. A longer lead may be provided where it is desirable to connect the electrode 600 to an energy source at the handle portion of the electrosurgical device.

The electrode 600 also comprises an electrically conductive element 604 and a knife slot 608. The electrically conductive element 604 of the flexible circuit electrode 600 also includes one or more electrically insulative elements 606 formed thereon to prevent the electrically conductive element 604 from electrically shorting when the jaw members are in a closed configuration and to prevent tissue from sticking to the electrically conductive element 604. The tissue contacts the electrically conductive element 604 in between the electrically insulative elements 606.

In one aspect, an electrically insulative layer 605 may be provided on the at least one electrically conductive element 604 to prevent electrically shorting the jaw member electrodes when they are in a closed configuration. In another aspect, the electrically insulative layer 605 defines at least one electrically insulative element 606 to establish a predetermined gap between the jaw electrodes of a bipolar electrosurgical instrument. In yet another aspect, the electrically insulative layer 605 may be configured as an electrically insulative cover that further defines the electrically conductive element 604 and can act as a spacer. The electrically insulative element 606 may be defined by the electrically insulative layer 605 and can be configured as an electrically insulative barrier between the jaw electrodes, provide a predetermined gap between the jaw electrodes, and/or assist tissue grasping between the jaw electrodes. In one aspect, the electrically insulative elements 606 may comprise a nonstick coating or may be formed of a nonstick material such as TEFLON to prevent tissue from sticking thereto. In one aspect, the electrically insulative elements 606 may be formed of a dielectric material.

In one aspect, the electrically insulative layer 605 may be formed by bonding a dielectric cover film on the electrically conductive element 604. In one aspect, the electrically insulative elements 606 may be formed by etching the dielectric cover film bonded to the electrically conductive element 604. In one aspect, at least one of the electrically insulative elements 606 may be configured as a spacer to provide a predetermined gap between upper and lower electrodes.

The electrically conductive element 604 comprises electrically conductive material such as copper, gold plated copper, silver, platinum, stainless steel, aluminum, or any suitable electrically conductive biocompatible material, for example. One or more than one of the electrically conductive elements 604 may be configured and arranged to define a conductive electrode.

The electrically insulative element 610 of the flexible circuit electrode 600 is formed of electrically insulative material such as a polymer and more specifically can be an electrically insulative material (e.g., polyimide, polyester, fluorocarbon, or any polymeric material, or any combinations thereof). The electrically insulative element 610 is generally attached to the tissue contacting side of the upper or lower jaw members of the clamp jaw assembly.

The knife portion of the electrosurgical instrument 2 (FIG. 1A) is slidably movable within the knife slot 608 to cut the tissue after it has been sealed using electrosurgical energy. The knife slot 608 extends along a length of the flexible circuit electrode 600. Although generally speaking the knife slot 608 is located along the lateral center of the flexible circuit electrode 600, this is not necessarily always the case. Thus, in other aspects, the knife slot 608 may be offset from the center to either side of the flexible circuit electrode 600.

Figure 36:
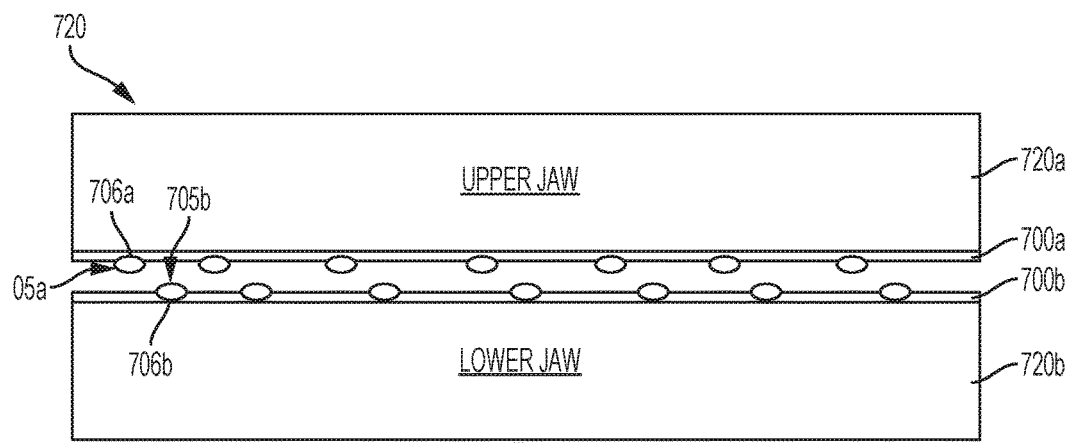
FIG. 36 is a schematic diagram of an end effector comprising an upper jaw and a lower jaw and flexible circuit electrodes attached to the corresponding upper and lower jaws where the flexible circuit electrodes comprise electrically insulative elements (e.g., insulative elements to establish desired gaps between electrodes in bipolar electrosurgical instruments), according to one aspect of the present disclosure.

Still with reference to FIGS. 35-36, utilizing flex circuit technology provides a means to manufacture the low cost electrode 600 assembly with control over the geometry of the elements 606. Tissue sticking may be a function of the surface area of the electrode 600. This manufacturing method provides a high degree of control over this variable. Thus, the low cost RF electrode 600 provides superior sealing with potentially less sticking.

The examples described in connection with FIGS. 36-40 illustrate various geometric patterns or configurations of electrically insulative elements to insulate the upper and lower jaw from shorting, provide a predetermined gap between the upper and lower jaw, and/or assist tissue gripping. Please not that the upper and lower jaws could both contain these patterns such that they offset from one another.

Figure 37:
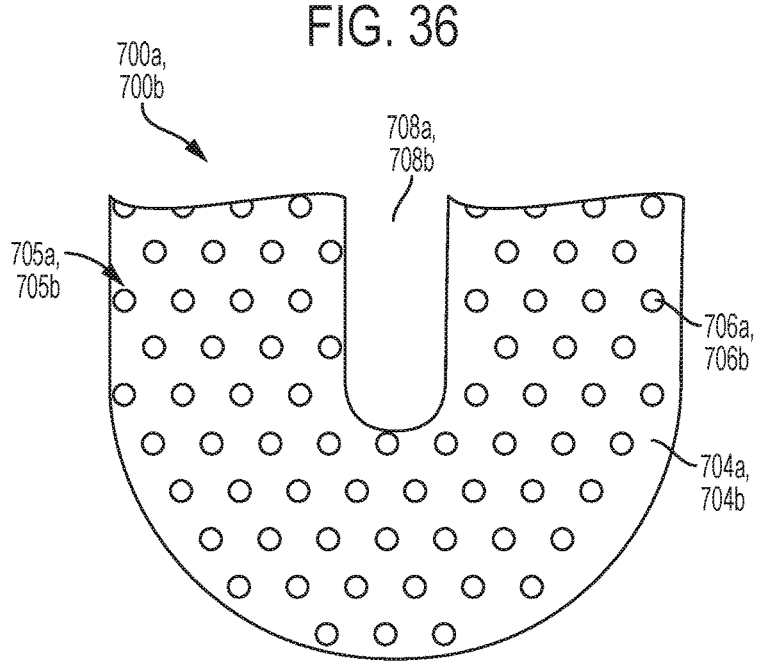
FIG. 37 is a plan view of the flexible circuit electrode comprising a macro pattern of electrically insulative elements showing the tissue contacting surface thereof, according to one aspect of the present disclosure.
Figure 38:
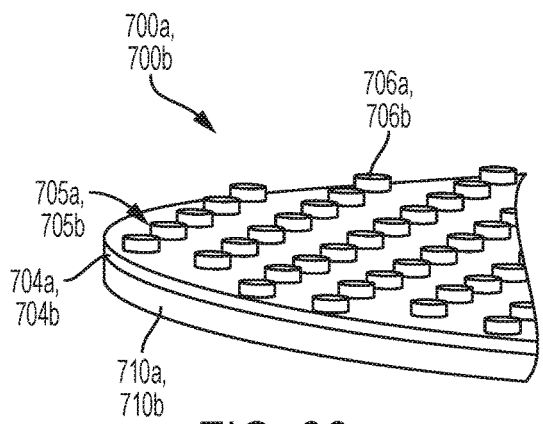
FIG. 38 is a detail view of the flexible circuit electrode shown in FIG. 37, according to one aspect of the present disclosure.

FIG. 36 is a schematic diagram of an end effector 720 comprising an upper jaw 720a and a lower jaw 720b and flexible circuit electrodes 700a, 700b attached to the corresponding upper and lower jaws 720a, 720b where the flexible circuit electrodes 700a, 700b comprise electrically insulative elements 706a, 706b (e.g., insulative elements to establish desired gaps between electrodes in bipolar electrosurgical instruments), according to one aspect of the present disclosure. FIG. 37 is a plan view of the flexible circuit electrode 700a, 700b comprising a macro pattern of electrically insulative elements 706a, 706b showing the tissue contacting surface thereof, according to one aspect of the present disclosure. FIG. 38 is a detail view of the flexible circuit electrode 700a, 700b shown in FIG. 37, according to one aspect of the present disclosure.

With reference to FIGS. 36-38, the end effector 720 comprises flexible circuit electrodes 700a, 700b on the upper and lower jaws 720a, 720b. The flexible circuit electrodes 700a, 700b each comprises an electrically conductive element 704a, 704b and a macro pattern of electrically insulative elements 706a, 706b formed on a surface of the As shown in FIG. 37, one or both of the electrically conductive elements 704a, 704b. The tissue contacts the conductive elements 704a, 704b between the electrically insulative elements 706a, 706b. As shown particularly in FIG. 38, electrically insulative elements 710a, 710b are attached or bonded to the conductive elements 704a, 704b on the side that is opposite side of the tissue contacting side.

In one aspect, electrically insulative layers 705a, 705b may be provided on the least one electrically conductive elements 704a, 704b to prevent electrically shorting the jaw member electrodes when they are in a closed configuration. In another aspect, the electrically insulative layers 705a, 705b defines electrically insulative elements 706a, 706b to establish a predetermined gap between the jaws 720a, 720b of a bipolar electrosurgical instrument. In yet another aspect, the electrically insulative layers 705a, 705b may be configured as an electrically insulative cover that further defines the electrically conductive elements 704a, 704b and can act as a spacer. The electrically insulative elements 706a, 706b may be defined by the corresponding electrically insulative layers 705a, 705b and can be configured as an electrically insulative barrier between the jaw electrodes, provide a predetermined gap between the jaw electrodes, and/or assist tissue grasping between the jaw electrodes. In one aspect, the electrically insulative elements 706a, 706b may comprise a nonstick coating or may be formed of a nonstick material such as TEFLON to prevent tissue from sticking thereto. In one aspect, the electrically insulative elements 706a, 706b may be formed of a dielectric material.

In one aspect, the electrically insulative layers 705a, 705b may be formed by bonding dielectric cover films on the electrically conductive elements 704a, 704b. In one aspect, the electrically insulative elements 706a, 706b may be formed by etching the dielectric cover films bonded to the electrically conductive elements 704a, 704b. In one aspect, at least one of the electrically conductive elements 704a, 704b may be configured as a spacer to provide a predetermined gap between upper and lower electrodes.

The electrically conductive elements 704a, 704b comprise electrically conductive material such as copper, gold plated copper, silver, platinum, stainless steel, aluminum, or any suitable electrically conductive biocompatible material, for example. One or more than one of the electrically conductive elements 704*a*, 704*b* may be configured and arranged to define a conductive electrode.

Figures 39, 40:
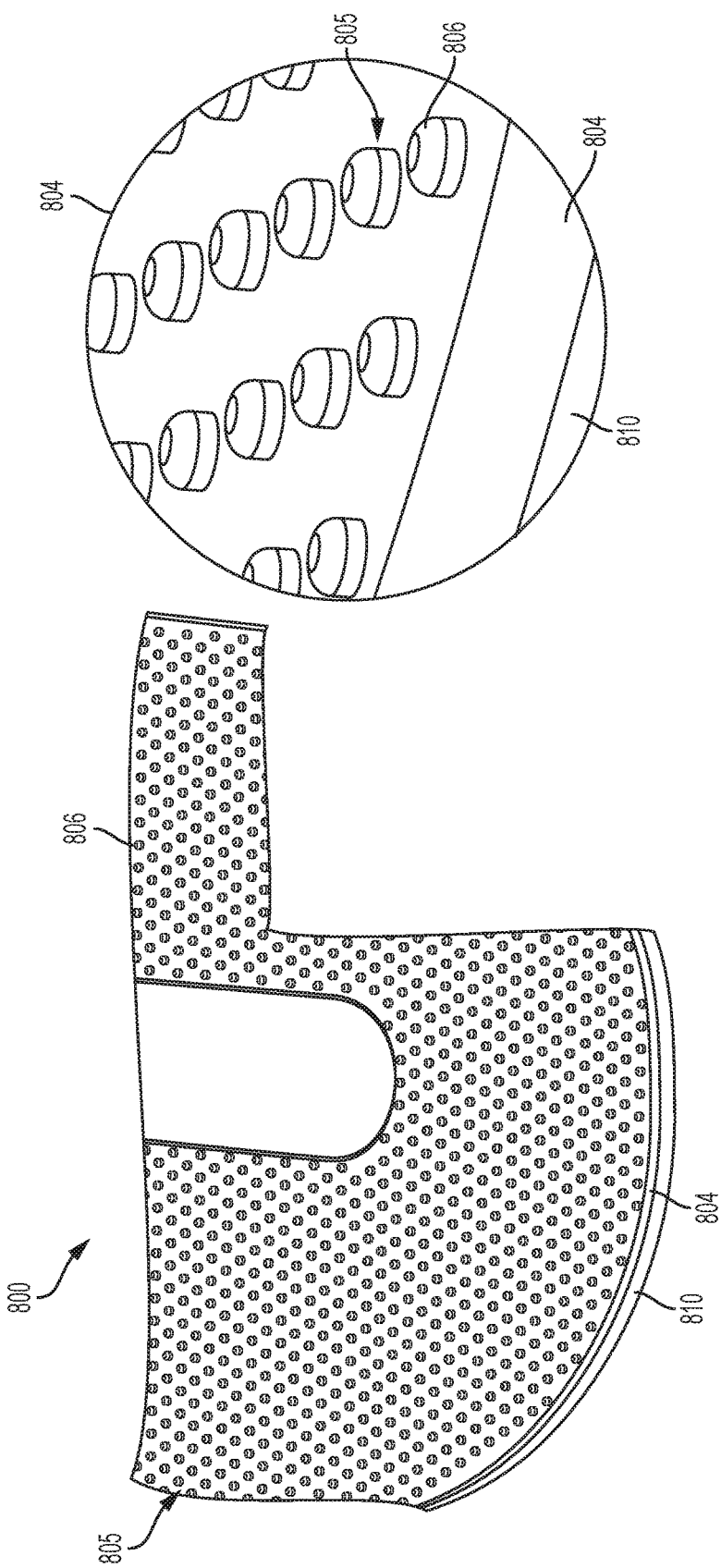
FIG. 39 illustrates a flexible circuit electrode comprising a pattern of electrically insulative elements, according to one aspect of the present disclosure.
FIG. 40 is a detail view of the flexible circuit electrode shown in FIG. 39, according to one aspect of the present disclosure.

FIG. 39 illustrates a flexible circuit electrode 800 comprising a pattern of electrically insulative elements 806 (e.g., insulative elements to establish desired gaps between electrodes in bipolar electrosurgical instruments), according to one aspect of the present disclosure. FIG. 40 is a detail view of the flexible circuit electrode 800 shown in FIG. 39, according to one aspect of the present disclosure.

With reference now to FIGS. 39 and 40, the flexible electrode 800 comprises a pattern of electrically insulative elements 806 formed on at least one electrically conductive element 804. The pattern of electrically insulative elements 806 can be uniform or substantially evenly distributed across the flexible circuit electrode 800 and comprises ten or more electrically insulative elements 806, for example. An electrically insulative element 810 is attached or bonded to the electrically conductive element 810 on the side that is opposite to the tissue contacting side. As shown particularly in FIG. 40, the electrically insulative elements 806 have a cylindrical lower portion and a dome-like upper portion with a flat section thereon. The electrically insulative elements 806 have a diameter ranging from ~0.001" to ~0.002" and a height ranging from ~0.002" to ~0.0025", for example.

In one aspect, an electrically insulative layer 805 may be provided on the at least one electrically conductive element 804 to prevent electrically shorting the jaw member electrodes when they are in a closed configuration. In another aspect, the electrically insulative layer 805 defines at least one electrically insulative element 806 to establish a predetermined gap between the jaw electrodes of a bipolar electrosurgical instrument. In yet another aspect, the electrically insulative layer 805 may be configured as an electrically insulative cover that further defines the electrically conductive element 804 and can act as a spacer. The electrically insulative element 806 may be defined by the electrically insulative layer 805 and can be configured as an electrically insulative barrier between the jaw electrodes, provide a predetermined gap between the jaw electrodes, and/or assist tissue grasping between the jaw electrodes. In one aspect, the electrically insulative elements 806 may comprise a nonstick coating or may be formed of a nonstick material such as TEFLON to prevent tissue from sticking thereto. In one aspect, the electrically insulative elements 806 may be formed of a dielectric material.

In one aspect, the electrically insulative layer 805 may be formed by bonding a dielectric cover film on the electrically conductive element 804. In one aspect, the electrically insulative elements 806 may be formed by etching the dielectric cover film bonded to the electrically conductive element 804. In one aspect, at least one of the electrically insulative elements 806 may be configured as a spacer to provide a predetermined gap between upper and lower electrodes.

The electrically conductive element 804 comprises electrically conductive material such as copper, gold plated copper, silver, platinum, stainless steel, aluminum, or any suitable electrically conductive biocompatible material, for example. One or more than one of the electrically conductive elements 804 may be configured and arranged to define a conductive electrode.

Figure 41:
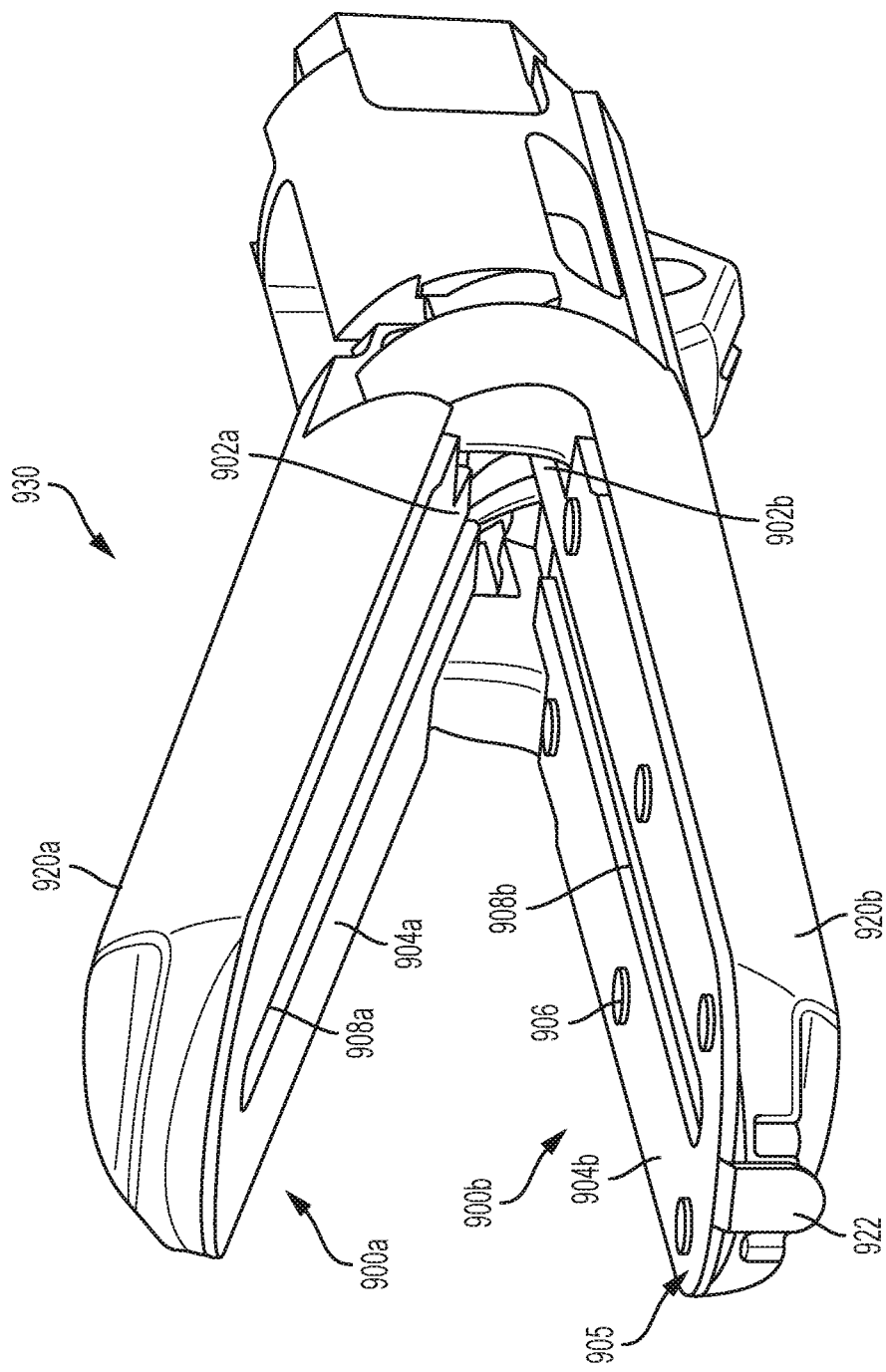
FIG. 41 illustrates an end effector comprising an upper jaw and a lower jaw and flexible circuit electrodes attached to the corresponding upper and lower jaws and where the with the flexible circuit electrode attached to the lower jaw comprises a thermal isolation and a distal electrode element, according to one aspect of the present disclosure.

V. Flexible Circuit Electrode Including Thermal Isolation and Distal Electrode Element A. End Effector Including Thermally Isolated Flexible Circuit Electrodes and Distal Electrode Element FIG. 41 illustrates an end effector 930 comprising an upper jaw 920*a* and a lower jaw 920*b* and flexible circuit electrodes 900*a*, 900*b* attached to the corresponding upper and lower jaws 920*a*, 920*b*, and where the flexible circuit electrode 900*b* attached to the lower jaw 920*b* comprises a thermal isolation and a distal electrode element 922 or element having a tongue configuration, according to one aspect of the present disclosure. The upper and lower electrode 900*a*, 900*b* comprises a knife slot 908*a*, 908*b*. The lower jaw 920*b* electrode 900*b* comprises a plurality of electrically insulative elements 906 (e.g., insulative elements to establish desired gaps between electrodes in bipolar electrosurgical instruments). Each of upper and lower jaw 920*a*, 920*b* electrodes 900*a*, 900*b* comprises a lead 902*a*, 902*b* to connect the electrodes 900*a*, 900*b* to an RF energy source.

During use of RF electrosurgical instruments, the thermal mass of the jaws can cause thermal imbalances of the heat flow from and into the tissue. Employing flexible circuit technology, the flexible circuit electrode 900*a*, 900*b* can be applied to both the upper and lower jaws 920*a*, 920*b* to thermally isolate the jaws 920*a*, 920*b* from the electrically conductive elements 904*a*, 904*b*, which define the electrode tissue sealing surfaces, thus ensuring that more heat is applied to the tissue and not lost through thermal conductivity in the jaws 920*a*, 920*b*. Examples of potential material for the electrodes 900*a*, 900*b* include Pyralux LF9250 and Pyralux LF9230 both sold by DuPont.

In one aspect, an electrically insulative layer 905 may be provided on the at least one electrically conductive element 904*b* to prevent electrically shorting the electrically conductive element 904*a*, 904*b* of the jaw member electrodes when they are in a closed configuration. In another aspect, the electrically insulative layer 905 defines at least one electrically insulative element 906 to establish a predetermined gap between the jaw electrodes of a bipolar electrosurgical instrument. In yet another aspect, the electrically insulative layer 905 may be configured as an electrically insulative cover that further defines the electrically conductive element 904*a*, 904*b* and can act as a spacer. The electrically insulative element 906 may be defined by the electrically insulative layer 905 and can be configured as an electrically insulative barrier between the jaw electrodes, provide a predetermined gap between the jaw electrodes, and/or assist tissue grasping between the jaw electrodes. In one aspect, the electrically insulative element 906 may comprise a nonstick coating or may be formed of a nonstick material such as TEFLON to prevent tissue from sticking thereto.

The electrically conductive elements 904*a*, 904*b* each comprises electrically conductive material such as copper, gold plated copper, silver, platinum, stainless steel, aluminum, or any suitable electrically conductive biocompatible material, for example. One or more than one of the electrically conductive elements 904*a*, 904*b* may be configured and arranged to define a conductive electrode.

Figure 42:
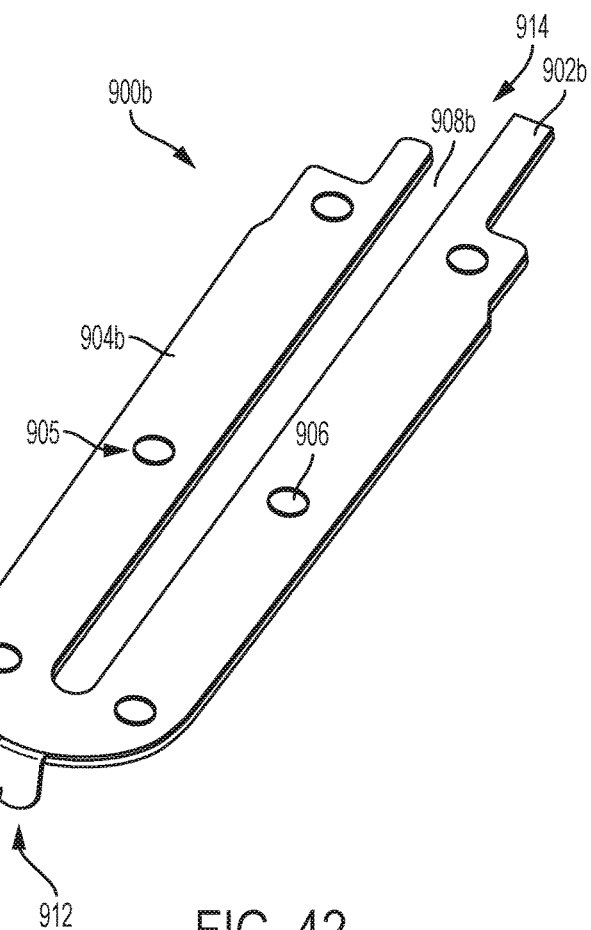
Figure 43:
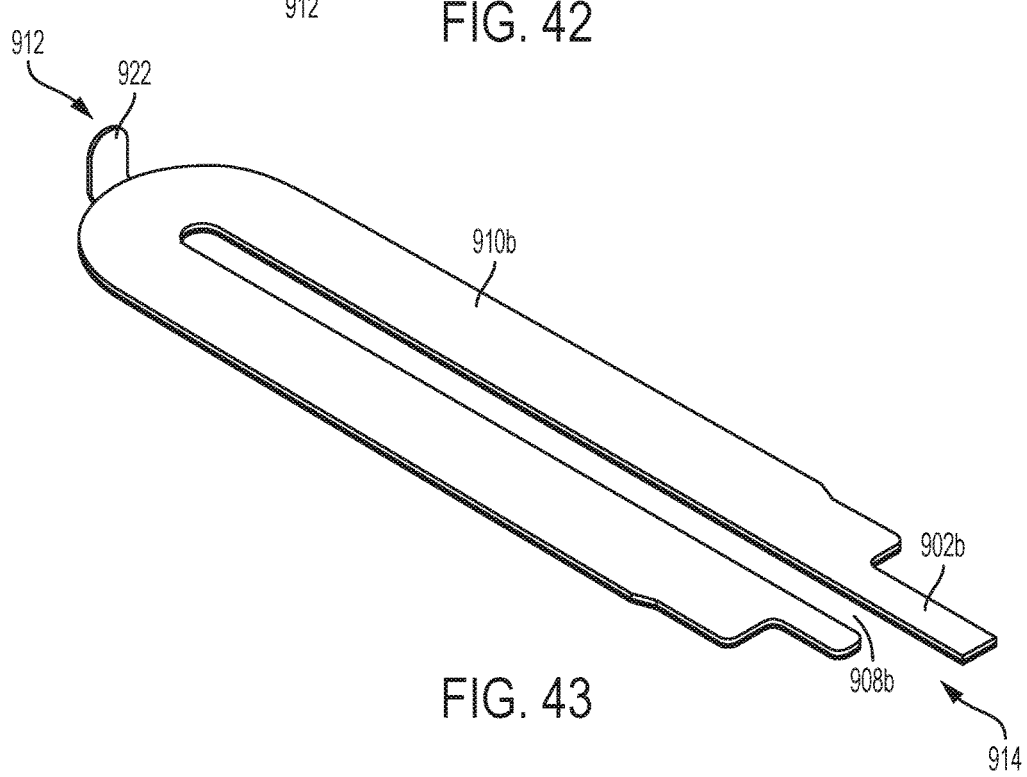

FIGS. 42-48 illustrate a flexible circuit electrode 900*b* comprising a distal electrode element 922 and electrically insulative elements 906, according to one aspect of the present disclosure. FIG. 42 is a perspective view of a flexible circuit electrode 900*b* comprising a distal electrode element 922 and electrically insulative elements 906 showing the electrically conductive element 904b that defines the electrode tissue sealing surface, according to one aspect of the present disclosure. FIG. 43 is a perspective view of the electrically insulative element 906 of the flexible circuit electrode 900b shown in FIG. 42, according to one aspect of the present disclosure.

FIG. 44 is a plan view of the electrically conductive element 904b side of the flexible circuit electrode 900b shown in FIG. 42, according to one aspect of the present disclosure. FIG. 45 is a plan view of the electrically insulative element 910b of the flexible circuit electrode 900b shown in FIG. 42, according to one aspect of the present disclosure.

FIG. 46 is a side elevation view of the flexible circuit electrode 900b shown in FIG. 42, according to one aspect of the present disclosure. FIG. 47 is an elevation view of the flexible circuit electrode 900b shown in FIG. 42 taken from a distal end 912, according to one aspect of the present disclosure. FIG. 48 is an elevation view of the flexible circuit electrode 900b shown in FIG. 42 taken from a proximal end 914, according to one aspect of the present disclosure.

With reference now to FIGS. 42-48, the flexible circuit electrode 900b comprises a lead 902b for connecting the electrode 900b to an energy source, such, for example, a radio frequency (RF) generator that outputs enough power to seal tissue. The short lead 902b enables the electrode 900b to be connected to the energy source near the distal end of the end effector. A longer lead may be provided where it is desirable to connect the electrode 900b to an energy source at the handle portion of the electrosurgical device.

The electrode 900b can be attached either to the upper jaw member, the lower jaw member, or both, of a clamp jaw assembly of the electrosurgical instrument, as shown in FIG. 41, for example. In one aspect, an electrically insulative layer 905 may be provided on the at least one electrically conductive element 904 to prevent electrically shorting the jaw member electrodes when they are in a closed configuration. In another aspect, the electrically insulative layer 905 defines at least one electrically insulative element 906 to establish a predetermined gap between the jaw electrodes of a bipolar electrosurgical instrument. In yet another aspect, the electrically insulative layer 905 may be configured as an electrically insulative cover that further defines the electrically conductive element 904b and can act as a spacer. The electrically insulative element 906 may be defined by the electrically insulative layer 905 and can be configured as an electrically insulative barrier between the jaw electrodes, provide a predetermined gap between the jaw electrodes, and/or assist tissue grasping between the jaw electrodes. In one aspect, the electrically insulative element 906 may comprise a nonstick coating or may be formed of a nonstick material such as TEFLON to prevent tissue from sticking thereto. In one aspect, the electrically insulative elements 906 may be formed of a dielectric material.

In one aspect, the electrically insulative layer 905 may be formed by bonding a dielectric cover film on the electrically conductive element 904b. In one aspect, the electrically insulative elements 906 may be formed by etching the dielectric cover film bonded to the electrically conductive element 904b. In one aspect, at least one of the electrically insulative elements 906 may be configured as a spacer to provide a predetermined gap between upper and lower electrodes.

The electrically conductive element 904b comprises the non-isolated distal electrode element 922. The electrically conductive element 904b comprises electrically conductive material such as copper, gold plated copper, silver, platinum, stainless steel, aluminum, or any suitable electrically conductive biocompatible material, for example. One or more than one of the electrically conductive elements 904a, 904b may be configured and arranged to define a conductive electrode.

The flexible circuit electrode 900b further comprises a knife slot 908b. The knife portion of the electrosurgical instrument 2 (FIG. 1A) is slidably movable within the knife slot 908b to cut the tissue after it has been sealed using electrosurgical energy. The flexible circuit electrode 900b defines the knife slot 908b and extends along a length of the electrode 900b. Although generally speaking the knife slot 908b is laterally centered, this is not necessarily always the case, and in other aspects, the knife slot 908b may be laterally offset from center.

The electrically insulative element 910b of the flexible circuit electrode 900b is formed of electrically insulative material such as a polymer and more specifically can be an electrically insulative material (e.g., polyimide, polyester, fluorocarbon, or any polymeric material, or any combinations thereof). The electrically insulative element 910b is generally attached to the tissue contacting side of the upper or lower jaw members of the clamp jaw assembly.

Figure 50:
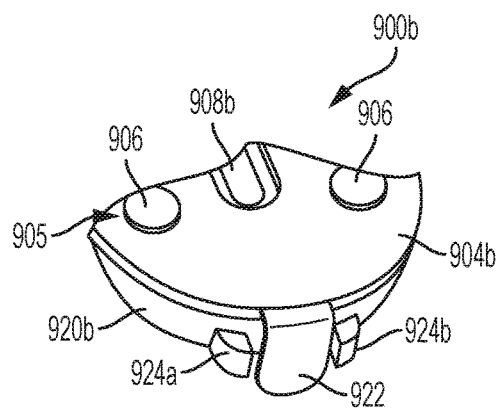
Figure 51:
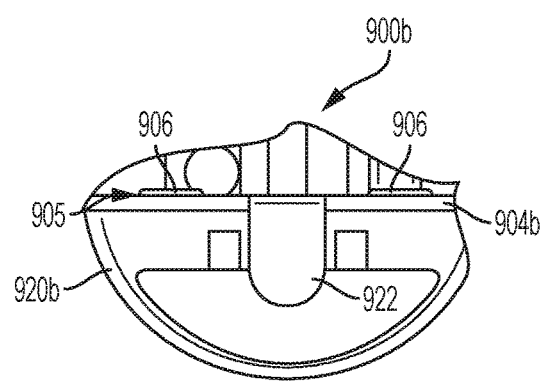

B. End Effector Including a Flexible Circuit Electrode Including Non-Isolated Distal Electrode Element and Electrically Insulative Elements FIGS. 49-51 illustrate detail views of a lower jaw portion 920b of the end effector 930 (FIG. 41) comprising a flexible circuit electrode 904b comprising a non-isolated distal electrode element 922 and electrically insulative elements 906, according to one aspect of the present disclosure.

Figure 49:
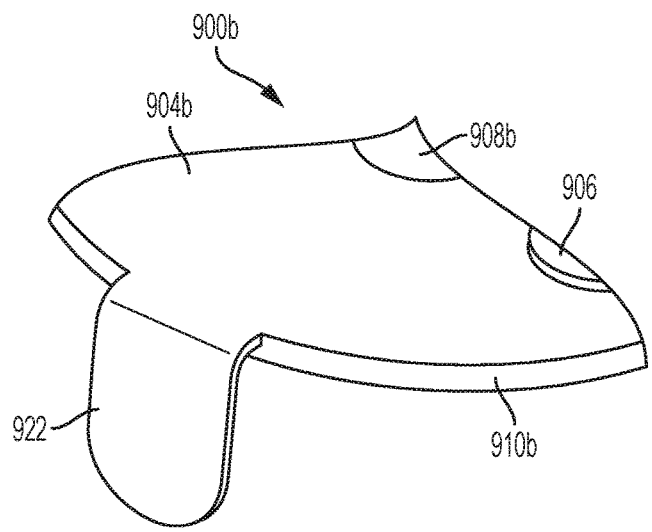
FIGS. 49-51 illustrate detail views of a lower jaw portion of an end effector comprising a flexible circuit electrode comprising a non-isolated distal electrode element and electrically insulative elements, according to one aspect of the present disclosure, where.

FIG. 49 is a perspective view of a flexible circuit electrode 904b comprising a non-isolated distal electrode element 922, electrically insulative elements 906, and a knife slot 908b according to one aspect of the present disclosure. FIG. 50 is a perspective view of the lower jaw 920b, according to one aspect of the present disclosure. FIG. 51 is an elevation view of the lower jaw 920b of the end effector 930 shown in FIG. 49 taken from a distal end, according to one aspect of the present disclosure. The distal end of the lower jaw 920b comprises projections 924a, 924b on either side of the non-isolated distal electrode element 922. As previously described, in one aspect, an electrically insulative layer 905 may be provided on the at least one electrically conductive element 904b to prevent electrically shorting the electrically conductive element 904a, 904b of the jaw member electrodes when they are in a closed configuration.

Figure 52:
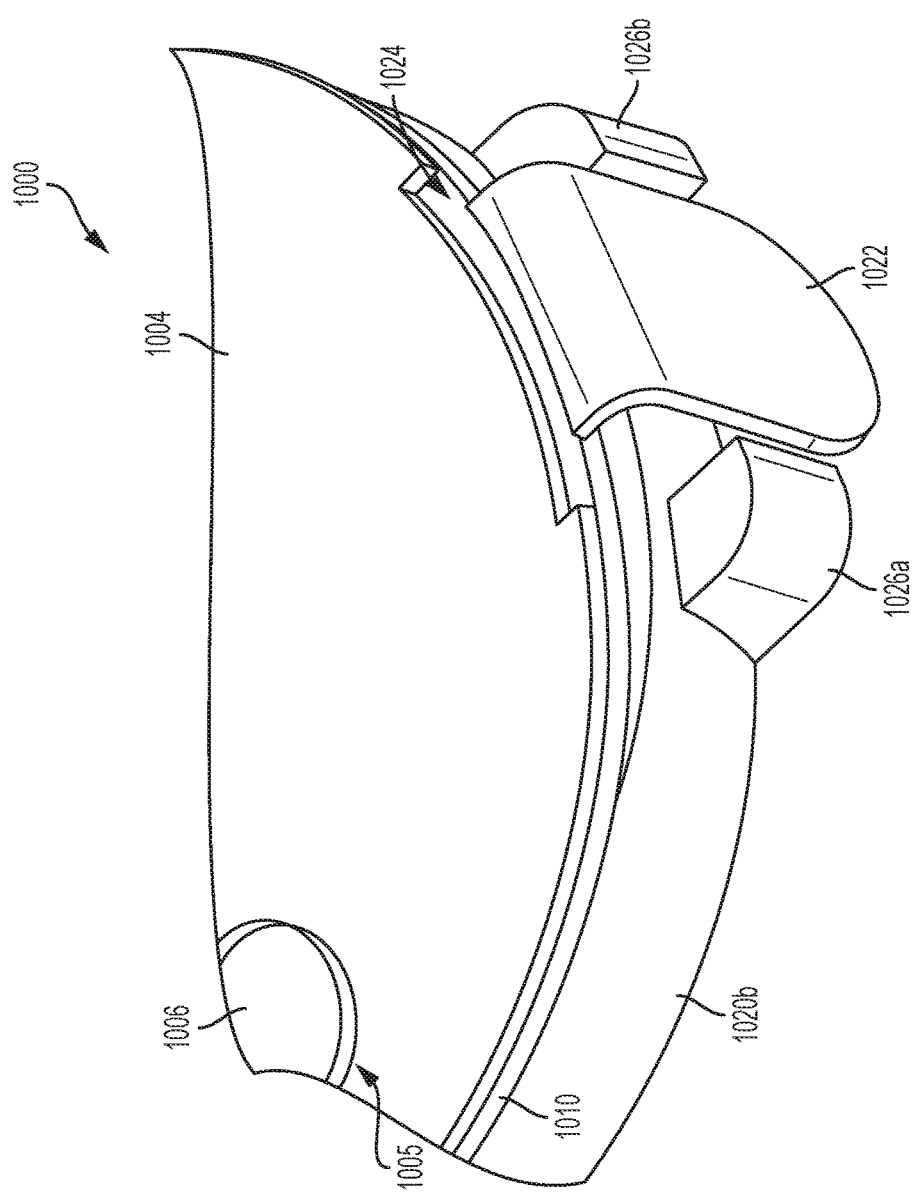
FIG. 52 is a perspective view of a lower jaw portion of an end effector comprising an isolated distal electrode element, according to one aspect of the present disclosure.

FIG. 52 is a perspective view of a lower jaw portion 1020b of an end effector comprising an isolated distal electrode element 1022, according to one aspect of the present disclosure. A flexible circuit electrode assembly 1000 comprises a primary electrode 1004 and a second electrode configured as an isolated distal electrode element 1022 at the distal end of the flexible circuit electrode assembly 1000. The distal electrode element 1022 is electrically and thermally isolated from the primary electrode 1004, which is employed as the main tissue sealing surface. An adhesive layer 1010 is provided between the primary electrode 1004 and the lower jaw member 1020b. The electrically insulative elements 1006 also are disposed on the tissue contacting surface of the flexible circuit electrode assembly 1000. The electrically insulative elements 1006 are sized and configured to prevent electrical shorting of the upper electrode with the primary electrode 1004 and to set a predetermined gap between the upper and lower jaw members 1020b (only the lower jaw member 1020b is shown for clarity of disclosure). A gap 1024 is provided between the distal electrode element 1022 and the primary electrode 1004 to thermally and electrically the distal electrode element 1022 and the primary electrode 1004. The distal end of the lower jaw 1020b comprises projections 1026a, 1026b on either side of the isolated distal electrode element 1022.

In one aspect, an electrically insulative layer 1005 may be provided on the at least one electrically conductive element 1004 to prevent electrically shorting the electrically conductive elements of the jaw member electrodes when they are in a closed configuration. In another aspect, the electrically insulative layer 1005 defines at least one electrically insulative element 1006 to establish a predetermined gap between the jaw electrodes of a bipolar electrosurgical instrument. In yet another aspect, the electrically insulative layer 1005 may be configured as an electrically insulative cover that further defines the electrically conductive element 1004 and can act as a spacer. The electrically insulative element 1006 may be defined by the electrically insulative layer 1005 and can be configured as an electrically insulative barrier between the jaw electrodes, provide a predetermined gap between the jaw electrodes, and/or assist tissue grasping between the jaw electrodes. In one aspect, the electrically insulative elements 1006 may comprise a nonstick coating or may be formed of a nonstick material such as TEFLON to prevent tissue from sticking thereto. In one aspect, the electrically insulative elements 1006 may be formed of a dielectric material.

In one aspect, the electrically insulative layer 1005 may be formed by bonding a dielectric cover film on the electrically conductive element 1004. In one aspect, the electrically insulative elements 1006 may be formed by etching the dielectric cover film bonded to the electrically conductive element 1004. In one aspect, at least one of the electrically insulative elements 1006 may be configured as a spacer to provide a predetermined gap between upper and lower electrodes.

The electrically conductive element 1004 each comprises electrically conductive material such as copper, gold plated copper, silver, platinum, stainless steel, aluminum, or any suitable electrically conductive biocompatible material, for example. One or more than one of the electrically conductive elements 1004 may be configured and arranged to define a conductive electrode.

VI. Flexible Circuit Electrodes with Flexure Bearing

A. Flexible Circuit Electrode Including Upper and Lower Electrodes Coupled by Lateral Flexure Bearing FIGS. 53-59 illustrate a flat flexible circuit electrode 1100 comprising an upper electrode 1100a and a lower electrode 1100b coupled by a flexure bearing 1128, according to one aspect of the present disclosure. The flexure bearing 1128 connects upper and lower flat flexible circuit electrodes 1104a, 1104b that are spaced apart laterally relative to the flexure bearing 1128.

FIG. 53 is a perspective view of the flat flexible circuit electrode 1100 comprising an upper flat flexible circuit electrode 1104a and a lower flat flexible circuit electrode 1104b showing the electrically conductive elements 1104a, 1104b side, which define the electrodes tissue sealing surfaces, according to one aspect of the present disclosure. FIG. 54 is a perspective view showing the electrically insulative element 1106a, 1106b side of the upper and lower flat flexible circuit electrodes 1104a, 1104b shown in FIG. 53, according to one aspect of the present disclosure.

Figure 55:
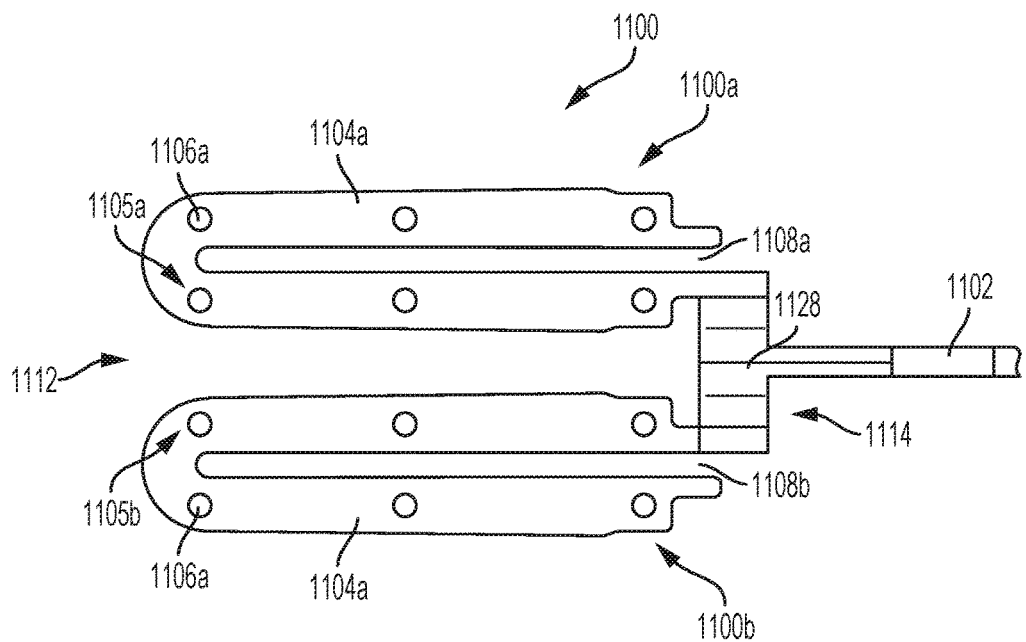
Figure 56:
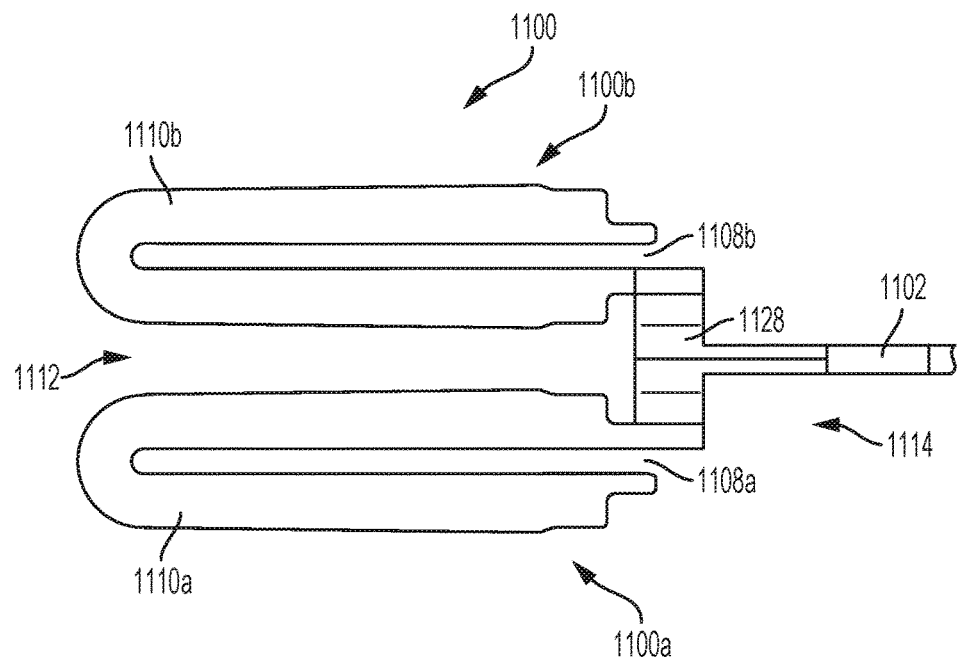

FIG. 55 is a plan view of the electrically conductive elements 1104a, 1104b side of the upper and lower flat flexible circuit electrodes 1100a, 1100b shown in FIG. 53, according to one aspect of the present disclosure. FIG. 56 is a plan view of the electrically insulative element side 1110a, 1110b of the upper and lower flat flexible circuit electrodes 1100a, 1100b shown in FIG. 53, according to one aspect of the present disclosure.

FIG. 57 is a side elevation view of the upper and lower flat flexible circuit electrodes 1100a, 1100b shown in FIG. 53, according to one aspect of the present disclosure. FIG. 58 is an elevation view of the upper and lower flat flexible circuit electrodes 1100a, 1100b shown in FIG. 53 taken from a distal end 1112, according to one aspect of the present disclosure. FIG. 59 is an elevation view of the upper and lower flat flexible circuit electrodes shown in FIG. 53 taken from a proximal end 1114, according to one aspect of the present disclosure.

With reference now to FIGS. 53-59, the flat flexible circuit electrode 1100 comprises two separate electrodes, an upper flat flexible electrode 1100a and a lower flat flexible electrode 1100b that are coupled by a flexure bearing 1128 connecting the two electrodes 1100a, 1100b. In one aspect the flexure bearing 1128 may be a flexure bearing. The flat flexible circuit electrode 1100 comprises a lead 1102 for connecting the upper and lower electrodes 1100a, 1100b to an energy source, such, for example, a radio frequency (RF) generator that outputs enough power to seal tissue. The long lead 1102 enables the upper and lower electrodes 1100a, 1100b to be connected to the energy source at the handle portion of the electrosurgical device. A shorter longer lead may be provided where it is desirable to connect the electrodes 1100a, 1100b to an energy source near the distal end of the end effector.

The upper electrode 1100a can be attached to the upper jaw member and the lower electrode 1100b can be attached to the lower jaw member of a clamp jaw assembly of the electrosurgical instrument, for example. The upper electrode 1100a comprises an electrically conductive element 1104a that includes electrically insulative elements 1106a (e.g., insulative rings to establish desired gaps between electrodes in bipolar electrosurgical instruments) and the lower electrode 1100b comprises an electrically conductive element 1104b that includes electrically insulative elements or 1106b provided thereon. The electrically insulative elements 1106a, 1106b prevent the electrically conductive elements 1104a, 1104b from electrically shorting when the jaw members are in a closed configuration. The electrically insulative elements 1106a, 1106b may be made of a dielectric nonstick material. The electrically conductive elements 1104a, 1104b comprise electrically conductive materials such as copper, gold plated copper, silver, platinum, stainless steel, aluminum, or any suitable electrically conductive biocompatible material, for example.

Each of the upper and lower flat flexible circuit electrodes 1100a, 1100b further comprise knife slots 1108a, 1108b. The knife portion of the electrosurgical instrument 2 (FIG. 1A) is slidably movable within the knife slots 1108a, 1108b to cut the tissue after it has been sealed using electrosurgical energy. The flat flexible circuit electrodes 1100a, 1100b each define a knife slot 1108a, 1108b and extends along a length of the electrode 1100. Although generally speaking the knife slots 1108a, 1108b are laterally centered, this is not necessarily always the case, and in other aspects, the knife slots 1108a, 1108b may be laterally offset from center.

The electrically insulative elements 1106a, 1106b of the flexible circuit electrode 1100a, 1100b are formed of electrically insulative materials such as a polymer and more specifically can be an electrically insulative material (e.g., polyimide, polyester, fluorocarbon, or any polymeric material, or any combinations thereof). The electrically insulative elements 1106a, 1106b are generally attached to the tissue contacting side of the upper or lower jaw members of the clamp jaw assembly.

In one aspect, electrically insulative layers 1105a, 1105b may be provided on the electrically conductive elements 1104a, 1104b to prevent electrically shorting the electrically conductive element 1104a, 1104b of the jaw member electrodes when they are in a closed configuration. In another aspect, the electrically insulative layers 1105a, 1105b define the electrically insulative elements 1106a, 1106b to establish a predetermined gap between the jaw electrodes of a bipolar electrosurgical instrument. In yet another aspect, the electrically insulative layers 1105a, 1105b may be configured as an electrically insulative cover that further defines the electrically conductive elements 1104a, 1104b and can act as a spacer. The electrically insulative element 906 may be defined by the electrically insulative layers 1105a, 1105b and can be configured as an electrically insulative barrier between the jaw electrodes, provide a predetermined gap between the jaw electrodes, and/or assist tissue grasping between the jaw electrodes. In one aspect, the electrically insulative elements 1106a, 1106b may comprise a nonstick coating or may be formed of a nonstick material such as TEFLON to prevent tissue from sticking thereto. In one aspect, the electrically insulative elements 1106a, 1106b may be formed of a dielectric material.

In one aspect, the electrically insulative layer 1105a, 1105b may be formed by bonding a dielectric cover film on the electrically conductive element 1104a, 1104b. In one aspect, the electrically insulative elements 1106a, 1106b may be formed by etching the dielectric cover film bonded to the electrically conductive element 1104a, 1104b. In one aspect, at least one of the electrically insulative elements 1106a, 1106b may be configured as a spacer to provide a predetermined gap between upper and lower electrodes.

The electrically conductive elements 1104a, 1104b each comprises electrically conductive material such as copper, gold plated copper, silver, platinum, stainless steel, aluminum, or any suitable electrically conductive biocompatible material, for example. One or more than one of the electrically conductive elements 1104a, 1104b may be configured and arranged to define a conductive electrode.

B. Flexible Circuit Electrode Including Upper and Lower Electrodes Coupled by Longitudinal Flexure Bearing FIGS. 60-66 illustrate a flexible circuit electrode 1200 comprising a flexure bearing 1228, according to one aspect of the present disclosure. The flexure bearing 1128 connects upper and lower flat flexible circuit electrodes 1200a, 1200b that are spaced apart longitudinally relative to the flexure bearing 1228.

Figure 60:
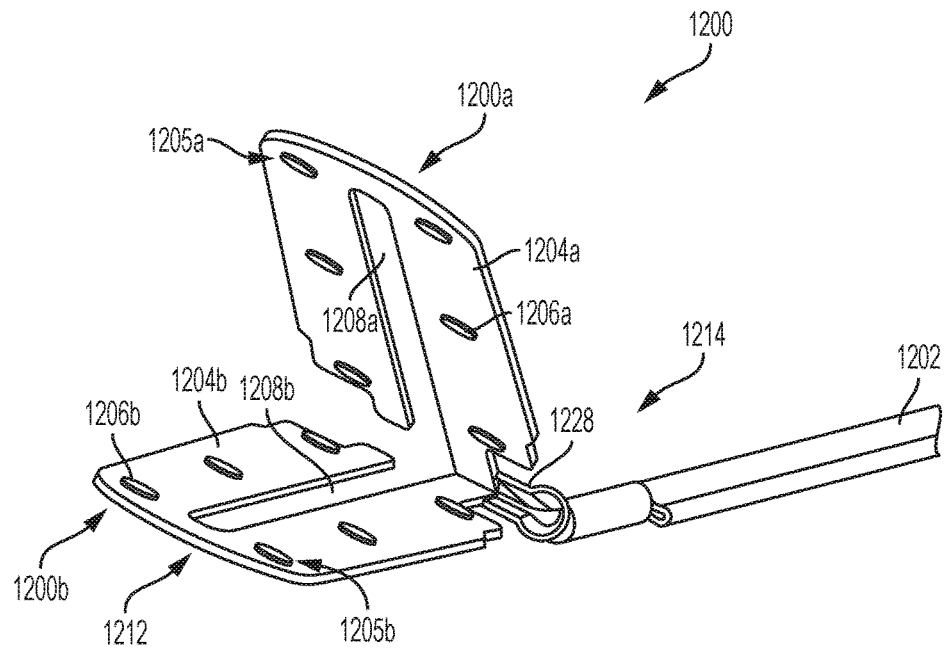
Figure 61:
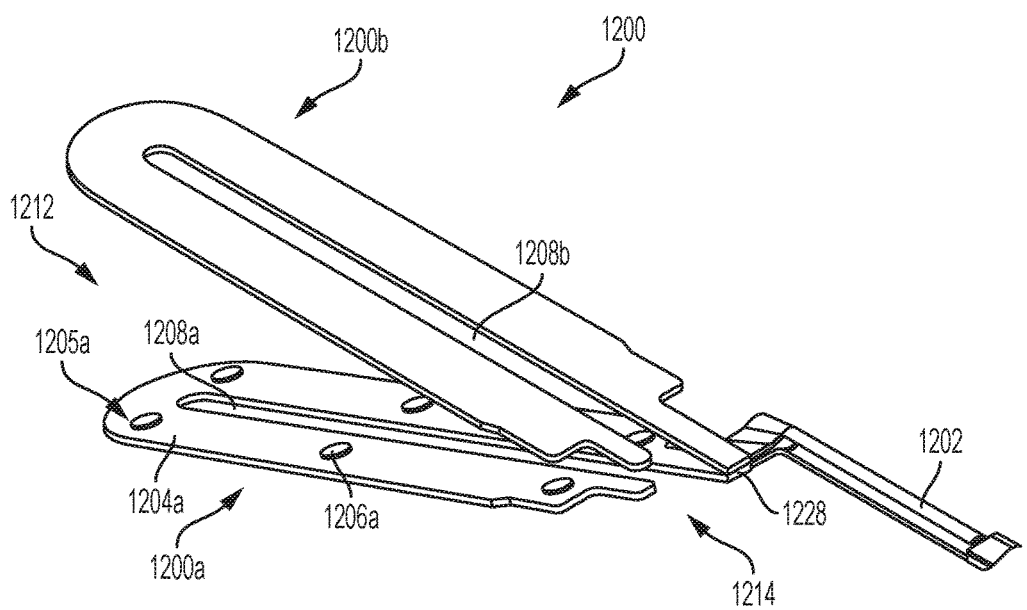

FIG. 60 is a perspective view of a flexible circuit electrode 1200 comprising upper and lower electrodes 1200a, 1200b coupled by a flexure bearing 1228 in an open configuration, according to one aspect of the present disclosure. FIG. 61 is another perspective view of the flexible circuit electrode 1200 shown in FIG. 60, according to one aspect of the present disclosure.

FIG. 62 is a plan view of the flexible circuit electrode 1200 shown in FIG. 60, according to one aspect of the present disclosure. FIG. 63 is a plan view of the flexible circuit electrode 1200 shown in FIG. 60, according to one aspect of the present disclosure.

Figure 64:
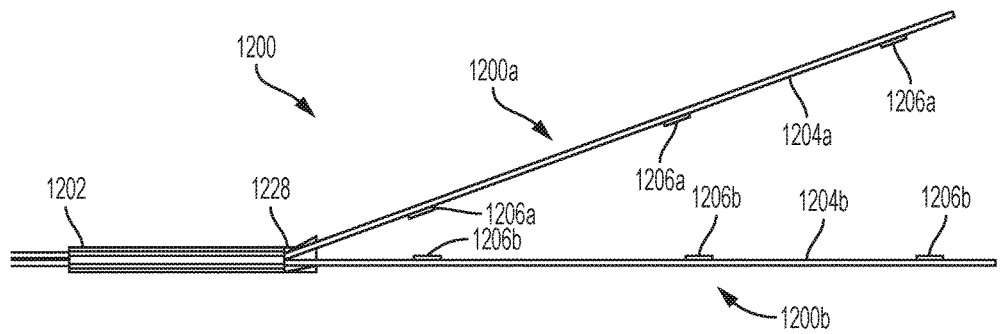
Figure 65:
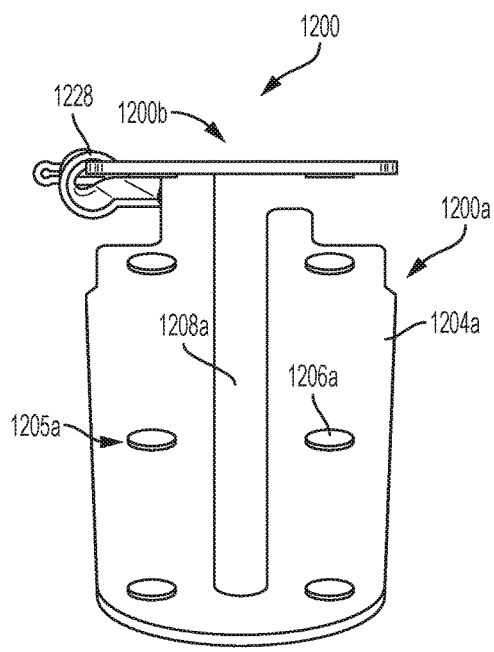

FIG. 64 is a side elevation view of the flexible circuit electrode 1200 shown in FIG. 60, according to one aspect of the present disclosure. FIG. 65 is an elevation view of the flexible circuit electrode 1200 shown in FIG. 60 taken from a distal end 1212, according to one aspect of the present disclosure. FIG. 66 is an elevation view of the flexible circuit electrode 1200 shown in FIG. 60 taken from a proximal end 1214, according to one aspect of the present disclosure.

With reference now to FIGS. 60-66 the flexible circuit electrode 1200 comprises two separate electrodes, an upper flexible electrode 1200a and a lower flexible electrode 1200b that are coupled by a flexure bearing 1228 connecting the two electrodes 1200a, 1200b. The flexible circuit electrode 1200 comprises a lead 1202 for connecting the upper and lower electrodes 1200a, 1200b to an energy source, such, for example, a radio frequency (RF) generator that outputs enough power to seal tissue. The long lead 1202 enables the upper and lower electrodes 1200a, 1200b to be connected to the energy source at the handle portion of the electrosurgical device. A shorter longer lead may be provided where it is desirable to connect the electrodes 1200a, 1200b to an energy source near the distal end of the end effector.

The upper electrode 1200a can be attached to the upper jaw member and the lower electrode 1200b can be attached to the lower jaw member of a clamp jaw assembly of the electrosurgical instrument, for example. The upper electrode 1200a comprises an electrically conductive element 1204a that includes electrically insulative elements 1206a (e.g., insulative rings to establish desired gaps between electrodes in bipolar electrosurgical instruments) and the lower electrode 1200b comprises an electrically conductive element 1204b that includes electrically insulative elements 1206b provided thereon. The electrically insulative elements 1206a, 1206b prevent the electrically conductive elements 1204a, 1204b from electrically shorting when the jaw members are in a closed configuration. The electrically insulative elements 1206a, 1206b may be made of a dielectric material, which may be coated with a nonstick material such as TEFLON. The electrically conductive elements 1204a, 1204b comprise electrically conductive materials such as copper, gold plated copper, silver, platinum, stainless steel, aluminum, or any suitable electrically conductive biocompatible material, for example.

Each of the upper and lower flexible circuit electrodes 1200a, 1200b further comprise knife slots 1208a, 1208b. The knife portion of the electrosurgical instrument 2 (FIG. 1A) is slidably movable within the knife slots 1208a, 1208b to cut the tissue after it has been sealed using electrosurgical energy. The flat flexible circuit electrodes 1200a, 1200b each define a knife slot 1208a, 1208b and extends along a length of the electrode 1200. Although generally speaking the knife slots 1208a, 1208b are laterally centered, this is not necessarily always the case, and in other aspects, the knife slots 1208a, 1208b may be laterally offset from center.

The electrically insulative elements 1206a, 1206b of the flexible circuit electrode 1200a, 1200b are formed of electrically insulative materials such as a polymer and more specifically can be an electrically insulative material (e.g., polyimide, polyester, fluorocarbon, or any polymeric material, or any combinations thereof). The electrically insulative elements 1206a, 1206b are generally attached to the tissue contacting side of the upper or lower jaw members of the clamp jaw assembly.

The flexible circuit electrode 1200 utilizes the flexible nature of the flexible-circuit electrode manufacturing technology to incorporate a variety of lead lengths and active/passive components in the electrode circuit. Exploiting the flexibility of configuration and potential cost savings of utilizing flexible circuits for bipolar electrodes 1200a, 1200b.

The flexible circuit electrode 1200 can be configured in a variety of ways. In one aspect, the length of the lead 1202 can be short, i.e., near the flexure bearing 1228 connecting the upper and lower electrodes 1200a, 1200b and enabling replaceable electrodes 1200a, 1200b and/or jaws. The length of the lead 1202 can be long, moving the termination point to the handle assembly of the electrosurgical instrument, reducing part count, electrical connection points, and enabling the inclusion of additional active components such as switches, EEPROM, etc. intimately associated with the upper and lower electrodes 1200a, 1200b.

In one aspect, an electrically insulative layers 1205a, 1205b may be provided on the electrically conductive elements 1204a, 1204b to prevent electrically shorting the electrically conductive elements of the jaw member electrodes when they are in a closed configuration. In another aspect, the electrically insulative layers 1205a, 1205b define electrically insulative elements 1206a, 1206b to establish a predetermined gap between the jaw electrodes of a bipolar electrosurgical instrument. In yet another aspect, the electrically insulative layers 1205a, 1205b may be configured as an electrically insulative cover that further defines the electrically conductive elements 1204a, 1204b and can act as a spacer. The electrically insulative elements 1206a, 1206b may be defined by the electrically insulative layers 1205a, 1205b and can be configured as an electrically insulative barrier between the jaw electrodes, provide a predetermined gap between the jaw electrodes, and/or assist tissue grasping between the jaw electrodes. In one aspect, the electrically insulative elements 1206a, 1206b may comprise a nonstick coating or may be formed of a nonstick material such as TEFLON to prevent tissue from sticking thereto. In one aspect, the electrically insulative elements 1206a, 1206b may be formed of a dielectric material.

In one aspect, the electrically insulative layers 1205a, 1205b may be formed by bonding a dielectric cover film on the electrically conductive element 1204a, 1204b. In one aspect, the electrically insulative elements 1206a, 1206b may be formed by etching the dielectric cover film bonded to the electrically conductive element 1204a, 1204b. In one aspect, at least one of the electrically insulative elements 1206a, 1206b may be configured as a spacer to provide a predetermined gap between upper and lower electrodes.

The electrically conductive elements 1204a, 1204b each comprises electrically conductive material such as copper, gold plated copper, silver, platinum, stainless steel, aluminum, or any suitable electrically conductive biocompatible material, for example. One or more than one of the electrically conductive elements 1204a, 1204b may be configured and arranged to define a conductive electrode.

VII. Vacuum Formed Flexible Circuit Electrodes

Figure 67:
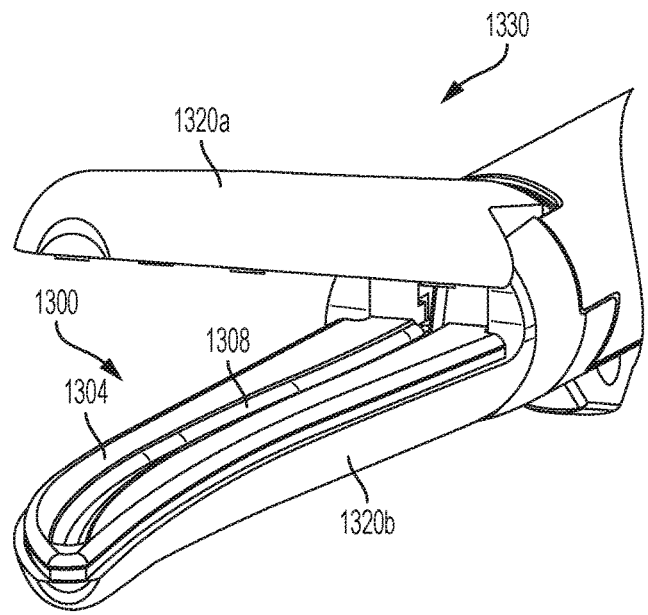
FIGS. 67-69 illustrate a vacuum formed flexible circuit electrode, according to one aspect of the present disclosure, where.
Figure 68:
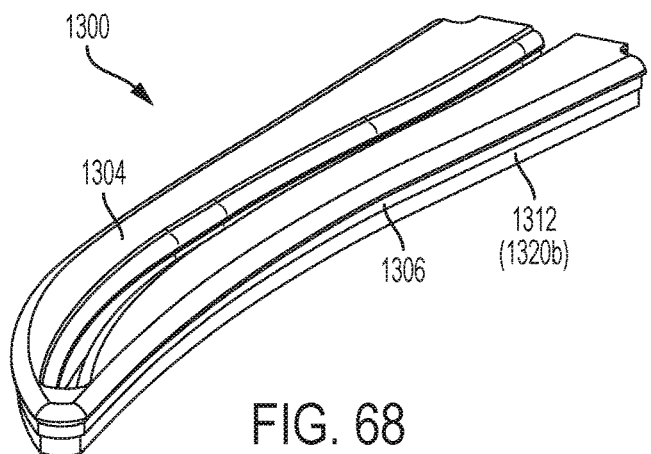
Figure 69:
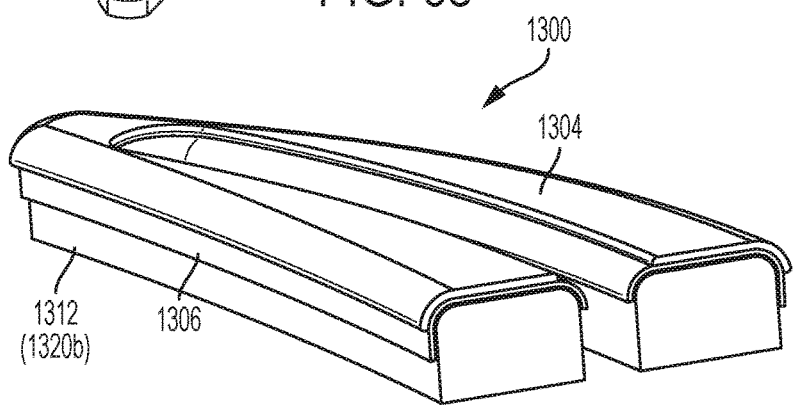

FIGS. 67-69 illustrate a vacuum formed flexible circuit electrode 1300, according to one aspect of the present disclosure. FIG. 67 is a perspective view of an end effector 1330 comprising a vacuum formed flexible circuit electrode 1300, according to one aspect of the present disclosure. The end effector 1330 comprises an upper jaw 1320a and a lower jaw 1320b. The upper and lower jaws 1320a, 1320b each may comprise vacuum formed flexible circuit electrode 1300. The end effector 1330 comprises a knife slot 1308. The upper jaw 1320a is movable from an open position to a closed position and vice-versa relative to the lower jaw 1320b.

FIG. 68 is a vacuum formed flexible circuit electrode 1300 disposed over a insert molded support 1312 or jaw 1320b, according to one aspect that can be inserted in an injection molding tool, according to one aspect of the present disclosure. FIG. 68 is another view of the vacuum formed flexible circuit electrode 1300 shown in FIG. 68, according to one aspect of the present disclosure. The vacuum formed flexible electrode 1300 comprises an electrical conductive element 1304 disposed over a flexible circuit substrate 1306 which is placed over an insert molded support 1312 or the jaw 1320b.

In one process, the vacuum formed flexible circuit electrode 1300 can be incorporated with the lower jaw 1320b, or the upper jaw 1320a (FIG. 67). First, the flexible circuit 1300 is vacuum formed to create a desired profile. That profile is then placed in an injection molding tool to create a substrate to support that shape. The flexible circuit electrode 1300 is then trimmed and the assembly is bonded to a jaw 1320a, 1320b by an adhesive, a second overmold step, or some other technique. A first manufacturing process can be carried out in accordance with the following steps:

Step 1—vacuum form flexible circuit to create a desired profile;

Step 2—place profile in an injection molding tool to create a substrate to support that shape;

Step 3—Trim the flexible circuit;

Step 4—Bond the flexible circuit to a jaw with adhesive, second overmold, or other technique.

In another process, the vacuum formed flexible circuit electrode 1300 is vacuum formed, trimmed, and then adhered directly to the lower jaw 1320b, or the upper jaw 1320a (FIG. 67), of the end effector 1330 (FIG. 67) jaw assembly, via adhesive, insert molding, or some other technique. In this aspect, the jaw 1320a, 1320b would have a complimentary profile to support the flexible circuit electrode 1300 profile. A second manufacturing process can be carried out in accordance with the following steps:

Step 1—vacuum form the flexible circuit;

Step 2—trim the flexible circuit;

Step 3—Adhere the flexible circuit directly to the jaw with adhesive, insert mold, or other technique.

Figure 72:
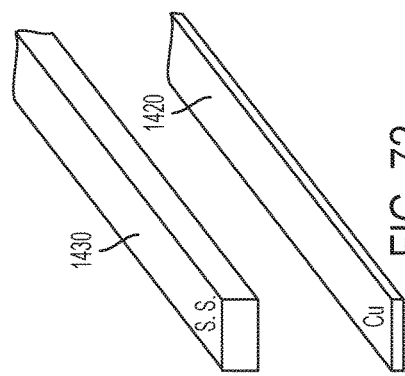

VIII. Comparison of Thin Flexible Circuit Electrodes and Thick Conventional Electrodes FIGS. 70-72 illustrate a comparison of a thin, copper flexible circuit electrode 1400 and a conventional stainless steel electrode 1430 from the standpoint of self-heating, according to one aspect of the present disclosure.

Figure 70:
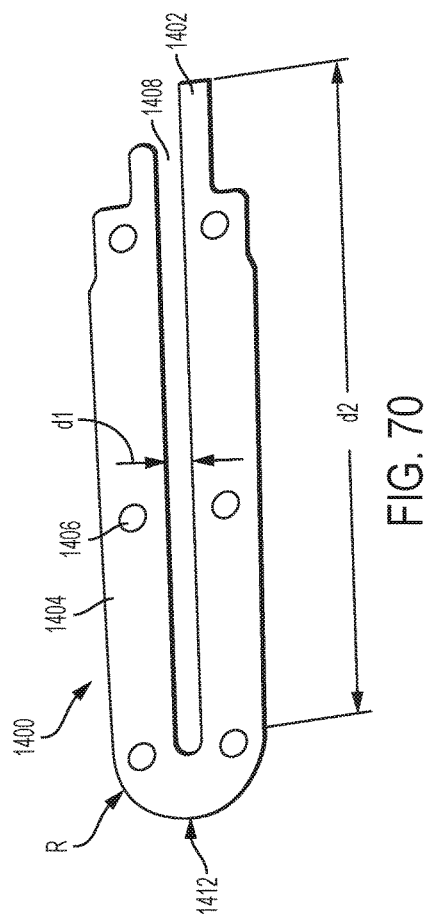
FIGS. 70-72 illustrate a comparison of a thin, copper flexible circuit electrode and a conventional stainless steel electrode from the standpoint of self-heating, according to one aspect of the present disclosure, where.
Figure 71:
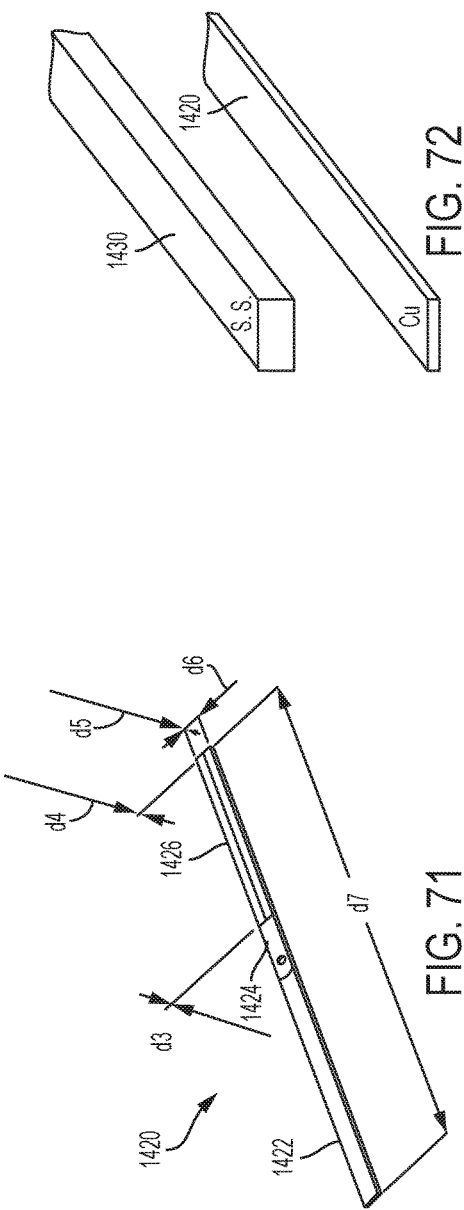

FIG. 70 illustrates a flexible circuit electrode 1400, according to one aspect of the present disclosure. The flexible circuit electrode 1404 comprises a lead 1402 to attach an electrically conductive element 1404, which defines the electrode tissue sealing surface, to an energy source. The electrode 1404 also comprises a plurality of electrically insulative elements 1406 (e.g., electrically insulative elements to establish desired gaps between electrodes in bipolar electrosurgical instruments). A knife slot 1408 is provided as a channel for a knife to translate along the slot 1408. An insulative element, not shown, is bonded to the opposite side of the electrically conductive element 1404.

In one aspect, the flexible circuit electrode 1400 may be implemented with the following dimensions:

R=0.097", where R is the radius of curvature of the distal end 1412 of the electrode 1400;

d1=0.036", where d1 is the width of the knife slot 1408;

d2=0.823", where d2 is the length of the straight portion of the 1400 to the end of the lead 1402.

FIG. 71 illustrates a flat conductive trace 1420 for a flexible circuit electrode, according to one aspect of the present disclosure. The flat conductive trace 1420 includes a dielectric insulator layer 1422 having a thickness d3=0.0020", a gold plated copper layer 1424 having a thickness d4=0.0028", and an electrically insulative layer 1426 (e.g., polyimide, polyester, fluorocarbon, or any polymeric material, or any combinations thereof) having a thickness d5=0.0050". The trace 1420 has a width d6=0.1560" and a length of d7=4.2274".

FIG. 72 is a comparison of a conventional stainless steel electrode 1430 versus the thin copper flexible circuit electrode 1420, according to one aspect of the present disclosure.

With reference now to FIGS. 70-72, in one aspect the flexible circuit electrode 1400 may be configured to reduce the self-heating of the electrode 1400 and allow the majority of the heat to be generated by the self-heat of the tissue. The superiority of using a thin copper conductor over thicker steel or stainless steel conductor will now be demonstrated.

The total resistance of a conductor is greater for alternating current than it is for continuous current due to induced EMFs (electromotive forces.) These forces are greater at the center of a conductor than they are at the surface and they resist the flow of current. This results in the current density to be greater at the surface of a conductor than at the center. This current density variation is referred to as the skin effect.

Several factors contribute to the skin effect and will subsequently affect the total resistance of a conductor. The conductor's resistivity value ($\rho$), frequency (f), and relative permeability ($\mu$) can be used to estimate the skin depth, where the skin depth is the distance from the surface of a conductor in which the current density is reduced to 1/e of the current density at the conductor's surface (approximately 37%.) Approximately 98% of the current moving in a conductor will be limited to the area defined by 4 times the skin depth.

For wires, tubes, and other compact shapes the skin depth ($\delta$) can be approximated by Equation 1:

$$\delta = \frac{1}{2\pi}\sqrt{\frac{10^7 \rho}{f\mu_r}} \quad \text{(Eq. 1)}$$

Table 1 provides material properties for some common materials:

Table 1: Properties of common materials

TABLE 1

| Material | $\rho$ ($\Omega \cdot m$) at 20° C. | Relative Permeability ($\mu_r$) |
|---|---|---|
| Silver | 1.59 × 10−8 | 0.999974 |
| Copper | 1.68 × 10−8 | 0.999991 |
| Gold | 2.44 × 10−8 | 0.999998 |
| Aluminum | 2.82 × 10−8 | 1.000022 |
| Tungsten | 5.60 × 10−8 | 1.000068 |
| Molybdenum | 5 × 10−8 | 1.000123 |
| Nickel | 6.99 × 10−8 | 100-600 |
| Lithium | 9.28 × 10−8 | 1.000014 |
| Iron | 1.00 × 10−7 | 6000-2000000 |
| Platinum | 1.06 × 10−7 | 1.000265 |
| Carbon steel (1010) | 1.43 × 10−7 | 100 |
| Titanium | 4.20 × 10−7 | 1.000182 |
| Stainless steel | 6.90 × 10−7 | 1.003 to 7 (Austenitic) 40-135 (Martensitic hardened) 750-950 (Martensitic annealed) 1000-1800 (Ferritic) |

Generally speaking the resistance of a conductor can be calculated by using Equation 2.

$$R = \frac{L x \rho}{A} \quad \text{(Eq. 2)}$$

where (L) is the length of the conductor, ($\rho$) is the resistivity and (A) is the area.

In the case where the current is confined to a small area near the surface of the conductor ($\delta$<<diameter), the subsequent resistance (R) can be estimated by Equation 3.

$$R \approx \frac{L x \rho}{\delta \pi D} \quad \text{(Eq. 3)}$$

where ($\pi D$) is the perimeter of a round conductor.

Typical Stainless Steel (assuming Austenitic) electrodes vs. flexible circuit electrodes self-heat performance. One of the significant factors in electrode material and geometry selection is the propensity to self-heat when current is passed through them. Table 2 shows calculations for a typical stainless steel electrode compared to a flex circuit electrode that has the same tissue contact area but significantly less cross-sectional area.

TABLE 2

| | Conventional Electrode |
|---|---|
| Frequency | 330000 |
| Electrode Length | 1 |
| Electrode Width | 0.2 |
| Electrode Height | 0.01 |
| Current | 3 |

TABLE 2-continued

| Material | $\rho$ ($\Omega \cdot m$) at 20° C. | Relative Permeability ($\mu$) | Reference for a range | 37% Depth, inches | 98% Depth, inches | Resistance | Power from Electrode |
|---|---|---|---|---|---|---|---|
| Silver | 1.59E−08 | 0.999974 | | 0.004352749 | 0.017410995 | 0.001826432 | 0.016437889 |
| Copper | 1.68E−08 | 0.999991 | | 0.004474206 | 0.017896824 | 0.001877428 | 0.016896853 |
| Gold | 2.44E−08 | 0.999998 | | 0.00539206 | 0.021568241 | 0.002262586 | 0.020363274 |
| Aluminum | 2.82E−08 | 1.000022 | | 0.005 | 0.023186711 | 0.002432428 | 0.02189185 |
| Tungsten | 5.60E−08 | 1.000068 | | 0.008168431 | 0.032673723 | 0.003427831 | 0.030850479 |
| Molybdenum | 5.00E−08 | 1.000123 | | 0.007718229 | 0.030872917 | 0.003239085 | 0.029151764 |
| Nickel | 6.99E−08 | 100-600 | 100 | 9.13E−04 | 0.003650547 | 0.038295629 | 0.344660662 |
| Lithium | 9.28E−08 | 1.000014 | | 0.01051551 | 0.042062039 | 0.00441253 | 0.039712768 |
| Iron | 1.00E−07 | 6000-200000 | 6000 | 1.41E−04 | 0.000563694 | 0.354802153 | 3.193219373 |
| Platinum | 1.06E−07 | 1.000265 | | 0.011237114 | 0.044948455 | 0.004716514 | 0.042448622 |
| Carbon Steel (1010) | 1.43E−07 | 100 | | 0.001305351 | 0.005221405 | 0.054774527 | 0.492970747 |
| Titanium | 4.20E−07 | 1.000182 | | 0.022368894 | 0.089475576 | 0.009388037 | 0.084492331 |
| Stainless Steel | 6.90E−07 | 1 | | 0.028673713 | 0.114694851 | 0.012031926 | 0.108287337 |
| Stainless Steel | 6.90E−07 | 7 | | 0.010837645 | 0.043350579 | 0.031833485 | 0.286501365 |
| Stainless Steel | 6.90E−07 | 0-135 (Martenstitic hardened) | 40 | 4.53E−03 | 0.018134848 | 0.076096584 | 0.684869256 |
| Stainless Steel | 6.90E−07 | 50-950 (Martenstitic annealed) | 750 | 1.05E−03 | 0.004188064 | 0.329507875 | 2.965570872 |
| Stainless steel | 6.90E−07 | 1000-1800 (Ferritic) | 1000 | 9.07E−04 | 0.00362697 | 0.38048292 | 3.424346282 |
| One Aspect Of A Proposed Flex Electrode | | | | | | | |
| Electrode Length | 1 | | | | | | |
| Electrode Width | 0.2 | | | | | | |
| Electrode Height | 0.0028 | | | | | | |
| Copper | 1.68E−08 | 0.999991 | | 4.47E−03 | 0.017896824 | 6.71E−03 | 0.060345902 |
| Stainless steel | 6.90E−07 | 7 | | 0.010837645 | 0.043350579 | 1.14E−01 | 1.023219161 |
| % Difference For Same Geometry | 4007% | 600% | | 142% | 142% | 1596% | 1596% |

A comparison of a conventional stainless steel electrode 1430 with a cross-section of 0.2×0.1" and a copper electrode 1420 with a cross-section of 0.2×0.0028". Assuming a 1" length and 3 A of current flowing (arbitrary) at a typical electrosurgical frequency of 330 kHz, the relative self-heat of the two designs are compared. The results indicate that the copper electrode 1420, even though the cross-section is significantly less, exhibits less self-heating than the thicker stainless steel electrode 1430. Accordingly, based on these results, one can conclude that the copper electrode 1420 in a flexible circuit arrangement is superior to a conventional stainless steel electrode 1430. Although, copper may be determined to be a sub-optimal choice for biocompatibility, the copper conductor can be clad or coated with another biocompatible material such as gold.

Table 3 shows the relative self-heat power of a conventional steel electrode vs. a flat copper flex electrode.

TABLE 3

Conventional Steel Electrode vs. Flat Copper Flex Electrode

| | |
|---|---|
| Relative self-heat power from 0.2 × 0.1 Steel Electrode | 0.29 |
| Relative self-heat power from Flat 0.2 × 0.0028 Copper Flex Electrode | 0.06 |

IX. Flexible Circuit Electrode Manufacturing Process

A. Mass Produced Cost Effective Flexile Circuit Electrode Sub-Assembly Including Insulative Barrier and Non-Conductive Stand-Offs FIGS. 73-80 illustrate a mass produced and cost effective flexile circuit electrode sub-assembly including insulative barrier and non-conductive stand-offs, according to one aspect of the present disclosure.

FIG. 73 is a perspective view of an assembly 1500 comprising an array 1502 of flexible circuit electrodes 1504, according to one aspect of the present disclosure. FIG. 74 is an elevation view of the assembly 1500 shown in FIG. 73, according to one aspect of the present disclosure.

Figure 75:
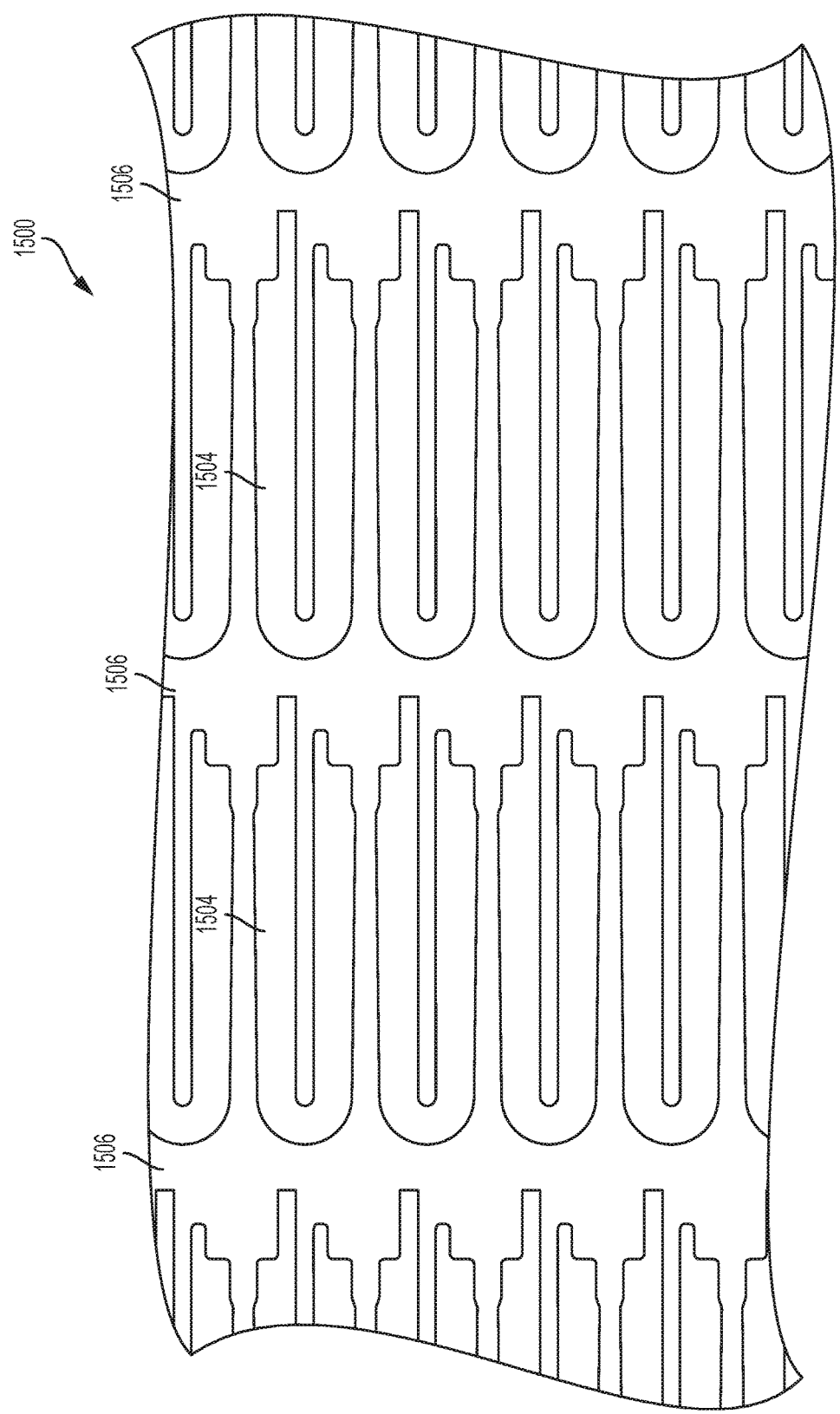

FIG. 75 is a detail plan view of the assembly 1500 shown in FIG. 73 showing individual flexible circuit electrodes 1504 fixed in a carrier web 1506 prior to die cutting, according to one aspect of the present disclosure. In one aspect, the carrier web 1506 may comprise fused links that are can be activated to sever the individual flexible circuit electrodes 1504 from the assembly 1500.

With reference to FIGS. 73-75, the following disclosure provides a technique of mass producing electrode assemblies 1500 for a bipolar medical device electrode 1504. In this assembly 1500 the final electrode 1504 is bonded to an electrically insulative backing material (e.g., polyimide, polyester, fluorocarbon, or any polymeric material, or any combinations thereof) and insulative elements are printed at two or more locations on the tissue sealing surface of the electrode 1504. These elements serve to prevent the electrode from shorting with the opposing jaws and serve to maintain a defined gap between the upper and lower electrodes.

The electrodes 1504 can be mass produced by laminating a metallic sheet to an electrically insulative film. Then the insulative elements are screen printed on the conductive face of the electrode. The shape of the electrode 1504 is formed by screen printing a protective barrier on the metallic film. This protective barrier allows the shape of the electrode to be formed by photoetching away the remaining material which does not make up the final shape of the electrode 1504. Finally, individual electrodes 1504 are die-cut out leaving electrode subassemblies that can be bonded to the jaws of the end effector. The electrically insulative backing material or barrier can have an adhesive or a brazeable surface on the back side of the electrically insulative backing material to allow for attachment to the lower or upper jaw depending on the device jaw construction.

Figure 77:
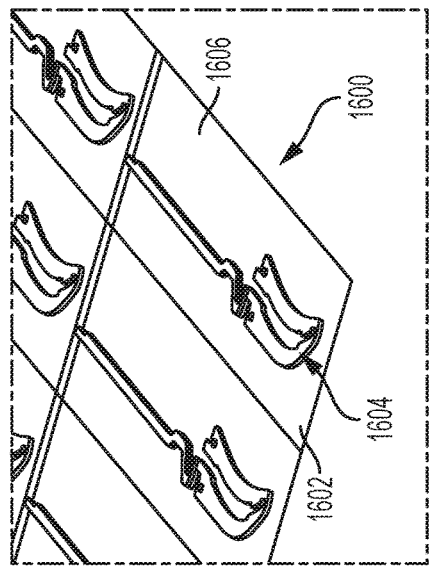
Figure 76:
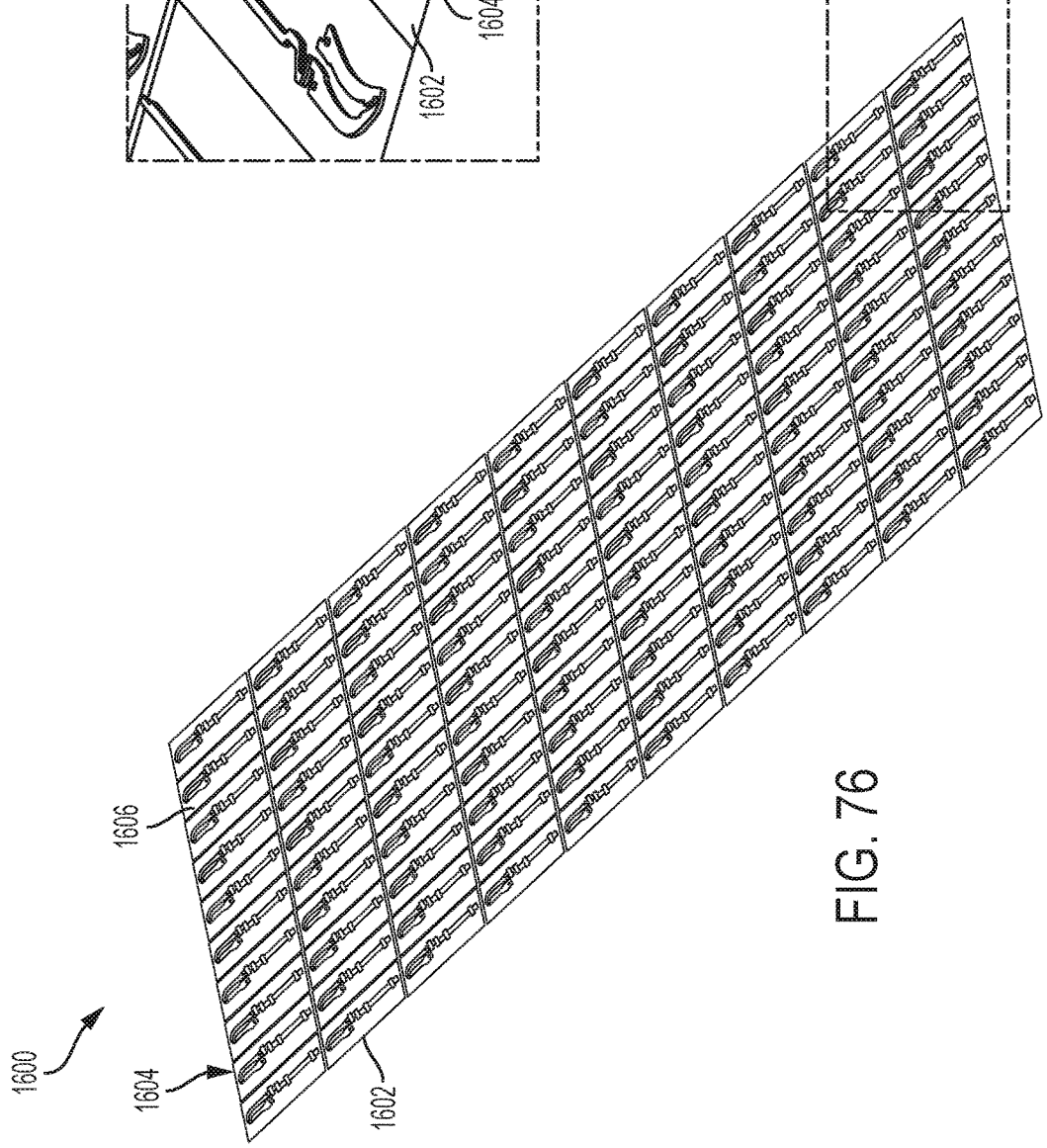

With reference to FIGS. 76-80, FIG. 76 is a perspective view of an assembly 1600 comprising an array 1602 of flexible circuit electrodes 1604 in a carrier web 1606, according to one aspect of the present disclosure. FIG. 77 is a detail view of the array 1602 of the flexible circuit electrodes 1604 in a carrier web 1606 shown in FIG. 76, according to one aspect of the present disclosure.

Figure 78:
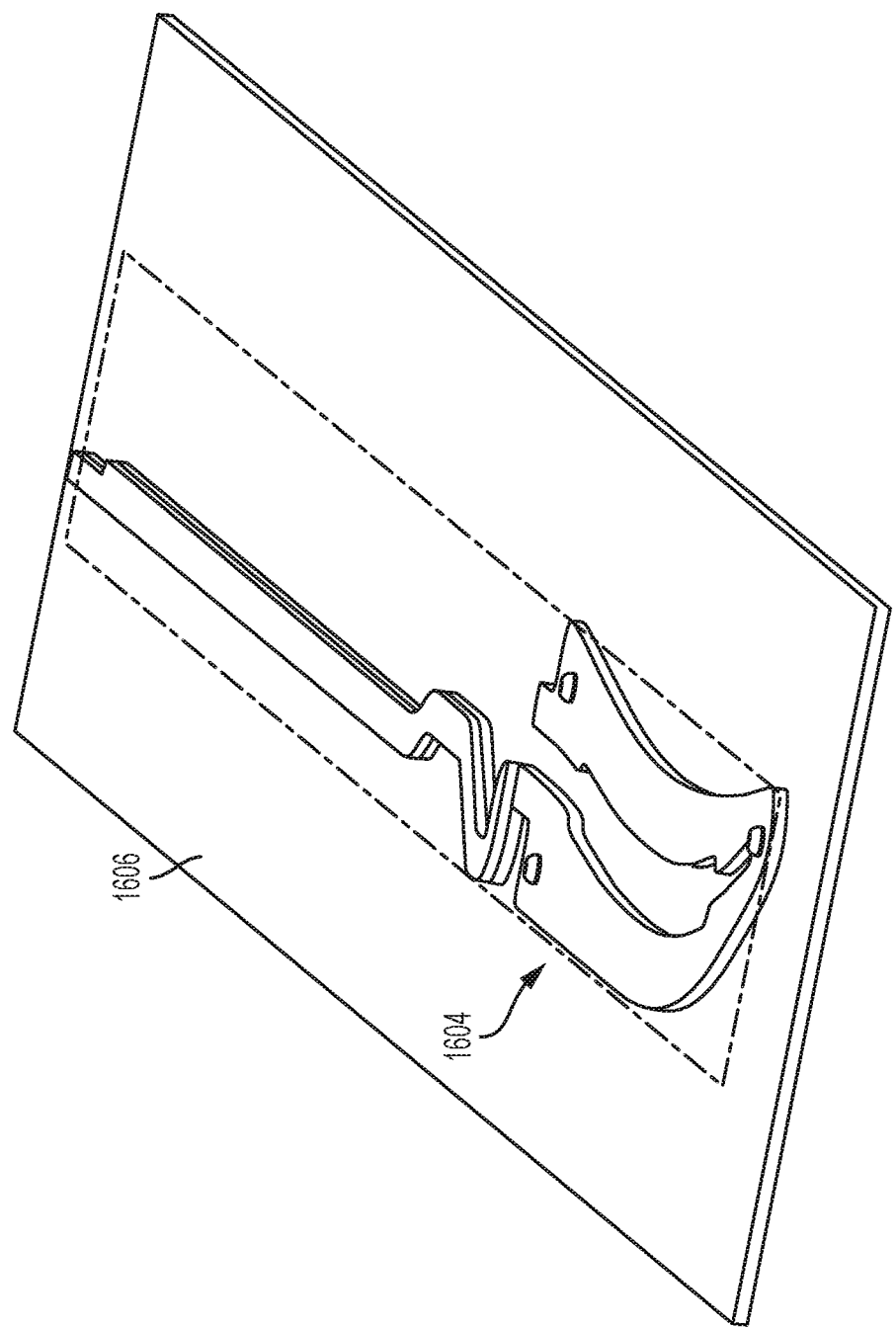
Figure 79:
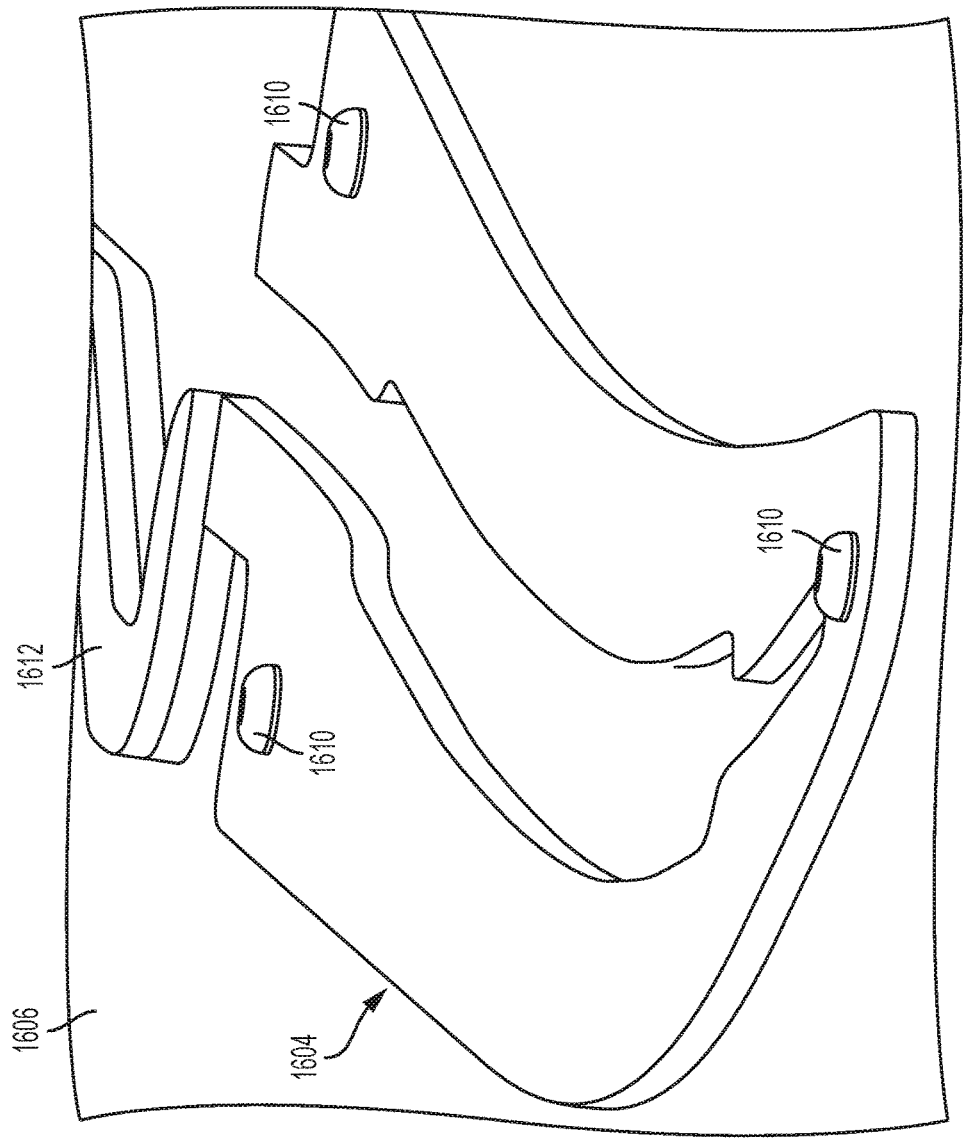

FIG. 78 is an individual flexible circuit electrode 1604 sub-assembly in a carrier web 1606 prior to die-cutting, according to one aspect of the present disclosure. FIG. 79 is a detail view of the individual flexible circuit electrode 1604 sub-assembly in a carrier web 1606 shown in FIG. 78, according to one aspect of the present disclosure.

Figure 80:
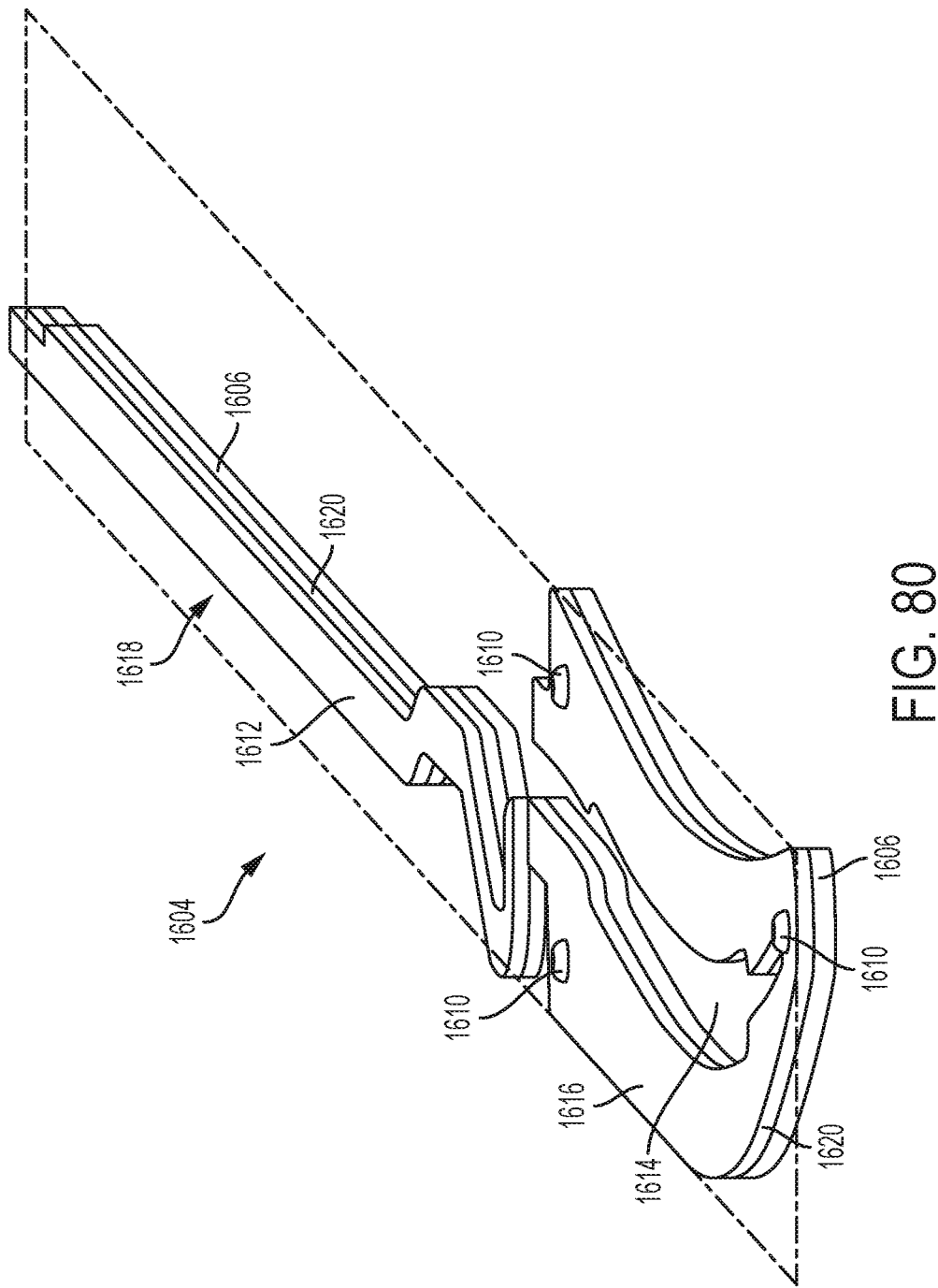

FIG. 80 is an individual flexible circuit electrode 1604 sub-assembly shown in FIG. 78 after die cutting and ready to be bonded to a jaw of an end effector, according to one aspect of the present disclosure. The electrode 1604 comprising an electrically conductive metal layer 1620, an electrically insulative layer 1606 (e.g., polyimide, polyester, fluorocarbon, or any polymeric material, or any combinations thereof) attached to one side of the conductive metal layer 1620. Dielectric insulative elements 1610 are printed on the tissue contacting surface 1616 of the conductive metal layer 1620. In one aspect, the dielectric insulative layer 1612 can be printed on the lead 1618 portion of the electrode 1604. A knife slot 1614 is provided in the electrode 1604 to receive the knife through the slot.

The following disclosure provides a technique of mass producing electrode assemblies 1600 for the bipolar medical device electrode 1604. In this assembly 1600 the final electrode 1604 is bonded to an electrically insulative backing 1606 (e.g., polyimide, polyester, fluorocarbon, or any polymeric material, or any combinations thereof) and insulative elements 1610 are printed at two or more locations on the tissue sealing surface 1616 of the electrode 1604. These elements 1610 serve to prevent the electrode 1604 from shorting with the opposing jaws and serve to maintain a defined gap between the upper and lower electrodes. The dielectric insulative layer 1612 used to print the elements 1610 can also be printed onto the lead portion 1618 of the electrode 1604.

The electrodes 1604 can be mass produced by laminating a metallic sheet 1620 to an electrically insulative film 1606 (e.g., polyimide, polyester, fluorocarbon, or any polymeric material, or any combinations thereof). Then the insulative elements 1610 are screen printed on the conductive face 1616 of the electrode 1604. The shape of the electrode 1604 is formed by screen printing a protective barrier on the metallic film 1620. This protective barrier allows the shape of the electrode to be formed by photoetching away the remaining material which does not make up the final shape of the electrode 1604. Finally, individual electrodes 1604 are die-cut out leaving electrode subassemblies that can be bonded to the jaws of the end effector. The electrically insulative barrier (e.g., polyimide, polyester, fluorocarbon, or any polymeric material, or any combinations thereof) can have an adhesive or a brazeable surface on the back side of the polyimide barrier to allow for attachment to the lower or upper jaw depending on the device jaw construction.

B. Flow Diagram of Process of Manufacturing Flexible Circuit Electrodes

Figure 81:
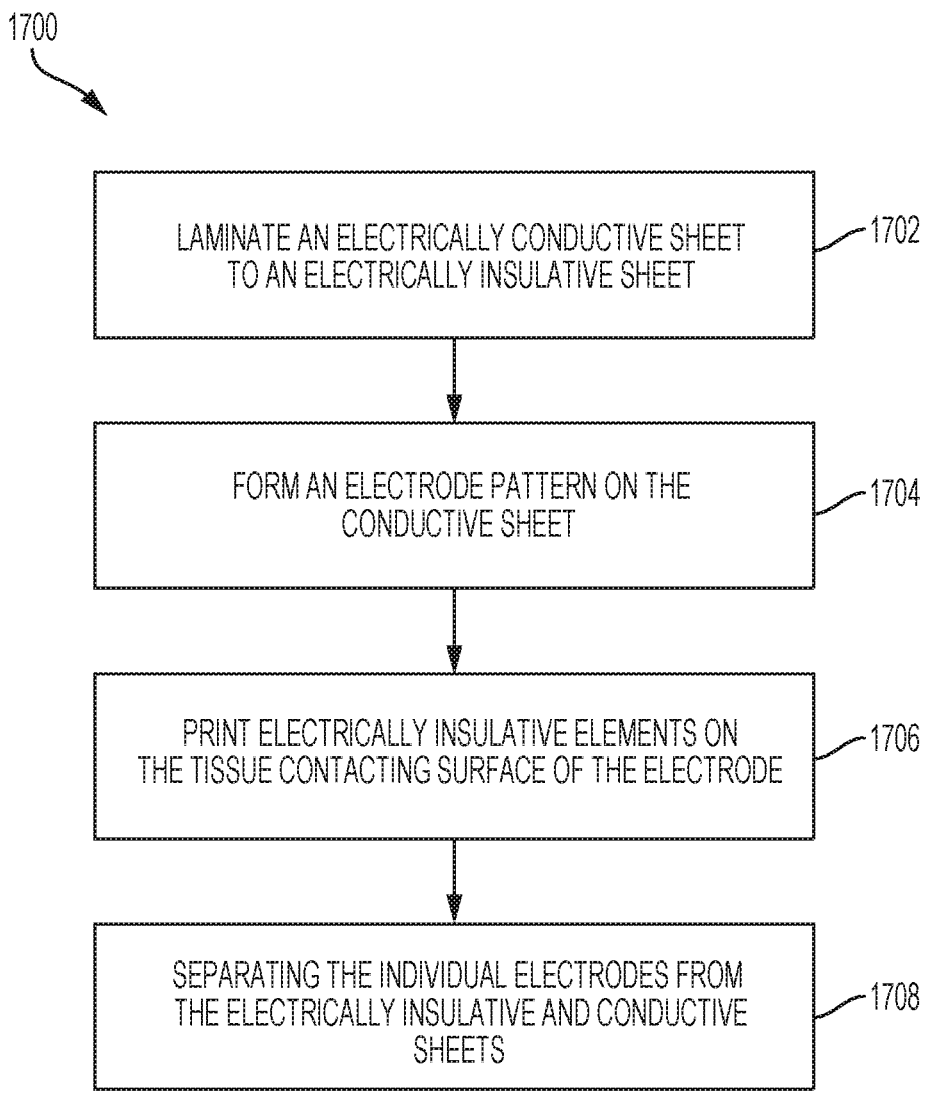
FIG. 81 is a flow diagram of a process of manufacturing flexible circuit electrodes, according to one aspect of the present disclosure.

FIG. 81 is a flow diagram 1700 of a process of manufacturing flexible circuit electrodes, according to one aspect of the present disclosure. An electrically conductive sheet is laminated 1702 to an electrically insulative sheet. The electrically conductive sheet may be a sheet made of copper, a gold plated copper, silver, platinum, stainless steel, aluminum, or any suitable electrically conductive biocompatible material, for example. The electrically insulative sheet may be a sheet of electrically insulative material (e.g., polyimide, polyester, fluorocarbon, or any polymeric material, or any combinations thereof).

An electrode is then formed 1704 on the electrically conductive sheet according to a predetermined pattern. This process may include for example etching an electrode on the electrically conductive sheet. In one aspect, a desired pattern may be formed by screen printing a protective barrier to the electrically conductive sheet. This protective barrier allows the shape of the electrode to be formed by photoetching away the remaining material which does not make up the final shape of the electrode.

Once the electrode is formed, electrically insulative elements are printed 1706 of the tissue contacting surface of the electrode. The electrically insulative elements may be formed of a dielectric material that can be screen printed on the tissue contacting surface of the electrode. The electrically insulative elements (e.g., insulative elements to establish desired gaps between electrodes in bipolar electrosurgical instruments).

Once the electrically insulative elements are printed on the tissue contacting surface of the electrode, the individual electrode are separated 1708 from the electrically insulative and conductive sheets that act as a web to hold the individual electrode elements in place during the processing phase. In one aspect, separating the electrodes comprises die cutting the electrodes, they can be attached to the jaws of the upper and/or lower electrode.

In accordance with the present disclosure, electrically insulative materials, such as dielectric materials, may be applied to a variety of flexible substrates by screen printing, stamping, dip coating, syringe dispensing, spraying, and/or pad printing, or combinations thereof. Suitable flexible substrates may include, without limitation, Kapton, Mylar, epoxy/glass, polycarbonate, treated and untreated polyester, glass, sputtered surfaces, Aluminum, and/or combinations thereof.

X. Thermal Assist for Advanced RF Electrodes

Figure 82:
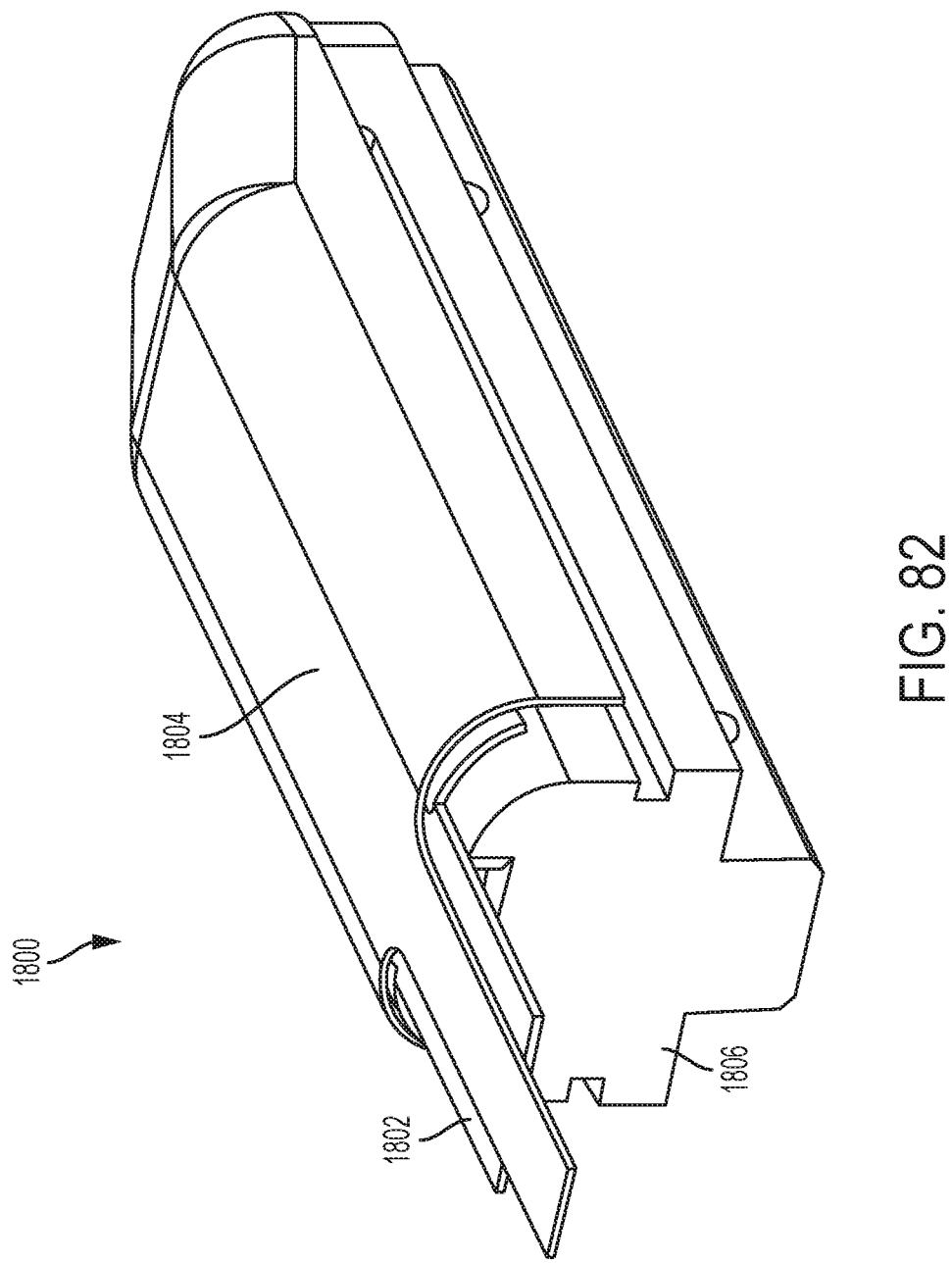
FIGS. 82-87 describe a thermal assist end effector, according to one aspect of the present disclosure, where.

FIGS. 82-87 describe a thermal assist end effector, according to one aspect of the present disclosure. FIG. 82 is a perspective view of an end effector jaw assembly 1800 comprising an electrode 1802 and a thermal assist heater 1804, according to one aspect of the present disclosure. The end effector jaw assembly 1800 also comprises a thermal and electrical insulator 1806. The resistive thermal heater 1804 is in the form of a foil attached to the electrode 1802. Use of the resistive thermal heater 1804 can reduce the time spent the low impedance (|Z|), high power, portion of the sealing cycle, that resemble a "bathtub" shape. Currently, when impedance is extremely low, the RF generator is limited in the power that can be transferred to the tissue electrically. By transferring power thermally to the tissue using the resistive thermal heater 1804, the tissue can be desiccated which will allow the cycle to finish more quickly. The resistive thermal heater 1804 foil can be integrated with the metal electrode or with a flexible circuit electrode 1802 as shown in FIG. 82.

Low impedance (|Z|) loads can cause long cycle sealing times. This is because the generator is limited in powering low |Z| loads. The generator or instrument can sense when the load is below a threshold where the generator is able to apply sufficient power to make a moderate cycle time. When this occurs, the resistive thermal heater 1804 can be turned on to give the tissue a boost into the coagulation cycle.

Once the power delivery from the generator is sufficient, then the resistive thermal heater 1804 can be turned off and the RF energy delivered by the generator can completed the seal. A threshold for the low impedance can be set such that when the generator cannot deliver 50 W or more of power then the resistive thermal heater 1804 heater is turned on. In one example, 3.5 A may be the maximum current available from a generator. Based on conventional power formulas $P=I^2R$ and $R=50/35^2 \cong 4$ Ohms. Once the generator is able to deliver ~200 W, then the resistive thermal heater 1804 can be turned off. In the above example, this is ~=16 Ohms.

Minimizing or reducing the time spent in the "bathtub" portion of the cycle will reduce the overall tissue sealing cycle time. Activation and deactivation of the thermal assist can be accomplished in several ways with varying benefits and trade-offs, some of which include a temperature based closed-loop control using peripheral-integral-derivative (PID) or other technique. A specific temperature-time profile is applied to the tissue while sensing tissue temperature or predicting tissue temperature based on jaw temperature. A time based control can be used to control thermal power applied for a predetermined period of time to assist in transitioning the bathtub. Temperature control using a bi-metal "thermostat" switch can be used to de-energize the thermal assist when a specific temperature has been achieved. An RF performance feedback technique can be used where the generator is employed to detect when impedance is too low to effectively drive current into the tissue, activating the thermal assist. When impedance rises, deactivating the thermal assist to rely on Advanced RF.

Figure 83:
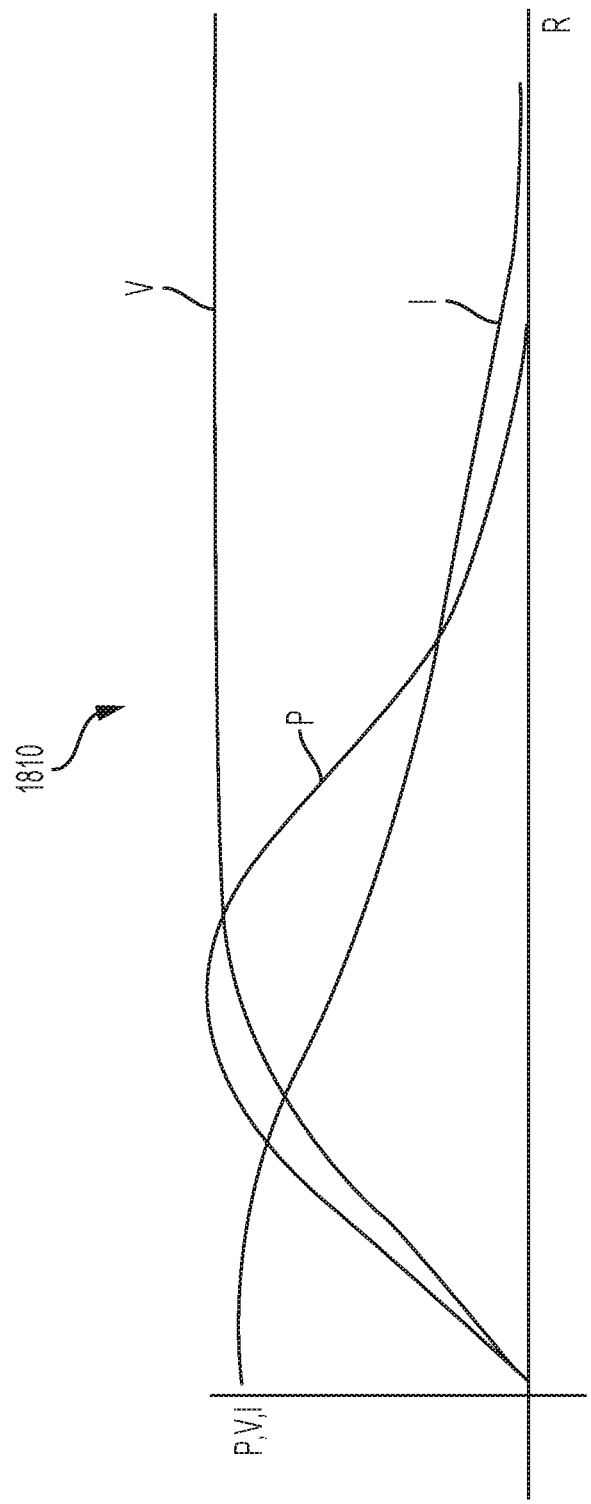

FIG. 83 is a graphical depiction 1810 of power, voltage, and current versus impedance, according to one aspect of the present disclosure. Power (P), voltage (V) and current (I) are depicted along the vertical axis and impedance (R) is depicted along the horizontal axis. As shown, wen the impedance (R) is low or near zero, current (I) is high or at its maximum and voltage (V) and power (P) are at their minimum or zero. As the impedance increases to right along the horizontal axis, current (I) gradually decreases and the power (P) and voltage (V) increase. As the impedance (R) increases further, the current (I) and power (P) drop to near zero and the voltage stabilizes to a maximum.

Figure 84:
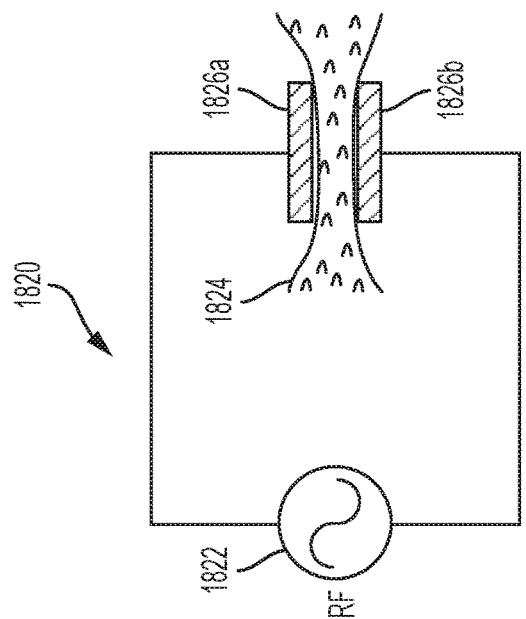

FIG. 84 is a schematic of a circuit 1820 of an RF energy source 1822 with a low impedance load between two electrodes 1826a, 1826b, according to one aspect of the present disclosure. The circuit 1820 is a conventional RF energy sealing circuit where an RF energy source 1822 is electrically coupled to first and second electrode 1826a, 1826b with tissue 1824 located therebetween. When the moisture content of the tissue 1824 positioned between the electrodes 1826a, 1826b is high, the impedance of the tissue is low. Accordingly, the RF energy source 1822 will output a high current. As RF energy is applied to the tissue 1824 moisture is driven out of the tissue due to the heating effect of the RF energy applied to the tissue 1824. As moisture is driven out of the tissue 1824, the tissue 1824 desiccates and the impedance increases, which reduces the amount of current through the tissue 1824. The process continues until the impedance reaches a predetermined quantity.

Figure 85:
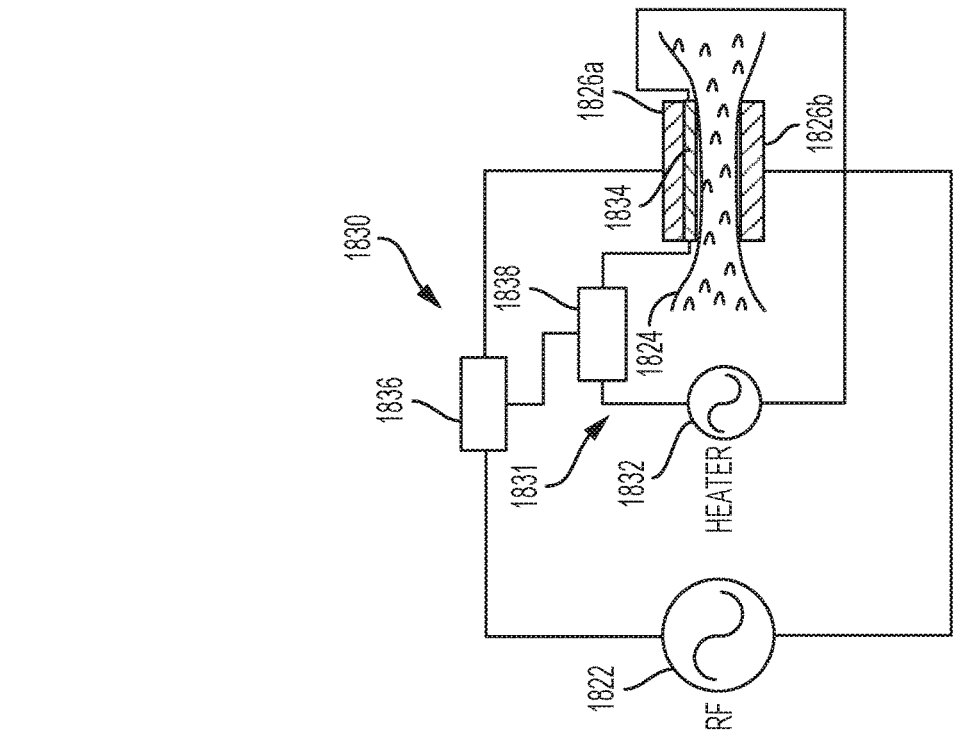

FIG. 85 is a schematic of a circuit 1830 comprising an RF energy source 1822 with a low impedance load between the electrodes 1826a, 1826b, a heater energy source 1832 with a heater 1834, and a thermal assist control circuit 1831, according to one aspect of the present disclosure. As shown, the circuit 1830 comprises an RF circuit comprising an RF energy source 1822 for driving the electrodes 1826a, 1826b and a control circuit 1836 to monitor tissue impedance $|Z_T|$ and control the RF energy source 1822 based on the measured impedance. The circuit 1830 also comprises a thermal assist control circuit 1831 comprising a heater energy source 1832 to drive the heater 1834 attached to one of the electrodes 1826a and a heater control circuit 1838 to control the heater energy source 1832 based on inputs from the RF control circuit 1836. The heater energy source 1832 applies energy to the heater 1834, which in turn heats the tissue to assist the RF energy source 1822 during low impedance load periods. The RF control circuit 1836 can turn the RF source ON and OFF and can send an instruction or a signal to the heater control circuit 1838, which can turn the heater source ON and OFF. The thermal assist control circuit 1831 powering the heater 1834 can be a single system that applies about 50 W to about 100 W of power through a battery, a separate mains supplied source, or from the generator output. See 2015/0190189, for example.

Figure 86:
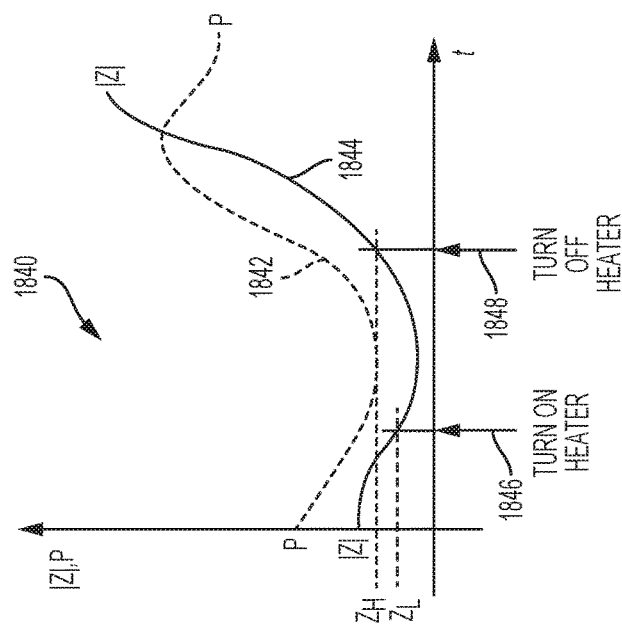

FIG. 86 is a graphical depiction 1840 of impedance (|Z|) 1844 and power (P) 1842 versus time (t), according to one aspect of the present disclosure. Impedance (|Z|) 1844 and power (P) 1842 are depicted on the vertical axis and time (t) is depicted on the horizontal axis. With reference also to FIG. 85, as the tissue 1824 impedance (|Z|) 1844 varies, the power (P) 1842 delivered to the tissue 1824 also varies. When the tissue impedance (|Z|) 1844 drops below a low impedance threshold $Z_L$ the heater control circuit turns ON 1846 the heater 1834 to apply heat to the tissue 1824. When the tissue impedance (|Z|) 1844 rises above a high impedance threshold $Z_H$ the heater control circuit turns OFF 1848 the heater 1834.

Figure 87:
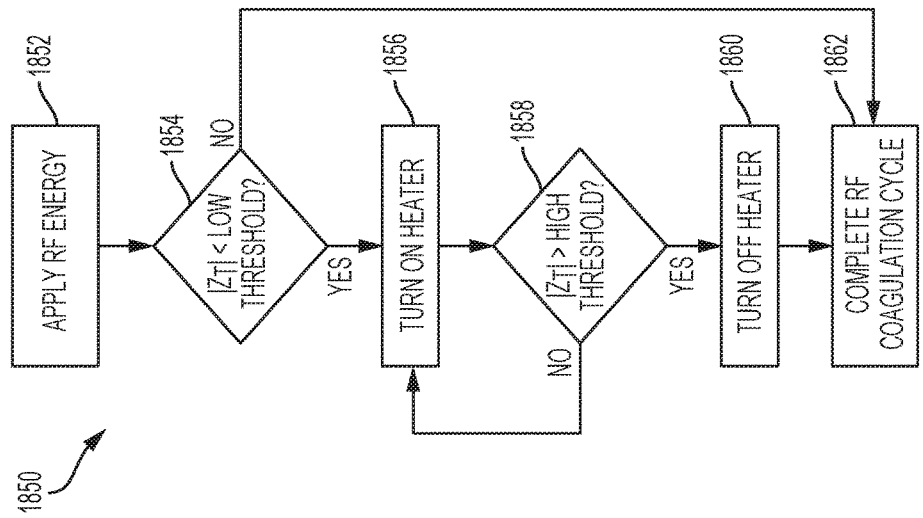

FIG. 87 is logic flow 1850 depicting a process for operating the thermal assist control circuit 1831 shown in FIG. 85, according to one aspect of the present disclosure. With reference also to FIGS. 85 and 86, after the surgeon grasps tissue between the jaws of the end effector RF energy is applied 1852 to the electrodes 1826a, 1826b. During the process the control circuit 1836 monitors the tissue impedance $|Z_T|$ and compares 1854 it to predetermined thresholds. When the tissue impedance $|Z_T|$ is less than the low tissue impedance threshold $Z_L$ the heater control circuit 1838 turns ON 1856 the heater 1834, otherwise the RF coagulation cycle is completed 1862. The control circuit 1836 continues comparing 1858 the measured tissue impedance to the predetermined thresholds. When the tissue impedance $|Z_T|$ is less than the high tissue impedance threshold $Z_H$ the heater 1834 stays on until the tissue impedance $|Z_T|$ is greater than the high tissue impedance threshold $Z_H$ and then the heater control circuit 1838 turns OFF 1860 the heater 1834 and completes 1862 the RF coagulation cycle.

The instrument and the generator can be configured to execute most any RF algorithm. One jaw algorithm is described in U.S. Pat. No. 9,060,776, for example.

XI. Optical Force Sensing for RF Sealing Process Monitoring

FIGS. 88-91 illustrate an optical force sensor 1900 based on measuring light transmission through micro-bent polymer optical fibers 1902 (POF) embedded in an elastomer strip 1904, according to one aspect of the present disclosure.

Figure 88:
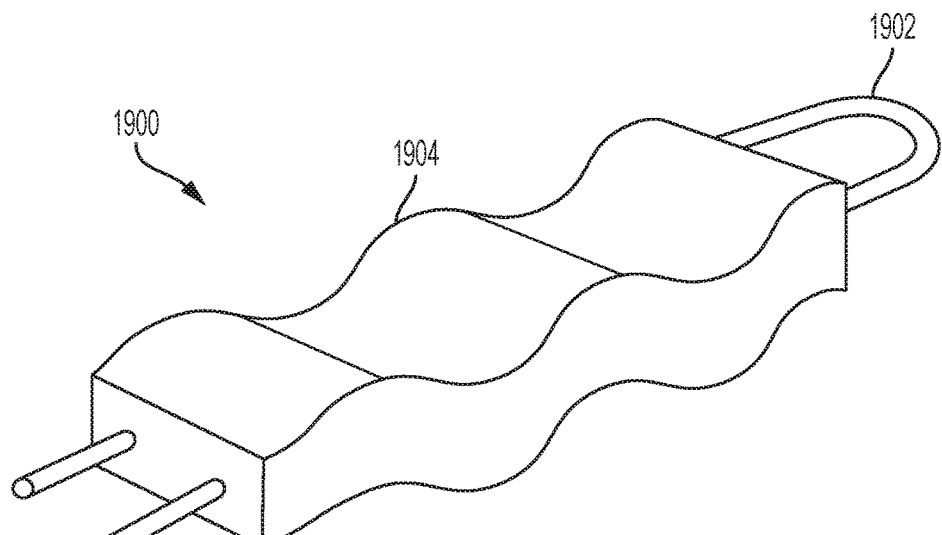
FIGS. 88-91 illustrate an optical force sensor based on a measuring light transmission through micro-bent polymer optical fibers (POF) embedded in an elastomer strip, according to one aspect of the present disclosure, where.
Figure 89:
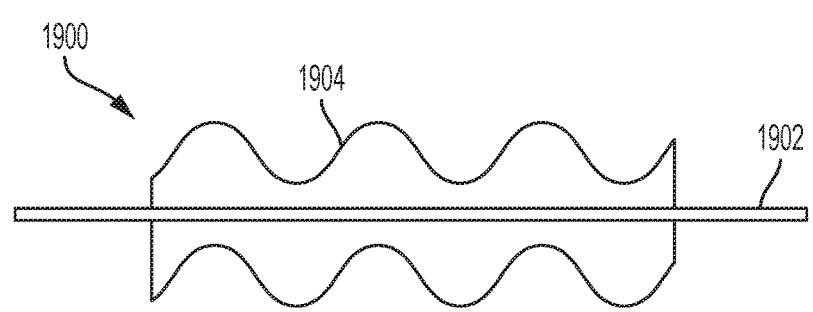

FIG. 88 is an optical force sensor 1900 in a relaxed state, according to one aspect of the present disclosure. FIG. 89 is a cross section of the optical force sensor 1900 shown in FIG. 88 in a relaxed state, according to one aspect of the present disclosure.

Figure 90:
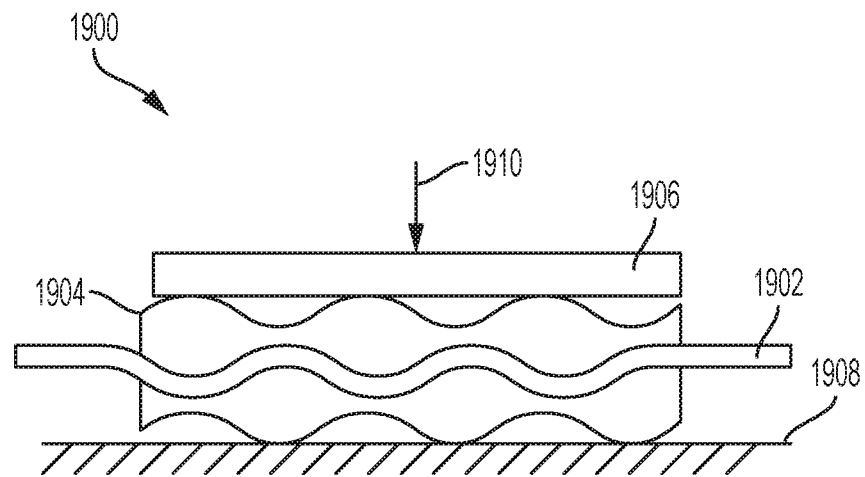
Figure 91:
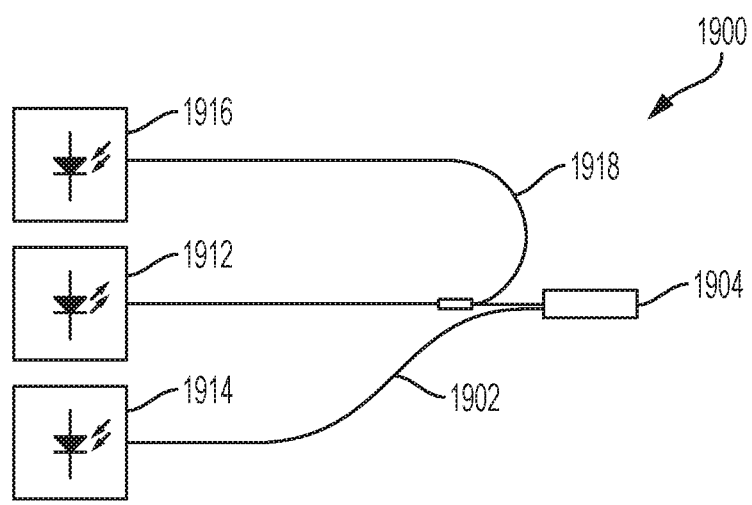

FIG. 90 is a cross section of the optical force sensor 1900 shown in FIG. 88 in a compressed state, according to one aspect of the present disclosure. FIG. 91 is a simplified schematic diagram of the optical force sensor 1900 shown in FIG. 88, according to one aspect of the present disclosure.

With reference now to FIGS. 88-91, this technique employs a force sensor 1900 based on measuring light transmission through micro-bent polymer optical fibers 1902 (POF). This technique provides improved flexibility of RF sealing algorithms to accommodate the variety of tissue properties and behavior encountered in practice. This technique also reduces the variability and improve strength of vessel seals by controlling the applied compressive force. The advantage of using an optical sensor is that it is undisturbed by RF fields. The advantage of POFs 1902 is that they are inexpensive and more flexible than silica optical fibers.

The sensor 1900 comprises a POF 1902 set in an elastomer strip 1904. The elastomer strip 1904 has a wavy shape while the fiber inside is straight, as shown in section view in FIG. 89. When the sensor 1900 is compressed between two flat surfaces 1906, 1908, as shown in FIG. 90, the POF 1902 is deformed into a series of micro-bends. When the POF 1902 is bent part of the light escapes from it. With the increase of compression force 1910 the deformation of the sensor 1900 elastomer strip 1904 varies and the light transmitted through the POF 1902 decreases monotonically. Thus the attenuation of transmitted light is a measure of the applied force 1910.

As shown in FIG. 91, the sensor 1900 is interrogated by sending light from an LED 1912 through a POF 1902 to the sensor strip 1904. The light returning from the strip 1904 is measured by a photodiode 1914. Another photodiode 1916 measures a fraction of the light from the LED 1912 carried by a POF 1918 coupled with the POF 1902 bringing light to the sensor 1900. The ratio of the signals from the two photodiodes 1914, 1916 can be calibrated versus the applied force 1910. The sensor 1900 can be inserted between the electrode and the jaw of an RF device such as an electrosurgical instrument 2 shown in FIG. 1A to monitor the applied force 1910.

XII. Polymer Optical Fiber (POF) on Flexible Circuit Electrode

Figure 92:
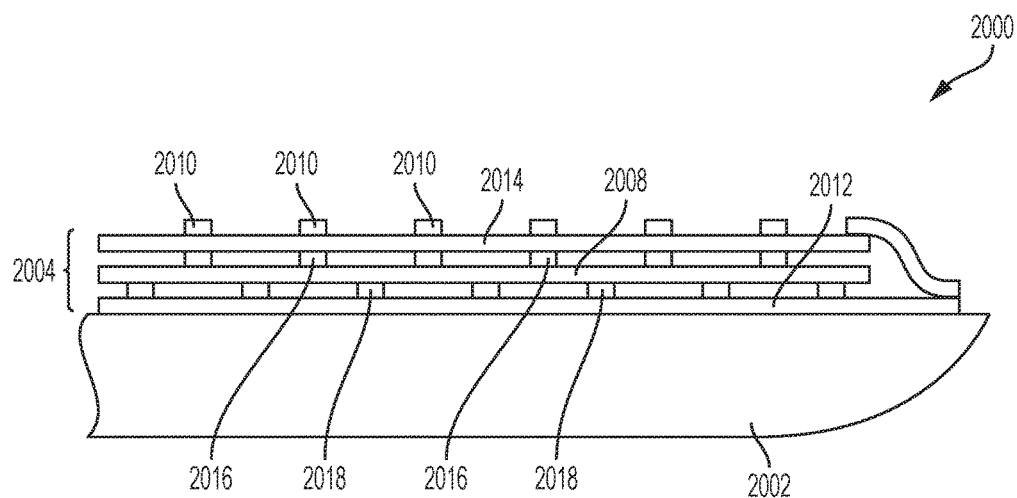
FIGS. 92-93 illustrate polymer optical fibers (POF) integrated with flexible circuit electrodes for sensing a pressure in a jaw of an end effector, according to one aspect of the present disclosure, where.
Figure 93:
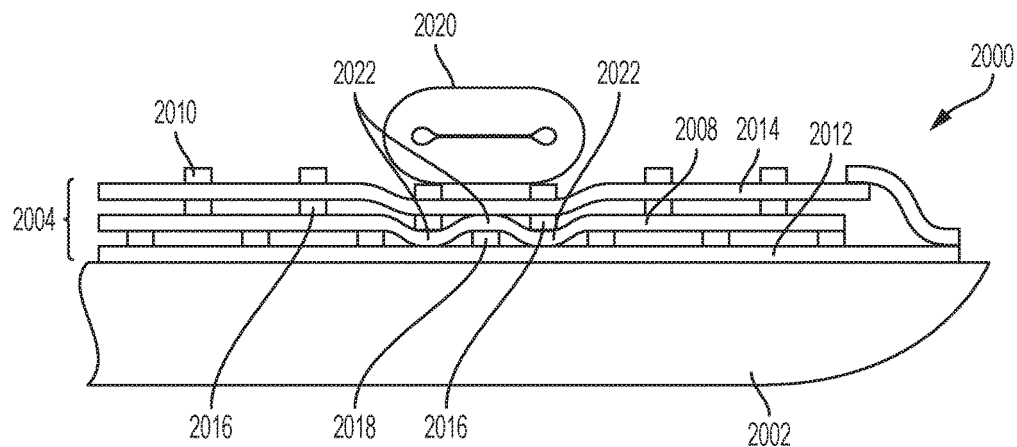

FIGS. 92-93 illustrate polymer optical fibers (POF) integrated with flexible circuit electrodes for sensing a pressure in a jaw of an end effector 2000, according to one aspect of the present disclosure. FIG. 92 is a section view of a lower jaw 2002 of the end effector 2000 comprising a POF force sensor 2004, according to one aspect of the present disclosure.

Turning now to FIG. 92, the POF force sensor 2004 is disposed on the lower jaw 2002 of the end effector 2000. The POF force sensor 2004 comprises first and second layers of electrically insulative film 2010, 2012, (e.g., polyimide, polyester, fluorocarbon, or any polymeric material, or any combinations thereof), such as Kapton, for example. A flexible electrode 2014 is located below the first electrically insulative film 2010. The lower side of the flexible electrode 2014 comprises a first plurality of trace layer segment conductors 2016. The upper of the second electrically insulative film 2012 comprises a second plurality of trace layer segment conductors 2018. Polymer optical fibers 2008 are integrated with the flexible electrode 2014 between the first and second plurality of the trace layer segment conductors 2016, 2018. Accordingly, the POF 2008 is located between what would otherwise be trace layer segments 2016, 2018 of the flexible electrode. The trace layer segment conductors 2016, 2018 are printed in an offset pattern as shown in FIG. 92, which causes the POF 2008 to bend when pressure is applied to the flexible electrode 2014. The flexible electrode 2014 configuration of the POF force sensor 2004 enables a pressure profile feedback from the end effector 2000 to be processed in the surgical instrument handle or electrosurgical generator.

FIG. 93 is a section view of the end effector 2000 shown in FIG. 92 with tissue 2020 disposed on the POF force sensor 2004, according to one aspect of the present disclosure. As the upper jaw (shown for clarity of disclosure) closes on the tissue 2020 and applies a force on the tissue 2020 against the lower jaw 2002, micro bends 2022 are developed in the POF 2008 layer. The POF force sensor 2004 is based on measuring light transmission through the micro bends 2022 of the POF 2008 layer. This technique provides improved flexibility of RF sealing algorithm to accommodate the variety of tissue properties and behavior encountered in practice. The POF force sensor 2004 also reduces the variability and improves the strength of vessel seals by controlling the applied compressive force. The POF force sensor 2004 operates on principles similar to the optical force sensor 1900 based on measuring light transmission through micro-bent POF 1902 embedded in an elastomer strip 1904, according to FIGS. 88-91.

The POF force sensor 2004 senses the pressure profile in the jaw 2002 as well as the position of the tissue 2020. The pressure applied to the tissue 2020 and the location of the tissue 2020 in the jaws 2002 are parameters that effect sealing performance. Obtaining information about the pressure profile in the jaws 2002 and the position of the tissue 2020 allows the algorithm to be adjusted in real time according to how the surgical instrument is being used and improves sealing performance due to the device receiving pressure feedback from the end effector 2000.

XIII. Flat Patterned Flexible Electrode Including Flexure Bearing

FIGS. 94-97 illustrate flat patterned flexible circuit electrodes comprising a flexure bearing, according to one aspect of the present disclosure. The flat patterned flexible circuit electrodes utilize the flexible nature of the flexible circuit electrode to incorporate a flexure bearing. This flat patterned flexible circuit electrodes enables both poles of the bipolar electrode to be fabricated in a single contiguous component. There are a variety of flat patterns which will allow the incorporation of both poles of a bipolar device into a single flexible circuit. These designs can be configured to include a flexure bearing within the flexible circuit. The introduction of a bipolar electrode consisting of a single flexible circuit enables a number of unique configurations and features as described herein in connection with FIGS. 94-95 and FIGS. 96-97.

Figure 94:
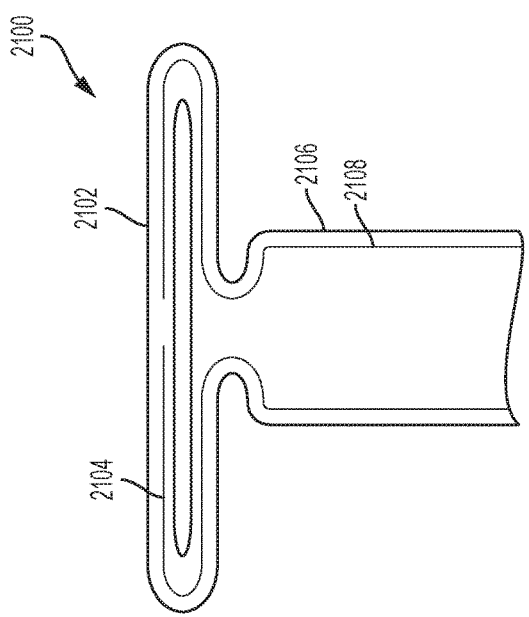

A. Flat Patterned Flexible Circuit Electrode where Upper and Lower Jaw Electrode Elements are in Transverse Orientation Relative to a Longitudinal Element FIG. 94 is a flat patterned flexible circuit electrode 2100 in a flat state where an upper jaw electrode element 2102 and a lower jaw electrode element 2104 are in transverse orientation relative to a longitudinal element, according to one aspect of the present disclosure. The flexible circuit 2100 comprises an upper jaw electrode element 2102, a lower jaw electrode element 2104, and a longitudinal element 2106 that extends from the junction of the upper and lower jaw electrode elements 2102, 2104 to a control circuit or a generator circuit. Electrically conductive traces 2108 extend along the longitudinal element 2106 and in the upper and lower jaw electrode elements 2102, 2104 to deliver electrical energy to an end effector. The flexible circuit electrode 2100 is manufactured in the flat state in a single contiguous component as shown in FIG. 94 and is folded in the state shown in FIG. 95 when disposed within the electrosurgical instrument.

Figure 95:
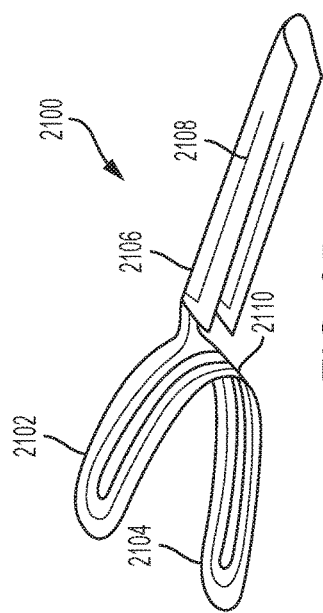

FIG. 95 illustrates the flat patterned flexible circuit electrode 2100 shown in FIG. 94 in a folded state where the upper and lower jaw electrode elements 2102, 2104 create a flexure bearing 2110, according to one aspect of the present disclosure. The flexible circuit electrode 2100 is folded in the state shown in FIG. 93 when it is disposed within a surgical instrument. The upper jaw electrode element 2102 is disposed in the upper jaw of an end effector and the lower jaw electrode element 2104 is disposed in the lower jaw of the end effector. The longitudinal element 2106 is disposed within a shaft of the electrosurgical instrument. The flexure bearing 2110 provides the necessary flexure when the upper and lower jaws of the end effector open and close.

Figure 96:
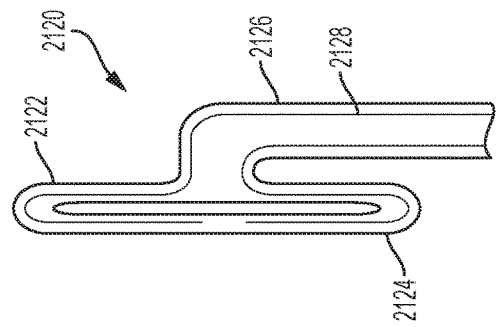
FIGS. 94-97 illustrate flat patterned flexible circuit electrodes comprising a flexure bearing, according to one aspect of the present disclosure, where.

B. Flat Patterned Flexible Circuit Electrode where Upper and Lower Jaw Electrode Elements are in Parallel Orientation Relative to a Longitudinal Element FIG. 96 is a flat patterned flexible circuit electrode 2120 in a flat state where the upper and lower jaw electrode elements 2122, 2124 are in parallel orientation relative to a longitudinal element 2126, according to one aspect of the present disclosure. The flexible circuit 2120 comprises an upper jaw electrode element 2122, a lower jaw electrode element 2124, and a longitudinal element 2126 that extends from the junction of the upper and lower jaw electrode elements 2122, 2124 to a control circuit or a generator circuit. Electrically conductive traces 2128 extend along the longitudinal element 2126 and in the upper and lower jaw electrode elements 2122, 2124 to deliver electrical energy to the end effector. The flexible circuit electrode 2120 is manufactured in the flat state in a single contiguous component as shown in FIG. 96 and is folded in the state shown in FIG. 97 when disposed within an electrosurgical instrument.

Figure 97:
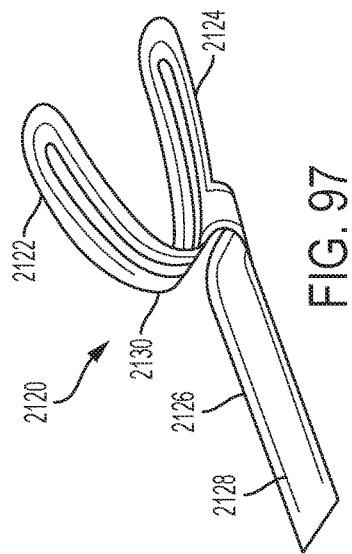

FIG. 97 illustrates the flat patterned flexible circuit electrode 2120 shown in FIG. 96 in a folded state where the upper and lower jaw elements 2122, 2124 create a flexure bearing 2130, according to one aspect of the present disclosure. The flexible circuit electrode 2120 is folded in the state shown in FIG. 97 when it is disposed within an surgical instrument. The upper jaw electrode element 2122 is disposed in the upper jaw of an end effector and the lower jaw electrode element 2124 is disposed in the lower jaw of the end effector. The longitudinal element 2106 is disposed within a shaft of the electrosurgical instrument. The flexure bearing 2110 provides the necessary flexure when the upper and lower jaws of the end effector open and close.

XIV. Switching and Control

Figure 98:
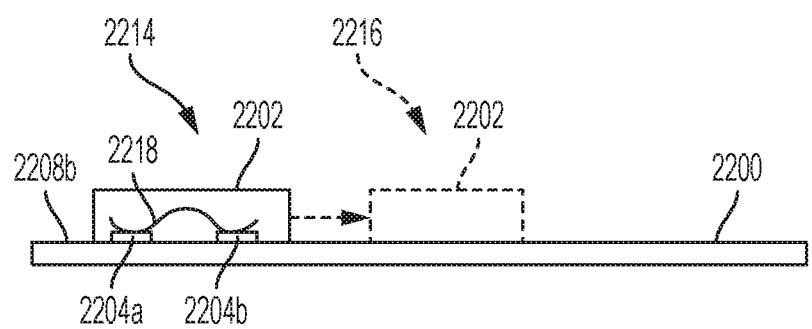
FIGS. 98-99 illustrate a flexible circuit integrated comprising an integrated slider switch to control switching modes, according to one aspect of the present disclosure, where.
Figure 99:
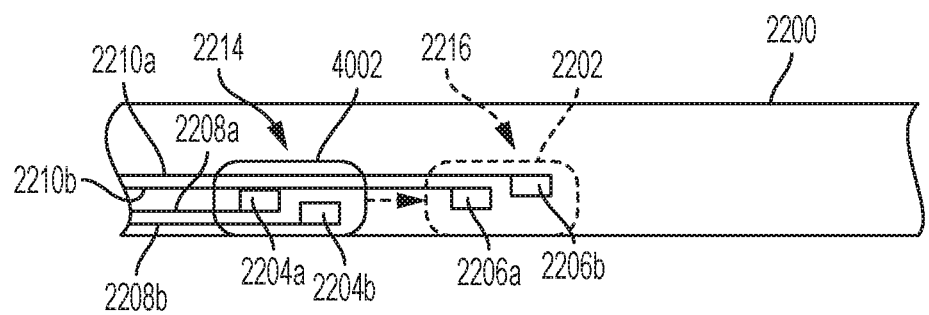

A. Flexible Circuit Including an Integrated Slider Switch to Control Switching Modes FIGS. 98-99 illustrate a flexible circuit comprising an integrated slider switch to control switching modes, according to one aspect of the present disclosure. The flexible circuit can be located proximally in a handle of an electrosurgical instrument and may contain a series of conductive pads with conductive traces. When the conductive pads are bridged with a slider switch different functionality can be obtained. In one aspect, the slider switch may be employed to switch between bipolar and monopolar RF operation.

FIG. 98 is a side elevation view of a flexible circuit electrode 2200 comprising an integrated slider switch 2202, according to one aspect of the present disclosure. FIG. 99 is a plan view of the flexible circuit electrode 2200 shown in FIG. 98 showing the integrated slider switch 2202, according to one aspect of the present disclosure. With reference now to FIGS. 98-99, the flexible circuit electrode 2200 can be positioned proximally in a handle of an electrosurgical instrument. The flexible circuit electrode 2200 comprises a series of conductive pads 2204a, 2204b, 2206a, 2206b with conductive traces 2208a, 2208b, 2210a, 2210b. When the conductive pads 2204a, 2204b, 2206a, 2206b are bridged with the contact 2218 of the slider switch 2202 different functionality can be obtained. In one aspect, the slider switch 2202 may be employed to switch between monopolar RF operation in a first position 2214 shown in solid line where the return path is disconnected and bipolar RF operation shown in a second position 2216 shown in phantom line.

B. Selectively Addressable Flexible Circuit Electrode Including Controlled Switching Areas and Switching Modes FIGS. 100-102 illustrate various flexible circuit electrode configurations including a controlled switching area to control various switching modes and enabling the flexible circuit electrode to be selectively turned on and off in different areas, according to one aspect of the present disclosure. The flexible circuit electrode can be turned on and off in different areas to enable the inside and outside portions of the end effector to be controlled separately. This enables control of the current density through the width of the electrode. Other aspects enable the distal electrode element to be used for touching up around bleeding areas at the surgical site. Other aspects enable control of the outside edges to enable touch up with the distal electrode element or allow the user to turn off the outer edges when operating around delicate structures.

FIG. 100 is a planar view of a flexible circuit electrode 2300 configured to enable inner and outer segments 2302, 2304 of the electrode 2300 to be controlled separately and independently, according to one aspect of the present disclosure. The flexible circuit 2300 comprises a knife slot 2306 and an inner electrode 2302 and an outer electrode 2304 surrounding the knife slot 2306. The inner and outer electrodes 2302, 2304 are separately and independently controllable. Accordingly, the inner and outer electrodes 2302, 2304 can be separately and independently energized. This configuration enables the flexible circuit electrode 2300 to be turned on and off in different areas to enable the inner and outer segments 2302, 2304 of the flexible circuit electrode 2300 to be controlled separately. This enables control of the current density through the width of the flexible circuit electrode 2300.

FIG. 101 is planar view of a flexible circuit electrode 2310 configured to enable separate and independent control of a distal tip 2318 of the electrode 2310, according to one aspect of the present disclosure. The flexible circuit electrode 2310 comprises one electrode 2312 disposed along lateral segments 2316a, 2316b of a jaw of an end effector separated by a knife slot 2317 and another electrode 2314 located at the distal tip 2318. The lateral and distal electrodes 2312, 2314 are separately and independently controllable. Accordingly, the lateral and distal electrodes 2312, 2314 can be separately and independently energized. This configuration enables the distal tip 2318 of the flexible circuit electrode 2310 to be used for touching up around bleeding areas at the surgical site.

FIG. 102 is a section view of a flexible circuit electrode 2320 configured to enable separate and independent control of the outer edges 2326a, 2326b of the flexible circuit electrode 2320, according to one aspect of the present disclosure. The flexible circuit electrode 2320 comprises a first electrode 2322 that is disposed along a planar surface of a jaw of an end effector and a second electrode 2324 that is disposed along the outer edges 2326a, 2326b. A knife slot 2328 is defined between the first and second electrodes 2322, 2324. The first and second electrodes 2322, 2324 are separately and independently controllable. Accordingly, the first and second electrodes 2322, 2324 can be separately and independently energized. This configuration enables control of the outside edges of the flexible circuit electrode 2320 to be used for touching up areas or to allow the user to turn off the second electrode 2324 at the outer edges 2326a, 2326b when operating around delicate structures.

It will be appreciated, that the various flexible circuit electrode configurations shown in FIGS. 100-102 can be incorporated in one aspect. Accordingly, any one of the various aspects of the electrode configurations shown in FIGS. 100-102 can be combined to control various switching areas and modes of an end effector. Accordingly, one aspect comprises a combination of the flexible circuits 2300 and 2310 as described in FIGS. 100 and 101. Another aspect, comprises a combination of the flexible circuits 2300 and 2320 as described in FIGS. 100 and 102. Another aspect, comprises a combination of the flexible circuits 2310 and 2320 as described in FIGS. 101 and 102. Finally, another aspect comprises a combination of the flexible circuits 2300, 2310, and 2320 as described in FIGS. 100-102. Thus, the flexible circuit electrode can be selectively turned on and off in different areas, according to one aspect of the present disclosure.

Figure 103:
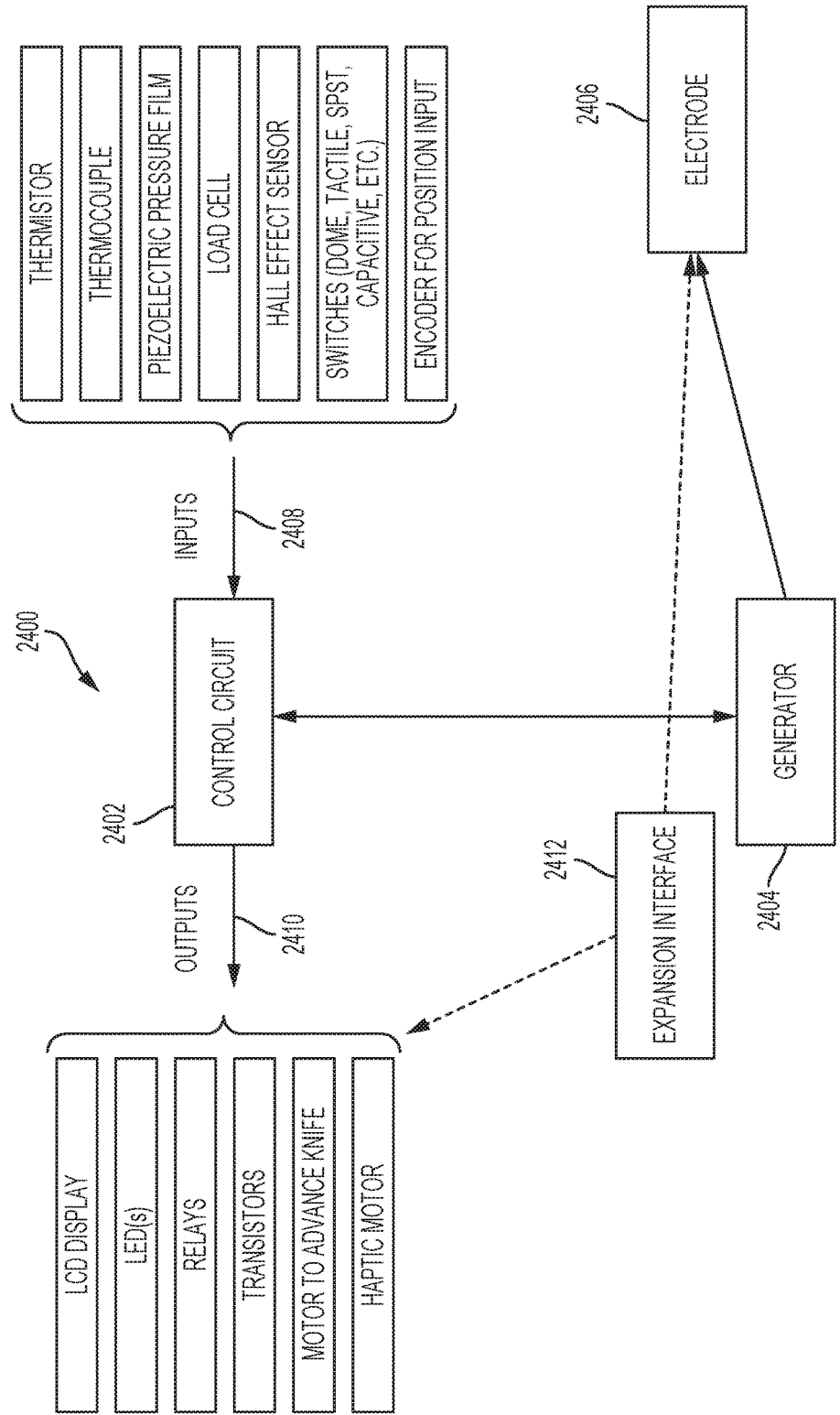
FIGS. 103-113 illustrates techniques for switching and controlling a radio frequency (RF) flexible circuit electrode, according to various aspects of the present disclosure, where.

C. Techniques for Switching and Controlling Radio Frequency (RF) Flexible Circuit Electrodes FIGS. 103-113 illustrate techniques for switching and controlling a radio frequency (RF) flexible circuit electrode, according to various aspects of the present disclosure. FIG. 103 is a diagram illustrating components and interconnections of a system 2400 of an electrosurgical instrument for switching and controlling a radio frequency (RF) flexible circuit electrode 2406, according to one aspect of the present disclosure. The interconnections between the switching and controlling can be electrically interconnected via a flexible circuit. The system 2400 comprises a control circuit 2402 coupled to a generator 2404. The control circuit 2402 may comprise an application specific integrated circuit (ASIC), microprocessor, microcontroller, field programmable gate array (FPGA), programmable logic device (PLD), among other digital and/or analog circuits. The generator 2404 is coupled to the flexible circuit electrode 2406. The control circuit 2402 is configured to receive one or more inputs 2408 and provide one or more control outputs 2410 to control the operation of the electrosurgical instrument. An optional expansion interface 2412 may be provided.

Some examples inputs 2408 to the control circuit 2402 include, without limitation, any sensor with analog, I$^2$C, serial communication, or digital interface. These sensors include, without limitation, thermistors, thermocouples, piezoelectric film temperature, pressure, force load cell for pressure or force measurement, Hall effect or encoder sensors to measure position of clamp arm or closer trigger, switch inputs (dome, tactile, capacitive). When the control circuit 2402 comprises an ASIC, microprocessor or FPGA, additional inputs 2408 can be incorporated into the electrosurgical instrument.

Some examples control outputs 2410 from the control circuit 2402 include, without limitation, solid or blinking LED's to indicate to the surgeon state of the instrument (RF energy delivery, high temperature of clamp arm, and seal complete. Additional outputs 2410 include haptic motor control to provide tactile feedback to surgeon. Stepper or pulse width modulation (PWM) outputs 2410 can be utilized for motor control of the knife to advance the knife after seal is complete or in conjunction with RF energy as the seal is completed for a particular electrode segment. Additional outputs 2410 may be employed to turn on relays or transistors to change the electrode (inside/outside, tip electrode, inner/outer, segment of the electrode). Display outputs 2410 include liquid crystal display (LCD) outputs to provide visual feedback to surgeon. When the control circuit 2402 comprises an ASIC, microprocessor or FPGA, additional control outputs 2410 can be incorporated into the electrosurgical instrument.

The system 2400 provides a means for switching and control of the RF flexible circuit electrode 2406. The circuit configurations of the system 2400 can be assembled on a flexible circuit or rigid flexible circuit that incorporates the RF flexible circuit electrodes 2406. The circuitry of the system 2400 may be located in the handle of the electrosurgical instrument and can be located on the flexible circuit in any location (i.e., the tail of the flexible circuit or near the RF flexible circuit electrode 2406) that enables the desired functionality. To enable the switching of energy to the RF flexible circuit electrode 2406 the user of the electrosurgical instrument can provide an input that the RF generator 2404 receives to switch the energy on to the RF output pins of the generator 2404 according to various algorithms. In one aspect, the generator 2404 receives the input on the handswitch wires of the generator 2404. In one aspect, the handswitch input to the generator 2404 can be an analog input (based on voltage measured being with in defined range for input) or it can be received digitally via a communication protocol.

Figure 104:
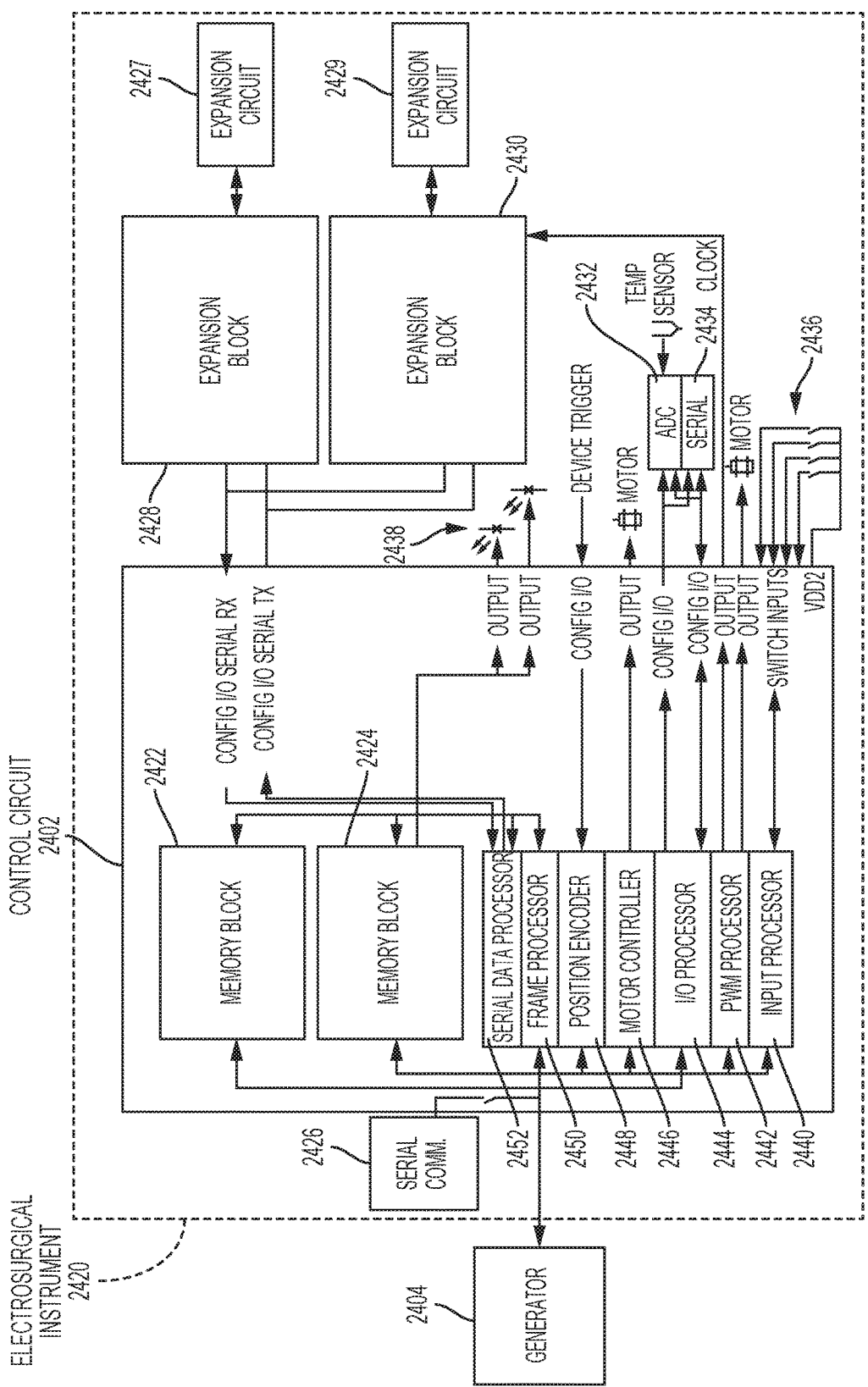

FIG. 104 is diagram of the system 2400 for switching and controlling a radio frequency (RF) flexible circuit electrode 2406 shown in FIG. 103 where an application specific integrated circuit (ASIC) is employed for the control circuit 2402, according to one aspect of the present disclosure. As shown in FIG. 104, an electrosurgical instrument 2420 is depicted in block diagram form. The electrosurgical instrument 2420 comprises a control circuit 2402 implemented as shown in FIG. 104 as an ASIC. The electrosurgical instrument 2420 also comprises a serial communication memory 2426, one or more expansion blocks 2428, 2430 each coupled to corresponding expansion circuits 2427, 2429. The electrosurgical instrument 2420 also comprises an analog-to-digital converter 2432 (ADC), a serial communication interface 2438, a bank of switches 2436 to indicate various states of the electrosurgical instrument 2420. The electrosurgical instrument 2420 also includes various LEDs 2436 to indicate states of the electrosurgical instrument 2420. The electrosurgical instrument 2420 is coupled to and receives energy signals and information from a generator 2404 and can communicate information to the generator 2404.

The control circuit 2402 comprises one or more memory blocks 2422, 2424. The first memory block 2422 is coupled to the second memory block 2424, to an input/output (I/O) processor 2444, and a frame processor 2450. The second memory block 2424 is coupled to a position encoder 2448, a motor controller 2446, a PWM processor 2442, and an input processor 2440. A serial data processor 2452 is coupled to first and second expansion blocks 2428, 2430, where each one is coupled to one or more expansion circuits 2427, 2429. The serial data processor 2452 controls the serial receiving (RX) and transmission (TX) functions.

The control circuit 2402 receives various inputs and outputs. In one aspect, for example, the frame processor 2450 of the control circuit 2402 is in two-way communication with the generator 2404. The input processor 2440 receives inputs from the switch bank 2436, where the switches indicate a state of the electrosurgical instrument 2420. Temperature sensors and other sensor inputs are provided to the ADC 2432, which is in coupled to the I/O processor 2444. A serial communication interface 2434 also is coupled to the I/O processor 2444. Device trigger inputs are coupled to the position encoder 2448. In one aspect, the input to the position encoder 2448 may be a quadrature encoder input, for example.

The control circuit 2402 also provides various control outputs. For example, the stepper motor controller 2446 provides control outputs to one or more motors of the electrosurgical instrument 2420. The PWM processor 2442 generates PWM waveforms and outputs the PWM waveforms to one or more motors of the electrosurgical instrument 2420. One or more outputs from one of the memory blocks 2424 is coupled to one or more LEDs 2438 of the electrosurgical instrument 2420. Additional functionality may include, without limitation, discrete inputs, discrete outputs, serial communication memory, and/or additional serial ports.

With reference now to FIGS. 103 and 104, the use of an ASIC, microprocessor, microcontroller, FPGA, and/or PLD for the control circuit 2402 provides the ability of processing input and output control occur locally (in the electrosurgical instrument 2420) rather than requiring the generator 2404 to process the input and output controls. This may provide faster real time control of outputs based on the inputs received by the expansion interface box. This expansion interface 2412 shown in FIG. 103, would enable the generator 2420 system to provide expanded capabilities such as high power, monopolar RF capability, combined RF/ultrasonic operation, control, or provide additional power to outputs such as motors, LCD displays, LED's 2438.

The ASIC implementation of the control circuit 2402 shown in FIG. 104, is configured to provide circuitry within the ASIC control circuit 2402 for interfacing and processing inputs and outputs. The ASIC control circuit 2402 can accept up to 8 or more discrete inputs and 8 or more discrete outputs (open drain [pull low] or totem pole type). The control circuit 2402 can interface with the generator 2404 utilizing any suitable communication protocol. The generator 2404 receives the status of the inputs and sends command to the ASIC control circuit 2402 to turn on outputs. This ASIC control circuit 2402 is placed on the flexible circuit or a rigid flexible circuit and is located within the handle of an electrosurgical instrument 2420 including, without limitation, monopolar and/or bipolar radio RF instruments, microwave instruments, reversible and/or irreversible electroporation instruments, and/or ultrasonic instruments, or any combination thereof.

Figure 105:
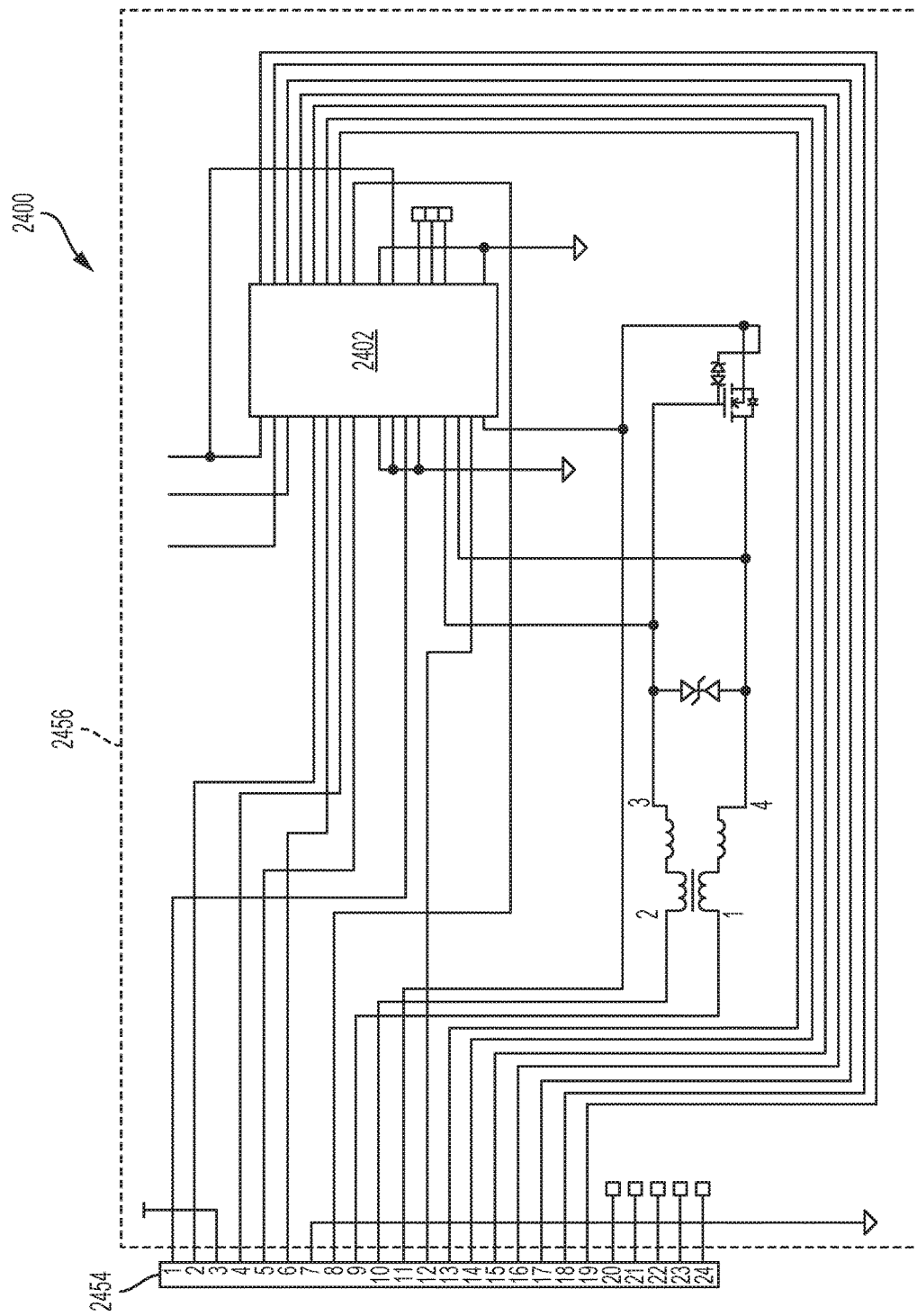

FIG. 105 is an electrical schematic of the system 2400 for switching and controlling a radio frequency (RF) flexible circuit electrode shown in FIGS. 103 and 104, according to one aspect of the present disclosure. The system 2400 comprises an ASIC control circuit 2402 and a connection 2454 to the system I/O. The electrically conductive interconnections can 2456 be formed on a flexible circuit or a rigid flexible circuit coupled to the flexible circuit electrode 2406.

Figure 106:
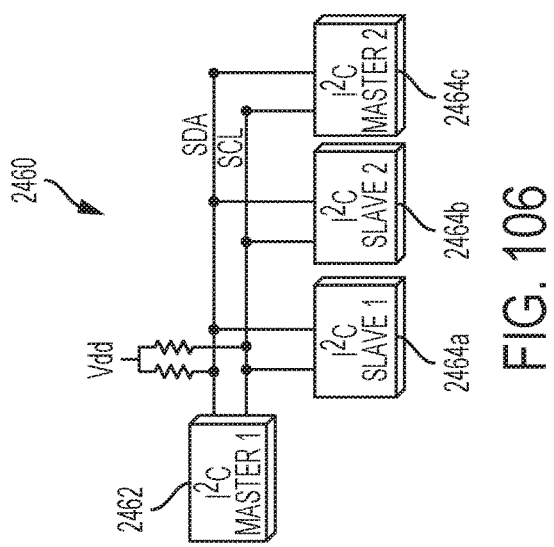

FIG. 106 is a diagram serial communication circuit 2460 that may be employed by the system 2400 shown in FIGS. 103, 104, according to one aspect of the present disclosure. The serial communication circuit 2460 may be an I²C serial communication interface comprising a multi-master 2462, multi-slave 2464a, 2464b, 2464c, single-ended, serial computer bus typically used for attaching lower-speed peripheral integrated circuits to processors and microcontrollers. The serial communication circuit 2460 provides a standard serial port used to communicate to a wide variety of commercial off-the-shelf electronic components. The serial communication circuit 2460 may be employed to communication to/from multiple components using a single 2-wire serial bus, as described in connection with FIGS. 103 and 104, for example. The serial communication circuit 2460 can be used to interact with I²C compatible temperature sensors, non-volatile memory (e.g., EEPROMs), motor controllers, analog-to-digital converters (ADC) and DAC (e.g., for tissue sensing, nerve stimulation, etc.), real time clocks, LCD drivers for displays, and/or position/angle sensors, for example. In one aspect, the I/O processor 2444 shown in FIG. 104 may be implemented using a circuit similar to the serial communication circuit 2460.

Figure 107:
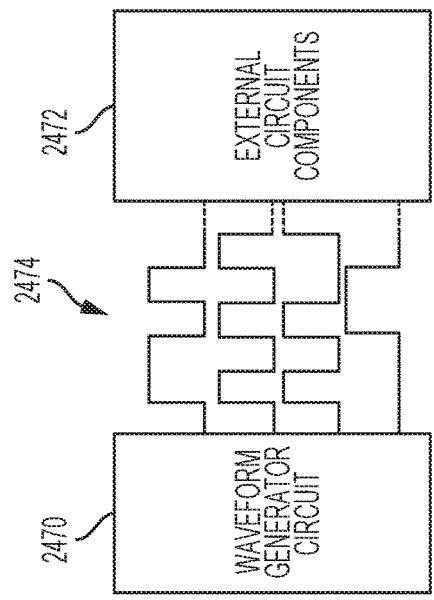

FIG. 107 is a waveform generator circuit 2470 configured to generate up to 4 synchronous arbitrary digital waveforms 2474 that may be employed by the system 2400 shown in FIGS. 103 and 104, according to one aspect of the present disclosure. As shown in FIG. 107, the 4 synchronous arbitrary digital waveforms 2474 generated by the waveform generator circuit 2470 are output to various external circuit components 2472. In one aspect, the waveform generator circuit 2470 may be employed as the PWM processor 2442 shown in FIG. 104. The synchronous arbitrary digital waveforms 2474 may be employed as custom digital communication protocol to the external components 2472. The synchronous arbitrary digital waveforms 2474 also may provide clocks or other required signals to the external components 2472 (e.g., to reduce the number of components required for expanded functionality). The synchronous arbitrary digital waveforms 2474 also may be provided to DAC converters (e.g., analog reference voltage, nerve stimulation), blinking LEDs, change tone of a sounder, and/or piezo driver, for example.

Figure 108:
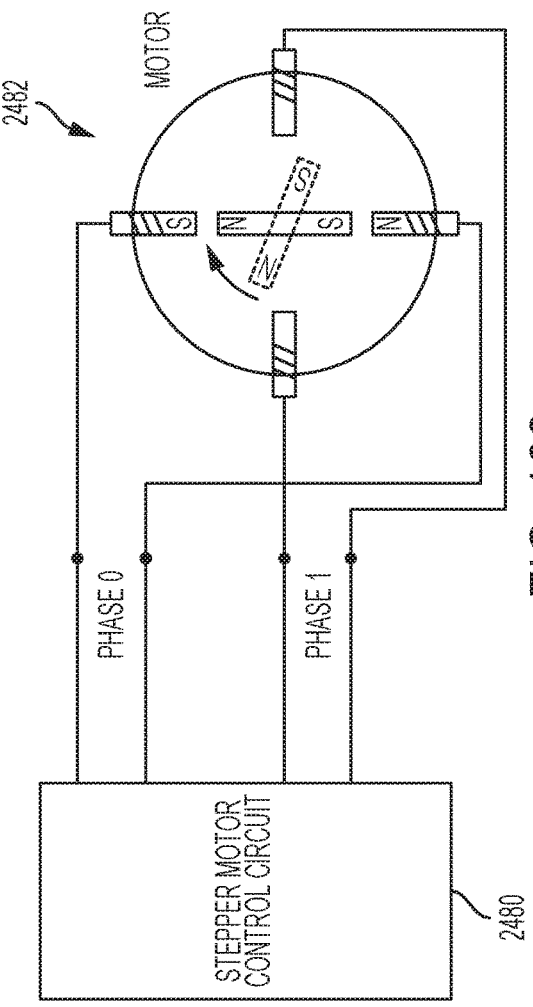

FIG. 108 is a stepper motor control circuit 2480 configured to drive a stepper motor 2482 that may be employed by the system 2400 shown in FIGS. 103 and 104, according to one aspect of the present disclosure. The stepper motor control circuit 2480 provides stepper motor control for the stepper motor 2482 and can drive a specified number of steps in a given direction OR drive until an external stop switch is thrown. The stepper motor control circuit 2480 also can control ramp rates, speed, number of steps, etc., configured by the generator 2404 as shown in FIGS. 103 and 104, for example. In one aspect the motor controller 2446 shown in FIG. 104 may be implemented as the stepper motor control circuit 2480, for example.

Figure 109:
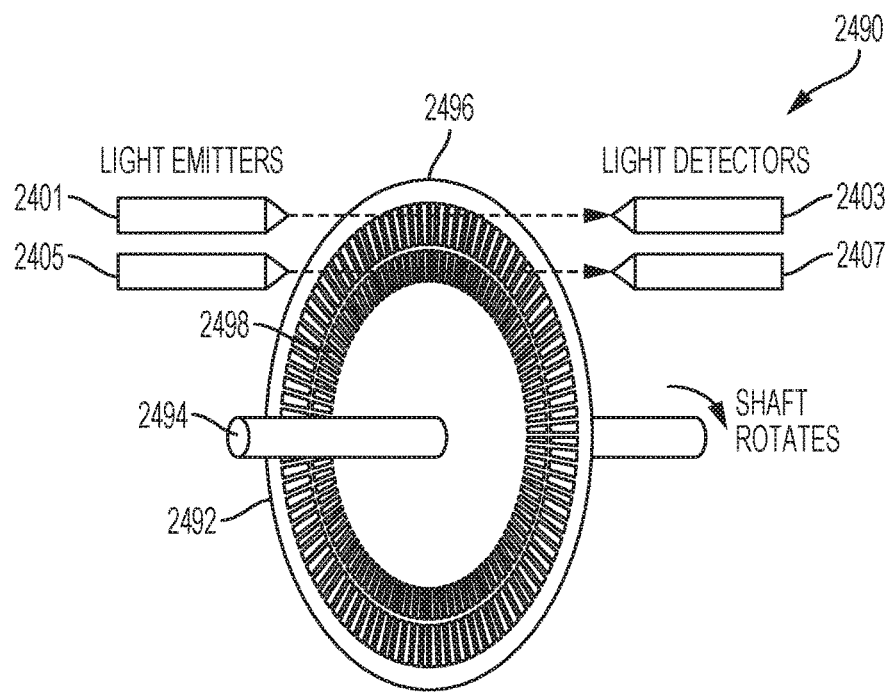
Figure 110:
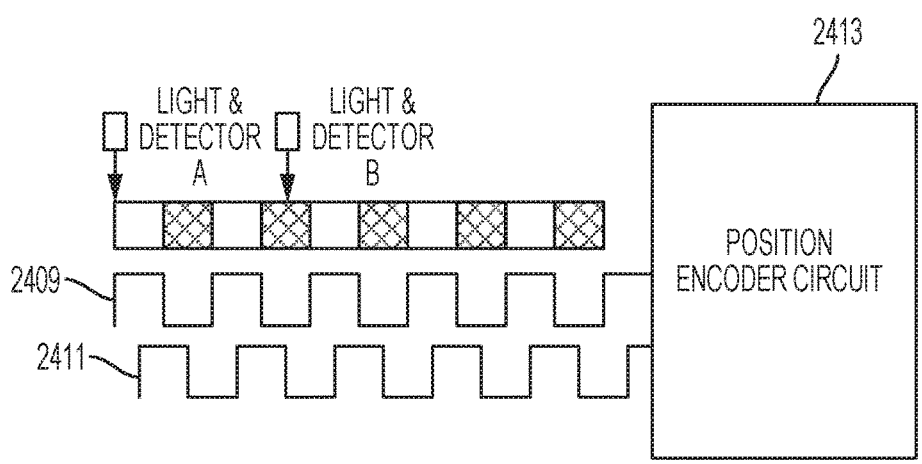

FIG. 109 is a quadrature encoder 2490 for sensing the position of a rotating disk 2492 that may be employed by the system 2400 shown in FIGS. 103 and 104, according to one aspect of the present disclosure. FIG. 110 is a schematic diagram of the quadrature encoder 2490 shown in FIG. 109, according to the present disclosure. With reference now to FIGS. 109 and 110, in one aspect the quadrature encoder 2490 comprises a disk 2492 configured to rotate about a shaft 2494. The disk 2492 comprises outer slits 2496 and inner slits 2498, where the outer and inner slits 2496, 2498 are alternating and where the outer slits 2496 are disposed about an outer diameter of the disk 2492 relative to the inner slits 2498, which are disposed about an inner diameter of the disk 2492. A first light emitter 2401 is positioned on one side of the disk 2492 to transmit light through the outer slits 2496 to be detected by a first light detector 2403 located on the other side of the disk 2492. A second light emitter 2405 is positioned on one side of the disk 2492 to transmit light through the inner slits 2498 to be detected by a second light detector 2407 located on the other side of the disk 2492.

As shown in FIG. 110, as the disk 2492 rotates the light detected at the first detector 2403 (A) and the light detected at the second detector 2407 (B) produce alternating waveforms 2409, 2411, respectively, that are in quadrature (i.e., 90° out phase relative to each other). These waveforms 2409, 2411 are provided to a position encoder circuit 2413 to determine the current position of a mechanism coupled to the shaft 2494 of the disk 2492. In one aspect, the position encoder circuit 2413 may be the position encoder circuit 2448 of the control circuit 2402 shown in FIG. 104 such that the control circuit 2402 can determine the current position of a mechanism coupled to the shaft 2494 of the disk 2492. The current position information can be communicated to the generator 2404 (FIG. 104) either automatically or upon request of the generator 2404. In one aspect, for example, the quadrature encoder 2492 may be employed to determine the position of the knife blade, among others.

Figure 111:
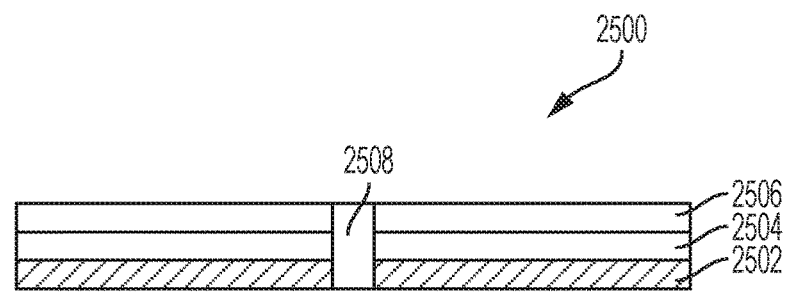

FIG. 111 is a section view of a flexible circuit electrode 2500 comprising a sensing layer 2502 disposed below an electrically insulative layer 2504 (e.g., polyimide, polyester, fluorocarbon, or any polymeric material, or any combinations thereof), which is disposed below an electrically conductive layer 2506, according to one aspect of the present disclosure. The flexible circuit electrode 2500 also comprises a knife slot 2508. With the electronics configuration described in connection with FIGS. 103 and 104, the control logic 2520 shown in FIG. 113 can be incorporated into the system 2400 (FIGS. 103, 104) of the electrosurgical instrument 2420 (FIG. 104) to measure the temperature of the end effector clamp. The sensing layer 2502 may comprise a temperature sensitive device or material such as, for example, a thermocouple, thermistor, or piezoelectric film that is mounted to the clamp arm between the electrically insulative layer 2504 of the flexible circuit and the electrode 2500 on the clamp arm, or any combination thereof. Once measured by the system 2400, the temperature can be displayed on an LCD or LED(s) lit solidly or blinking to indicate that the temperature is above a threshold where damage to surrounding tissue could result if the clamp arm comes into contact with this tissue. The measured temperature could also be utilized in an algorithm running in the generator 2404 (FIGS. 103, 104) to adjust the current provided to the RF flexible circuit electrode 2500 to prevent undesirable damage to tissue.

Figure 112:
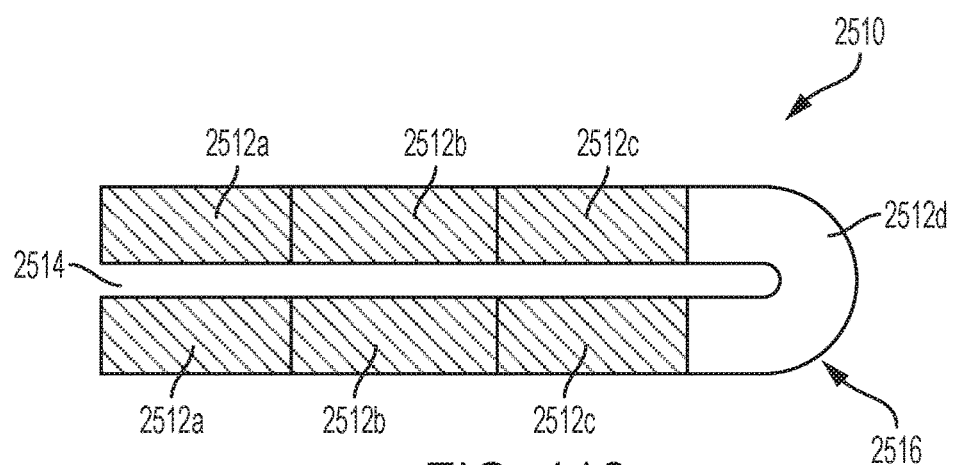

FIG. 112 is a plan view of a segmented flexible circuit electrode 2510 comprising four segments 2512a, 2512b, 2512c, 2512d, according to one aspect of the present disclosure. In various aspects, the segmented flexible electrode 2506 can be segmented into multiple zones. Although the example segmented flexible circuit electrode 2510 shown in FIG. 111 comprises four independently controllable segments or zones, a segmented flexible circuit electrode according to the present disclosure may comprise at least two segments or zones. One or more of the segments 2512a-2512d may comprise a separate LED to indicate its activation status. Accordingly, the RF energy to one of the segments 2512a-2512d may be switched on or off independently as required by an algorithm based on the measured temperature. In one aspect, the segmented flexible circuit electrode 2506 also may comprise the sensing layer 2502 of the flexible circuit electrode 2500 as described in connection with FIG. 111. The first three segments 2512a-2512c are separated by a knife slot 2514 and the fourth segment 2512d is located at the distal tip 2516 of the flexible circuit electrode 2510.

Figure 113:
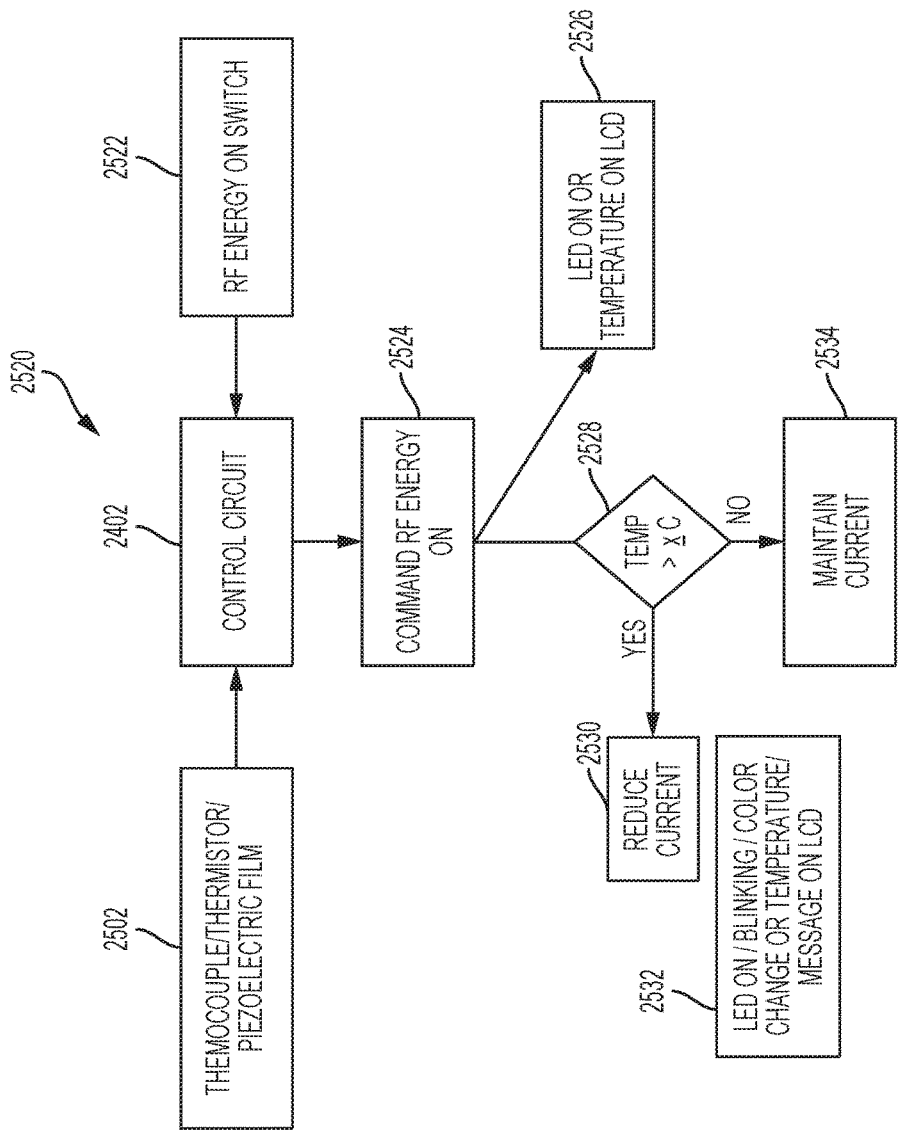

FIG. 113 is a logic diagram 2520 for controlling a segmented flexible circuit electrode that may be employed by the system shown in FIGS. 103 and 104, according to one aspect of the present disclosure. According to one of the logic diagram 2520, a control circuit 2402, such as the control circuit 2402 described in connection with FIGS. 103 and 104, receives various inputs such as inputs from a temperature sensing layer 2502 disposed on a flexible circuit electrode 2500, 2510 as described in connection with FIGS. 111 and 112. The control circuit 2402 also may receive an energy activation/deactivation signal from a switch disposed on the electrosurgical instrument. As shown in FIG. 113, the control circuit 2402 receives a signal from the switch to turn on 2522 or activate the RF energy. The control circuit 2402 provides 2524 a command to turn on the RF energy and thus electrical current flows to the flexible circuit electrode 2500, 2510 to treat tissue. The control circuit 2402 monitors the temperature of the flexible circuit electrode 2500, 2510 by monitoring the temperature sensing layer 2502. The control circuit 2402 indicates 2526 the measured temperature either by turning on or off selected LEDs or simply displaying the temperature on a LCD. The control circuit 2402 compares 2528 the temperature to a predetermined value and when the temperature exceeds a predetermined threshold, the process continues along Yes branch to reduce 2530 the current to the flexible circuit electrode 2500, 2510. At which point, the control circuit 2402 may indicate 2532 the over temperature condition by turning an LED on, blinking the LED, changing the color of the LED, displaying change or temperature or some other message on the LCD. When the temperature does not exceed the predetermined threshold, the process continues along No branch to maintain 2534 the current level.

D. Flexible Circuit Electrode for Switching and Controlling Data Storage

In various aspects, the flexible circuit electrode for switching and controlling data storage may be configured to store use data for root cause investigation. Utilizing a flex circuit electrode, sensors, and a controller (ASIC, Microprocessor, or FPGA), additional inputs and output controls may be enabled. Storing this information in the device handle, or generator, would allow users that are performing a root cause investigation on a returned device, full access to the detailed inputs and outputs that were utilized with the instrument during the procedure.

Figure 114:
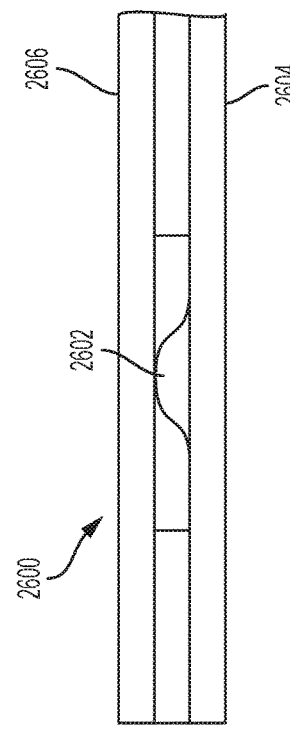
FIGS. 114-118 illustrate a mechanical temperature switch embedded in a multi layer flexible circuit electrode to implement flexible circuit switching electrodes based on the bimetal temperature principle, according to one aspect of the present disclosure, where.
Figure 115:
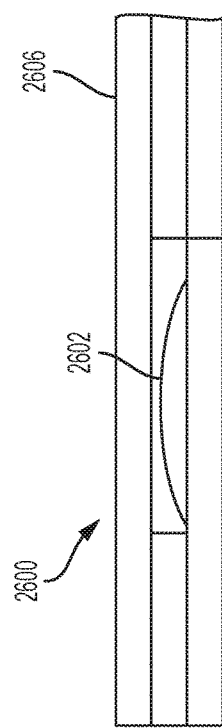
Figure 116:
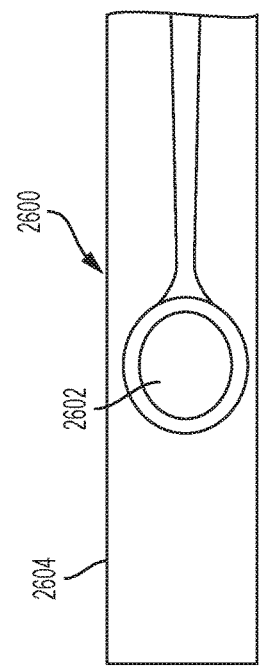

E. Multi Layer Flexible Circuit Electrode Including Embedded Mechanical Temperature Switch FIGS. 114-118 illustrate a mechanical temperature switch embedded in a multi layer flexible circuit electrode to implement flexible circuit switching electrodes based on the bimetal temperature principle, according to one aspect of the present disclosure. FIG. 114 is a cross section view of a multilayer flexible circuit electrode 2600 comprising a mechanical switch in the form of a dome 2602 disposed on the lowest layer 2604 of the multilayer flexible circuit electrode 2600 in a non-contact state, according to one aspect of the present disclosure. The dome 2602 is configured to expand and contract in response to changes in temperature. For example, in one aspect the dome 2602 may expand in response to an increase in temperature and in another aspect, the dome 2602 may contract in response to a decrease in temperature. The temperature control element, such as the dome 2602, is thus incorporated into the flexible circuit electrode 2600 for electrosurgical device applications. The dome 2602 mechanical switch is embedded in the layers of the multilayer flexible circuit electrode 2600. In the example shown in FIG. 114, the dome 2602 expands to make contact when a predetermined temperature is reached. Using a multilayer flexible circuit electrode 2600, a contact dome 2602 is placed on the lowest layer 2604. In a low temperature state, the dome 2602 does not make contact with a circuit on an adjacent layer 2606. When the temperature increase, the dome 2602 expands and makes electrical contact with a circuit on the adjacent layer 2606. FIG. 115 is a lower plan view of the multilayer flexible circuit electrode 2600 shown in FIG. 114, according to one aspect of the present disclosure. FIG. 116 is an upper plan view of the multilayer flexible circuit electrode 2600 shown in FIG. 114, according to one aspect of the present disclosure.

FIG. 117 is a cross section view of the multilayer flexible circuit electrode 2600 showing the dome 2602 disposed on the lowest layer 2604 of the multilayer flexible circuit electrode 2600 in an electrical contact state, according to one aspect of the present disclosure. As shown in FIG. 117, the dome 2602 is in an expanded state and in is electrical communication with a circuit on an adjacent layer 2606 of the multilayer flexible circuit electrode 2600.

FIG. 118 is a cross section view of a multilayer flexible circuit electrode 2610 comprising a mechanical switch in the form of a spring 2612 disposed on the lowest layer 2614 of the multilayer flexible circuit electrode 2610 in a non-contact state, according to one aspect of the present disclosure. The spring 2612 is configured to expand and contract in response to changes in temperature. For example, in one aspect the spring 80012 may expand in response to an increase in temperature and in another aspect, the spring 2612 may contract in response to a decrease in temperature. The temperature control element, such as the spring 2612, is thus incorporated into the flexible circuit electrode 2610 for electrosurgical device applications. The dome 2602 mechanical switch is embedded in the layers of the multilayer flexible circuit electrode 2610. In the example shown in FIG. 118, the spring 2612 expands to make contact when a predetermined temperature is reached. Using a multilayer flexible circuit electrode 2610, a contact spring 2612 is placed on the lowest layer 2614. In a low temperature state, the spring 2612 does not make contact with a circuit on an adjacent layer 2616. When the temperature increase, the spring 2612 expands and makes electrical contact with a circuit on the adjacent layer 2616.

F. Segmented Flexible Circuit Electrode Including Sensor Configured to Provide Feedback to a Motorized Knife Control Circuit to Control Position of Motorized Knife FIGS. 119-121 illustrate a segmented flexible circuit electrode 2700 including a sensor configured to provide feedback to a motorized knife control circuit for controlling the position of the motorized knife 2702, according to one aspect of the present disclosure. Position control of the knife 2702 may be implemented utilizing the control circuit 2402 of the electrosurgical instrument 2420 control system 2400 described in connection with FIGS. 103 and 104 and the position and motor controlled circuits described in connection with FIGS. 108-110, for example. The motorized knife 2702 is configured to reciprocate within a knife slot 2706.

The segmented flexible circuit electrode 2700 comprises four separate and distinct electrode segments 2704a, 2704b, 2704c, 2704d that can be independently energized. Each of the electrode segments 2704a, 2704b, 2704c, 2704d comprises sensor elements 2708a, 2708b, 2708c, 2708d to detect tissue presence and/or tissue seal. The sensor elements 2708a-2708d may comprise pressure or thermal sensors to detect tissue presence and tissue seal may be determined by tissue impedance feedback techniques. The sensors 2708a-2708d may be embedded in or disposed on the segmented electrode elements 2704a-2704d, respectively. For example, prior to applying energy to the tissue via one of the segmented flexible electrode segments 2704a-2704d the tissue is rich in moisture and the impedance of the tissue is very low. Applying RF energy to the tissue to effect a seal desiccates the tissue making it less conductive and thus increases the tissue impedance. Upon completion of the seal, the desiccated tissue will generally have a very high impedance. Impedance may be measured by the control circuit 2402 by measuring the drive current through the segmented flexible electrode segments 2704a-2704d and the voltage between the segmented flexible electrode segments 2704a-2704d and a return path.

The control circuit 2402 employs feedback from the sensor elements (pressure, thermal) and the tissue impedance measurements to control the position of the motor driven knife 2702. In one aspect, for example, the control circuit 2402 will drive the knife 2702 only as far as tissue is located within the jaw of the end effector. This technique provides knife 2702 travel along the knife slot 2706 permitting simultaneous cutting and sealing of tissue while preventing the knife 2702 from advancing distally along the slot 2706 until the pressure or thermal sensor 2708a-2708d "detects" the presence of tissue within the jaws of the end effector and/or further detecting when a tissue seal is effected by measuring the tissue impedance.

FIG. 119 illustrates the segmented flexible circuit electrode 2700 where only the proximal electrode segment 2704a is activated, according to one aspect of the present disclosure. The proximal electrode segment 2704a is activated once tissue (not shown for clarity of disclosure) is detected by the pressure or thermal sensor 2708a located in the proximal electrode segment 2704a. Activation of the proximal electrode segment 2704a seals the tissue and signals the control circuit 2402 (FIG. 104) to advance the motor controlled knife 2702 longitudinally to coincide with the proximal electrode segment 2704a by the control circuit 2402 (FIG. 104). A pressure sensor 2708a located in the proximal electrode segment 2704a detects the presence of tissue. The control circuit 2402 receives the feedback signal from the sensor and activates the proximal electrode segment 2704a. The control circuit 2402 advances the knife 2702 along the extent of the proximal electrode segment 2704a upon receiving the tissue presence feedback signal from the pressure sensor 2708a. Alternately, the feedback signal to the control circuit 2402 is provided by a thermal sensor 2708a that indicates the completion of a tissue seal. Upon receiving the tissue seal feedback signal, the control circuit 2402 advances the knife 2702 along the extent of the proximal electrode segment 2704a where the tissue is located. Once tissue is detected, the proximal electrode segment 2704a is energized to seal the tissue and the knife 2702 is advanced through the slot 2706.

FIG. 120 illustrates a segmented flexible circuit electrode 2700 where the intermediate electrode segment 2704b is activated, according to one aspect of the present disclosure. The motor controlled knife 2702 is now extended beyond the extent of the proximal electrode segment 2704a and extends longitudinally into the intermediate electrode segment 2704b by the control circuit 2402 (FIG. 104). As previously discussed, advancement of the knife 2702 into the intermediate electrode segment 2704b is controlled by the control circuit 2402 when tissue is detected in the intermediate electrode segment 2704b. Once tissue is detected by the sensor 2708b, the intermediate electrode segment 2704b is energized to seal the tissue and the knife 2702 is advanced through the slot 2706.

FIG. 121 illustrates a segmented flexible circuit electrode 2700 where the distal electrode segment 2704c is activated, according to one aspect of the present disclosure. The motor controlled knife 2702 is now extended beyond the extent of the proximal and intermediate electrode segments 2704a, 2704b and extends longitudinally into the distal electrode segment 2704c by the control circuit 2402 (FIG. 104). As previously discussed, advancement of the knife 2702 into the distal electrode segment 2704c is controlled by the control circuit 2402 when tissue is detected in the intermediate electrode segment 2704b. Once tissue is detected by the sensor 2708c, the distal electrode segment 2704c is energized to seal the tissue and the knife 2702 is advanced through the slot 2706.

It will be appreciated that when tissue spans two or more electrode segments, the two or more electrode segments will be activated and the knife 2702 will be driven forward by the motor under control of the control circuit 2402 (FIG. 104). Further, the distal electrode element segment 2704d also may comprise a sensor 2708d and may be energized independently whether or not tissue is detected by the sensor 2708d at the location of the distal tip.

G. Multi-Zone Segmented Flexible Circuit Electrode Configured to Output Different Algorithms and Treat for Each of the Zones Independently FIG. 122 illustrates a multi-zone (1, 2, 3) segmented flexible circuit electrode 2800 configured to output different algorithms for each of the zones 1-3 and treat tissue in each of the zones 1-3 independently, according to one aspect of the present disclosure. The disclosed multi-zone segmented flexible circuit electrode 2800 comprises three separate electrode segments 2802a, 2802b, 2802c that defines three separate and independently activatable zones 1-3. A different algorithm can be outputted to each of the electrode segments 2802a-2802c in each zone 1-3 to treat tissue located in each of the different zones 1-3 independently based on tissue type. Since tissue is not homogenous, the disclosed multi-zone segmented flexible circuit electrode 2800 enables the electrode segments 2802a-2802c to apply a different algorithm in different zones 1-3 to enable at least three different types of tissue to be treated therapeutically differently.

In an effort to achieve an algorithm that is suitable for treating a variety of tissue types, the multi-zone segmented flexible circuit electrode 2800 technique enables the treatment of tissue located in zones 1, 2, or 3 in a full byte of the jaw assembly differently. Thus a different algorithm can be employed to treat each tissue type and output multiple algorithms simultaneously for an optimized outcome. Accordingly, the disclosed multi-zone segmented flexible circuit electrode 2800 enables the selective treatment of tissue within zones 1-3 to optimize tissue sealing and reduce thermal damage.

The multi-zone segmented flexible circuit electrode 2800 can be layered and function independently. Utilizing tissue sensing techniques, each electrode segment 2802a-2802c can then output a separate algorithm that is specifically configured for the tissue that is being treated in that zone. Treating zones 1-3 independently provides optimized tissue effects and minimize unintended damage. It will be appreciated that the multi-zone segmented flexible circuit electrode 2800 may comprise at least two electrode segments 2802a-2802b and in other aspects may comprise more than three electrode segments 2802a-2802c, without departing from the scope of the present disclosure.

H. Technique for Implementing a Multiplexer with Flexible Electronic Circuits to Provide Improved Control Methods FIGS. 123-124 illustrate a technique for implementing a multiplexer 2900 with flexible electronic circuits to provide improved control methods, according to one aspect of the present disclosure.

FIG. 123 illustrates a two line multiplexer 2900 (MUX) implemented with flexible electronic circuits, according to one aspect of the present disclosure. A multiplexer is a device that selects one of several analog or digital input signals and forwards the selected input into a single output line. Generally, a multiplexer may comprise n select lines to select $2^n$ input lines to send to a single output line. For the multiplexer 2900 (MUX), n=2, thus two input select lines S0, S1 are used to multiplexed inputs provides $2^2=4$ select lines (1-4) that are forwarded to a single output line (Output). A multiplexer can increase the functionality of an electrosurgical instrument over a fixed hardware environment. Accordingly, in one aspect, the multiplexer 2900 may be employed to switch algorithm control between RF and ultrasonic energy in an electrosurgical instrument.

In one aspect the control circuit 2402 (FIG. 104) of the generator 2404 (FIG. 104) has eight inputs/outputs. If one input is dedicated to a single activation button, seven inputs remain available to a multiplexer to provide $2^7=128$ different combinations of lines that can be selected to forward to a single output line. This multiplexer configuration can simplify the use of transistors or relays to act as switches on power lines, to enable/disable undesired lines. The multiplexer, however, can be used for more than just the power lines and can be used for signal lines as well.

FIG. 124 illustrates a jaw configuration 2910 with independently actuatable electrodes 2912a-2912h, according to one aspect of the present disclosure. A knife slot 2914 is provided between banks of independently actuatable electrodes 2912a-2912h and a distal tip electrode 2916, which also can be independently actuated. A flexible electronic circuit based multiplexer can be employed to select multiple outputs to the segmented electrodes 2912a-2912h. This technique provides additional output control for turning on and off additional features of the electrosurgical instrument by making use of flexible circuit electrode electronics, specifically sensors, transducers and more.

Referring now to FIGS. 123-124, in various aspects, a 128-to-1 a multiplexer can select one of 128 combinations of lines for switching on and off based on eight input select lines. The multiplexer configuration can enable multiple combinations of the segmented electrodes 2912a-2912h to sense tissue presence, provide profile of impedance in tissue, better characterize tissue, determine orientation in the jaw, provide "smarter" switching between ultrasonic and RF, apply heat only in low impedance sections of tissue instead of across entire load in jaws to improve speed or reduce charring/inadvertent burning, better allow spot coagulation and scoring and use the multiplexer for auto-detection and provide a separate switch that the user presses, energize segmented electrodes. Additionally, the multiplexer configuration can turn sensors or transducers on/off, enable or disable a multi-transducer model, apply power to and read force sensors, pressure sensors, and temperature sensors, determine upperology of tissue. The multiplexer configuration also can turn lights or LEDs on/off and make better use of buttons, among other features.

In some aspects, employing a multiplexer in combinations with the segmented electrode 2910 provides multiple combinations of electrodes to limit the number of power transistors or isolation relays by putting a single transistor or relay on each output of the multiplexer which can be located by the control circuit 2402 (FIG. 104). The output of the transistors or relays can be on the hand switch circuit, which can then allow for the portion of the flexible circuit to go down the shaft of the instrument. In other aspects, a multiplexer may enable the user to imitate monopolar RF operation when the tip electrode 2916 only activated or when the sides of the segmented electrode 2910 are electrified. In yet other aspects, a multiplexer may be provided advanced bipolar RF energy such that the generator 2404 (FIG. 104) can switch through electrode pairs to allow the generator 2404 to identify where the tissue is located in the jaws. Also, the generator 2404 can identify impedances to know when all of the tissue or only a portion of the tissue requires additional energy or more time effect a seal. This technique can be employed to activate only on sections of tissue that need to be activated upon or when a short circuit is present, the generator 2404 can switch to ultrasonic energy drive. Additionally, there are other ultrasonic techniques to determine the occurrence of a true short circuit versus the presence of low impedance tissue (frequency changes on metal, in addition to auditory change from metal-on-metal contact). Finally, in one aspect, when the tissue impedance is greater than the termination impedance but less than an open circuit impedance across all electrode combinations, ultrasonic energy may be delivered by the generator 2404 to effect the seal rather than bipolar RF energy.

I. Flexible Circuit Segmented Electrode Including Inner and Outer Materials Having Different Thermal Conductivity Properties for Altering Tissue Effects FIG. 125 illustrates a flexible circuit segmented electrode 3000 comprising an inner material 3002 and an outer material 3004 that have different thermal conductivity properties for altering tissue effects, according to one aspect of the present disclosure. The inner and outer materials 3002, 3004 are disposed on an electrically insulative film 3006 (e.g., polyimide, polyester, fluorocarbon, or any polymeric material, or any combinations thereof). The flexible circuit segmented electrode 3000 may be mass produced for electrosurgical instruments. The inner and outer materials 3002, 3004 are bonded to the electrically insulative film 3006 backing to produce a sub-assembly. The inner and outer materials 3002, 3004 can be produced by laminating metallic sheets to the electrically insulative film 3006. The shape of the electrode can be formed by screen printing a protective barrier to the metallic film. This protective barrier permits the shape of the inner and outer materials 3002, 3004 to be formed by photoetching away the remaining material which does not make up the final shape of the inner and outer materials 3002, 3004. Finally the flexible circuit segmented electrode 3000 is die-cut out leaving an electrode sub-assembly that can be bonded to the jaws of the end effector. The electrically insulative film 3006 can have an adhesive or a braze-able surface on the back side of the electrically insulative film 3006 thus allowing for means of attachment to the lower or upper jaw elements depending on the device jaw construction.

Separation of the electrode 3000 with different materials 3002, 3004 permits different impedance and power levels to be controlled. The inner and outer materials 3002, 3004 may be selected to have different heating characteristics such that either the inner material 3002 or the outer material 3004 faster than the other. For example, the thermal affected zone may be reduced by selecting an inner material 3002 that heats faster than an outer material 3004.

XV. Pressure Sensing

A. Flexible Circuit Electrode Including Integrated Pressure Sensor

FIGS. 126-130 illustrates an integrated thin flexible circuit electrode 3100 comprising a pressure sensor 3102 integrated with the flexible circuit electrode 3100, according to one aspect of the present disclosure. FIG. 126 illustrates a thin and flexible circuit electrode 3100 comprising a switching pressure sensor 3102, according to one aspect of the present disclosure. A pressure sensor 3102 (such as a thin flexible sensor known under the tradename TEKSCAN) is attached (e.g., laminated) to the one side of an electrically insulative layer 3104 (e.g., polyimide, polyester, fluorocarbon, or any polymeric material, or any combinations thereof) of the flex circuit electrode 3100. The other side of the electrically insulative layer 3104 comprises electrically conductive traces 3106 made of copper, silver, gold, and similar conductive element s or alloys. A knife slot 3108 is provided such that the knife can reciprocate therein. The thin and flexible circuit electrode 3100 comprising a switching pressure sensor 3102 can enable a closed loop system in the device where the control circuit 2402 (FIG. 104) reads the pressure in the jaw elements of the end effector to adjust the duty cycle and/or current of the drive energy. When the pressure is low, the control circuit 2402 can apply more power without any additional programming required in the generator 2404 (FIG. 104).

FIG. 127 is a lower plan view of the flexible circuit electrode 3100 shown in FIG. 126 showing the pressure sensor 3102, according to one aspect of the present disclosure. FIG. 128 is a side view of the flexible circuit electrode 3100 shown in FIG. 126 with an embedded pressure sensor, according to one aspect of the present disclosure. FIG. 129 is a plan view of the flexible circuit electrode 3100 shown in FIG. 126 with a tissue bundle 3110 present thereon, according to one aspect of the present disclosure. FIG. 130 is a plan view of the flexible circuit electrode 3100 shown in FIG. 126 with a vessel present 3112, according to one aspect of the present disclosure.

With reference now to FIGS. 126-130, the thin flexible pressure sensor 3102 can be integrated with a flexible circuit electrode 3100 to drive a generator based on load feedback. For example, an RF generator feedback can be customized based on a pressure profile/compression in the end effector jaws. In one aspect, the thin flexible pressure sensor 3102 may be in the form of a tape (such as the type provided by TEKSCAN) is integrated with a flexible layered circuit electrode 3100 to enable detection of a pressure profile in jaw/compression force and drive the RF generator in response thereto based on the tissue type. For example, when a large bundle of tissue is detected, the RF generator is driven at greater power and when a small vessel is detected in the center of the jaws, the RF generator is driven according to a sealing algorithm.

B. Flexible Circuit Electrode Including Integrated Pressure Sensor to Localize or Adjust Closure Pressure The integrated thin flexible circuit electrode 3100 comprising a pressure sensor 3102 described in connection with FIGS. 126-130, may be employed to localize or adjust closure pressure by controlling the force on the tissue and pressure regulation using the pressure sensor 3102 feedback to the control circuit 2402 (FIG. 104). In other aspects, a flexible circuit electrode may incorporate single, or multiple separate layers that include small bimetallic discs, interfaced with a current delivering wire. As current is applied to the disc, it heats up, and the bimetallic layer causes it to expand. As it expands, the jaw or electrode would deliver more compression in that area of the jaw. Additionally, utilizing multiple layers, or selectively isolated sections of a single layer provides a selectably controlled closure force at unique points of the jaws. This system could be used in conjunction with other systems to generate many different desired outcomes. Some possible implementations are described below:

In one aspect, a dynamic pulse closure pressure technique may be employed. An initial very heavy closure force on activation to ensure mechanical movement of musculature layer is provided before easing off to slow transection to generate optimum hemostasis.

In another aspect, a layer of different compression profiles in different sections of jaw may be enabled to selectively engage tissue. One example is to create high tip compression when not activating the device to generate good grasping, and then reduce it during energy activation to ensure uniform treatment.

In yet another aspect, on either the same of different layer, a wire mesh may be arranged to simulate a strain gauge in series with the bimetallic disc system. As a section receives additional pressure from tissue resistance or other closure load, it will deform the strain gauge, increasing its resistance. This results in less current for the discs, reducing the force that they will produce. This feature will collectively allow the device to automatically balance the closure pressure uniformly along jaws.

In another aspect, a layer of different discs in patterns radiating outward from blade or cut location are provided. Pressure is initially pulsed, to start inward and then moves outwardly to facilitate fluid transfer outward away from the upcoming cut, thus allowing the electrosurgical instrument to apply energy directly to tissue without excess fluid at or near the cut line.

C. Flexible Circuit Electrode Including Selective Electrode Zones (1-3) Activation Employing Piezoelectric Pressure Detection FIGS. 131-133 illustrate a flexible circuit electrode 3200 comprising selective electrode zones (1-3) activation employing piezoelectric pressure detection, according to tone aspect of the present disclosure. FIG. 131 illustrates a segmented flexible circuit electrode 3200 divided into three activation segments 3202a, 3202b, 3202c, and a knife slot 3216, according to one aspect of the present disclosure. FIG. 132 is a section view of the segmented flexible circuit electrode 3200 shown in FIG. 131 showing a layer electrode 3204, a circuit layer 3206, a piezoelectric ceramic sensor layer 3214, according to one aspect of the present disclosure. FIG. 133 schematically illustrates a load pressure 3210 from tissue being applied to the electrode segments 3202a, 3202b (sections 2-3) and a reaction pressure 3211 applied to underlying ceramic piezoelectric sensors 3208b, 3208c, according to one aspect of the present disclosure.

With reference to FIGS. 131-133, in one aspect, the piezoelectric ceramic sensor layer 3214 comprises piezoelectric ceramic sensors 3208a, 3208b, 3208c are located in corresponding segmented electrodes 3202a, 3202b, 3202c in sections 1-3 of the electrode 3200. The piezoelectric ceramic sensor layer 3214 is located below each defined electrode segments 3202a-3202c or zones (1-3). As pressure is applied to the electrode 3200, the underlying ceramic piezoelectric sensors 3208a-3208c detect the pressure applied in the sections 1-3. The electrode segments 3202a-3202c of the electrode 3200 are then activated or enabled. For example, as tissue contacts sections 2 and 3 of the distal tip 3212 of the electrode 3200, the electrode segments 3202b and 3202c in sections 2 and 3 are enabled while the electrode 3202a in section 1 remains inactive.

The two electrode segments 3202b, 3202c are activated when a voltage difference $\Delta V$, produced by the tissue load pressure 3210 is applied to the two electrode segments 3202b, 3202c and a reaction pressure 3211 is applied to the two piezoelectric ceramic sensor 3208b, 3208c and to sections 2-3. The voltage difference ΔV developed is response to the applied pressure 3210, 3211 is detected by the control circuit 2402 (FIG. 104). In one aspect, the flexible circuit electrode 3200 is configured such that the electrode segments 3202a-3202c can be selectively enabled only where tissue is located thereon. This technique minimizes heat generation in non-tissue containing sections. In various aspects, additional sections can be utilized as needed.

In one aspect, the flexible circuit electrode 3200 is coupled to the control circuit 2402 (FIG. 104) that selectively activates sections 1-3 of energy delivery by activating the electrode segments 3202a-3202c based on pressure sensed by the piezoelectric ceramic sensor 3208a-3208c. The flexible circuit electrode 3200 incorporates the piezoelectric ceramic sensor 3208a-3208c to detect pressure in a finite number of sections (1-3). Pressure applied to this piezoelectric ceramic layer 3214 indicates the presence of tissue in the jaws in that specific section due to the delta voltage created by the applied pressure. This section is then allowed to be active. Sections where no tissue is present remain inactive and heat generation is minimized.

XVI. Temperature Sensing

A. Flexible Circuit Electrode Including Embedded Optical Temperature Sensor

FIGS. 134-136 illustrate an optical temperature sensor 3300 embedded in a flexible circuit electrode 3302 according to one aspect of the present disclosure. FIG. 134 is a plan view of an optical temperature sensor 3300 embedded in the flexible circuit electrode 3302, according to one aspect of the present disclosure. FIG. 135 is as section view of the optical temperature sensor 3300 embedded in a flexible circuit electrode 3302 taken along section line 135-135 as shown in FIG. 134, according to one aspect of the present disclosure. The optical temperature sensor 3300 comprises a flexible circuit electrode 3302 with a light pipe 3304 embedded therein. The embedded optical temperature sensor 3300 can be incorporated in the flexible electrode 3302 by printing a light pipe 3304 of a high index transparent material on a substrate 3310 with a lower index of refraction. A photodiode 3306 and an LED 3308 light source are fixed and optically coupled at each end of the light pipe 3304. Measuring the amount of transmitted light can be used to measure temperature. The flexible circuit electrode 3302 also defines a knife slot 3314 to enable a knife to reciprocate therealong.

As shown in FIG. 135, the light pipe 3304 is disposed on a substrate 3310 and is covered by a compliant material 3312. The optical temperature sensor 3300 can be embedded in the flexible electrode 3302 by printing a light pipe 3304 of a transparent material with a refraction index higher than the index of the substrate 3310. The light pipe 3304 is covered with the compliant material 3312 having a lower refraction index than that of the light pipe 3304. This way the equivalent of an optical fiber is achieved. The light transmitted by the light pipe 3304 depends on the refraction indices of the substrate and compliant materials involved. The refraction indices depend on temperature, thus allowing temperature measurement.

In one aspect, the optical temperature sensor 3300 works on the principle of variation of transmitted light through an optical fiber, e.g., the light pipe 3304, due to changes of the index of refraction with temperature. The embedded optical temperature sensor 3300 enables monitoring the temperature of the flexible circuit electrode 3302 during tissue sealing operations. During sealing, the flexible circuit electrode 3302 may overheat, causing damage to adjacent tissue. Feedback of electrode temperature to the control circuit 2402 (FIG. 104) can be used to adjust the RF power applied to the flexible circuit electrode 3302. This also permits minimizing damage to neighboring tissue.

FIG. 136 is a schematic of a bent fiber section 3320 curved with a radius of curvature R, according to one aspect of the present disclosure. FIG. 136 shows a schematic of a curved multimode step index optical fiber [19]. The radius of curvature is R and the core diameter is $2\rho_{Core}$. The refractive indices of the core and cladding are $n_{Core}$, and $n_{Cladding}$, respectively. Optical power is launched at the beginning of the rectilinear region of the fiber. The geometrical description of the core rays in a step-index optical fiber is more complex than in a planar waveguide [20], due to the presence of the skew rays. The guidance of the core rays is achieved by ensuring that the propagation angle, α, satisfies the condition: $0 \le \alpha \le \alpha_c$, where the critical angle ($\alpha_c$) is given by: $\alpha_c = \sin^{-1}(n_{Cladding}/n_{Core})$. The expression of the numerical aperture (NA) for the rectilinear region is given by:

$$NA = n_{Core} \cdot \sin \alpha \le (n_{Core}^2 - n_{Cladding}^2)^{1/2} \quad (1)$$

However, in the bend optical fiber, the guidance of the core rays can follow two ways. Only the rays entering the bent part of the fiber in the meridional plane remain with the same angle of incidence along a given ray path. On the other hand, the skew rays entering this plane after the successive reflections within the core, do not follow a simple repeatable pattern because of the asymmetry introduced by bending the fiber. So when the optical fiber is bent, the local numerical aperture changes at a given location of the bent optical fiber. The dependence of the numerical aperture with the bend is given by [19]:

$$NA(R, \rho, \phi) = n_{Core}\left[1 - \frac{n_{Cladding}^2}{n_{Core}^2}\left(\frac{R + \rho_{Core}}{R - \rho \cdot \cos\phi}\right)^2\right]^{1/2} \quad (2)$$

where ϕ is the ray angle at the beginning of the bend, which varies from 0° to 180°, $\rho_{Core}$ is the fiber core radius and p is the radial position in the core satisfying the relation $0 \le \rho \le \rho_{Core}$.

The optical fiber sensor proposed in this paper is based on a macro-bend POF. In this intensity sensor, the losses induced by the bending effect depend on the numerical aperture that changes with temperature. The refractive index of the core and cladding POF depend on the temperature. The POF used in the experiments is a Rayon® Eska® SH-4001 (Mitsubishi, Tokyo, Japan) with core and cladding manufactured using polymethyl methacrylate (PMMA) and fluorinated polymer, respectively. The temperature dependence of the core refractive index can be expressed as [21]:

$$n_{Core}(T) = K_2 \cdot T^2 + K_1 \cdot T + n_0 \quad (3)$$

where $K_1 = -1.15 \cdot 10^{-4} (° C.)^{-1}$ is the thermo-optic (TO) co efficient of the core, $K_2 = -5.173 \cdot 10^{-7} (° C.)^{-2}$ is the second order temperature dependence term of the core and $n_0 = 1.49538$ is the core refractive index at 0° C. On the other hand, the temperature dependence of the cladding refractive index is given by [22.]:

$$n_{Cladding}(T) = n_{Cladding}(T_0) + K_3 \cdot (T - T_0) \quad (4)$$

where $K_3 = -3.5 \cdot 10^{-4} (° C.)^{-1}$ is the TO coefficient of the cladding and $n_{Cladding}(T_0) = 1.403$ is the cladding refractive index at the reference temperature ($T_0 = +25°$ C.)

It can be seen that $|K_3|>|K_1|$. Finally, from Equation (2), the local numerical aperture in the bent section of the fiber versus the temperature can be expressed as:

$$NA(T, R, \rho, \phi) = n_{Core}(T)\left[1 - \frac{n_{Cladding}^2(T)}{n_{Core}^2(T)}\left(\frac{R+\rho_{Core}}{R-\rho\cdot\cos\phi}\right)^2\right]^{1/2} \quad (5)$$

A detailed explanation of a similar sensor is given in the attached article. *A Temperature Sensor Based on a Polymer Optical Fiber Macro-Bend*, Alberto Tapetado Moraleda, Carmen Vázquez García, Joseba Zubia Zaballa and Jon Arrue, Sensors 2013, 13, 13076-13089; doi:10.3390/s131013076; ISSN1424-8220.

B. Flexible Circuit Bladder Sensor for Sensing Pressure and Temperature

FIGS. 137-138A illustrate a flexible circuit bladder sensor 3400 for sensing pressure and temperature, according to one aspect of the present disclosure. FIG. 137 is an exploded view of the flexible circuit bladder sensor 3400, according to one aspect of the present disclosure. FIG. 138 is an elevation view of the flexible circuit bladder sensor 3400 attached to a jaw member 3410 of an end effector, according to one aspect of the present disclosure. The flexible circuit bladder sensor 3400 is configured to measure force during closure and measure temperature during treatment using a bladder element 3402 adhered to the back side 3404 of a flexible circuit electrode 3406. The back side 3404 of the electrode 3406 comprises a plastic flexible layer usually made of an electrically insulative material (e.g., polyimide, polyester, fluorocarbon, or any polymeric material, or any combinations thereof). The other side of the electrode 3406 is the tissue contacting side 3408. As shown in FIG. 138, the flexible bladder element 3402 is located somewhere on the tissue contacting portion of the flexible circuit in order to sense pressure changes when tissue is contacted, clamped, and treated. In one aspect, the actual pressure sensing element (e.g., pressure sensing element 3434, see FIG. 138A) can be co-located on the flexible circuit. In other aspects, however, the pressure sensing element can be located somewhere else in the device.

The flexible circuit bladder sensor 3400 can be configured to measure force during closure and temperature during treatment employing a flexible micro bladder element 3402 adhered to the back side 3404 of a flexible circuit electrode 3406. Thus, both force and temperature can be measured on the flexible circuit electrode 3406 in an electrosurgical device, as referenced herein.

In one aspect, the flexible bladder element 3402 may be fabricated by adhering a flexible sheet to the back of side 3404 of a flexible circuit electrode 3406 to create a flexible bladder element 3402 of any desired shape, size, or location on the electrode 3406 area of the flexible circuit 3406. In one aspect a tube 3412 is formed between the flexible sheet and the back side of the flexible circuit electrode 3406. The tube 3412 and the bladder element 3402 are in fluid communication and define a volume. The bladder element 3402 and the tube 3412 may be formed as a single piece unit. In another aspect, the tube 3412 may be formed using two flexible sheets.

The flexible bladder element 3402 is in fluid communication with the tube 3412, which is configured to transmit the pressure in the bladder element 3402 to a pressure sensing element of a circuit 3420 via an open end 3414 of the tube 3412. The open end 3414 is sealed to the input port 3422 of the pressure sensing integrated circuit 3420. Thus, the pressure is contained within a closed system. The tube 3412 extends to a point where the pressure sensing integrated circuit 3420 is located. In one aspect, a pressure sensing integrated circuit 3420 is attached to the flexible circuit electrode 3406 and converts the pressure to an electrical signal. In one aspect, the pressure sensing integrated circuit 3420 may be mounted on the surface of the flexible circuit electrode 3406.

In operation, when the jaws of the end effector are closed, the bladder 3402 compresses and increases pressure in the tube 3412 created by the flexible sheet against the back side 3404 of the flexible circuit electrode 3406. When the temperature increases, the pressure increases in the bladder and therefore senses pressure at jaw closure and temperature during treatment. The circuit is in communication with the control circuit 2402 (FIG. 104).

FIG. 138A is a section view of the pressure sensing integrated circuit 3420, according to one aspect of the present disclosure. The pressure sensing integrated circuit 3420 comprises an input port P1 to receive the input pressure from the tube 3412 and a second port P2, which is normally open to atmospheric pressure, but can be closed to a vacuum to measure absolute pressure applied to the input port P1. The pressure sensing integrated circuit 3420 comprises fluorosilicone gel die coat 3424 disposed over an integrated circuit die 3426. A stainless steel cap 3428 and a thermoplastic case 3430 enclose the die 3426 and pressure chamber. The die 3426 is bonded 3432 to the thermoplastic case 3430. The die 3426 comprises a differential pressure sensing element 3434. As pressure is applied to port P1, the differential pressure sensing element 3434 deforms and generates a voltage proportional to the applied pressure. The voltage is coupled to an external lead frame 3436 by way of wire bonds 3438. In one aspect, the pressure sensing integrated circuit 3420 may be a MPXV6115V series sensor integrates on-chip, bipolar op-amp circuitry and thin film resistor networks to provide a high output signal and temperature compensation. The pressure sensing integrated circuit 3420 has a small form factor and benefits from the high reliability of on-chip integration. The differential pressure sensing element 3434 comprises a monolithic, signal conditioned, silicon pressure sensor. The sensor combines advanced micromachining techniques, thin film metallization, and bipolar semiconductor processing to provide an accurate, high level analog output signal that is proportional to applied pressure.

C. Flexible Circuit Thermocouple Sensor

FIGS. 139-140 illustrate a flexible circuit thermocouple sensor 3500, according to one aspect of the present disclosure. FIG. 139 is a schematic diagram of the flexible circuit thermocouple sensor 3500, according to one aspect of the present disclosure. FIG. 140 is a section view of the flexible circuit thermocouple sensor 3500, according to one aspect of the present disclosure. With reference now to FIGS. 139 and 140, a thermocouple 3502 is provided in a flexible circuit electrode 3504 by creating a contact between two dissimilar metals 3506, 3508. To reduce electromagnetic interference (EMI), the thermocouple 3502 layer is sandwiched. The flexible circuit thermocouple sensor 3500 can be employed to monitor the temperature of the flexible circuit electrode 3504 during sealing.

The thermocouple 3502 can be built in a flexible circuit. If the flexible circuit also contains an RF electrode, special precautions should be taken to avoid EMI noise in the thermocouple circuit. Since the flexible circuit electrode 3504 may overheat during sealing and cause damage to neighboring tissue, feedback from the flexible circuit electrode 3504 can be used to adjust the power applied by the generator 2404 (FIG. 104). Thus the flexible circuit thermocouple sensor 3500 can be used to minimize damage to neighboring tissue during sealing.

As shown schematically in FIG. 139, the flexible circuit thermocouple sensor 3500 comprises a thermocouple 3502 formed by creating a contact between two dissimilar metals 3506, 3508. The dissimilar metals 3506, 3508 are coupled to an instrumentation amplifier 3510, which amplifies the low level signal produced by the thermocouple 3502. A guard 3514 surrounds the thermocouple metals 3506, 3508 and is driven by the output 3516 of a buffer amplifier 3518 to shield the low level signal produced of the thermocouple 3502.

The low level signal produced by the thermocouple 3502 can be masked by EMI when the RF power is applied. EMI noise may be coupled in several ways: (1) Common Mode Noise Coupled by Ground Loop; (2) Capacitive Coupling; and (3) Magnetic Coupling. For the first two modes, insulating the thermocouple and shielding it with the driven guard 3514 is a common method. Having the guard 3514 surrounding the thermocouple 3502 connected to a low impedance buffer amplifier 3518 that keeps it at a fixed voltage (e.g., ground) makes it very effective in preventing noise coupling by stray capacitance and leak resistance in the thermocouple 3502. The simplified schematic illustrates the canceling of induced currents 3520 due to EMI. Avoiding a large area loop in the thermocouple circuit is the most effective method to prevent induced noise currents. In a flat geometry, like the flexible circuit, this can be achieved by balanced canceling loops.

FIG. 140 is a section view of the flexible circuit thermocouple sensor 3500, according to one aspect of the present disclosure. The flexible circuit thermocouple sensor 3500 comprises an electrically insulative material 3522 (e.g., polyimide, polyester, fluorocarbon, or any polymeric material, or any combinations thereof). The first metal 3506 of the thermocouple 3502 is embedded in the electrically insulative material 3522 and is coupled to the second metals 3508, which also are embedded in the electrically insulative material 3522. The thermocouple 3502 metals 3506, 3508 are surrounded by the guard 3514 conductors, which may be copper, for example.

XVII. Optical Tissue Sensing

A. Flexible Circuit Electrode Including Integrated Pulse-Oximeter Sensor

FIGS. 141-142 illustrate a pulse-oximeter sensor integrated in a flexible circuit electrode for identifying blood flow in tissue located between jaw members of an end effector prior to clamping and cutting, according to one aspect of the present disclosure. The pulse-oximeter sensor and/or i-watch technology, LED light sources, and photodiode optical sensors positioned within a flexible circuit electrode may be employed to notify the end user of blood flow within tissue located between the jaw members of an end-effector.

FIG. 141 illustrates a system 3600 comprising an electrosurgical instrument 3602 coupled to a generator 3604, according to one aspect of the present disclosure. The electrosurgical instrument 3602 comprises an LED light 3620 located on the handle 3622. The electrosurgical instrument 3602 also comprises an end effector 3606 comprising a pulse-oximeter sensor 3608 integrated in flexible circuit electrodes 3610a, 3610b comprising an element 3610a located in the upper jaw member 3614a and another element 3610b located in the lower jaw member 3614b. In another aspect, a wearable device sensor may be integrated in the flexible circuit electrodes 3610a, 3610b. In one aspect, the wearable device sensor comprises i-watch technology, for example.

FIG. 142 is a detail view of the end effector 3606 shown in FIG. 141 comprising a pulse-oximeter sensor 3608 integrated in the flexible circuit electrodes 3610a, 3610b, according to one aspect of the present disclosure. The pulse-oximeter sensor 3608 comprises LED light sources 3616 attached to the flexible circuit electrode 3610a located in the upper jaw member 3614a and a photodiode optical sensor 3618 is attached to the flexible circuit electrode 3610b located in the lower jaw member 3614b. The LED light sources 3616 and the photodiode optical sensor 3618 are coupled to the control circuit 2402 (FIG. 104) and/or the generator 3604 (e.g., the generator 2404 shown in FIG. 104). Similarly, the electrodes 3610a, 3610b may be coupled to the control circuit 2402 and/or to the generator 3604. The control circuit 2402 drives the LED light sources 3616 and the light 3626 is received by the photodiode optical sensor 3618. The output voltage produced by the photodiode optical sensor 3618 is indicative of the blood flow 3624 and/or oxygen ($O_2$) levels in the vessel 3612. The control circuit 2402 and/or the generator 3604 can be used to determine the blood flow and/or oxygen ($O_2$) 3624 levels in the vessel 3612 based on the amount of light 3626 transmitted by the LED lights sources 3616 is received by the photodiode optical sensor 3618, where the difference is absorbed by blood flow 3624 in the vessel 3612. Blood can be optically monitored based on the absorption of 350-600 nm light by hemoglobin in the blood.

FIG. 141 shows a blood vessel 3612 located between the jaw members 3614a, 3614b of the end effector 3606. The pulse-oximeter sensor 3608 can be configured to identify vessels 3612 that may or may not have been identified in a tissue bite with a monopolar or bipolar electrosurgical instrument 3602. The pulse-oximeter (or i-watch) sensor 3608 enables the identification of blood flow 3624 within tissue 3612 located between the jaw members 3614a, 3614b prior to cutting the tissue 3612.

A surgeon cannot identify the type of tissue 3612 located between the jaw members 3614a, 3614b with certainty. The pulse-oximeter sensor 3608 comprising LED light sources 3616 and photodiode optical sensors 3618, as well as flexible circuit technology can be employed to detect blood flow and/or $O_2$ 3624 levels in the tissue 3612. Thus, the surgeon would know when a blood vessel is located in the jaw members 3614a, 3614b of the electrosurgical instrument 3602. This technique may be employed to identify the tissue type and determine when blood is present in a vessel within the tissue 3612 located between the jaw members 3614a, 3614b. Knowledge of this information may be helpful to surgeons that like to march quickly through the tissue 3612.

In operation, the LED light sources 3616 located on one flexible circuit electrode sends light 3626 through the tissue 3612 and is received by the photodiode optical sensors 3618. Blood flow and/or $O_2$ 3624 is recognized (e.g., similar to a pulse oximeter or i-watch). The information is sent to the generator 3604. The generator 3604 sends a message to the LED light 3620 on the handle 3622 of the electrosurgical instrument 3602, which illuminates when appropriate. The pulse-oximeter 3618 and/or i-watch could also be configured to communicate with smart phones or wearables such as the i-watch, fit-bit, among other applications to signal information.

B. Flexible Circuit Electrode Including Integrated Electro Optical Sensors for Sensing Tissue Properties FIGS. 143-147 illustrate electro optical sensors 3700 for sensing tissue properties integrated with a flexible circuit electrode 3702, according to one aspect of the present disclosure. Turning to FIG. 143, which illustrates an exploded view of an electro optical sensor 3700 for sensing of tissue properties integrated with a flexible circuit electrode 3702, according to one aspect of the present disclosure. The electro optical sensor 3700 is integrated in a flexible circuit electrode 3702 and comprises a multilayer coating 3704 positioned over an optically transparent window 3706, which is positioned above a diffraction grating 3708. A lens 3710 is positioned between the diffraction grating 3708 and a photo diode 3712. The photo diode 3712 is electrically coupled to control circuits by way of conductive traces 3714 formed on the flexible circuit electrode 3702. A flexible opaque electrically insulative layer 3716 is disposed over the optical assembly comprising the window 3706, the diffraction grating 3708, the lens 3710, and the photo diode 3712. In one aspect, the flexible opaque electrically insulative layer 3716 may be made of a polyimide film, such as Kapton, or polyester, fluorocarbon, or any polymeric material, or any combinations thereof.

FIG. 144 is a plan view of the flexible circuit electrode 3702 comprising an electro optical sensor 3700 for sensing of tissue properties shown in FIG. 143 integrated in a via 3718 of the flexible circuit electrode 3702, according to one aspect of the present disclosure. The flexible circuit electrode 3702 comprises a plurality of traces 3720 and a plurality of vias 3718 to electrically interconnect different layers of the flexible circuit electrode 3702. As with other aspects of flexible circuit electrodes described herein, a knife slot 3722 is defined by the flexible circuit electrode 3702 to enable a knife to reciprocate therealong. The electro optical sensor 3700 is disposed in one or more of the plurality of vias 3718.

FIG. 145 is a section view of the electro optical sensor 3700 integrated in a via 3718 of a flexible circuit electrode 3702 for sensing of tissue properties, according to one aspect of the present disclosure. As shown in FIG. 145, the electro optical sensor 3700 is inserted inside a cavity 3724 defined by the via 3718. The electro optical sensor 3700 is electrically coupled to control circuitry by way of spring loaded electrical contacts 3726 to conductive traces 3728 of the flexible circuit electrode 3702. An optically transparent window 3706 and is disposed between an upper layer of an electrically insulative film 3716a and a lower layer of electrically insulative film 3716b, where the upper and lower layers of electrically insulative materials 3716a, 3716b can be made of polyimide, polyester, fluorocarbon, or any polymeric material, or any combinations thereof.

FIG. 146 is an elevation view of an end effector 3730 with a flexible circuit electrode 3702 comprising an electro optical sensor 3700 integrated therewith, according to one aspect of the present disclosure. The end effector 3730 comprises an upper jaw member 3732a and a lower jaw member 3732b. The flexible circuit electrode 3702 is disposed on the lower jaw member 3732b. A plurality of electro optical sensors 3700 are disposed on the flexible circuit electrode 3702 located in the lower jaw member 3732b. Additionally, the electro optical sensors 3700 are positioned on the flexible circuit electrode 3702 such that they extend above the plane defined by the flexible circuit electrode 3702 and thus can function as stop members to set a defined gap "G" between the upper and lower jaw members 3732a, 3732b when they are in a closed configuration.

FIG. 147 is a plan view of a flexible circuit electrode 3702 comprising a plurality of electro optical sensors 3700 integrated with, according to one aspect of the present disclosure. A plurality of electro optical sensors 3700 comprising photo diodes 3712 (see FIG. 143) are disposed on the flexible circuit electrode 3702. Analog processing electronic circuits 3734 to power and condition signals received from the photo diodes 3712 are located proximal to a tissue stop 3736. Traces 3738 connect the analog processing electronic circuits 3734 to the digital control circuit 2402 (see FIG. 104 for details) located either in the handle of the electrosurgical instrument or the generator 2404 (FIG. 104).

With reference now to FIGS. 143-147, bipolar or monopolar RF surgical instruments may use various tissue parameters, such as impedance, to determine the effect of RF electricity has had on the tissue. Providing additional feedback to the generator can improve the confidence level to the surgeon that a seal has been created in tissue bundles treated by the end effector 3730 of the electrosurgical instrument.

The photo diodes 3712 disposed on the flexible circuit electrode 3702 can be used to determine when the seal is complete, the location of tissue within the jaw members 3732a, 3732b (distal vs. proximal), and also tissue type. The electro optical sensor 3700 can serve a secondary purpose of setting the gap between the flexible circuit electrode 3702 and the other jaw member or return electrode, which is shown as the upper jaw member 3732a in FIG. 146. The electro optical sensor 3700 is incorporated into the flexible circuit electrode 3702 to determine changes in tissue condition.

This disclosure illustrates how an electro optical sensor 3700 can be integrated with a flexible circuit electrode 3702 for the purpose of sensing tissue sensing in a monopolar or bipolar RF electrosurgical instrument. In one aspect, the electro optical sensor 3700 may be an infrared (IR) photo diode 3712, however, other electro optical sensors may be used in a similar manner. The photo diode 3712 is mounted to the trace layer of the flexible circuit electrode 3702 where individual conductors are photo etched from copper or another conductor. The photo diode 3712 is located in a distal portion of the flexible circuit electrode 3702 such that the tissue being treated is within the optical field of view of the electro optical sensor 3700. Blood can be optically monitored based on the absorption of 350-600 nm light by hemoglobin in the blood.

The photo diode 3712 is covered by an optical window 3706 selected for its transmission of wavelengths generating a large response in the photo diode 3712. The optical window 3706 may employ optical coatings to enhance transmission of the desired wavelengths while rejecting unwanted wavelengths. Coatings also may be used to enhance the durability of the optical window 3706. The optical window 3706 also may include diffraction gratings 3708 or lenses 3710 to focus and further concentrate photons from the tissue being treated. Traces 3714 of the flexible circuit electrode 3702 are connected to the photo diode 3712 and routed proximally to carry the sensor current to analog processing electronic circuits 3734. These processing electronic circuits 3734 may consist of pass band filters, amplifiers, and analog-to-digital converts. The most likely location for the analog electronics is proximal to the tissue stop 3736 such that they are within close proximity to the electro optical sensor 3700, but do not interfere with the treatment of tissue in the end effector 3730.

C. Flexible Circuit Electrode Including LED and Photodiode Based Vascular Sensor FIG. 148 illustrates a flexible circuit electrode 3800 comprising a vascular sensor 3802 comprising a LED 3804 and photodiode 3806 arrangement integrated therewith for sensing vascularity, according to one aspect of the present disclosure. The vascular sensor 3802 utilizes pairs of LEDs 3804a, 3804b, 3804c and photodiodes 3806a, 3806b, 3806c to define multiple zones 1-3 in a jaw member of an end effector to determine the vascularity of the tissue located in each of the zones 1-3 for optimal tissue treatment. The vascular sensor 3802 is electrically coupled to the control circuit 2402 (FIG. 104) to process the signals provided by the vascular sensor 3802. Based on the vascularity sensed by the vascular sensor 3802, an algorithm can be selected by the control circuit 2402 to treat each of the zones 1-3 in an independent manner to enable better sealing and hemostasis. The vascular sensor 3802 employs the pairs of LEDs 3804a-3804c and photodiodes 3806a-3806c to sense the vascularity of the tissue within each of the zones 1-3 in a manner similar to how a pulse oximeter works. Vascularity can be determined based on how much infrared or red light is absorbed by blood in the tissue. Each of the zones 1-3 can then be treated independently by executing a unique algorithm to maximize tissue sealing and minimizing unintended damage for an optimal patient outcome. Blood can be optically monitored based on the absorption of 350-600 nm light by hemoglobin in the blood.

D. Flexible Circuit Electrode Including Integrated Vascular Tissue Sensor

FIGS. 149-150 illustrate a vascular tissue sensor 3900 integrated with a flexible circuit electrode 3902, according to one aspect of the present disclosure. FIG. 149 is an end effector 3904 comprising upper and lower jaw members 3906a, 3906b and a vascular tissue sensor 3900 integrated with a flexible circuit electrode 3902, according to one aspect of the present disclosure. The upper jaw member 3906a of the end effector 3904 comprises the vascular tissue sensor 3900. The vascular tissue sensor 3900 comprises a LED 3908 and a photo sensor 3910, such as a photo diode, for example. In addition, a visual LED 3912 is located on a surface of the upper jaw member 3906a to indicate detection of vascular tissue. The lower jaw member 3906b of the end effector 3904 comprises a flexible circuit electrode 3902. Electrical energy to power the vascular sensor 3900 elements is received by a first electrical conductive element 3914 and electrical energy to power the electrode 3902 is received by a second electrical conductive element 3916. The return path 3918 is provided through electrically conductive portions of the upper jaw member 3906a. The vascular tissue sensor 3900 configuration illustrated in FIG. 149 may be employed to detect vascular tissue to aid in anatomical identification and reduction of unintended tissue damage.

Remission phoupperlethysmography (PPG) is a technique that uses non invasive monitoring of skin blood vessel pulsations. It is known that mobile heart rate monitoring can be optically monitored based on the absorption of 350-600 nm light by hemoglobin in the blood. The amount of blood can be measured by irradiating a living body with light in that wavelength range and measuring changes in the time needed for the light to reflect back. Counting the number of rhythmic peaks in the amount of blood gives the heart rate. A smart sensor for this application can be composed of a green LED with 530 nm emission, a silicon photo diode, and appropriate circuits.

Based on the configuration illustrated in FIG. 149, a remission PPG method may be implemented using the LED 3912 and photo diode 3910, and appropriate circuits could be installed on the distal end in either upper or lower jaw members 3906a, 3906b of an RF bipolar electrosurgical instrument and be used as a detection method to confirm the presence of vascular tissue. For example, the vascular sensor 3900 may electrically coupled to the control circuit 2402 (FIG. 104). This PPG circuit can be mounted to an independent layer of the flexible circuit electrode 3902 and can have its own geometric pattern to be fitted in the upper or lower jaw member 3906a, 3906b and an independent power/communication source to utilize the detection signal.

The detection signal could trigger the visual LED 3912 located on the upper jaw member 3906a of the end effector 3904 and/or an audible tone from the generator 2404 (FIG. 104). Detection of vascular tissue could then be used to avoid unintended tissue damage, or to confirm the location of vessels and aid in anatomical identification. The PPG technology can integrated with the flexible circuit electrode 3902 to identify vascular tissue and provide a signal to the end user and avoid unintended tissue damage and anatomical/vessel identification.

The LED 3908 and the photosensor 3910 can be located on a separate leg of the flexible circuit electrode 3902 and can be connected to the distal tip 3920 of the upper jaw member 3906a to detect vascular tissue and provide a detection signal. The detection signal can be visual, audible, and/or vibratory to aid end user in use of the electrosurgical device.

FIG. 150 is a schematic diagram of a sensor 3922 for mobile heart rate monitoring, according to one aspect of the present disclosure. A smart sensor 3922 for this application comprises and LED 3924, a photodiode 3926, and a processing circuit 3928 mounted on a substrate 3930. In one aspect, the LED 3924 is a green LED with 530 nm emission and the photodiode 3926 is a Silicon photodiode. The LED 3924 transmits a beam of light 3932 to the tissue 3934 and a portion of the light 3936 is reflected form the tissue 3934 and is detected by the photodiode 3926. The processing circuit 3928 control the operation of driving the LED 3924 and processing the signal produced by the photodiode 3926 in response to detecting the reflected light 3936.

Heart rates can be optically monitored based on the absorption of 350-600 nm light by hemoglobin in the blood. The amount of blood can be measured by irradiating a living body with light in that wavelength range from the LED 3924 and measuring changes in the time needed for the light 3936 to reflect back using the photodiode 3926 and the processing circuit 3928. Counting the number of rhythmic peaks in the amount of blood gives the heart rate.

XVIII. Connection and Attachment Techniques for Flexible Circuit Electrodes

A. Techniques for Connecting and Disconnecting Flexible Circuits to Wiring on Re-Usable Instrument Connections FIGS. 151-157 illustrate various attachment techniques to connect and disconnect flexible circuits to wiring on reusable instrument connections, according to one aspect of the present disclosure. Termination of the electrical signals of a flexible circuit can come in the form of simple pins, holes, or fingers as shown in FIGS. 151-152 where FIG. 151 illustrates a flexible circuit termination 4000 comprising supported fingers 4002, according to one aspect of the present disclosure, and FIG. 152 illustrates a flexible circuit termination 4004 comprising unsupported fingers 4005, according to one aspect of the present disclosure.

FIG. 153 illustrates an example flexible circuit electrode 4006 with four supported fingers 4008 exposed on the proximal end 4010, according to one aspect of the present disclosure. The four supported fingers 4008 could be inserted into a simple female connector 4012 as shown in FIG. 154. In an alternate aspect, both of the two legs of the flexible circuit electrode can have two supported fingers instead of all four on a single leg, as shown above. This could be necessary due to the small width of the electrode and the limitations of electrical connector size.

FIG. 154 is the frontside of a female electrical connector 4012 configured to receive a flexible circuit electrode, according to one aspect of the present disclosure, such as, for example, the flexible circuit electrode 4006 (FIG. 153). The connector 4012 has angled internal side walls 4014a, 4014b to more easily receive the male portion of the flexible circuit electrode 4006 during assembly, and four biased electrical retaining metallic contacts 4015 that are biased to ensure electrical continuity is retained. FIG. 155 illustrates the backside 4016 of the electrical connector 4012 shown in FIG. 154, according to one aspect of the present disclosure. The backside of the electrical connector 4012 is soldered to wiring 4017 to connect to processing circuits such the control circuit 2402 (FIG. 104) and the generator 2404 (FIG. 104).

FIG. 156 is an internal section view of biased contacts 4018 of the connector 4012 shown in FIG. 154 connected to the supported finger 4008 shown in FIG. 153, according to one aspect of the present disclosure. The biased contacts 4018 connect to the supported finger 4008. FIG. 157 is a full flexible circuit electrode assembly 4020 comprising the flexible circuit electrode 4006 shown in FIG. 153 connected to the connector 4012 shown in FIG. 154, according to one aspect of the present disclosure.

B. Flexible Circuit Electrode Attachment Features for Connection and Mechanical Attachment to Processing Circuits and Energy Sources FIGS. 158-164 illustrate flexible circuit electrode attachment features for connection and mechanical attachment to processing circuits and energy sources, according to one aspect of the present disclosure. Using a flexible circuit electrode on an RF electrosurgical instrument can save space and reduce cost. The attachment/alignment features are configured to be attached and aligned the flexible circuit electrode to the jaw members of an end effector. An RF electrosurgical instrument comprising a flexible circuit for an electrode may employ attachment/alignment features soldered onto the flexible circuit electrode for attachment to the jaw member, alignment on the jaw member, provide structural support, or make electrical connections.

FIG. 158 is a perspective view of a flexible circuit electrode 4100 with attachment/alignment features 4102 provided on a surface 4104 thereon, according to one aspect of the present disclosure. The attachment/alignment features 4102 are soldered to the flexible circuit electrode 4100 to facilitate attachment of the flexible circuit electrode 4100 to a jaw member, such as, the jaw member 4106 shown in FIG. 159. The attachment/alignment features 4102 could be multiple parts or a single hook that fits into a slot on the jaws. It could also be soldered on electrical connectors. A knife slot 4103 is provided in the flexible circuit electrode 4100 to enable the knife to reciprocate therealong.

FIG. 159 is a section elevation view of a lower jaw member 4106 with the flexible circuit electrode 4100 shown in FIG. 158 with attachment/alignment features 4102 shown in FIG. 158 prior to being disposed thereon, according to aspect of the present disclosure. The lower jaw member 4106 comprises a plurality of recesses 4107 sized and configured to receive the attachment/alignment features 4102 attached to the flexible circuit electrode 4100.

FIG. 160 is a section view of the lower jaw member 4106 shown in FIG. 159 with the flexible circuit electrode 4100 with the attachment/alignment features 4102 shown in FIG. 159 prior to being disposed thereon, according to aspect of the present disclosure.

FIG. 161 is a partial perspective view of the flexible circuit electrode 4100 disposed shown in FIG. 158 disposed on an insulative flexible substrate 4105 with a solder point 4108 for connecting the attachment/alignment feature 4102 shown in FIG. 158 to the flexible circuit electrode, according to one aspect of the present disclosure;

FIG. 162 is an exploded view of the flexible circuit electrode 4100 with multiple attachment/alignment features 4102 shown removed from the flexible circuit electrode 4100, according to aspect of the present disclosure. The attachment/alignment features 4102 are soldered to solder points 4108 formed on the substrate of the flexible circuit electrode 4100.

FIG. 163 is an exploded view of a flexible circuit electrode with a single attachment/alignment feature 4110 shown removed from the flexible circuit electrode 4112, according to aspect of the present disclosure. A knife slot 4113 is provided in the flexible circuit electrode 4112 to enable the knife to reciprocate therealong.

FIG. 164 is a perspective view of a flexible circuit electrode 4114 comprising an attachment feature 4116 for a wire/cable connector 4118, according to one aspect of the present disclosure.

C. Flexible Circuit Electrode Including Alternate Contacts for Routing and Wring Multiple Electrode Paths to Monopolar or Bipolar Instruments FIGS. 165-173 illustrate a flexible circuit electrode including alternate contacts for routing and wiring multiple electrode paths to monopolar or bipolar instruments for spot coagulation, according to one aspect of the present disclosure. A flexible circuit electrode with the main electrode formed on an upper surface and multiple electrode paths formed on a lower surface can be used for monopolar or bipolar RF spot coagulation. These paths can run lengthwise along the flexible circuit electrode back to the handle of the electrosurgical instrument. The flexible circuit electrode can be coiled around a tube in the handle with rings to transmit the RF energy. A flexible circuit electrode for an RF electrosurgical instrument is provided where one surface of the circuit is an RF sealing surface of exposed metal and another surface is the same or a different exposed electrode or electrodes in an area that is not the main sealing surface. A flexible circuit electrode is provided with an electrode surface where the flexible circuit electrode terminates in a handle of the electrosurgical instrument where the circuit forms rings to transmit RF through a rotating contact. These various aspects are described hereinbelow.

FIG. 165 is a perspective view of an end effector 4200 comprising an upper and lower jaw member 4202a, 4202b comprising a flexible circuit electrode 4204 with a distal monopolar electrode 4206 and lateral bipolar electrodes 4208a, 4208b, 4208c, according to one aspect of the present disclosure. By using a flexible circuit and printing the main electrode 4204 on the surface and using the lower of the flexible circuit multiple electrode paths for monopolar or bipolar spot coagulation can be used. These paths can run along the flexible circuit back to the handle of the electrosurgical instrument. The distal monopolar electrode 4206 and the lateral bipolar electrodes 4208a-4208c are electrically connected to the control circuit 2402 (FIG. 104) and the generator 2404 (FIG. 104). A knife slot 4210 is provided in the lower jaw member 4202b and the flexible circuit electrode 4204 to enable the knife to reciprocate therealong.

FIG. 166 is a plan view of the flexible circuit electrode 4204 shown in FIG. 165, according to one aspect of the present disclosure. The flexible circuit electrode 4204 is shown unfolded showing both sides of the lateral bipolar electrode 4208a-4208c and the distal monopolar electrode 4206. Details of the electrically conductive traces at the proximal end 4212 of the flexible circuit electrode 4204 are shown in FIG. 167.

FIG. 167 is a detail section view of the proximal end of the flexible circuit electrode 4204 shown in FIG. 166 showing the electrically conductive traces 4214a, 4214b, 4214c which are electrically coupled to the lateral bipolar electrodes 4208a, 4208b, 4208c and electrically conductive trace 4215 which is electrically coupled to the distal monopolar electrode 4206, according to one aspect of the present disclosure.

FIG. 168 is a perspective view of a lower jaw member 4216 of a jaw assembly comprising a fold over flexible circuit electrode 4218, according to one aspect of the present disclosure. A knife slot 4220 is provided in the fold over flexible circuit electrode 4218 to enable the knife to reciprocate therethrough.

FIG. 169 is a detail view of the fold over flexible circuit electrode 4218 shown in FIG. 166, according to one aspect of the present disclosure. The flexible circuit electrode 4218 comprises exposed lateral sealing surfaces 4222a, 4222b and an upper main sealing surface 4222c. The sealing surfaces 4222a-4222c are exposed metal electrodes that are sized and configured to conduct RF electricity that contact tissue and provide sealing surfaces.

FIG. 170 is a perspective view of a rotating contact assembly 4230 disposed about the outer surface 4234 of an inner tube 4236 of a shaft component of the electrosurgical instrument, according to one aspect of the present disclosure. The rotating contact assembly 4230 is formed on a flexible circuit 4232 that is coupled to the electrode. The flexible circuit 4232 terminates in a handle of the electrosurgical instrument where the circuit forms rings such as a plurality of rotating contacts 4236a, 4236b, 4236c, 4236d configured to transmit RF electrical energy through the rotating contact assembly 4230. The flexible circuit can be coiled around the inner tube 4236. FIG. 1A illustrates a shaft 10 of an electrosurgical instrument 2. The inner tube 4236 is typically disposed within the shaft 10. Turning back to FIG. 170, in one aspect the rotating contact assembly 4230 comprises a plurality of rotating contacts 4236a-4236d formed on the flexible circuit 4232 and disposed about the inner tube 4236, for example. An exposed electrically conductive element 4238 (e.g., copper) is located behind the plurality of rotating contacts 4236a-4236d and is adhered about the outer surface 4234 of the inner tube 4236 and extends distally towards the jaw assembly or end effector.

With reference now also to FIG. 170, FIG. 171 is a detail section view of electrical contact wipers 4240a, 4240b, 4240c, 4240d electrically and rotatably coupled to the plurality of rotating contacts 4236a-4236d of the rotating contact assembly 4230 disposed about the outer surface 4234 of the inner tube 4236, according to one aspect of the present disclosure.

FIG. 172 is a perspective view of the rotating contact assembly 4230, according to one aspect of the present disclosure. FIG. 173 is a perspective view of the rotating contact assembly 4230 comprising an outer tube 4242, an inner tube 4236, and a plurality of rotating contacts 4236a-4236d formed on a flexible circuit electrode and disposed about the inner tube 4236, according to one aspect of the present disclosure. The rotating contact assembly 4230 is rotatably disposed within the outer tube 4242.

D. Flexible Circuit Including Snap in Electrode Assembly and Grasping/Gap Setting Elements at a Distal End FIGS. 174-176 illustrate flexible circuit 4300 comprising a snap in electrode assembly 4302 and grasping/gap setting elements 4304 at a distal end 4306, the elements having various geometries to aid in grasping and setting the gap "G" between the upper jaw member 4308a and the lower jaw member 4308b members of a clamp jaw assembly 4310, and a connecting scheme to couple the snap in electrode assembly 4302 to the clamp jaw assembly 4310, according to one aspect of the present disclosure. The flexible circuit 4300 comprising the snap in electrode assembly 4302 is a replaceable component and can provide multiple options of clamp assemblies for an electrosurgical instrument during manufacturing. The interchangeable configuration provides various levels of grasping (i.e., atraumatic for liver or general surgery) and various levels of gap setting features for marching versus sealing. The proximal end 4314 of the interchangeable flexible circuit 4300 electrode comprises an edge connector 4312 that contains an identification card such that control circuit can identify the type of flexible circuit 4300 connected to the shaft 4316 of the electrosurgical instrument.

FIG. 174 is a perspective view of a flexible circuit 4300 comprising a snap in electrode assembly 4302 at a distal end 4306 and an edge connector 4312 that contains an identification card at a proximal end 4314, according to one aspect of the present disclosure. The snap in electrode assembly 4302 comprises multiple layers. An upper layer 4318 is an electrically conductive layer 4326 that act as the electrode to apply energy to tissue located in the clamp jaw assembly 4310. The electrode 4326 comprises a plurality of elements 4304 printed thereon to provide various gaps or to various grasping features. The middle layer 4320 provides the electrical connection to the circuitry back to the edge connector 4312. A lower layer 4322 is an overmolded component that connects via snap features 4306 to the lower jaw member 4308b of the clamp jaw assembly 4310. The snap fit features 4306 are formed on lateral surfaces of the snap in electrode assembly 4302 to snap fit connect the electrode assembly 4302 to snap fit features 4338 to the lower jaw member 4308b (FIG. 176). The edge connector 4312 comprises an identification circuit element such that the control circuit can identify the type of flexible circuit 4300 connected to the shaft 4316 of the device. A knife slot 4336 is provided in the snap in electrode assembly 4302

FIG. 174A is a detail view of two types of elements 4304, according to various aspects of the present disclosure. A first type of elements 4332 terminate in a pointed edge. As second type of elements 4334 terminate in a flat edge. The elements 4332, 4334 are configured to set a gap "G" between the upper and lower jaw members 4308a, 4308b of the clamp jaw assembly 4310 (FIG. 176).

FIG. 175 is a section view of the proximal end 4314 of the flexible circuit 4300 taken along section line 175-175, as shown in FIG. 174, showing a T-slot 4328 configuration for alignment of the flexible circuit 4300 with the shaft 4316 (FIG. 176) of the electrosurgical instrument, according to one aspect of the present disclosure.

FIG. 176 is an elevation view of the clamp jaw assembly 4310 showing the female end of an edge connector 4330 located on the shaft 4316 for electrically and mechanically coupling the edge connector 4312 of the flexible circuit 4300 (FIG. 174) to a control circuit and/or a generator, according to one aspect of the present disclosure. Snap fit features 4338 are sized and configured to receive the snap fit features 4306 formed on the lateral surfaces of the snap fit electrode assembly 4302 (FIG. 174). The snap fit features 4306, 4338 mechanically connect the snap in electrode assembly 4302 to the lower jaw member 4308b of the clamp jaw assembly 4310.

XIX. Automatic Electrode Renewal System for Flexible Circuit Electrodes

FIGS. 177-178 illustrate an automatic electrode renewal system 4400 for flexible circuit electrodes, such as spools of flexible circuit electrodes 4404a, 4404b wind about corresponding rollers 4406a, 4406b, according to one aspect of the present disclosure. FIG. 177 is an elevation view of a clamp jaw assembly 4407 comprising an upper jaw element 4414a and a lower jaw element 4414b and a renewable flexible circuit electrode system 4400 for unwinding and advancing clean flexible circuit electrodes 4404a, 4404b from a proximal end 4408 pair of upper and lower rollers 4406a, 4406b and winding used flexible circuit electrodes about a distal end 4410 pair of upper and lower spools 4412a, 4412b in a distal direction 4422a, 4422b, according to aspect of the present disclosure. The flexible circuit electrodes 4404a, 4404b can be automatically fed into contact with tissue. In one aspect, the flexible circuit electrodes 4404a, 4404b can be configured for a specific tissue type also can be fed to be in contact with the specific tissue type.

A pair of upper and lower spools 4406a, 4406b of clean flexible circuit electrodes 4404a, 4404b is located at the proximal end 4408 of the clamp jaw assembly 4407 and a pair of upper and lower rollers 4412a, 4412b of used flexible circuit electrodes is located as the distal end 4410 of the clamp jaw assembly 4407. As the flexible circuit electrodes 4404a, 4404b are used, clean electrodes can be advanced in a counterclockwise direction 4416a and a clockwise direction 4416b by winding the used electrodes at the distal rollers 4412a, 4412b and unwinding clean electrodes from the proximal rollers 4406a, 4406b.

To provide a clean electrode, the rollers 4406a, 4406b, 4412a, 4412b are rotated to expose tissue to a new electrode surface. This configuration enables the use of different sections of a surface of the flexible circuit electrodes 4404a, 4404b to treat different types of tissue. This technique can provide a specialized electrode type for different tissues. This technique also can eject tissue from the jaw members 4414a, 4414b to create a peeling release as opposed to a shearing release.

FIG. 178 is an elevation view of the automatic electrode renewal system 4400 shown in FIG. 177 comprising an electrical brush contact 4420 to electrically couple to a flexible circuit electrode 4404a disposed about the lower roller 4406b at the proximal end 4408, according to one aspect of the present disclosure. Although the upper roller 4406a (FIG. 177) is not shown in FIG. 178, a similar brush contact 4420 may be coupled to the flexible circuit electrode 4404a disposed about the upper roller 4406a at the proximal end 4408. The electrical contact for the upper and lower spools 4406a, 4406b of flexible circuit electrodes 4404a, 4404b can be provided by brush contacts or the rollers 4406a, 4406b. The rollers 4406a, 4406b can be used as electrical contact provided between the flexible circuit electrodes 4404a, 4404b and the structural support portion of the clamp jaw assembly 4407.

XX. Flexible Circuit Electrode Including Vibratory Elements to Mitigate Tissue Sticking to the Clamp Jaw Members A. Vibratory Element Including Vibrating Piezoelectric Bimorph Transducer to Release Tissue from the Jaw Members FIGS. 179-184 illustrate a flexible circuit comprising an electrode and a vibratory element to mitigate tissue sticking to the clamp jaw members, according to one aspect of the present disclosure. The vibratory element comprises a piezoelectric bimorph transducer that vibrates to release tissue from the jaw members of the clamp jaw assembly. During use, tissue adheres to the electrode surface in RF electrosurgical instruments. Vibrations, e.g., acoustic energy, can be employed to release the tissue from the electrode surface. Vibratory energy can be applied in proportion to the amount of tissue sticking seen thereby not treating the tissue with acoustic energy if it is not necessary.

Vibratory energy can be used to release tissue from the surface of a flexible circuit electrode. However, acoustic vibration also can damage tissue and or the tissue seal if it is not necessary. In one technique, acoustic energy is applied in proportion to the sticking force experienced when opening the jaws. For example, if no sticking force is detected, then no acoustic vibration is applied and if a high sticking force is detected, then high acoustic vibration is applied. Piezoelectric bimorph transducers that are 180° out of phase are placed in the upper and lower jaws. Flexible circuit electrodes can bend with the piezoelectric bimorph transducers.

FIG. 179 is a section view of a piezoelectric bimorph transducer 4500 attached to a flexible circuit electrode 4502, according to one aspect of the present disclosure. The piezoelectric bimorph transducer 4500 comprises a metal layer 4504 sandwiched between two piezoelectric layers 4506a, 4506b. In one aspect, the piezoelectric layers 4506a, 4506b may be lead zirconate titanate, an intermetallic inorganic compound with the chemical formula $Pb[Zr_xTi1-x]O3$ ($0 \leq x \leq 1$). Also called PZT, it is a ceramic perovskite material that shows a marked piezoelectric effect, meaning that the compound is used in a number of practical applications in the area of electroceramics. In one aspect, the metal layer 4504 may comprise brass, or other metal. The first piezoelectric layer 4506a is driven by a first high voltage time varying signal v1 and the second piezoelectric layer 4506b is driven by second high voltage time varying signal v2 that is 180° out of phase relative to the first high voltage time varying signal v1.

FIG. 180 is a schematic illustration of the displacement of the piezoelectric bimorph transducer 4500 shown in FIG. 179, where a first mode of deflection is shown in solid line 4508 and a second mode of deflection is shown in dashed line 4510, according to one aspect of the present disclosure. Accordingly, with the end portions 4512a, 4512b of the piezoelectric bimorph transducer 4500 are anchored, the piezoelectric layers 4506a, 4506b are electrically activated to cause one piezoelectric layer 4506a to extend and the other piezoelectric layer 4506a layer to contract. This may be implemented by driving one piezoelectric layer 4506a with a first high voltage time varying signal and driving the other piezoelectric layer 4506b with a second high voltage time varying signal that is 180° out of phase relative to the first high voltage time varying signal. The total displacement is indicated as "D". Repeated electrical actuation causes the piezoelectric bimorph transducer 4500 to vibrate or oscillate. This technique can be use to vibrate the flexible circuit electrode 4502 to release any tissue stuck to the electrode 4502 during the sealing process.

FIG. 181 is a section view of a clamp jaw assembly 4514 comprising upper and lower bimorph transducers 4500a, 4500b located in respective upper and lower jaw members 4516a, 4516b, according to one aspect of the present disclosure. A layer of rubberized polymer 4518a is attached to the upper jaw member 4516a. A bimorph transducer 4500a is attached to the rubberized polymer 4518a on one side and to a flexible circuit electrode 4502a on the other side. Similarly, a layer of rubberized polymer 4518b is attached to the lower jaw member 4516b. A bimorph transducer 4500b is attached to the rubberized polymer 4518b on one side and to a flexible circuit electrode 4502b on the other side. As shown in FIG. 181, the bimorph transducers 4500a, 4500b are in the first mode 4508 (FIG. 180) of maximum deflection. The upper and lower bimorph transducers 4500a, 4500b located in the clamp jaw assembly 4514 oscillate between the first mode 4508 and second mode 4510 of deflection, as shown in FIG. 180, to release tissue.

FIG. 182 is a section view of the clamp jaw assembly 4514 shown in FIG. 181, where the bimorph transducers 4500a, 4500b located in the respective upper and lower jaw members 4516a, 4516b are in the second mode 4510 of maximum deflection (FIG. 180), according to one aspect of the present disclosure.

FIG. 183 is a section view of the lower bimorph transducer 4500b located on a lower jaw member 4516b of the clamp jaw assembly 4514 configured in sensor mode to measure the adhesion force "F" of tissue sticking to the lower jaw member 4516b, according to one aspect of the present disclosure. Although not shown in FIG. 183, the same technique applies to measuring the adhesion force F tissue sticking to the upper jaw member 4516a using the upper bimorph transducer 4500a. It is known that a bimorph piezoelectric transducer can operate in actuator mode and sensor mode. In actuator mode, a voltage applied to the transducer causes the transducer to displace and in sensor mode, displacement of the transducer generates a voltage. The bimorph transducer 4500 can be operated in sensor mode to measure the sticking force F. The sticking force "F" drives the bimorph transducer 4500 in the second mode of deflection. The sticking force "F" shows the displacement "d" of the lower bimorph transducer 4500b due to tissue sticking to the lower flexible circuit electrode 4502b and to the upper flexible circuit electrode 4502a (not shown) or simply sticking to the upper jaw member 4516a (not shown).

Accordingly, the bimorph transducer 4500 can become a force sensor when force is applied to it. The bimorph transducer 4500 can produce a voltage under a sticking load. The bimorph transducer 4500 can be configured to switch between a force measuring bimorph sensor and a driving bimorph transducer to result in mechanical vibrations that are proportional to the sticking force "F". The mechanical vibrations may be employed in proportion to the adhesion force "F" of the tissue sticking to the electrode 4502.

FIG. 184 is a logic flow diagram 4520 of a technique for operating a bimorph transducer by switching between a force measuring bimorph sensor to a driving bimorph transducer resulting in vibrations proportional to the adhesion force, according to one aspect of the present disclosure. A control circuit, such as the control circuit 2402 shown in FIG. 104, can be programmed and configured to execute an algorithm to implement the logic flow diagram 4520. Accordingly, the control circuit 2402 is configured to stop driving the bimorph element 4500a, 4500b and measure 4522 the voltage (v) on the bimorph element 4500a, 4500b, where the voltage (v) is proportional to the tissue adhesion force "F" on the flexible circuit electrode 4502 as described in connection with FIG. 183. The control circuit 2402 then drives 4524 the bimorph element 4500a, 4500b in proportion to the measured voltage (v) according to the function P=f(v) for a period of time "t" and the cycle is repeated a predetermined frequency selected from the range of 100 Hz to 1000 Hz, or 250 Hz to 750 Hz, or preferably approximately 500 Hz. Thus, the control circuit 2402 vibrates or oscillates the bimorph element 4502a, 4502b in proportion to the tissue adhesion force "F". The total work done by the bimorph element 4500a, 4500b to release the tissue adhered to the flexible circuit electrode 4502 can be represented by the following equation:

$$w = \int_0^t f(v) dt \qquad (6)$$

where w is work defined by the integral over the period "t" of f(v).

B. Flexible Circuit Electrode Including a Vibratory Element Configured to Vibrate to Reduce Tissue Adhesion on Electrode or Remove Tissue Adhered to Electrode FIGS. 185-186 illustrate a jaw member 4700 comprising a flexible circuit electrode assembly 4702 comprising a vibratory element configured to vibrate to reduce tissue adhesion on an electrode 4704 or remove tissue adhered to the electrode 4704, according to one aspect of the present disclosure. FIG. 187 illustrates a circuit configured to actuate the vibratory element, according to one aspect of the present disclosure.

FIG. 185 is a plan view of a vibrating jaw member 4700 comprising a flexible circuit electrode assembly 4702 configured to vibrate to reduce tissue adhesion to the electrode 4704 or remove tissue adhered to the electrode 4704, according to one aspect of the present disclosure. FIG. 186 is a section view of the vibrating jaw member 4700 shown in FIG. 185 taken along section 186-186, according to one aspect of the present disclosure. During sealing/fastening/adhering tissue together between bipolar jaw members of an electrosurgical instrument, the tissue affected has a tendency to stick to one or both jaw members. Accordingly, the vibrating jaw member 4700 provides a laminated grooved flexible circuit electrode assembly 4702 disposed across an upper surface 4716 of one of the two jaw members 4700. As shown in FIG. 186, the flexible circuit electrode assembly 4702 is positioned on upper portion of a sheet of piezoelectric element 4712, which may be in the form of a sheet, that when energized will create vibrations and displacement of the flexible circuit electrode assembly 4702, which in turn will reduce sticking of tissue to the flexible circuit electrode 4704. Alternatively, if sticking occurs, actuation of the piezoelectric element 4712 will loosen the stuck tissue. A knife slot 4724 is provided to enable a knife to reciprocate therealong.

With reference still to FIGS. 185-186, the flexible circuit electrode assembly 4702 is disposed over the jaw member 4700 of a clamp jaw assembly of an electrosurgical instrument. The jaw member 4700 may represent either an upper jaw member or a lower jaw member of the clamp jaw assembly. The flexible circuit assembly 4702 may be attached to the upper jaw member, lower jaw member, or both. The flexible circuit electrode assembly 4702 comprises a first flexible electrically insulative substrate 4714 (e.g., polyimide, polyester, fluorocarbon, or any polymeric material, or any combinations thereof), and insulator 4706 disposed over the insulative substrate 4714, and conductive traces or pads (e.g., copper) formed on the insulator 4706. The conductive traces define the electrode 4704. A second flexible electrically insulative substrate 4710 is disposed over the insulator 4706 except where the electrode 4704 is exposed to enable tissue treatment, where a groove 4711 is defined between the electrodes 4704 and the second flexible electrically insulative substrate 4710.

A piezoelectric element 4712 (e.g., transducer) is laminated on a lower surface 4715 of the first flexible electrically insulative substrate 4714 of the flexible circuit electrode assembly 4702. The piezoelectric element 4712 is positioned on upper of the jaw member 4700 body 4726, which may be a rigid structure. Thus, when used with another armature/jaw member in opposing position and then actuated towards each other, they will clamp and hold tissue therebetween. The electrode 4704 may be energized in bipolar or monopolar RF mode. The piezoelectric element 4712 can be actuated by a circuit 4718, as described in more detail in connection with FIG. 187.

FIG. 187 is a schematic diagram of a circuit 4718 configured to activate the flexible circuit electrode assembly 4702 (FIGS. 185-186) and the piezoelectric element 4712 (FIG. 186) simultaneously, according to one aspect of the present disclosure. The circuit 4718 is configured to actuate the piezoelectric element 4712 and the electrode 4708 (FIGS. 185-186) at the same time. The circuit 4718 comprises an energy source 4720 configured to provide a high voltage alternating current voltage. The energy source 4720 is applied to the electrode 4708 to treat tissue. A sub-circuit 4722 is used to drive the piezoelectric element 4712.

In other aspects, the electrode 4708 may be energized separately using two separate circuits, one to energize the piezoelectric element 4714 and one to energize the electrode 4708. In another aspect, a single circuit may be used to apply power between the piezoelectric element 4714 and the electrode 4708 alternately rather than simultaneously to affect tissue in the jaw members. In other aspects, power may be applied to the piezoelectric element 4714 and the electrode 4708 to affect tissue in different ways.

XXI. Flexible Circuit Electrodes for Therapy, Sensing, Power, and Proximity Detection FIGS. 188-189 illustrate a jaw member 4600 of clamp jaw assembly comprising a flexible circuit 4602 comprising an inner electrode 4604 for applying therapy to tissue and an outer electrode 4608 for sensing, powering accessory functions, and proximity detection among other functions, according to one aspect of the present disclosure. These functions include: visualizing the tip of the jaw member 4600 via lighting, confirming that the jaw member 4600 has engaged the tissue, determining the presence of tissue in the jaw member 4600, determining where tissue is located in the jaw member 4600, and determining whether a nerve tissue is present in close proximity to the jaw member 4600

FIG. 188 is a perspective view of a jaw member 4600 comprising a flexible circuit 4602 comprising an inner electrode 4604 and an outer electrode 4608, according to one aspect of the present disclosure. The inner electrode 4604 is disposed on and defines a tissue grasping surface 4606 of the jaw member 4600. The inner electrode 4604 is configured to apply therapeutic levels of energy to tissue to seal and/or coagulate tissue. The outer electrode 4608 is disposed on an outer rim 4610 of the jaw member 4600. The outer electrode 4608 is configured to sense and power accessory functions.

FIG. 189 is a detail view of the jaw member 4600 shown in FIG. 188, according to one aspect of the present disclosure. As shown in FIG. 189, the flexible circuit 4602 comprises a first electrically insulative layer 4616 (e.g., polyimide, polyester, fluorocarbon, or any polymeric material, or any combinations thereof) attached to the jaw member 4600 structure. The outer electrode 4608 is disposed over the first insulative layer 4616. A second electrically insulative layer 4618 (e.g., polyimide, polyester, fluorocarbon, or any polymeric material, or any combinations thereof) is disposed over the outer electrode 4608. The inner electrode 4604 is disposed over the second insulative layer 4618 and defines the tissue grasping surface 4606 comprising a knife slot 4620 to enable a knife to reciprocate therein. The flexible circuit 4602 may be disposed over the upper jaw member, lower jaw member, or both, of a clamp jaw assembly.

With reference now to FIGS. 188 and 189, in one aspect, the outer electrode 4608 disposed on the outer rim 4610 of the jaw member 4600 is configured to sense and power accessory functions such as providing direct current (DC) voltage to power LEDs when both upper and lower jaws contact electrically conductive media, detecting tissue presence in the jaw member 4600, the distal end 4612 of the jaw member 4600, the proximal end 4614 of the jaw member 4600. The outer electrode 4608 also is configured to apply DC biphasic power for nerve stimulation. A grounding pad may be employed to complete the circuit with the inner or outer electrodes 4604, 4608.

XXII. Lighting and Illuminating

A. Flexible Circuit Electrode Including LEDS for Illuminating Tissue

FIGS. 190-192 illustrate a flexible circuit electrode assembly 4804 comprising electrodes 4806 for tissue treatment and LEDs 4808 for illuminating tissue, according to one aspect of the present disclosure. In one aspect, the LEDs 4808 can be provided on the periphery of the flexible circuit electrode assembly 4804 to provide visualization at the surgical site. A layer may be added to the flexible circuit electrode assembly 4804 where the LEDs 4808 are printed/connected along the periphery thereof to emit light at the surgical site. A separate power source for the LED 4808 from the flexible circuit electrode 4806 permits lighting at all times and adds another functional feature for the end user to increase their visualization.

FIG. 190 is an elevation view of a clamp jaw assembly 4800 comprising an upper jaw member 4802a and a lower jaw member 4802b comprising a flexible circuit electrode assembly 4804 in the lower jaw member 4802b, according to one aspect of the present disclosure. The upper and lower jaw members 4802a, 4802b are movable relative to each such that either the upper or lower jaw member 4802a, 4802b is movable or both are movable. The flexible circuit electrode assembly 4804 comprises an electrode 4806 and a plurality of LEDs 4808 positioned around the periphery of the lower jaw member 4802b.

FIG. 191 is a plan view of the flexible circuit electrode assembly 4804 comprising the electrode 4806 and the plurality of LEDs 4808 positioned around the periphery of the lower jaw member 4802b, according to one aspect of the present disclosure. The LEDs 4808 may be printed along the perimeter or periphery 4816 of the flexible circuit electrode assembly 4804. Power to the electrode 4806 is provided by a first electrical conductive element 4810 and power to the LEDs 4808 is provide by a second electrical conductive element 4812. The conductive elements 4810, 4812 are coupled to the control circuit 2402 and/or the generator 2404 (FIG. 104). A knife slot 4814 is provided to enable a knife to reciprocate therealong.

To provide improved visualization at the surgical site and to reduce risk of inadvertent tissue damage, the flexible circuit electrode assembly 4804 can be constructed in multiple layers of conductive and insulating materials. On one such layer LEDs 4808 can be embedded along the outer edge 4816 of the flexible circuit electrode assembly 4804 or on the entire conductive layer 4818 to provide illumination directly at the surgical site where the jaws of the clamp jaw assembly 4800 (FIG. 190) of the electrosurgical instrument. A company that produces such LEDs 4808 is Rohinni, which produces LEDs 4808 using diodes about the size of a red blood cell. The LED 4808 light layer may be supplied its own power source through the second conductive element 4812 to provide illumination 100% of the time thus adding a level of additional functionality to the device as a visualization tool. The electrode 4806 can be powered with an independent power source through the first electrically conductive element 4810.

FIG. 192 is a section view of the flexible circuit electrode assembly 4804 taken along section line 192-192 as shown in FIG. 191, according to one aspect of the present disclosure. The flexible circuit electrode assembly 4804 comprises conductive layers 4820 (e.g., copper) between the electrically insulative layers 4822 (e.g., polyimide, polyester, fluorocarbon, or any polymeric material, or any combinations thereof). The electrode 4806 is the exposed conductor layer on upper of the flexible circuit electrode assembly 4804. The LEDs 4808 are located about the periphery 4816 of the flexible circuit electrode assembly 4804.

B. Flexible Circuit Electrode Including LED for Signaling Status

FIGS. 193-194 illustrate a flexible circuit electrode assembly 4904 comprising an electrode 4906 and an LED 4908 for signaling status, according to one aspect of the present disclosure. FIG. 193 is a perspective view of a clamp jaw assembly 4900 comprising an upper jaw member 4902a and a lower jaw member 4902b and a flexible circuit electrode assembly 4904, according to one aspect of the present disclosure. The upper and lower jaw members 4902a, 4902b are movable relative to each such that either the upper or lower jaw member 4902a, 4902b is movable or both are movable. An LED section 4910 of the flexible circuit electrode assembly 4904 comprises a plurality of LEDs 4908 to provide improved visualization at the surgical site. The LED section 4910 is positioned in the upper jaw member 4902a and the electrode 4906 is located in the lower jaw member 4902b to provide visual indication of tissue sealing status. Signaling at the surgical site enables the surgeon to see the LED signal without having to look at the device outside the surgical site. Power and communication to the LED section 4910 is provided through a first conductive element 4914 and power to the electrode 4906 is provided through a second conductive element 4916. The conductive elements 4914, 4916 are coupled to the control circuit 2402 and/or the generator 2404 (FIG. 104). A knife slot 4912 is provided to enable a knife to reciprocate therealong.

In one aspect, the LEDs section 4910 comprises colored LEDs 4908. In one aspect, three LEDs 4908 are provided. A red LED 4908a, a yellow LED 4908b, and a green LED 4908c, for example. Additional or fewer LEDs 4908 may be employed as well as different colors. The colored LEDs 4910 provided on a separate leg of the flexible circuit electrode assembly 4904 can be connected back to a control circuit 2402 or generator 2404 (FIG. 104). The red LED 4908a/yellow Led 4908b/green LED 4908c on the upper jaw member 4902a may be combined with tones to indicate different conditions at the surgical site. Visualization can be linked to other sensor feedback such as tissue status via temperature, photo optics, jaw position, among others. Improved visual communication at the surgical site provides consistent tissue performance and improved communication to user of device status—generator status and tissue status.

FIG. 194 is a plan view of the flexible circuit electrode assembly 4904 shown in FIG. 193, according to one aspect of the present disclosure. The flexible circuit electrode assembly 4904 comprises two sections, an electrode section 4918 and an LED section 4910 such that the LED section 4910 can be located in one jaw member and the electrode section 4918 can be located in the other jaw member. The LED section 4910 comprises a first group of colored LEDs 4908: red LED 4908a, a yellow LED 4908b, and a green LED 4908c on one side, and a second group of colored LEDS 4908': red LED 4908a', a yellow LED 4908b', and a green LED 4908c' on the other side to provide added visibility of the LEDS signals to the surgeon. The conductive elements 4914, 4916 coupled to the electrode and LED section 4910 on one side and the control circuit 2402 and/or the generator 2404 (FIG. 104) on the other and the knife slot 4912 are also shown.

With reference now to FIGS. 193 and 194, the flexible circuit electrode assembly 4904 can be constructed in multiple layers of conductive and insulating materials and each layer may have different geometrical patterns and different power sources. On one such layer, independent of the electrode 4906, may comprise the colored LED 4908 lights embedded along the periphery 4920 and can extend in such a way that it may be routed and secured into the jaw member 4902a, 4902b of a monopolar or bipolar RF electrosurgical instrument that is opposite to the jaw member 4902a, 4902b that contains the electrode 4906. The LED 4908 layer can have its own power/communication source through conductive element 4916 linked back to the control circuit 2402 and/or the generator 2404 (FIG. 104). The colored lighting would provide a visual signal in the surgical field and would not require the user to move their focus outside of the surgical field. The colored lighting could be synced to communicate the power state of the electrosurgical instrument, including tones, or other sensor feedback driven tissue status updates related to temperature, photo optics, jaw position, among others.

C. Flexible Circuit Electrode Assembly Including Optical Sensing System

FIGS. 195-196 illustrate a flexible circuit electrode assembly 5004 comprising an optical sensing system 5014 comprising at least one light emitting diode 5008 (LED) and photo sensor 5010 to provide an indication of tissue status and visualization of the surgical site, according to one aspect. FIG. 195 is an elevation view of a clamp jaw assembly 5000 comprising an upper jaw member 5002a and a lower jaw member 5002b and a flexible circuit electrode assembly 5004, according to one aspect of the present disclosure. The upper and lower jaw members 5002, 5002b are movable relative to each such that either the upper or lower jaw member 5002a, 5002b is movable or both are movable. The flexible circuit electrode assembly 5004 comprises an upper jaw portion 5004a and a lower portion 5004b. The upper jaw portion 5004a comprises one component of the optical sensing system 5014, a plurality of LEDs 5008, and also may comprise an electrode. The lower jaw portion 5004b comprises an electrode 5006 and another component of the optical sensing system 5014, a photo sensor 5010, such as a photodiode, to detect the light emitted 5016 by the LEDs 5008. The LEDs 5008, electrode 5006, and optical sensor 5010 are coupled back to the control circuit 2402 and/or the generator 2404 (FIG. 104).

In one aspect, one or more than one optical sensor 5010 can be incorporated into a flexible circuit electrode assembly 5004 to determine changes in tissue 5012 condition. The monopolar or bipolar RF electrosurgical instruments generally may use one tissue parameter, impedance, to determine the effect that the RF electricity has had on the tissue 5012. Providing additional feedback to the control circuit 2402 and/or the generator 2404 (FIG. 104) can improve the confidence level of the surgeon that a tissue seal has been created in the tissue bundles treated between the clamp jaw assembly 5000 of the end effector of the electrosurgical instrument.

At least one LED 5008 located on one jaw member 5002a, 5002b in combination with an optical sensor 5010 (e.g., photodiode) located on another jaw member 5002a, 5002b can be used to determine when the tissue seal is complete. The location of the tissue 5012 within the jaw members 5002a, 5002b (distal vs. proximal), blood pressure, and force within the jaw members 5002a, 5002b. The LED 5008 can serve a second purpose of providing lighting and furthering surgeon visibility.

The LED 5008 can either be comprised of organic polymers and small molecules or inorganic structures. In this illustration, patternable organic LEDs 5008 are formed by vapor thermal evaporation and patterned using stencil lithography on the flexible circuit electrode assembly 5004. The photodiode optical sensor 5010 can be covered by an optical window which permits only selected wavelength transmissions. The window also may be coated for durability, or contain one or more lenses for different diffraction gradients. The photodiode optical sensor 5010 or the LED 5008 is mounted to the trace layer of a separate flexible printed circuit of the flexible circuit electrode assembly 5004 where individual conductors are photo etched from copper or another conductor. Traces in the flexible circuit, which are connected to the photodiode optical sensor 5010 or the LED 5008 are routed proximally to carry the sensor current to the analog processing electronics located either in the handle of the instrument and/or the generator. These electronics may comprise of amplifiers, digital converters, and pass band filters, and be part of the control circuit 2402 (FIG. 104) or the generator 2404 (FIG. 104). The location and intensity of light reception by the photodiode optical sensor 5010 can indicate the tissue thickness as well as tissue location within the jaw members 5002a, 5002b of the clamp jaw assembly 5000, while the LEDs 5008 can provide a secondary function of further enhancing surgeon visualization in confined spaces.

FIG. 196 is a logic diagram 5020 of operating the optical sensing system 5014 described in connection with FIG. 195, according to one aspect of the present disclosure. The optical sensing system 5014 controlled by the control circuit 2402 (FIG. 104). The logic diagram 5020 will now be described in connection with FIG. 195. Power is applied 5022 to the LEDs 5008 and the photo sensor 5010 via a trace in the flexible circuit electrode assembly 5004. Accordingly, light 5016 is transmitted from the LEDs 5008 through the tissue 5012 and light that is not absorbed by the tissue 5012 is detected 5024 by the photo sensor 5010. The photo sensor 5010 generates an analog signal proportional to the light sensed by the photo sensor 5010. The control circuit 2402 receives 5026 the analog signal from the photo sensor 5010. The analog signal is filtered 5028 and is provided to an digital signal processing circuits located in the handle of the electrosurgical instrument. The digital signal processing circuits include at least one analog-to-digital converter and a digital signal processor. The analog signal is converted to a digital signal and is processed 5030 by the digital signal processing circuits. The process described above, can be applied to a plurality of LEDs 5008 and/or a plurality of photo sensors 5010 may be provided to evaluate tissue 5012 in different location in the clamp jaw assembly 5000.

D. Flexible Circuit Electrode Including Light Pipe and LED Light Source

FIG. 197 illustrates a flexible circuit electrode assembly 5100 comprising an electrode 5102 and a light pipe 5104, according to one aspect of the present disclosure. A light source 5106 is provided to transmit light into the light pipe 5104 to illuminate the surgical site and enhance the visibility of the surgical field of view. An LED light source 5106 is used in conjunction with a polymer layer acting as a light pipe 5104 to provide better illumination at the surgical site and improved visibility of the surgical field of view. As a result this technique should minimize unintended tissue damage. A polymer layer 5108 is incorporated into a flexible circuit electrode assembly 5100. The polymer layer 5108 comprises geometric features 5110 to refract the incoming light source 5106 outward to provide light 5112 to illuminate the distal end of the electrosurgical instrument as well as the surrounding surgical field of view.

E. Flexible Circuit Electrode Including Light Pipe and Optical Fiber Light Source FIG. 198 illustrates a flexible circuit electrode assembly 5200 comprising an electrode 5202 and a light pipe 5204, according to one aspect of the present disclosure. The light pipe 5204 comprises an optical fiber light source 5206 to illuminate the surgical site and enhance the visibility of the surgical field of view. The flexible circuit electrode assembly 5200 comprises an optical fiber in conjunction with a polymer layer 5208 acting as a light pipe 5204 to illuminate the surgical site and enhance the visibility of the surgical field of view and as a result can minimize unintended tissue damage. The polymer layer 5208 is incorporated into the flexible circuit electrode assembly 5200. The polymer layer comprises geometric features 5210 to refract the incoming light source 5206 outward to provide light 5212 to illuminate the distal end of the instrument as well as the surrounding surgical field.

XXIII. Proximity Sensing

A. Electrosurgical Instrument Equipped with Inductive Element Based Proximity Sensor The end effector portion of an electrosurgical instrument can be equipped with an inductive element to implement an inductance based proximity sensor. It is advantageous to understand the position of a moving jaw member of the clamp jaw assembly of an end effector portion of an electrosurgical instrument relative to the opposite jaw member. This information allows the electrosurgical instrument to determine or infer the location of the tissue, the tissue type, or the intended use, and adjust the output of the electrosurgical instrument accordingly A flexible circuit electrode assembly may comprise a continuous wire looped through multiple layers that can be accomplished by printing one layer and folding over to create an inductive coil. The circuit comprises a lead and return as two connections to the proximal end of the electrode and is anchored to two separate insulated wires that run proximally to the handle. No additional circuitry is needed at the distal end of the electrode. A small current is applied by the control circuit 2401 and/or the generator 2404 (FIG. 104) to the inductive coil and to monitor its return. The return from the inductive coil will be indicative of the position of other metallic objects near the electrode, mainly the other jaw member of the electrosurgical instrument. If the inductor indicates an excessively large distance for the other jaw member it can infer that extraordinarily thick tissue is present, or that the surgeon is intentionally feathering on thick tissue without over compressing it. The electrosurgical instrument can use this information to increase its output current knowing that there will be more resistance due to the tissue thickness.

Additionally, the inductor can be custom calibrated for how much the field is modified based on the position of the jaw member during the manufacturing process. Equipment could control the position of the jaw member, either as a sub-assembly, or a full device assembly, and monitor the inductive response at different positions. The resultant calibration can be recorded as a parameter on the device's specific EEPROM.

B. Proximity Sensor System Including Inductive Element Formed on a Flexible Circuit FIGS. 199-208 illustrate a proximity sensor system 5300 comprising an inductive element 5302 formed on a flexible circuit 5304, according to one aspect of the present disclosure. The proximity sensor system 5300 also comprises an inductance-to-digital converter circuit 5306.

FIG. 199 is a schematic diagram of a proximity sensor system 5300 configured to measure axial distance "d" to a target 5322, according to one aspect of the present disclosure. The proximity sensor system 5300 comprises an inductive element 5302 formed on a flexible circuit 5304. The inductive element 5302 is coupled to an inductance-to-digital converter circuit 5306 to convert the analog signal from the inductive element 5302 to a digital signal, which can then be digitally processed by the control circuit 2402 (FIG. 104).

FIG. 200 is a functional block diagram of the proximity sensor system 5300, according to one aspect of the present disclosure. The inductive element 5302 can be modeled as an inductor L in series with a resistor Rp and in parallel with a capacitor C. The inductive element 5302 is coupled to the inductance-to-digital converter circuit 5306. The signal is received by an inductance-to-digital converter 5308. The digital output of the inductance-to-digital converter 5308 is coupled to a threshold detector 5310, a proximity data register 5312, and a frequency counter data register 5314. The outputs from the threshold detector 5310, proximity data register 5312, and frequency counter data register 5314 are provided to a 4-wire serial interface 5320 for communication purposes. A frequency counter 5316 is coupled to the frequency counter data register 5314. The inductance-to-digital converter circuit 5306 comprises a power section 5318 to condition the power for the inductive element 5302.

The inductance-to-digital converter 5308 measures the parallel impedance of the LC resonator of the inductive element 5302. It accomplishes this task by regulating the oscillation amplitude in a closed-loop configuration to a constant level, while monitoring the energy dissipated by the resonator. By monitoring the amount of power injected into the resonator, the circuit 5308 can determine the value of Rp and it returns this as a digital value which is inversely proportional to Rp. The threshold detector 5310 block provides a comparator with hysteresis. With the threshold registers programmed and comparator enabled, the proximity data register 5312 is compared with threshold registers and indicates the output. The circuit 5308 has a simple 4-wire serial interface 5320.

FIG. 201 is a simplified circuit model of the proximity sensor system 5300 and a proximal metal target 5322, according to one aspect of the present disclosure. An AC source 5323 provides an alternating current that flows through a coil L will generate an alternating current (AC) magnetic field. If a conductive material, such as a metal target 5322, is brought into the vicinity of the coil L, this magnetic field will induce circulating currents (eddy currents) on the surface of the target. These eddy currents are a function of the distance, size, and composition of the target 5322. The eddy currents then generate their own magnetic field, which opposes the original field generated by the coil L. This mechanism is best compared to a transformer, where the coil is the primary core and the eddy current is the secondary core. The inductive coupling between both cores depends on distance and shape. Hence the resistance and inductance of the secondary core (eddy current), shows up as a distant dependent resistive and inductive component on the primary side (coil).

FIG. 202 is a simplified circuit model of a metal target 5322 modeled as an inductor $L_T$ and resistor $R_T$ with circulating eddy currents 5325, according to one aspect of the present disclosure. The eddy currents 5325 generated on the surface of the target 5322 can be modeled as a transformer. The coupling 5324 between the primary and secondary coils is a function of the distance "d" and the conductor's characteristics. The inductance Ls is the inductance of the coil L shown in FIG. 201 and Rs is the parasitic series resistance of the coil L shown FIG. 201. The inductance L(d), which is a function of distance "d" is the coupled inductance of the metal target 5322. Likewise, R(d) is the parasitic resistance of the eddy currents and is also a function of distance.

FIG. 203 is a schematic diagram of a linear position sensing system 5330 comprising an inductive element 5302 formed on a flexible circuit 5304 and an inductance-to-digital converter circuit 5308, according to one aspect of the present disclosure. The inductive element 5302 can be formed on a flexible circuit 5304 and installed in a jaw member of a clamp arm assembly in accordance with the present disclosure. The inductive element 5302 is coupled to the inductance-to-digital converter circuit 5308 by a capacitor C. The output of the inductance-to-digital converter circuit 5308 is a linear representation of the position of a conductive target 5332 relative to the inductive element 5302.

FIG. 204 is a graphical representation 5334 of the linear position sensing system 5330 shown in FIG. 203, according to one aspect of the present disclosure. The vertical axis is the digital output of the inductance-to-digital converter circuit 5308 and the horizontal axis represents the position of the conductive target 5332 relative to the inductive element 5302.

FIG. 205 is a schematic diagram of an angular position sensing system 5340 comprising a flexible circuit inductive element 5302 formed on a flexible circuit 5304 and an inductance-to-digital converter circuit 5308, according to one aspect of the present disclosure. The inductive element 5302 can be formed on a flexible circuit and installed in a jaw member of a clamp arm assembly. The inductive element 5302 is coupled to the inductance-to-digital converter circuit 5308 by a capacitor C. The output of the inductance-to-digital converter circuit 5308 is a saw tooth waveform that represents the angular position of a conductive target 5342 relative to the inductive element 5302. The saw tooth graph that is linear output over a 360° range.

FIG. 206 is a graphical representation 5346 of the angular position sensing system 5340 shown in FIG. 203, according to one aspect of the present disclosure. The vertical axis is the digital output of the inductance-to-digital converter circuit 5308 and the horizontal axis represents the angular position (deg) of the conductive target 5342 relative to the inductive element 5302.

FIG. 207 is an upper layer layout 5350 of the inductive element 5302 formed on a flexible circuit 5304 and an inductance-to-digital converter circuit 5308 and FIG. 208 is a lower layer layout 5352 of the inductive element 5302 formed on a flexible circuit 5304 and an inductance-to-digital converter circuit 5308.

XXIV. Flexible Circuit Electrodes Coated with Insulation

FIGS. 209-210 illustrate examples of flexible circuit electrodes coated with ultraviolet (U.V.) cured paint insulation systems, according to one aspect of the present disclosure.

FIG. 209 illustrates a coating process 5400 for applying a dielectric material 5402 on an electrical connection 5404 or joint between a flexible circuit electrode assembly 5406 and an electrical conductor 5408 with, according to one aspect of the present disclosure. A first mask 5410 is provided over the flexible circuit electrode assembly 5406 and a second mask 5412 is provided over the other circuit elements such as the electrical conductor 5408, which is tied to ground 5414 during the coating process. An electrospray nozzle 5416 is used for a localized application of a small amount of dielectric material 5402 in paint on the electrical connection 5404. Spraying the dielectric material 5402 in paint form or lacquer form leaves no gaps in the coating. In one aspect, transfer windings are coated in lacquer to prevent shorting. The electrical connection 5404 is coated in lacquer and all exposed metal surfaces all electro-sprayed.

FIG. 210 is an electrical schematic diagram 5420 of the electrospray process, according to one aspect of the present disclosure. As shown in FIG. 210, an electrospray nozzle 5416 is positively charged to a high voltage, e.g., +100V. An active rod target 5422, such as the electrical connection 5404 shown in FIG. 209, to be coated is tied to ground 5414. When the electrospray nozzle 5410 is activated, it releases charged lacquer particles 5424, which coat the target 5422.

XXV. Heating, Cutting with Heat, and Cooling

A. Temperature Sensor Overmolded with Flexible Circuit Electrode

FIGS. 211-215 illustrate temperature sensor overmolded with a flexible circuit electrode assembly located in a jaw member to provide a biocompatible clamp jaw assembly, according to one aspect of the present disclosure. Temperature sensors can be disposed in a clamp jaw assembly to provide real time accurate measurement of temperature at the jaw member and can provide improved tissue temperature control when used to control device power output and seal termination. Biocompatibility of sensor material, wire protection and routing, and assembly difficulties prevent simple integration of temperature sensors (or other sensors: force, light etc.) in the jaw member. Biocompatibility of thermistor material, wire protection and routing, and assembly difficulties prevent simple integration of temperature sensor or other sensors types.

Thermistors would provide real time accurate measurement of temperature at the jaw and can provide improved tissue temperature control when used to control device power output and seal termination. The temperature sensors can be soldered, adhered, or placed on the electrode lower with an injection molding tool to inject insulator material (glass filled polyamide for example) around wires to lock them in place. Encapsulated sensors and wires keep patient safe and improve assembly. Better control of power can improve seal strength and procedural efficiency. In one aspect, a configuration and method of manufacturing a flexible circuit electrode assembly comprising embedded temperature sensor in a monopolar or bipolar RF vessel sealer clamp jaw assembly are provided.

FIG. 211 is a perspective view of a clamp jaw assembly 5500 configured for an electrosurgical instrument tissue sealer comprising an embedded temperature sensor 5506, according to one aspect of the present disclosure. The clamp jaw assembly 5500 comprises an upper jaw member 5502*a* and a lower jaw member 5502*b*. The upper and lower jaw members 5502*a*, 5502*b* are movable relative to each other. One or both jaw member 5502*a*, 5502*b* may be movable. The temperature sensor 5506 can be overmolded with a flexible circuit electrode assembly 5504. The flexible circuit electrode assembly 5504 may be located in at least one of the jaw members 5502*a*, 5502*b* or both. A knife slot 5508 is provided in at least one jaw member 5502*b* to enable a knife to reciprocate therealong. A plurality of elements or stop members 5518 are formed on the tissue contacting surface 5512 of the flexible circuit electrode assembly 5504.

FIG. 212 is a plan view of the flexible circuit electrode assembly 5504 comprising an embedded temperature sensor 5506 overmolded therewith, according to one aspect of the present disclosure. The flexible circuit electrode assembly 5504 comprises an electrode 5510 on a tissue contacting surface 5512 and one or more embedded temperatures sensor 5506 located just below the tissue contacting surface 5512. A first electrical connector 5514 is provided to supply power to and read a signal from the temperature sensor 5506. A second connector 5516 is provided to supply power to the electrode 5510.

FIG. 213 is a perspective view from the proximal end of the flexible circuit electrode assembly 5504 with a temperature sensor 5506 overmolded therewith, according to one aspect of the present disclosure. The knife slot 5508, the tissue contacting surface 5512, and the first and second electrical connectors 5514, 5516 also are shown.

FIG. 214 is a section view of the flexible circuit electrode assembly 5504 with a temperature sensor 5506 overmolded therewith taken along section line 214-214 as shown in FIG. 213, according to one aspect of the present disclosure. The section view illustrates the electrical contact elements 5514 that supply power to and carry signals to and/or from the temperature sensor 5506 located just below the tissue contacting surface 5512.

FIG. 215 is a section view of the flexible circuit electrode assembly 5504 with a temperature sensor 5506 overmolded therewith taken along section line 215-215 as shown in FIG. 214, according to one aspect of the present disclosure. This view shows the lower portion 5524 of the flexible circuit electrode assembly 5504 that is attached to the lower jaw member 5502*b* of the clamp arm assembly 5500. Recesses or apertures 5520 are formed in the lower portion 5524 of the flexible circuit electrode assembly 5502*b* that houses the temperature sensor 5506. FIG. 215 also provides another view of the electrical contact elements 5514 located below the tissue contacting surface 5512 and the knife slot 5508.

B. Flexible Circuit Electrode Including RF Electrode with Tissue Contacting Surface and Heater Element to Create Dual Energy Source for Treating Tissue FIG. 216 illustrates a flexible circuit electrode assembly 5600 comprising a RF electrode 5602 with a tissue contacting surface and a heater element 5604 thus creating a dual energy source for treating tissue, according to one aspect of the present disclosure. In one aspect, a vapor film with high resistance zones is deposited on a layer beneath the exposed RF electrode 5602 to form a resistive heating layer 5604. The electrode 5602 may be formed of copper or other electrically conductive metal. Accordingly, the electrode 5602 defines a first heating zone to seal tissue and the resistive heating layer 5604 defines a second heating zone to raise the tissue temperature. The resistive heating layer 5604 comprises a plurality of resistive heating elements 5606. When low impedance tissue is detected on the tissue contacting surface of the electrode 5602, the resistive heating layer 5604 can be activated. Heat from the resistive heating layer 5604 works in conjunction with the RF energy from the electrode 5602 to raise the tissue temperature to a water desiccating temperature. This provides a technique for heating low impedance tissues in an RF electrosurgical instrument tissue sealer. An electrically insulative layer 5608 is disposed between the electrode 5602 and the resistive heating layer 5604. The flexible circuit electrode assembly 5600 is coupled to the control circuit 2402 and/or the generator 2404 (FIG. 104) to detect the low impedance tissue disposed on the electrode 5602 and to drive a current through the resistive heating layer 5604 to control its temperature.

C. Process of Sealing, Cooling, and Cutting Tissue while Cooling

Electrosurgical instruments generally depend on mechanical force input from the surgeon to drive a knife to cut tissue. An electric knife increases ease of operation, but a conventional electric knife may be subject to excessive heat spread to the tissue. Thus, an electrical knife alone may not provide the best results because of tissue overheating concerns. Employing flexible circuit technology, however, it is more practical to incorporate MEMS based cooling cells to offset increased heat spread from the electric knife. The surgeon would experience ease of use because they only need to push a button to activate the electric knife and the cooling cells.

FIGS. 217-219 illustrate a process of sealing, cooling, and cutting tissue while cooling, according to one aspect of the present disclosure. The process may be carried out with a clamp jaw assembly comprising an upper jaw member and a lower jaw member and a flexible circuit electrode assembly comprising an electric knife, one or more cooling cells, and one or more electrodes disclosure. The electrodes may be disposed either in the upper or lower jaw member, or both, and are provided to make a tissue seal. The upper and lower jaw members are movable relative to each other, where either one of the upper and lower jaws are movable or both are movable. The electric knife and/or the cooling cells can be implemented with superconducting heat and/or microelectromechanical systems (MEMS) cooling cells. The electrosurgical instrument employs a flexible circuit electrode assembly that contains multiple circuits such as electrodes for sealing the tissue, an electric knife for cutting the tissue, and cooling cells the cooling the tissue. The electrodes, electric knife, and cooling cells ae coupled to the control circuit 2402 and/or the generator 2404 (FIG. 104) to control the operation of each of the separate circuits controlling sealing, cooling, and cutting tissue.

FIG. 217 is a section view of a clamp jaw assembly 5700 in the process of performing a first step of sealing tissue disposed in the clamp jaw assembly 5700, according to one aspect of the present disclosure. The circuits disposed on the flexile circuit electrode are configured as electrodes to seal tissue using RF energy via electrodes 5702*a*, 5702*b*.

FIG. 218 is a section view of the clamp jaw assembly 5700 shown in FIG. 217 in the process of performing a second step of cooling the tissue disposed in the clamp jaw assembly, according to one aspect of the present disclosure. The circuits disposed on the flexile circuit electrode are configured as cooling cells 5704*a*, 5704*b* to cool the tissue by activating the MEMS elements. Next both pads would activate MEM cooling cells, which would have thermal reservoirs attached to a super conductive bar that runs the length of the shaft to a cold reservoir in the handle. This bar would be insulated along the length of the shaft.

FIG. 219 is a section view of the clamp jaw assembly 5700 shown in FIG. 217 in the process of performing a third step of cooling and cutting the tissue disposed in the clamp jaw assembly, according to one aspect of the present disclosure. The circuits disposed on the flexile circuit electrode are configured as a MEMS electric knife between electrode 5706*a*, 5706*b* to cut the tissue while limiting the thermal spread in the tissue with cooling cells 5708, and thus eliminating the need for a mechanical knife. While the cooling cells 5708 are activated, a third circuit is triggered to transect or cut the tissue between electrodes 5706a, 5706b, isolating thermal energy to the region intended to be cut. Thus transecting tissue with minimal thermal spread to neighboring tissue. This would make an electric knife a viable solution without excessive tissue damage.

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Aspects of the devices disclosed herein can be designed to be disposed of after a single use, or they can be designed to be used multiple times. Aspects may, in either or both cases, be reconditioned for reuse after at least one use. Reconditioning may include any combination of the steps of disassembly of the device, followed by cleaning or replacement of particular pieces, and subsequent reassembly. In particular, aspects of the device may be disassembled, and any number of the particular pieces or parts of the device may be selectively replaced or removed in any combination. Upon cleaning and/or replacement of particular parts, aspects of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various aspects of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, aspects, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

While various details have been set forth in the foregoing description, it will be appreciated that the various aspects of the flexible circuits for electrosurgical instrument may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one aspect," or "an aspect" means that a particular feature, structure, or characteristic described in connection with the aspect is included in at least one aspect. Thus, appearances of the phrases "in one aspect," "in an aspect," "in one aspect," or "in an aspect" in various places throughout the specification are not necessarily all referring to the same aspect. Furthermore, the particular features, structures or characteristics may be combined in any suitable manner in one or more aspects.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

Some or all of the aspects described herein may generally comprise technologies for flexible circuits for electrosurgical instrument, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various aspects of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), or other integrated formats. Those skilled in the art will recognize, however, that some aspects of the aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative aspect of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

In summary, numerous benefits have been described which result from employing the concepts described herein. The foregoing description of the one or more aspects has been presented for purposes of illustration and description. It is not intended to be exhaustive or limiting to the precise form disclosed. Modifications or variations are possible in light of the above teachings. The one or more aspects were chosen and described in order to illustrate principles and practical application to thereby enable one of ordinary skill in the art to utilize the various aspects and with various modifications as are suited to the particular use contemplated. It is intended that the claims submitted herewith define the overall scope.

What is claimed is:

1. A flexible circuit electrode formed by a process, comprising:
    laminating a flexible electrically conductive sheet to a flexible electrically insulative sheet with adhesive therebetween to produce a flexible laminate;
    forming at least one electrode on the flexible electrically conductive sheet, wherein the at least one electrode comprises at least two electrode segments connected by a flexure bearing, and wherein each of the two electrode segments has a tissue contacting surface;

forming at least one electrically insulative layer on the tissue contacting surface of at least one of the two electrode segments, wherein the at least one electrically insulative layer comprises a dielectric, nonstick element; and separating the at least one electrode from the flexible laminate.

2. The flexible circuit electrode of claim 1, wherein the flexible electrically conductive sheet is selected from any one of copper, gold plated copper, silver, platinum, stainless steel, or aluminum, or alloys thereof.

3. The flexible circuit electrode of claim 1, wherein the flexible electrically insulative sheet is selected from any one of polyimide, polyester, fluorocarbon, or any polymeric material, or any combinations thereof.

4. The flexible circuit electrode of claim 1, wherein forming the at least one electrode on the flexible electrically conductive sheet comprises etching the at least one electrode on the flexible electrically conductive sheet.

5. The flexible circuit electrode of claim 4, wherein etching comprises:
    screen printing a protective barrier on the flexible electrically conductive sheet; and
    photoetching away any remaining material which does not make up a final shape of the at least one electrode.

6. The flexible circuit electrode of claim 5, wherein the at least one electrically insulative layer further defines the at least one electrode.

7. The flexible circuit electrode of claim 1, wherein the at least one electrically insulative layer defines at least one electrically insulative element.

8. The flexible circuit electrode of claim 7, wherein the at least one electrically insulative element is configured as a spacer.

9. The flexible circuit electrode of claim 1, wherein forming the at least one electrically insulative layer comprises printing the dielectric, nonstick element on the at least one of the tissue contacting surfaces of the at least one of the two electrode segments.

10. The flexible circuit electrode of claim 1, wherein forming the at least one electrically insulative layer comprises bonding the dielectric, nonstick element on the at least one of the tissue contacting surfaces of the at least one of the two electrode segments.

11. The flexible circuit electrode of claim 10, further comprising forming a spacer by etching the dielectric, nonstick element bonded to the at least one of the tissue contacting surfaces of the at least one of the two electrode segments.

12. The flexible circuit electrode of claim 1, wherein forming the at least one electrically insulative layer comprising the dielectric, nonstick element comprises printing the dielectric, nonstick element on the at least one of the tissue contacting surfaces of the at least one of the two electrode segments.

13. The flexible circuit electrode of claim 12, wherein printing the dielectric, nonstick element comprises printing an annular wall on the at least one of the tissue contacting surfaces of the at least one of the two electrode segments, and wherein the annular wall defines a cavity.

14. The flexible circuit electrode of claim 1, wherein forming the at least one electrically insulative layer on the at least one of the tissue contacting surfaces of the at least one of the two electrode segments comprises printing the dielectric, nonstick element sized and configured to define a predetermined gap between opposing jaw members of a clamp jaw assembly.

15. The flexible circuit electrode of claim 1, wherein forming the at least one electrically insulative layer on the at least one tissue contacting surface of the at least one of the two electrode segments comprises printing at least one dielectric, nonstick pattern on the at least one tissue contacting surface of the at least one of the two electrode segments.

16. The flexible circuit electrode of claim 1, wherein separating the at least one electrode comprises die cutting the at least one electrode from the flexible laminate.

17. The flexible circuit electrode of claim 1, wherein forming the at least one electrode comprises forming a distal electrode element on a distal end of the at least one electrode.

18. The flexible circuit electrode of claim 17, wherein forming the distal electrode element comprises forming a distal electrode element that is electrically coupled to the at least one electrode.

19. The flexible circuit electrode of claim 17, wherein forming the distal electrode element comprises forming a distal electrode element that is electrically isolated from the at least one electrode.

20. The flexible circuit electrode of claim 1, wherein forming the least two electrode segments connected by the flexure bearing comprises forming the at least two electrode segments spaced apart laterally relative to the flexure bearing on the at least one electrode.

21. The flexible circuit electrode of claim 1, wherein forming the least two electrode segments connected by a flexure bearing comprises forming the at least two electrode segments are spaced apart longitudinally relative to the flexure bearing on the at least one electrode.

22. The flexible circuit electrode of claim 1, wherein:
    forming at least one electrode on the flexible electrically conductive sheet comprises forming a plurality of electrodes on the flexible electrically conductive sheet; and
    forming at least one electrically insulative layer comprising the dielectric, nonstick element on the at least one tissue contacting surface of the least one of the two electrode segments comprises forming the at least one electrically insulative layer comprising the dielectric, nonstick element on at least one of the tissue contacting surfaces of each of the plurality of electrodes.

\* \* \* \* \*